(12) United States Patent
Holloway et al.

(10) Patent No.: US 8,216,999 B2
(45) Date of Patent: *Jul. 10, 2012

(54) HCV NS3 PROTEASE INHIBITORS

(75) Inventors: M. Katharine Holloway, Lansdale, PA (US); Nigel J. Liverton, Harleysville, PA (US); Steven W. Ludmerer, North Wales, PA (US); John A. McCauley, Maple Glen, PA (US); David B. Olsen, Lansdale, PA (US); Michael T. Rudd, Collegeville, PA (US); Joseph P. Vacca, Telford, PA (US); Charles J. McIntyre, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 416 days.

This patent is subject to a terminal disclaimer.

(21) Appl. No.: 12/325,965

(22) Filed: Dec. 1, 2008

(65) Prior Publication Data

US 2009/0124661 A1    May 14, 2009

Related U.S. Application Data

(63) Continuation of application No. 11/484,925, filed on Jul. 12, 2006, now Pat. No. 7,470,664.

(60) Provisional application No. 60/700,764, filed on Jul. 20, 2005, provisional application No. 60/724,566, filed on Oct. 7, 2005.

(51) Int. Cl.
*A61K 38/12* (2006.01)
*C07K 7/50* (2006.01)

(52) U.S. Cl. ......... 514/4.3; 514/21.1; 530/331; 540/455

(58) Field of Classification Search .................. None
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,184 B2 | 10/2005 | Friedrichs et al. | |
| 7,470,664 B2 * | 12/2008 | Holloway et al. | 514/1.1 |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0038872 A1 | 2/2004 | Campbell et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| GB | 2337262 A | 11/1999 |
| GB | 2430621 A | 4/2007 |
| WO | 97/041211 A1 | 11/1997 |
| WO | 98/022496 A2 | 5/1998 |
| WO | 98/046630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |

(Continued)

OTHER PUBLICATIONS

Brian W. Dymock et al., "Novel Approaches to the Treatment of Hepatitis C Virus Infection," 11 Antiviral Chemistry & Chemotherapy 79-96 (2000). Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

(Continued)

*Primary Examiner* — Jeffrey E Russel
(74) *Attorney, Agent, or Firm* — Julie M. Lake; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections.

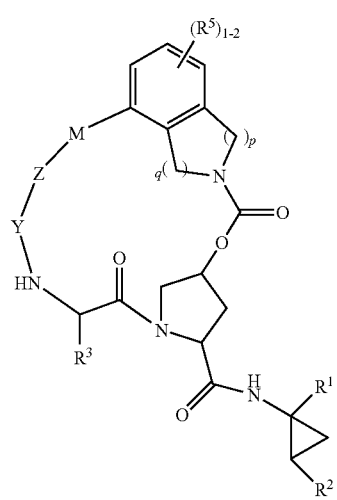

18 Claims, No Drawings

FOREIGN PATENT DOCUMENTS

| | | |
|---|---|---|
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | WO03/053349 A2 | 7/2003 |
| WO | 03/064455 A2 | 8/2003 |
| WO | 03/068244 A1 | 8/2003 |
| WO | WO03/066103 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | WO2004/037855 A1 | 5/2004 |
| WO | 2004/093915 A1 | 11/2004 |
| WO | WO2004/099203 A1 | 11/2004 |
| WO | 2004/103996 A1 | 12/2004 |
| WO | WO2005/010029 A1 | 2/2005 |
| WO | WO2005/095403 A2 | 10/2005 |
| WO | 2007/131966 A1 | 11/2007 |
| WO | WO2008/019303 A2 | 2/2008 |
| WO | 2008/057208 A2 | 5/2008 |
| WO | 2009/064955 A1 | 5/2009 |
| WO | 2009/064975 A1 | 5/2009 |

OTHER PUBLICATIONS

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., "The occurrence of a hydride shift in the aromatization of 1,4-epoxy-1,2-dihydronaphthalenes," 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

* cited by examiner

HCV NS3 PROTEASE INHIBITORS

CROSS-REFERENCE TO RELATED APPLICATIONS

This application is a continuation application of U.S. patent application Ser. No. 11/484,925, filed Jul. 12, 2006 now U.S. Pat. No. 7,470,664 which claims priority to U.S. Provisional Patent Application No. 60/700,764, filed Jul. 20, 2005, and to U.S. Provisional Patent Application No. 60/724,566, filed Oct. 7, 2005.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock et al., "Novel approaches to the treatment of hepatitis C virus infection," 11 *Antiviral Chem. & Chemotherapy* 79-96 (2000); H. Rosen et al., "Hepatitis C virus: current understanding and prospects for future therapies," 5 *Molec. Med. Today* 393-399 (1999); D. Moradpour et al., "Current and evolving therapies for hepatitis C," 11 *Euro. J. Gastroenterol. Hepatol.* 1189-1202 (1999); R. Bartenschlager, "Candidate Targets for Hepatitis C Virus-Specific Antiviral Therapy," 40(5-6) *Intervirology* 378-393 (1997); G. M. Lauer & B. D. Walker, "Hepatitis C Virus Infection," 345 *N. Engl. J. Med.* 41-52 (2001); B. W. Dymock, "Emerging therapies for hepatitis C virus infection," 6 *Emerging Drugs* 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. Patent Application Publication Nos. US 2005/0020503, US 2004/0229818, and US 2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I) and/or a pharmaceutically acceptable salt or hydrate thereof:

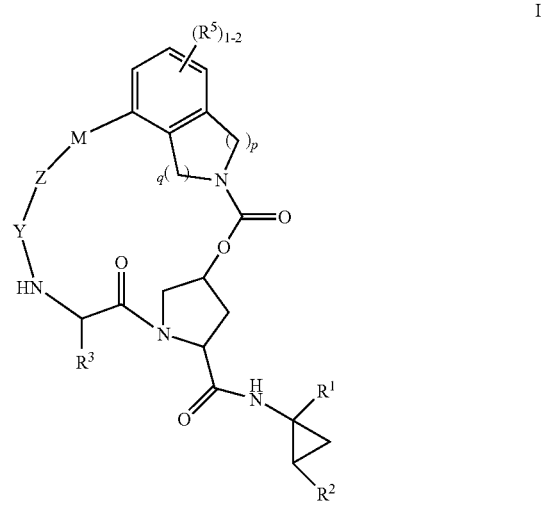

wherein:
p and q are independently 1 or 2;
$R^1$ is $CO_2R^{10}$, $CONR^{10}SO_2R^6$, $CONR^{10}SO_2NR^8R^9$, or tetrazolyl;
$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;
$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

Het is a 5- or 6-membered saturated cyclic ring having 1 or 2 heteroatoms selected from N, O and S, wherein said ring is optionally substituted with 1 to 3 substituents selected from halo, $OR^{10}$, $SR^{10}$, $N(R^{10})_2$, $N(C_1-C_6$ alkyl)$O(C_1-C_6$ alkyl), $C_1-C_6$ alkyl, $C_1-C_6$ haloalkyl, halo($C_1-C_6$ alkoxy), $NO_2$, CN, $CF_3$, $SO_2(C_1-C_6$ alkyl), $S(O)(C_1-C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^4$ is H, $C_1-C_8$ alkyl, $C_3-C_8$ cycloalkyl($C_1-C_8$)alkyl, or aryl ($C_1-C_8$)alkyl; wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1-C_6$ alkyl)$O(C_1-C_6$ alkyl), $C_1-C_6$ alkyl, $C_1-C_6$ haloalkyl, halo($C_1-C_6$ alkoxy), $NO_2$, CN, $CF_3$, $SO_2(C_1-C_6$ alkyl), $S(O)(C_1-C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^5$ is H, halo, $OR^{10}$, $C_1-C_6$ alkyl, CN, $CF_3$, $SR^{10}$, $SO_2(C_1-C_6$ alkyl), $C_3-C_8$ cycloalkyl, $C_3-C_8$ cycloalkoxy, $C_1-C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1-C_6$ alkyl)$O(C_1-C_6$ alkyl), $C_1-C_6$ alkyl, $C_1-C_6$ haloalkyl, halo($C_1-C_6$ alkoxy), $C_3-C_6$ cycloalkyl, $C_3-C_6$ cycloalkoxy, $NO_2$, CN, $CF_3$, $SO_2(C_1-C_6$ alkyl), $NR^{10}SO_2R^6$, $SO_2N(R^6)_2$, $S(O)(C_1-C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

$R^6$ is $C_1-C_6$ alkyl, $C_3-C_6$ cycloalkyl, $C_3-C_6$ cycloalkyl($C_1-C_5$)alkyl, aryl, aryl($C_1-C_4$)alkyl, heteroaryl, heteroaryl($C_1-C_4$ alkyl), heterocyclyl, or heterocyclyl($C_1-C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is C(=O), $SO_2$, or C(=N—CN);

Z is $C(R^{10})_2$, O, or $N(R^4)$;

M is $C_1-C_{12}$ alkylene or $C_2-C_{12}$ alkenylene, wherein said alkylene or alkenylene is optionally substituted with 1 or 2 substituents selected from the group consisting of $C_1-C_8$ alkyl, $C_3-C_8$ cycloalkyl($C_1-C_8$ alkyl), and aryl($C_1-C_8$ alkyl); and the 2 adjacent substituents of M are optionally taken together to form a 3- to 6-membered cyclic ring containing 0-3 heteroatoms selected from N, O and S;

each $R^7$ is independently H, $C_1-C_6$ alkyl, $C_3-C_6$ cycloalkyl, $C_3-C_6$ cycloalkyl($C_1-C_5$)alkyl, aryl, aryl($C_1-C_4$)alkyl, heteroaryl, heteroaryl($C_1-C_4$ alkyl), heterocyclyl, or heterocyclyl($C_1-C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1-C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1-C_6$ alkyl), $S(O)(C_1-C_6$ alkyl), $C_3-C_8$ cycloalkyl, $C_3-C_8$ cycloalkoxy, $C_1-C_6$ haloalkyl, $N(R^{10})_2$, $N(C_1-C_6$ alkyl)$O(C_1-C_6$ alkyl), halo($C_1-C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1-C_8$ alkyl, $C_3-C_8$ cycloalkyl, $C_3-C_8$ cycloalkyl($C_1-C_8$ alkyl), aryl, aryl($C_1-C_4$ alkyl), heteroaryl, heterocyclyl, heteroaryl($C_1-C_4$ alkyl), or heterocyclyl($C_1-C_8$ alkyl), wherein said alkyl, cycloalkyl, aryl, heteroaryl or heterocyclyl is optionally substituted with 1 to 4 substituents selected from the group consisting of aryl, $C_3-C_8$ cycloalkyl, heteroaryl, heterocyclyl, $C_1-C_6$ alkyl, halo($C_1-C_6$ alkoxy), halo, $OR^{10}$, $SR^{10}$, $N(R^{10})_2$, $N(C_1-C_6$ alkyl)$O(C_1-C_6$ alkyl), $C_1-C_6$ alkyl, $C(O)R^{10}$, $C_1-C_6$ haloalkyl, $NO_2$, CN, $CF_3$, $SO_2(C_1-C_6$ alkyl), $S(O)(C_1-C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

$R^9$ is $C_1-C_8$ alkyl, $C_3-C_8$ cycloalkyl, $C_3-C_8$ cycloalkyl($C_1-C_8$ alkyl), $C_1-C_8$ alkoxy, $C_3-C_8$ cycloalkoxy, aryl, aryl($C_1-C_4$ alkyl), heteroaryl, heterocyclyl, heteroaryl($C_1-C_4$ alkyl), or heterocyclyl($C_1-C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3-C_8$ cycloalkyl, heteroaryl, heterocyclyl, $C_1-C_6$ alkyl, halo($C_1-C_6$ alkoxy), halo, $OR^{10}$, $5R^{10}$, $N(R^{10})_2$, $N(C_1-C_6$ alkyl)$O(C_1-C_6$ alkyl), $C_1-C_6$ alkyl, $C(O)R^{10}$, $C_1-C_6$ haloalkyl, $NO_2$, CN, $CF_3$, $SO_2(C_1-C_6$ alkyl), $S(O)(C_1-C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0-3 heteroatoms selected from N, O and S;

or $R^8$ and $R^9$ are optionally taken together, with the nitrogen atom to which they are attached, to form a 4- to 8-membered monocyclic ring containing 0-2 additional heteroatoms selected from N, O and S; and each $R^{10}$ is independently H or $C_1-C_6$ alkyl.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts and/or hydrates thereof. These compounds and their pharmaceutically acceptable salts and/or hydrates are HCV protease inhibitors (e.g., HCV NS3 protease inhibitors). The present invention also includes compounds of formulae II, II-a, II-b, II-c, II-d, III, III-a, III-b, III-c, and III-d wherein all variables are as defined for formula I.

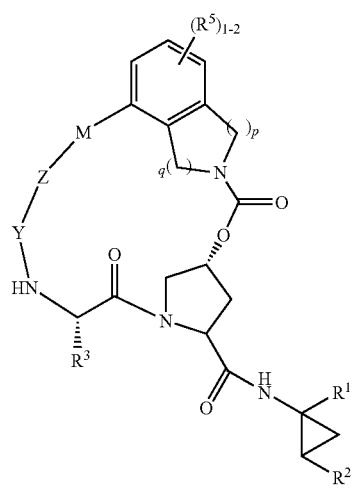

II

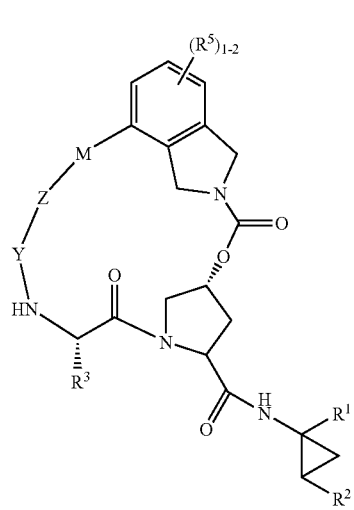

II-a

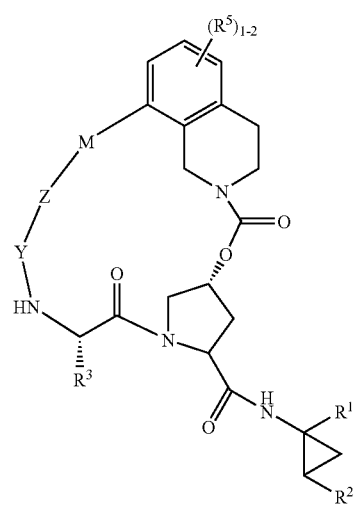

II-b

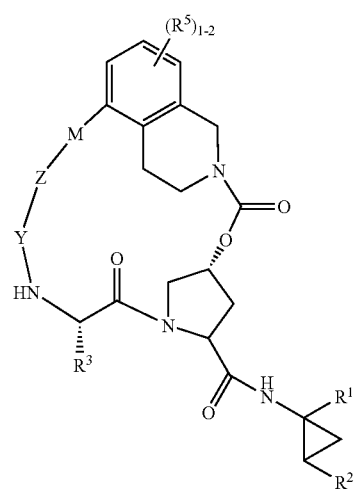

II-c

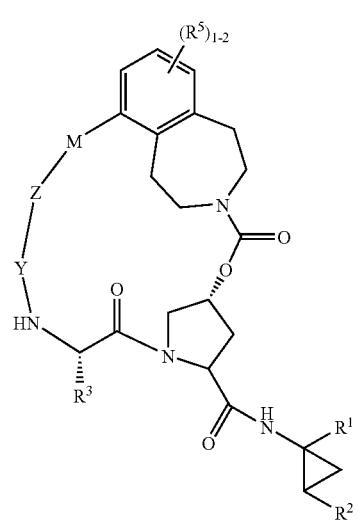

II-d

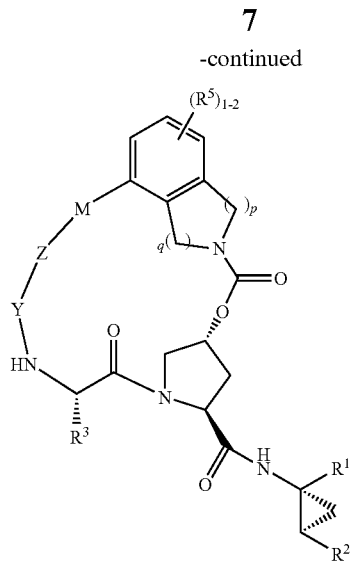

III-a

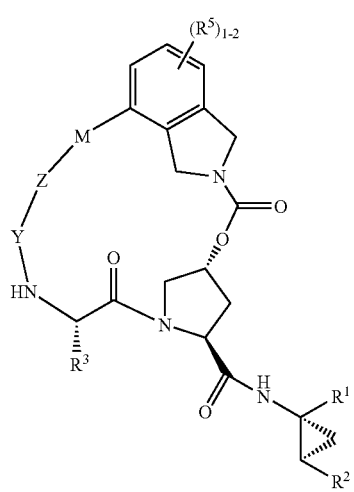

III-b

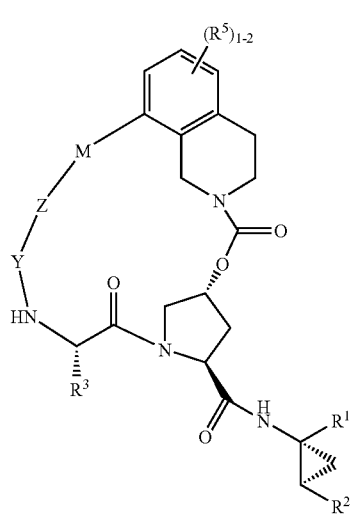

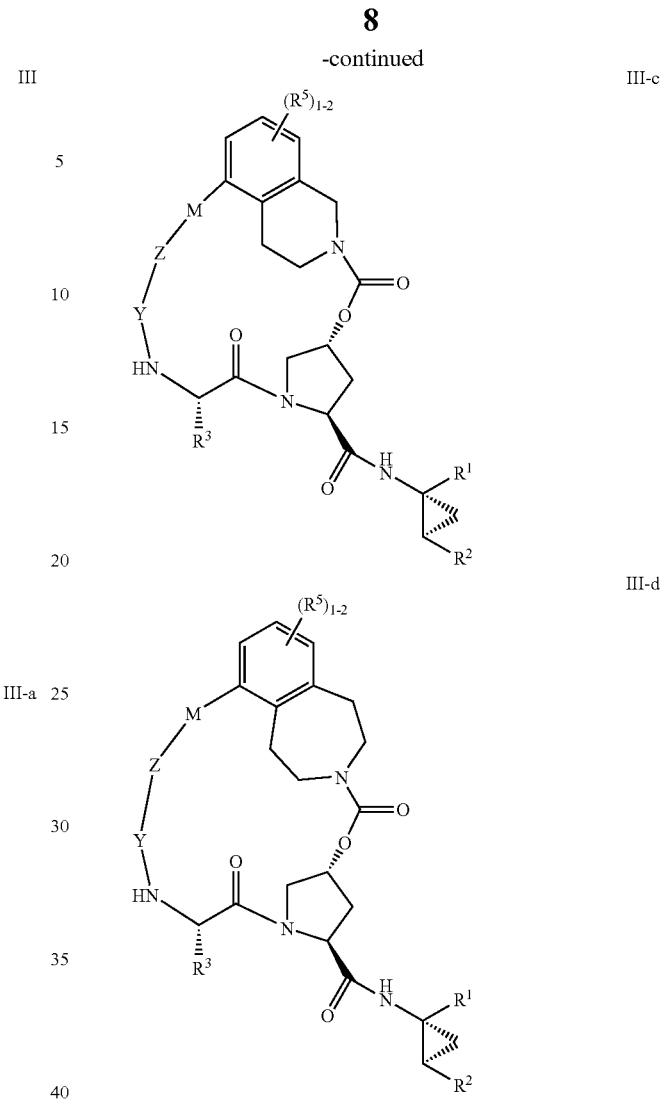

A first embodiment of the present invention is a compound of formula I, II, II-a, II-b, II-c, II-d, III, III-a, II-b, III-c, or III-d, or a pharmaceutically acceptable salt or hydrate thereof, wherein $R^1$ is $CO_2R^{10}$ or $CONR^{10}SO_2R^6$, and all other variables are as originally defined (i.e., as defined in the Summary of the Invention). In a first aspect of the first embodiment, $R^1$ is $CONR^{10}SO_2R^6$; and all other variables are as defined in the first embodiment. In a feature of the first aspect of the first embodiment, $R^1$ is $CONHSO_2R^6$ wherein $R^6$ is $C_3$-$C_8$ cycloalkyl; and all other variables are as defined in the first embodiment. In a second feature of the first aspect of the first embodiment, $R^1$ is $CONHSO_2R^6$ wherein $R^6$ is cyclopropyl; and all other variables are as defined in the first embodiment. In a second aspect of the first embodiment, $R^1$ is $CO_2R^{10}$; and all other variables are as defined in the first embodiment. In a feature of the second aspect of the first embodiment, $R^{10}$ is $CO_2H$; and all other variables are as defined in the first embodiment.

A second embodiment of the present invention is a compound of formula I, II, II-a, I-b, II-c, II-d, III, III-a, II-b, III-c, or III-d, or a pharmaceutically acceptable salt or hydrate thereof, wherein $R^1$ is $CONHSO_2NR^8R^9$; and all other variables are as originally defined. In a first aspect of the second embodiment, $R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R^8$ and $R^9$ is optionally substituted with 1 to 4 substituents selected from the group consisting of aryl, heteroaryl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3- to 6-membered cyclic ring containing 0-3 heteroatoms selected from N, O and S; or $R^8$ and $R^9$ are optionally taken together, with the nitrogen atom to which they are attached, to form a 4- to 8-membered monocyclic ring containing 0-2 additional heteroatoms selected from N, O and S; and all other variables are as defined in the second embodiment.

In a second aspect of the second embodiment, $R^8$ is $C_1$-$C_8$ alkyl, $C_3$-$C_8$ cycloalkyl($C_1$-$C_8$ alkyl), aryl, aryl($C_1$-$C_4$ alkyl), heteroaryl, or heteroaryl($C_1$-$C_4$ alkyl); and $R^9$ is $C_1$-$C_8$ alkyl, $C_3$-$C_8$ cycloalkyl($C_1$-$C_8$ alkyl), $C_1$-$C_8$ alkoxy, aryl, aryl($C_1$-$C_4$ alkyl), heteroaryl, or heteroaryl($C_1$-$C_4$ alkyl), wherein said alkyl, cycloalkyl, alkoxy, aryl, or heteroaryl in both $R^8$ and $R^9$ is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$, wherein each aryl is independently phenyl or naphthyl and each heteroaryl is independently a 5- or 6-membered aromatic ring having 1, 2 or 3 heteroatoms selected from N, O and S, attached through a ring carbon or nitrogen, and wherein the 2 adjacent substituents of said cycloalkyl, aryl, or heteroaryl are optionally taken together to form a 3- to 6-membered cyclic ring containing 0-3 heteroatoms selected from N, O and S; or $R^8$ and $R^9$ are optionally taken together, with the nitrogen atom to which they are attached, to form a 4- to 6-membered monocyclic ring containing 0-2 additional heteroatoms selected from N, O and S; and all other variables are as defined in the second embodiment.

In a first feature of the second aspect of the second embodiment, $R^3$ is $C_1$-$C_3$ alkyl, wherein said alkyl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; and $R^9$ is $C_1$-$C_3$ alkyl, $C_1$-$C_3$ alkoxy, phenyl, or $—(CH_2)_{1-2}$-phenyl, wherein said alkyl or alkoxy is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; or $R^8$ and $R^9$ are optionally taken together, with the nitrogen atom to which they are attached, to form a 4- to 6-membered monocyclic saturated ring containing 0-1 additional heteroatoms selected from N and O; and all other variables are as defined in the second embodiment. In a second feature of the second aspect of the second embodiment, $R^8$ is methyl; and all other variables are as defined in the second embodiment. In a third feature of the second aspect of the second embodiment, $R^9$ is methyl, methoxy, ethyl, i-propyl, phenyl, or benzyl; and all other variables are as defined in the second embodiment. In a fourth feature of the second aspect of the second embodiment, $R^8$ and $R^9$ are taken together to form a heteocyclic ring selected from the following:

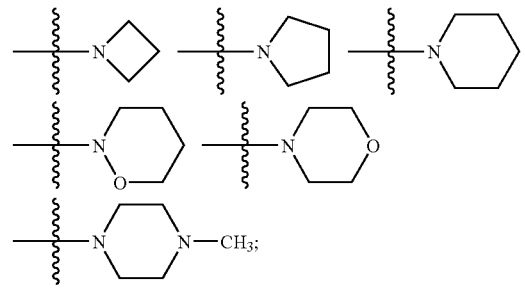

and all other variables are as defined in the second embodiment. In a fifth feature of the second aspect of the second embodiment, $R^8$ is methyl and $R^9$ is methoxy; and all other variables are as defined in the second embodiment.

A third embodiment of the present invention is a compound of formula I, II, II-a, II-b, II-c, II-d, III, III-a, II-b, III-c, or III-d, or a pharmaceutically acceptable salt or hydrate thereof, wherein $R^2$ is $C_1$-$C_6$ alkyl or $C_2$-$C_6$ alkenyl; and all other variables are as originally defined or as defined in any one of the preceding embodiments. In a first aspect of the third embodiment, $R^2$ is $C_1$-$C_4$ alkyl or $C_2$-$C_4$ alkenyl; and all other variables are as originally defined or as defined in any one of the preceding embodiments. In a second aspect of the third embodiment, $R^2$ is $C_2$-$C_4$ alkenyl; and all other variables are as originally defined or as defined in any one of the preceding embodiments. In a feature of the second aspect of the third embodiment, $R^2$ is vinyl; and all other variables are as defined in the second embodiment or as defined in any one of the preceding embodiments. In a third aspect of the third embodiment, $R^2$ is $C_1$-$C_4$ alkyl; and all other variables are as originally defined or as defined in any one of the preceding embodiments. In a feature of the third aspect of the third embodiment, $R^2$ is ethyl; and all other variables are as defined in the third embodiment or as defined in any one of the preceding embodiments.

A fourth embodiment of the present invention is a compound of formula I, II, II-a, II-b, II-c, II-d, III, III-a, III-b, III-c, or III-d, or a pharmaceutically acceptable salt or hydrate thereof, wherein $R^3$ is $C_3$-$C_8$ cycloalkyl optionally substituted with $C_1$-$C_6$ alkyl; Het; or $C_1$-$C_8$ alkyl optionally substituted with 1 to 3 substituents selected from halo and $OR^{10}$; and all other variables are as originally defined or as defined in any one of the preceding embodiments. In a first aspect of the fourth embodiment, $R^3$ is $C_5$-$C_7$ cycloalkyl, piperidinyl, pyrrolidinyl, tetrahydrofuranyl, tetrahydropyranyl, or $C_1$-$C_8$ alkyl optionally substituted with 1 to 3 halo substituents; and all other variables are as defined in the fourth embodiment or as defined in any one of the preceding embodiments. In a second aspect of the fourth embodiment, $R^3$ is $C_5$-$C_6$ cycloalkyl or $C_1$-$C_8$ alkyl optionally substituted with 1 to 3 halo substituents; and all other variables are as defined in the fourth embodiment or as defined in any one of the preceding embodiments. In a third aspect of the fourth embodiment, $R^3$ is propyl or butyl; and all other variables are as defined in the fourth embodiment or as defined in any one of the preceding embodiments. In a feature of the third aspect of the fourth embodiment, $R^3$ is i-propyl, n-butyl or t-butyl; and all other variables are as defined in the fourth embodiment or as defined in any one of the preceding embodiments. In a fourth aspect of the fourth embodiment, $R^3$ is cyclopentyl or cyclohexyl; and all other variables are as defined in the fourth embodiment or as defined in any one of the preceding embodiments. In a fifth aspect of the fourth embodiment, $R^3$ is $CH_2CF_3$ or $CH_2CHF_2$; and all other variables are as defined in the fourth embodiment or as defined in any one of the preceding embodiments. In a sixth aspect of the fourth embodiment, $R^3$ is $C_3$-$C_8$ cycloalkyl, Het, or $C_1$-$C_8$ alkyl optionally substituted with 1 to 3 halo substituents; and all other variables are as originally defined or as defined in any one of the preceding embodiments. In a seventh aspect of the fourth embodiment, $R^3$ is $C_3$-$C_8$ cycloalkyl substituted with $C_1$-$C_6$ alkyl, or $C_1$-$C_8$ alkyl substituted with 1 to 3 $OR^{10}$ substituents; and all other variables are as originally defined or as defined in any one of the preceding embodiments. In an eighth aspect of the fourth embodiment, $R^4$ is cyclohexyl substituted with methyl; and all other variables are as originally defined or as defined in any one of the preceding embodiments. In a ninth aspect of the fourth embodiment, $R^4$ is $CH_2O$-t-Bu; and all other variables are as originally defined or as defined in any one of the preceding embodiments.

A fifth embodiment of the present invention is a compound of formula I, II, II-a, II-b, II-c, II-d, III, III-a, III-b, III-c, or III-d, or a pharmaceutically acceptable salt or hydrate thereof, wherein $R^5$ is H or halo; and all other variables are as originally defined or as defined in any one of the preceding embodiments. In one aspect of the fifth embodiment, $R^5$ is H, F, or Cl; and all other variables are defined in the fifth embodiment or as defined in any one of the preceding embodiments.

A sixth embodiment of the present invention is a compound of formula I, II, II-a, II-b, II-c, II-d, III, III-a, III-b, III-c, or III-d, or a pharmaceutically acceptable salt or hydrate thereof, wherein $R^5$ is $C_1$-$C_6$ thioalkyl, aryl, heteroaryl, or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, or thioalkyl is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; and all other variables are as originally defined or as defined in any one of the preceding embodiments.

In one aspect of the sixth embodiment, $R^5$ is aryl wherein aryl is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; and all other variables are as defined in the sixth embodiment or as defined in any one of the preceding embodiments. In a second aspect of the sixth embodiment, $R^5$ is $C_1$-$C_6$ thioalkyl,

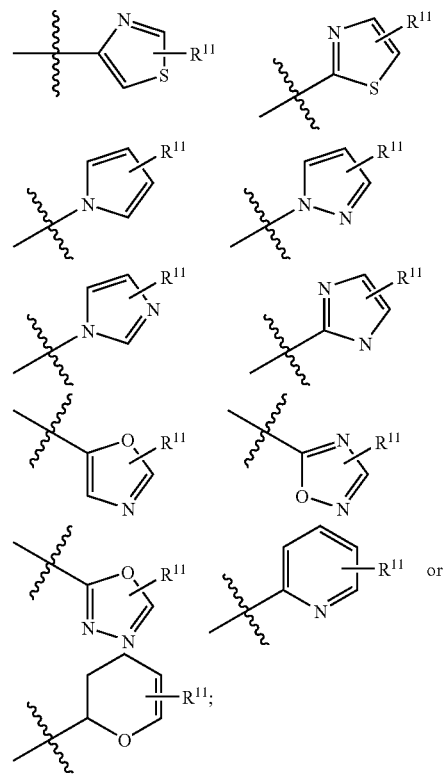

wherein $R^{11}$ is H, $C_1$-$C_6$ alkyl, $NHR^7$, $NHCOR^{12}$, $NHCONHR^{12}$ or $NHCOOR^{12}$ and each $R^{12}$ is independently $C_1$-$C_6$ alkyl or $C_3$-$C_6$ cycloalkyl; and all other variables are as defined in the sixth embodiment or as defined in any one of the preceding embodiments. In a third aspect of the sixth embodiment, $R^5$ is

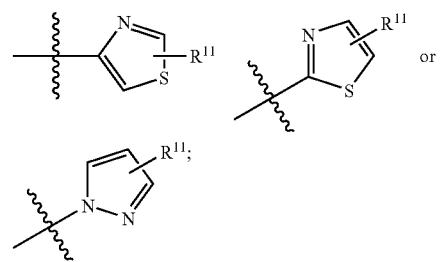

wherein $R^{11}$ is H, $C_1$-$C_6$ alkyl, $NHR^7$, $NHCOR^{12}$, $NHCONHR^{12}$ or $NHCOOR^{12}$ and each $R^{12}$ is independently $C_1$-$C_6$ alkyl or $C_3$-$C_6$ cycloalkyl; and all other variables are as defined in the sixth embodiment or as defined in any one of the preceding embodiments.

In a fourth aspect of the sixth embodiment, $R^5$ is unsubstituted phenyl; and all other variables are as defined in the sixth embodiment or as defined in any one of the preceding embodiments A seventh embodiment of the present invention is a compound of formula I, II, II-a, II-b, II-c, II-d, III, III-a, II-b, III-c, or III-d, or a pharmaceutically acceptable salt or hydrate thereof, wherein $R^5$ is $C_1$-$C_6$ alkyl, $C_1$-$C_6$ alkoxy, hydroxy, or $N(R^7)_2$ wherein $R^7$ is H or $C_1$-$C_6$ alkyl; and all other variables are as originally defined or as defined in any one of the preceding embodiments. In one aspect of the seventh embodiment, $R^5$ is $C_1$-$C_6$ alkoxy; and all other variables are as defined in the seventh embodiment or as defined in any one of the preceding embodiments. In a second aspect of the seventh embodiment, $R^5$ is methoxy; and all other variables are as defined in the seventh embodiment or as defined in any one of the preceding embodiments.

An eighth embodiment of the present invention is a compound of formula I', II' or III', or a pharmaceutically acceptable salt or hydrate thereof, wherein all variables are as originally defined or as defined in any one of the preceding embodiments.

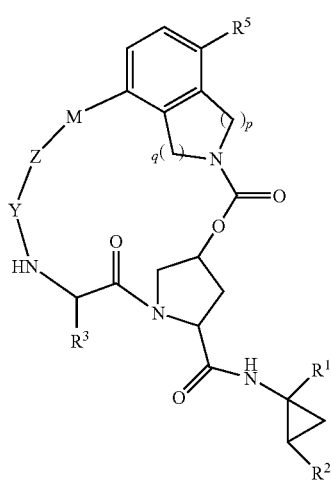

I'

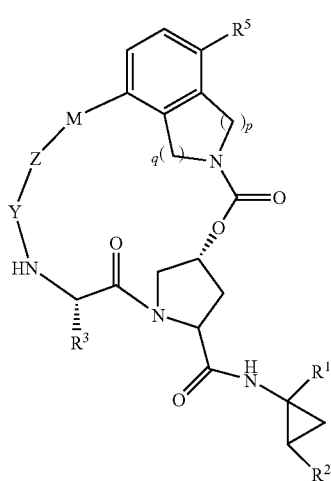

II'

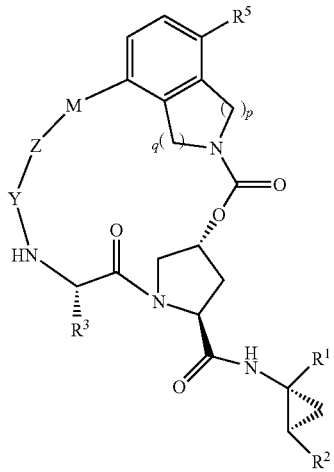

III'

A ninth embodiment of the present invention is a compound of formula I, II, II-a, II-b, II-c, II-d, III, III-a, II-b, III-c, or III-d, or a pharmaceutically acceptable salt or hydrate thereof, wherein Y is C=O or $SO_2$; and all other variables are as originally defined or as defined in any one of the preceding embodiments. In one aspect of the ninth embodiment, Y is C=O; and all other variables are as defined in the ninth embodiment or as defined in any one of the preceding embodiments.

A tenth embodiment of the present invention is a compound of formula I, II, II-a, II-b, II-c, II-d, III, III-a, III-b, III-c, or III-d, or a pharmaceutically acceptable salt or hydrate thereof, wherein Z is O, $C(R^{10})_2$, NH or $N(C_1$-$C_8$ alkyl); and all other variables are as originally defined or as defined in any one of the preceding embodiments. In one aspect of the tenth embodiment, Z is O, $CH_2$, NH, or $N(CH_3)$; and all other variables are as defined in the tenth embodiment or as defined in any one of the preceding embodiments. In another aspect of the tenth embodiment, Z is N(i-Pr) or N(n-Pr); and all other variables are as defined in the tenth embodiment or as defined in any one of the preceding embodiments.

An eleventh embodiment of the present invention is a compound of formula I, II, II-a, I-b, II-c, II-d, III, III-a, II-b, III-c, or III-d, or a pharmaceutically acceptable salt or hydrate thereof, wherein M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), or aryl($C_1$-$C_8$ alkyl); and the 2 adjacent substituents of M are optionally taken together to form a 3- to 6-membered cyclic ring containing 0-2 heteroatoms selected from N, O and S; and all other variables are as originally defined or as defined in any one of the preceding embodiments. In a first aspect of the eleventh embodiment, M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), or aryl($C_1$-$C_8$ alkyl); and all other variables are as originally defined or as defined in any one of the preceding embodiments. In a first feature of the first aspect of the eleventh embodiment, M is unsubstituted $C_1$-$C_8$ alkylene or unsubstituted $C_2$-$C_8$ alkenylene; and all other variables are as defined in the eleventh embodiment or as defined in any one of the preceding embodiments. In a second feature of the first aspect of the eleventh embodiment, M is unsubstituted $C_4$ alkylene or unsubstituted $C_4$ alkenylene; and all other variables are as defined in the eleventh embodiment or as defined in any one of the preceding embodiments. In a third feature of the first aspect of the eleventh embodiment, M is unsubstituted $C_5$ alkylene or unsubstituted $C_5$ alkenylene; and all other variables are as defined in the eleventh embodiment or as defined in any one of the preceding embodiments. In a fourth feature of the first aspect of the eleventh embodiment, M is unsubstituted $C_6$ alkylene or unsubstituted $C_6$ alkenylene; and all other variables are as defined in the eleventh embodiment or as defined in any one of the preceding embodiments. In a fifth feature of the first aspect of the eleventh embodiment, M is unsubstituted $C_7$ alkylene or unsubstituted $C_7$ alkenylene; and all other variables are as defined in the eleventh embodiment or as defined in any one of the preceding embodiments. In a sixth feature of the first aspect of the eleventh embodiment, M is unsubstituted $C_8$ alkylene or unsubstituted CS alkenylene; and all other variables are as defined in the eleventh embodiment or as defined in any one of the preceding embodiments. In a seventh feature of the first aspect of the eleventh embodiment, M is:

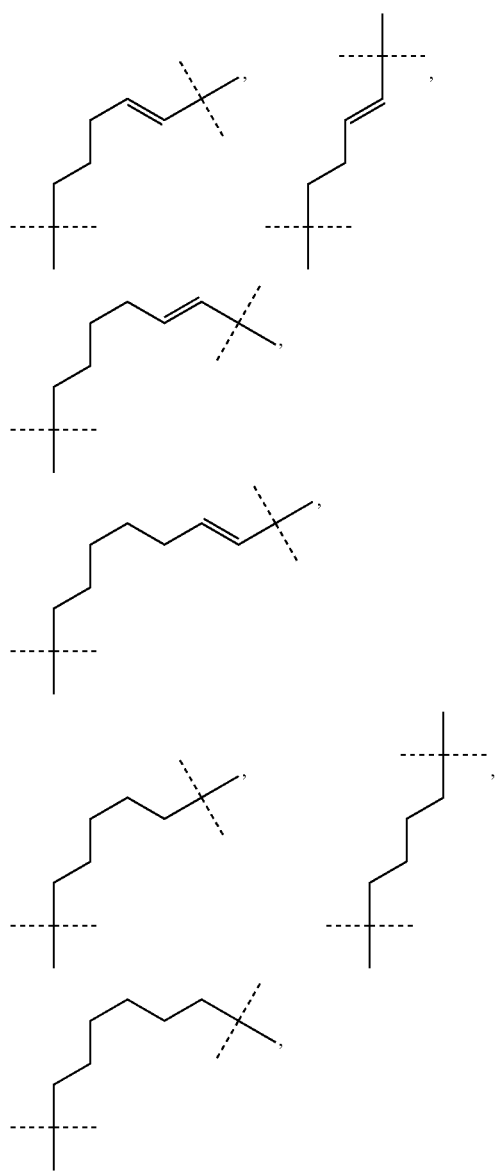

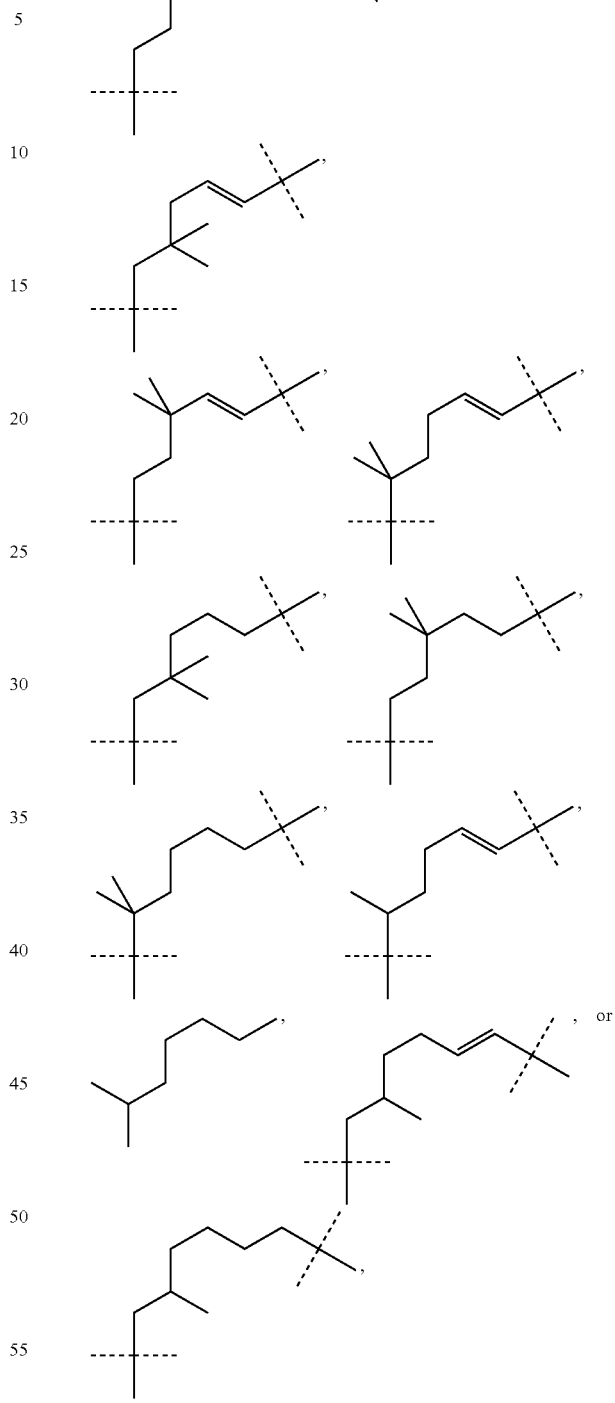

In a second aspect of the eleventh embodiment, M is $C_1$-$C_8$ alkylene or $C_2$-$C_8$ alkenylene, wherein said alkylene or alkenylene is optionally substituted with 1 or 2 substituents selected from $C_1$-$C_8$ alkyl, $C_3$-$C_8$ cycloalkyl($C_1$-$C_8$ alkyl), or aryl($C_1$-$C_8$ alkyl); and the 2 adjacent substituents of M are taken together to form a 3- to 6-membered cyclic ring containing 0 heteroatoms; and all other variables are as originally defined or as defined in any one of the preceding embodiments.

A twelfth embodiment of the present invention is a compound, or a pharmaceutically acceptable salt or hydrate thereof, selected from the group consisting of the compounds III-1 to III-240.
III-1
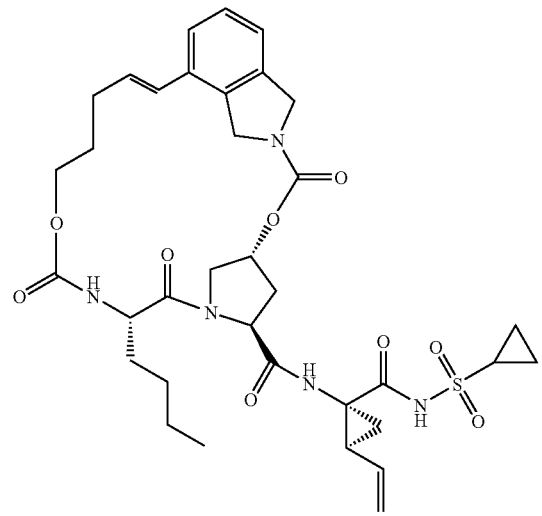
III-2
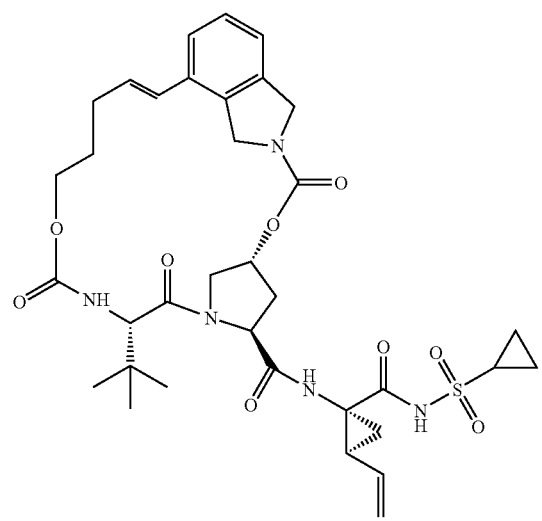
III-3
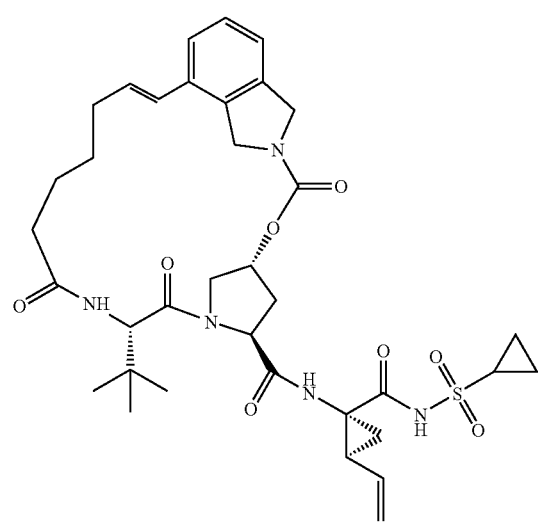
-continued
III-4
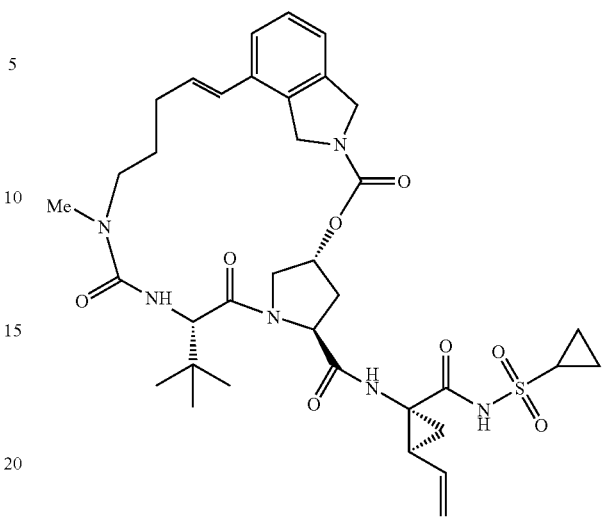
III-5
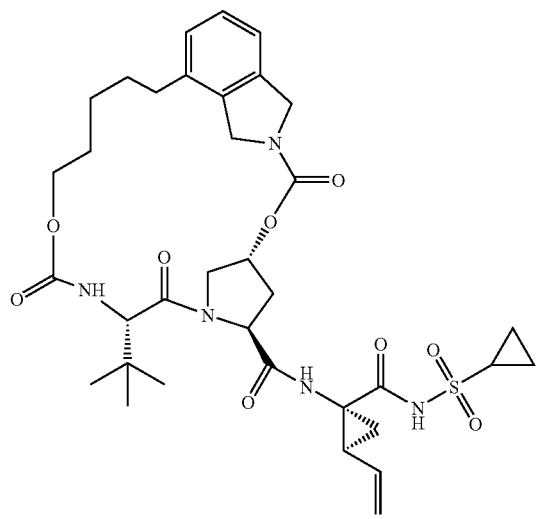
III-6
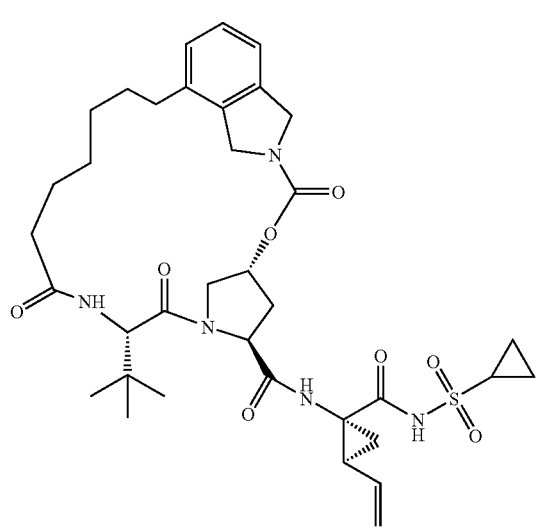

III-7
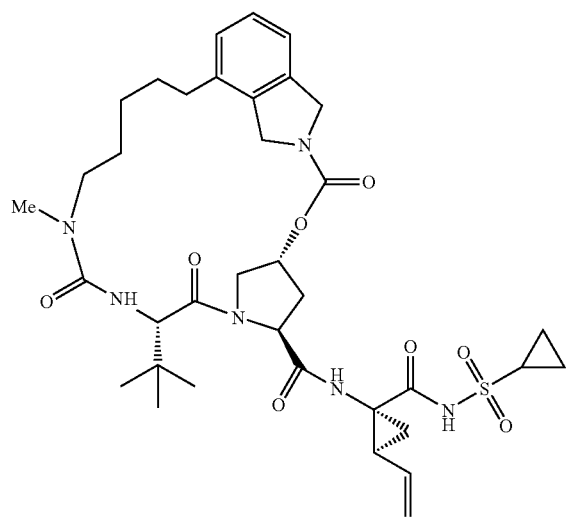
III-10
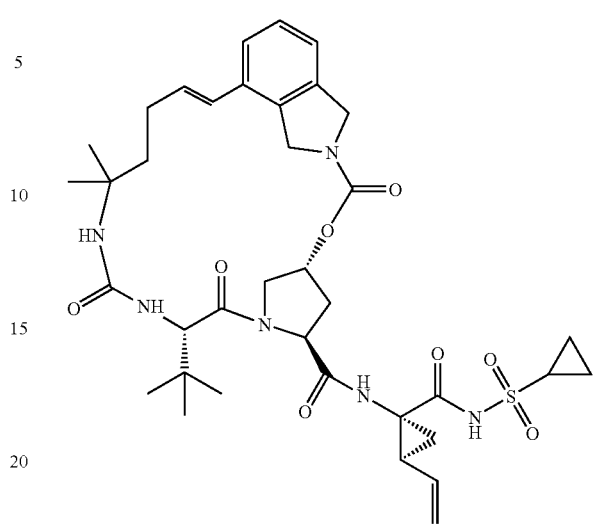
III-8
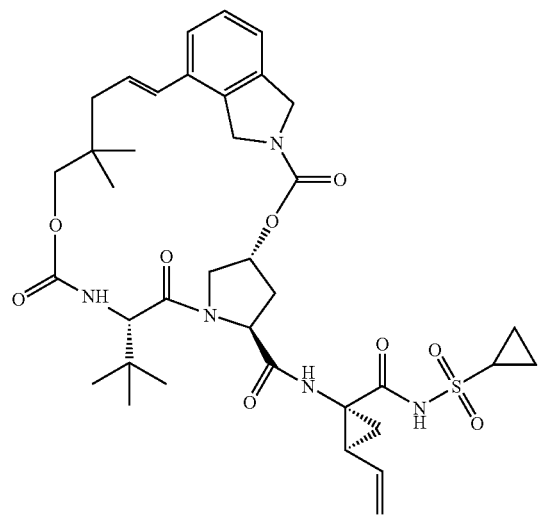
III-11
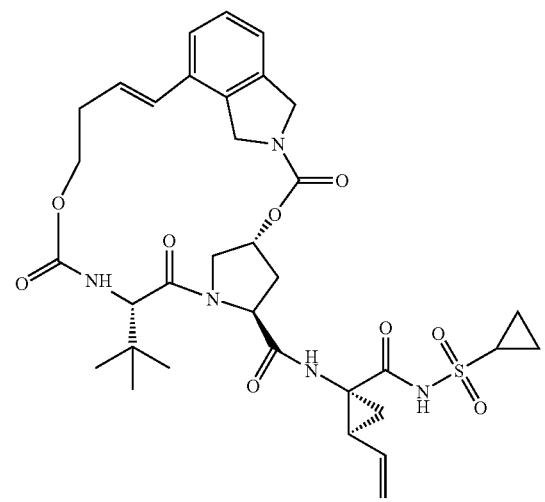
III-9
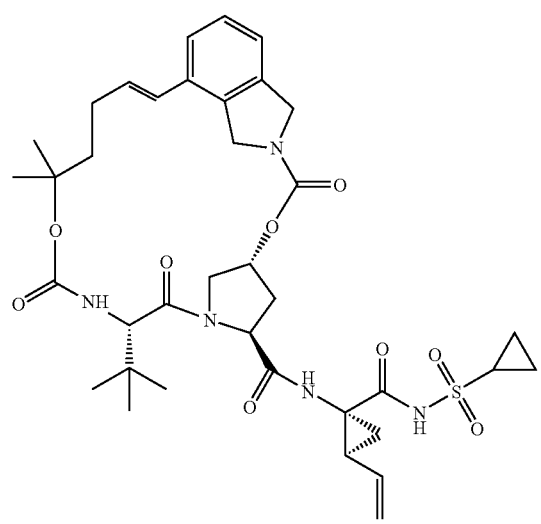
III-12
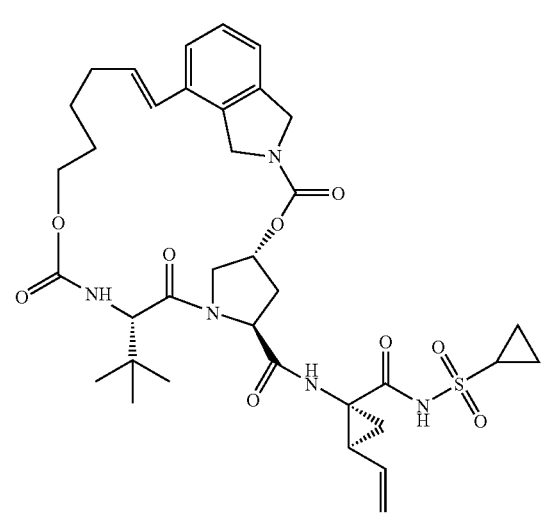

III-13
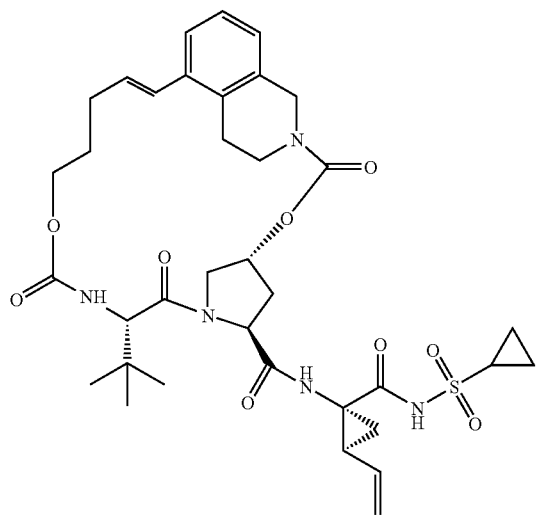
III-14
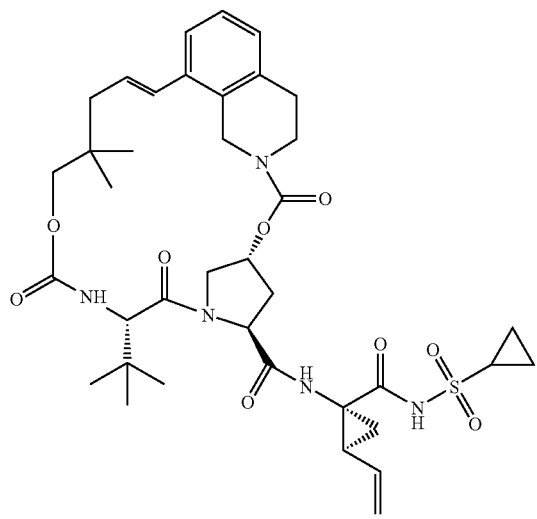
III-15
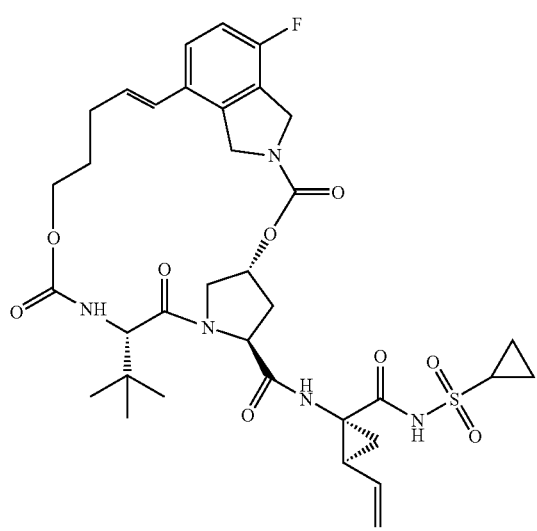
III-16
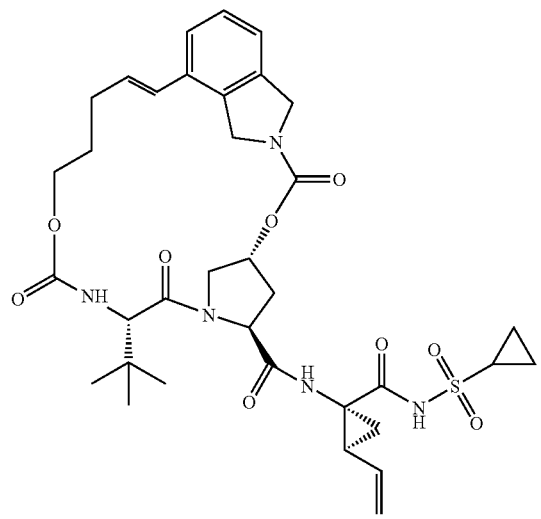
III-17
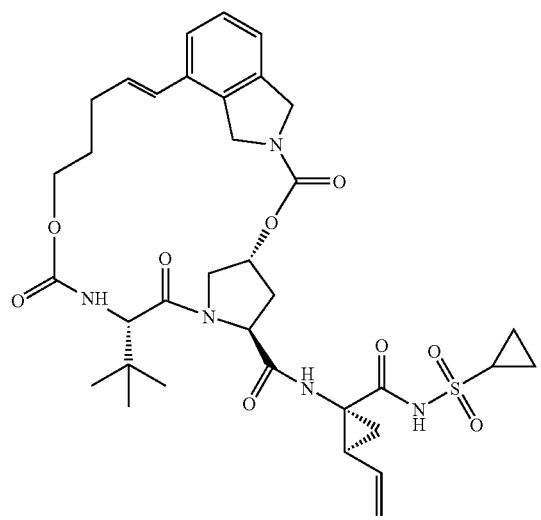
III-18
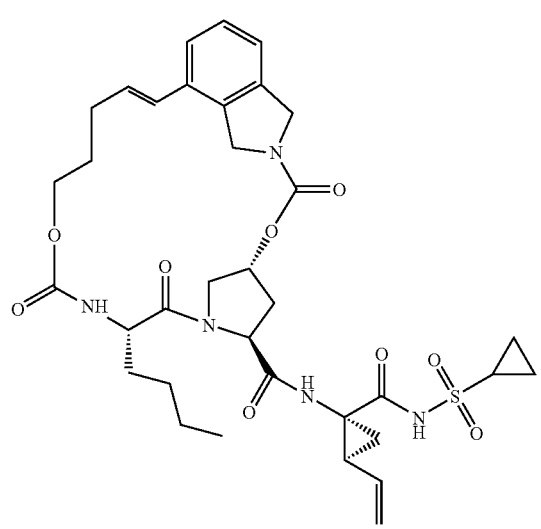

III-19
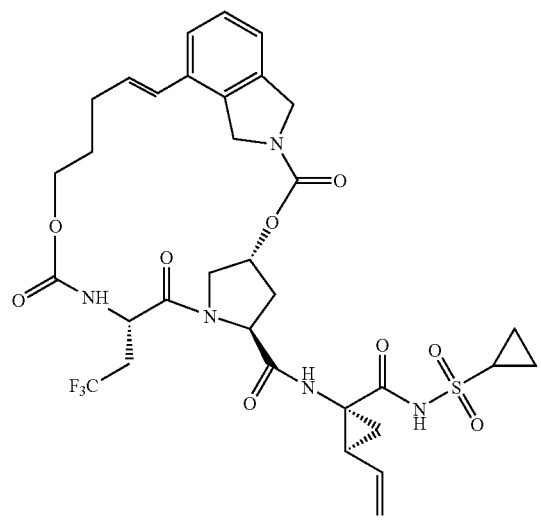
III-20
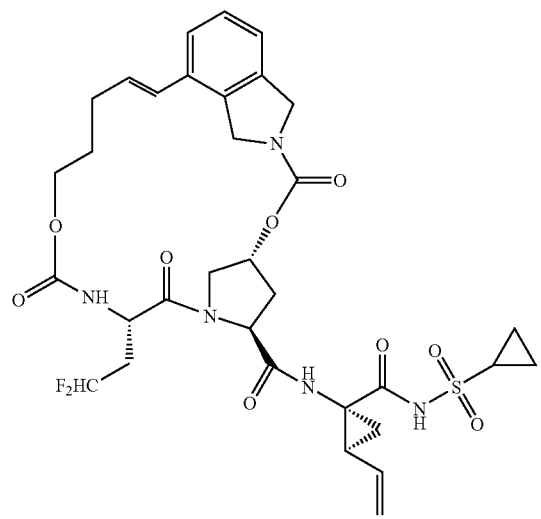
III-21
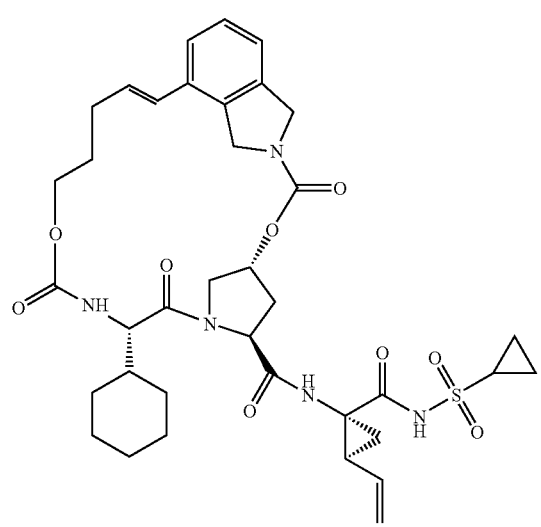
III-22
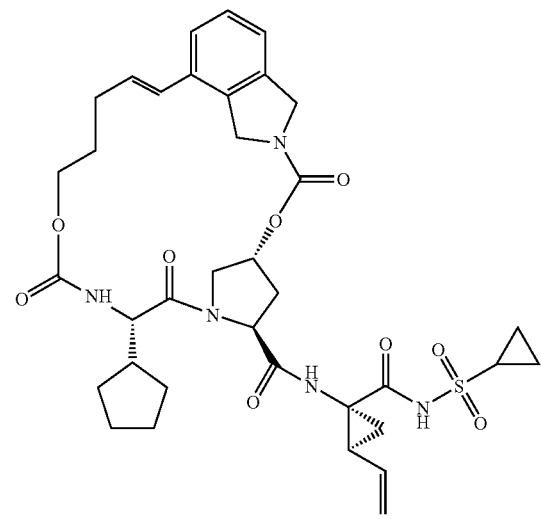
III-23
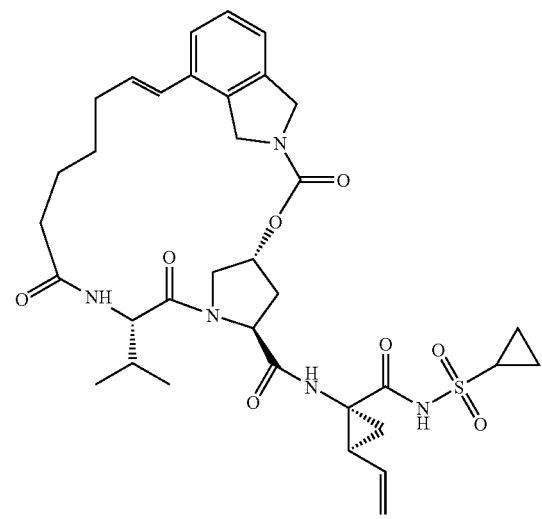
III-24
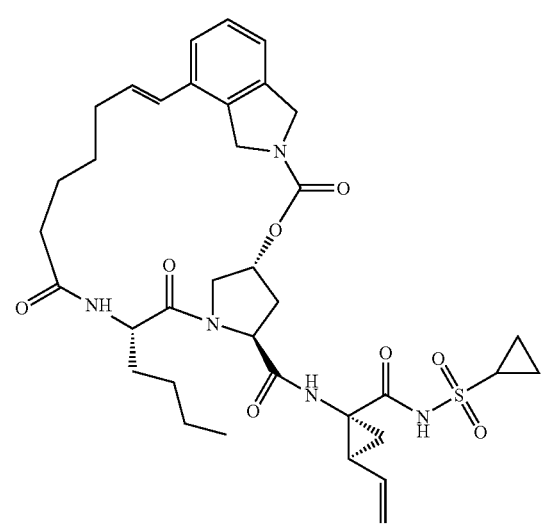

-continued
III-25
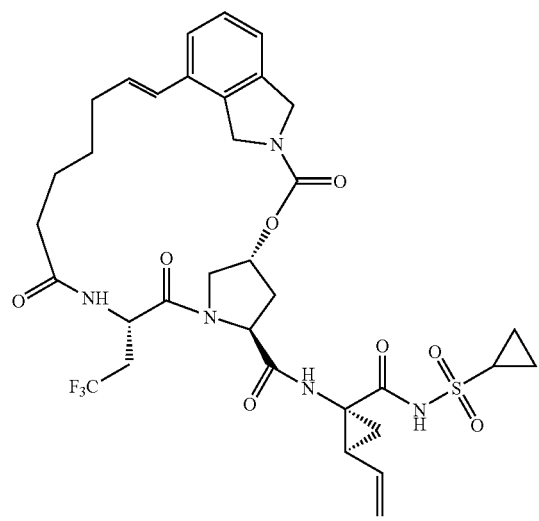
III-26
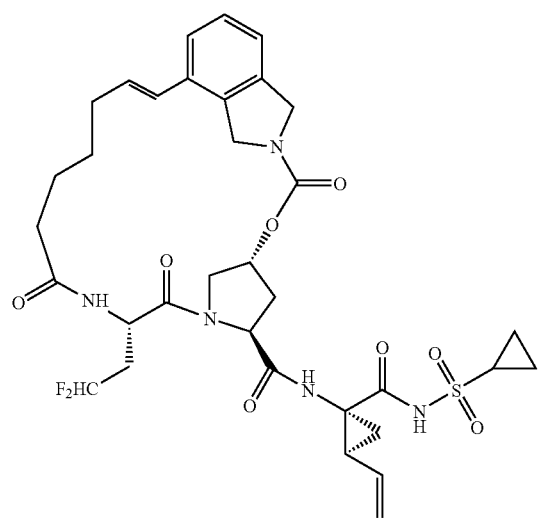
III-27
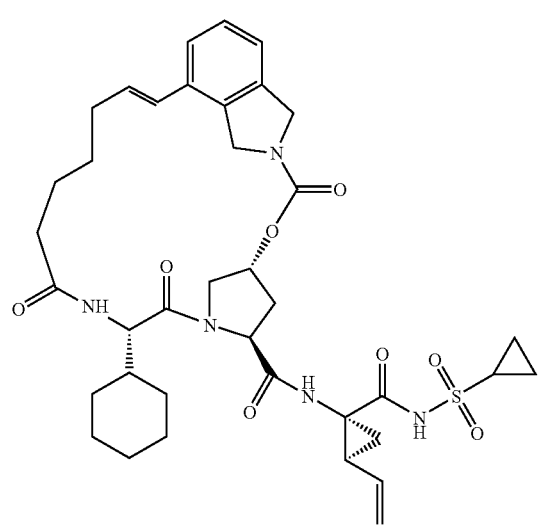
-continued
III-28
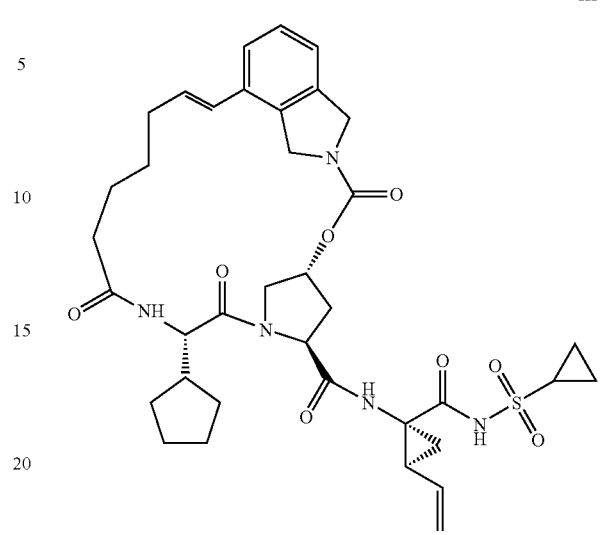
III-29
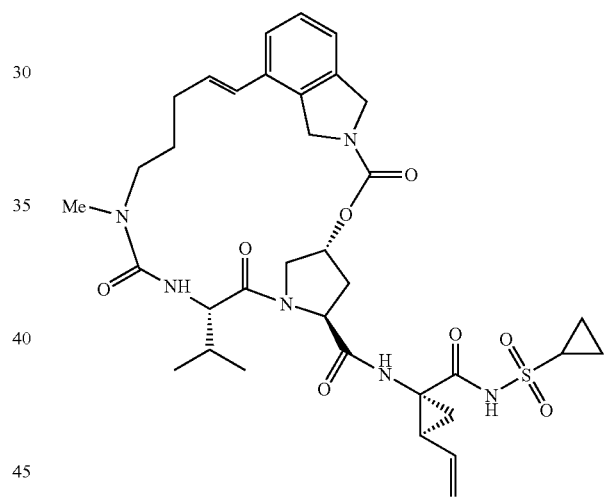
III-30
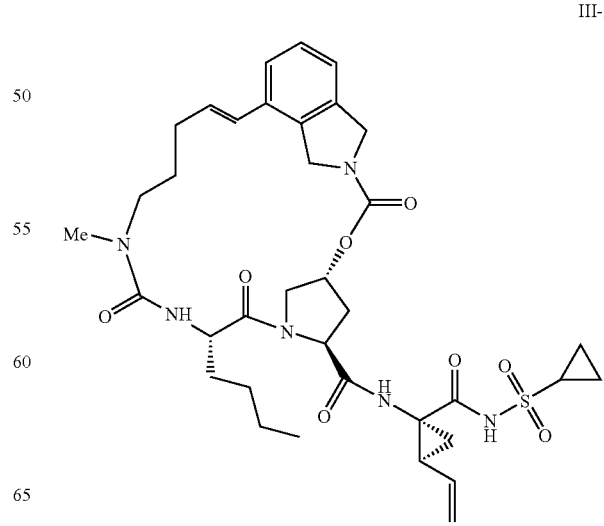

III-31
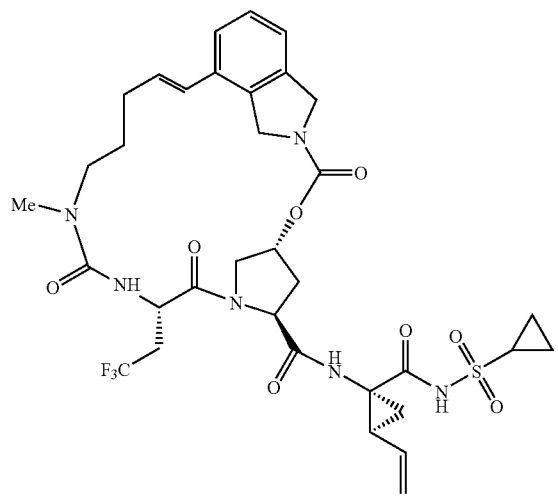
III-32
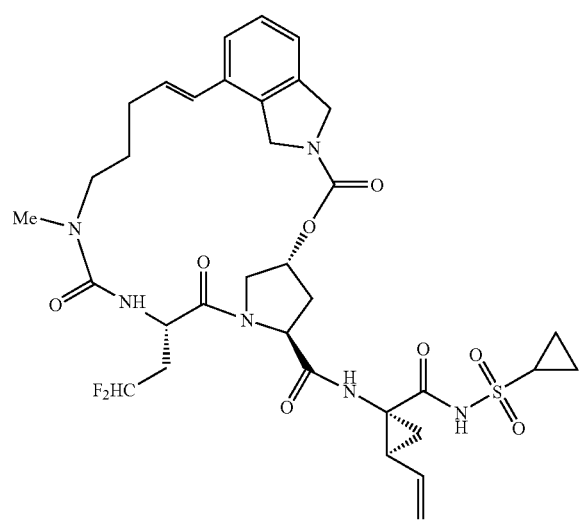
III-33
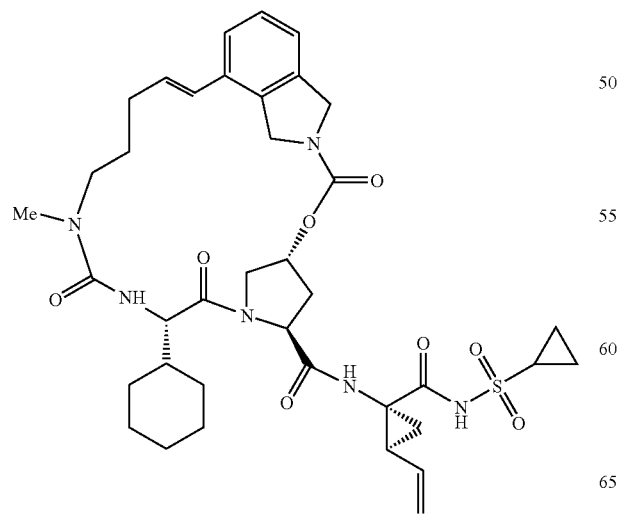
III-34
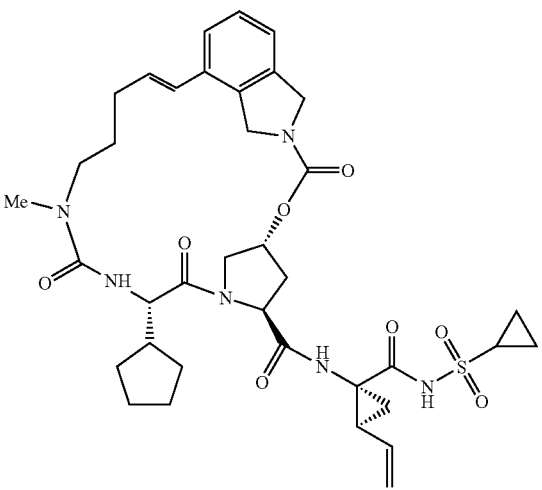
III-35
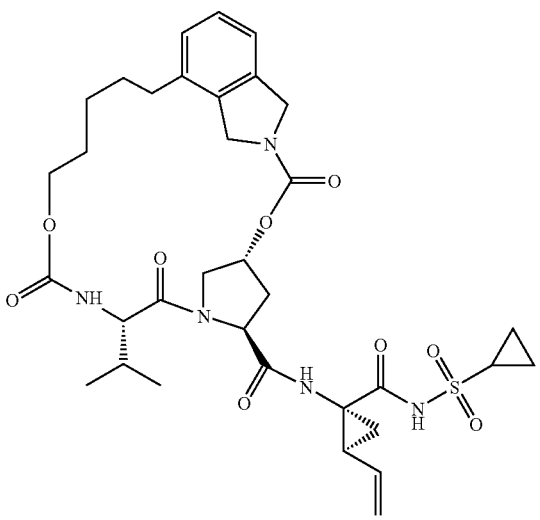
III-36
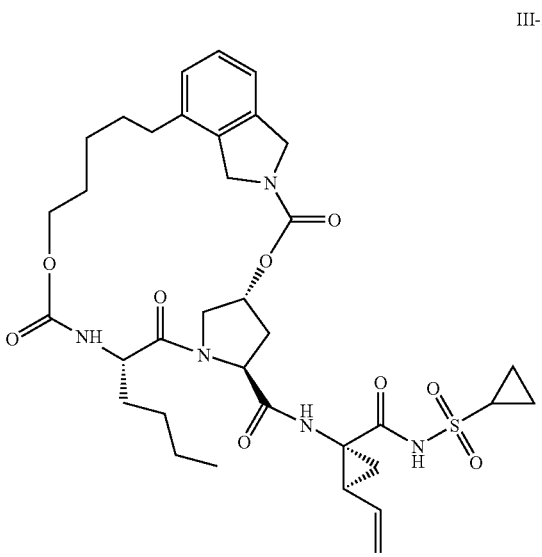

III-37
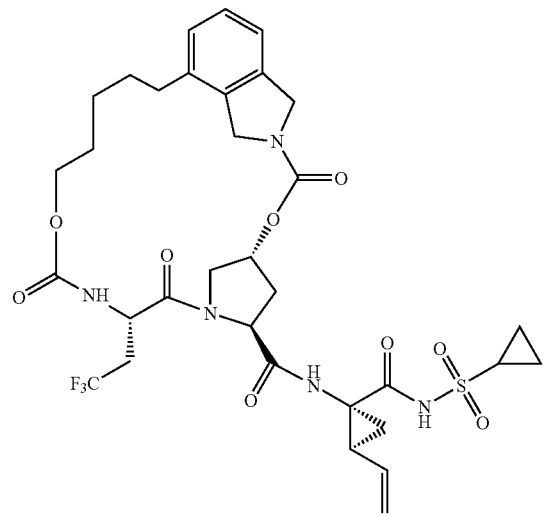
III-38
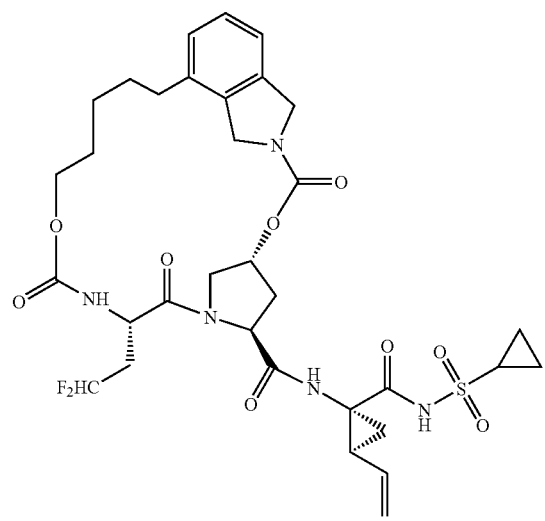
III-39
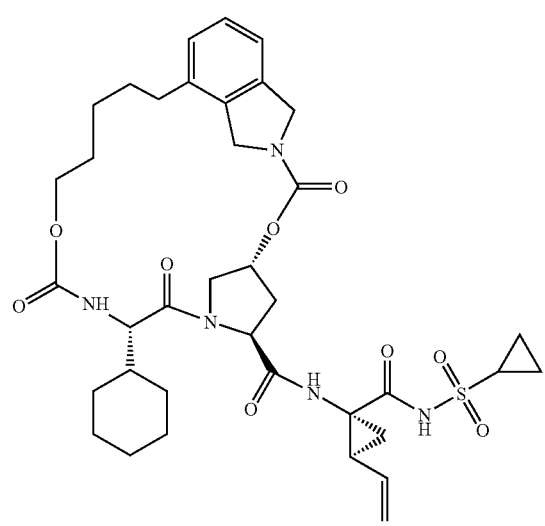
III-40
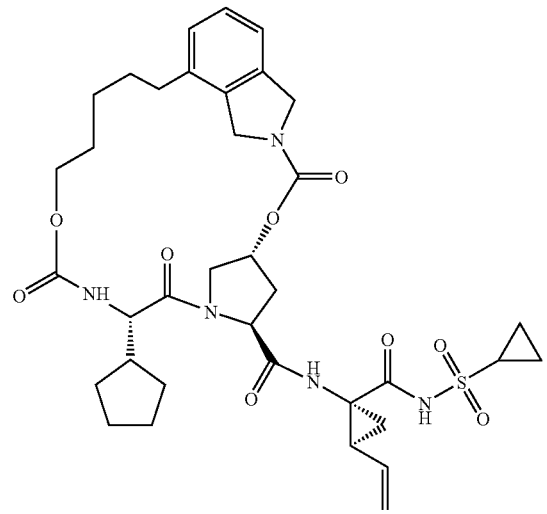
III-41
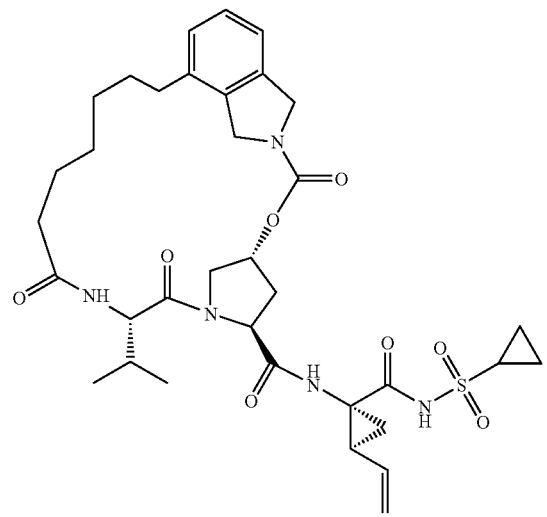
III-42
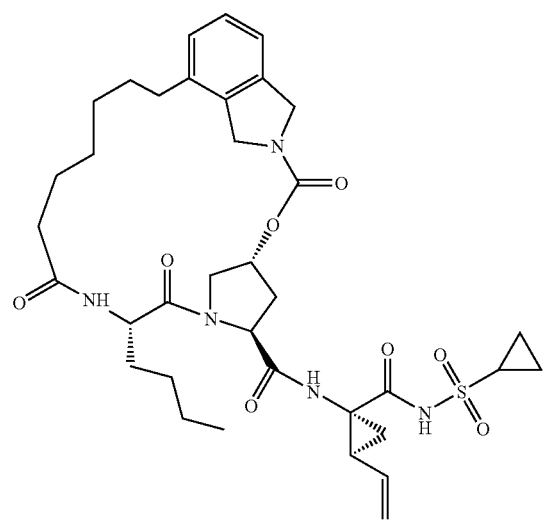

III-43
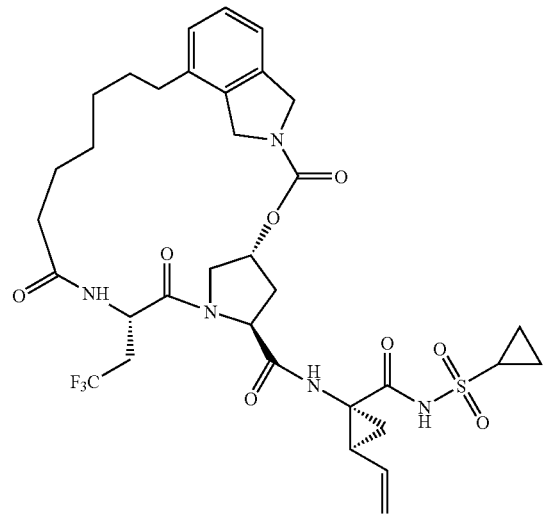
III-46
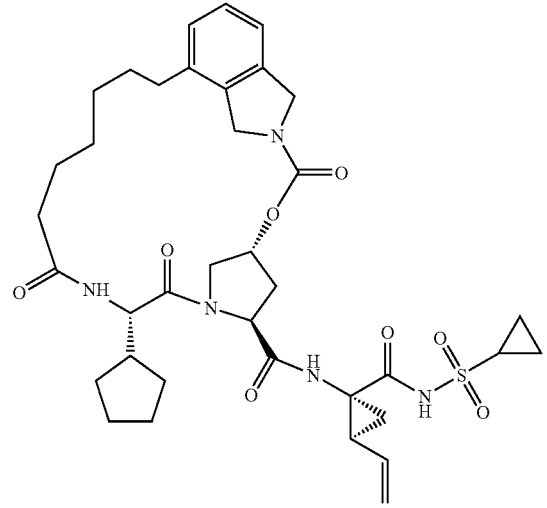
III-44
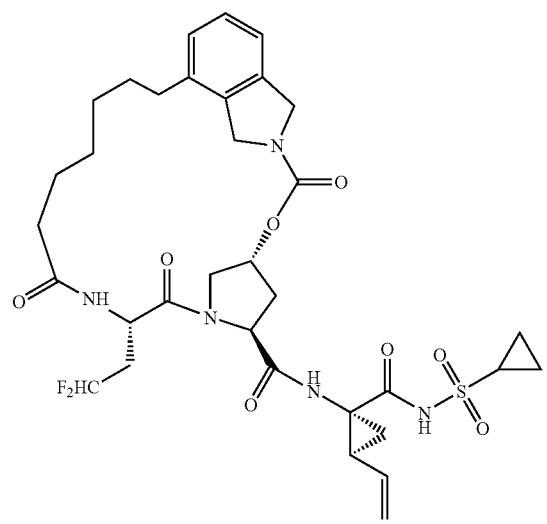
III-47
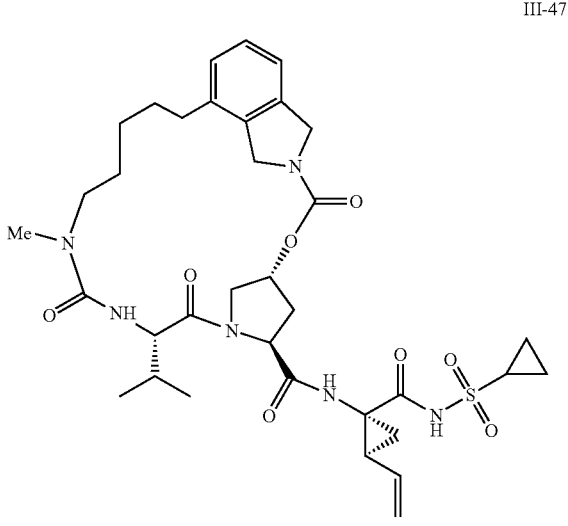
III-45
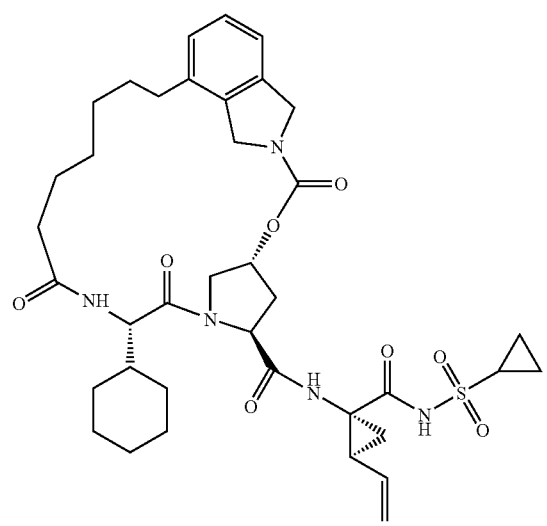
III-48
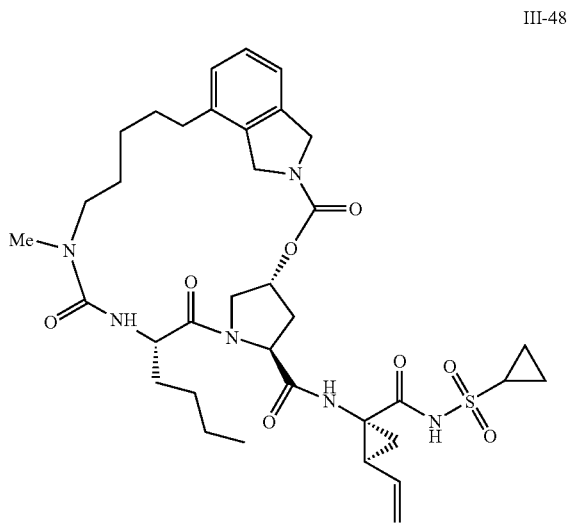

III-49
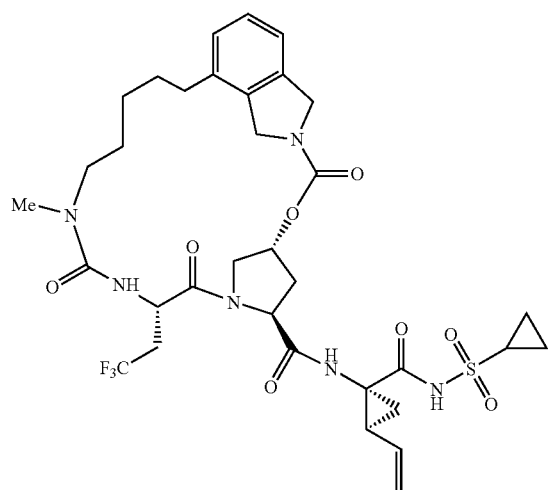
III-50
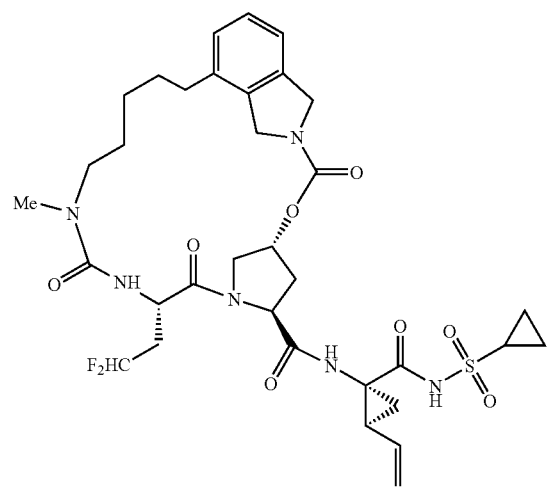
III-51
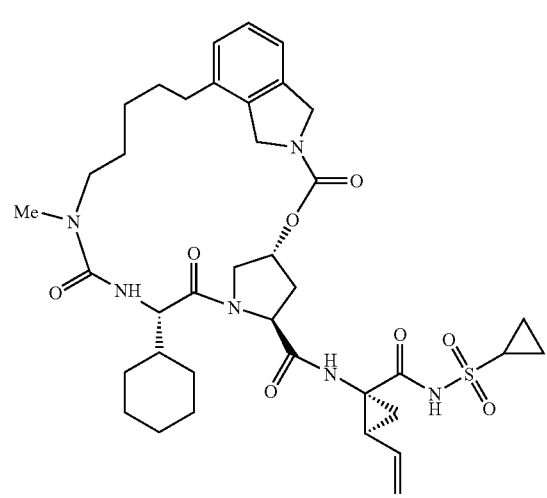
III-52
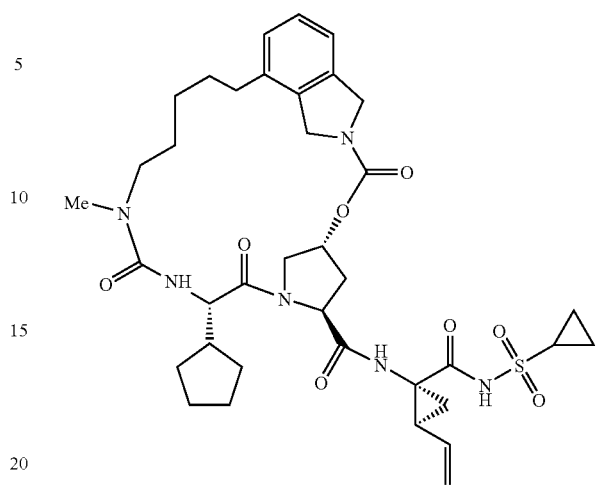
III-53
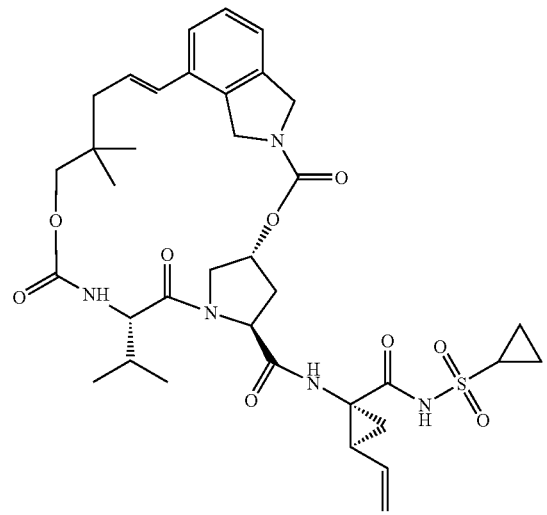
III-54
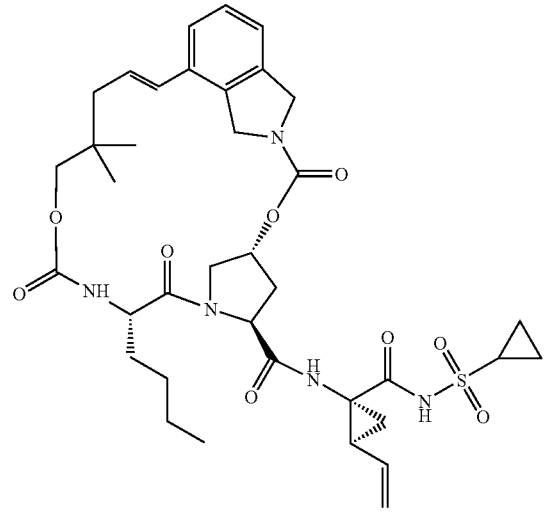

-continued
III-55
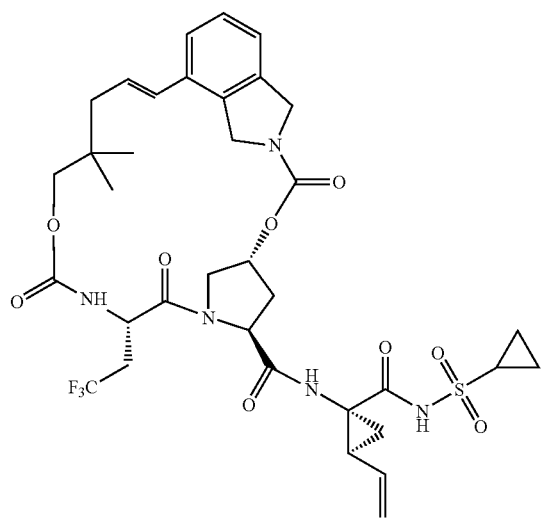
III-56
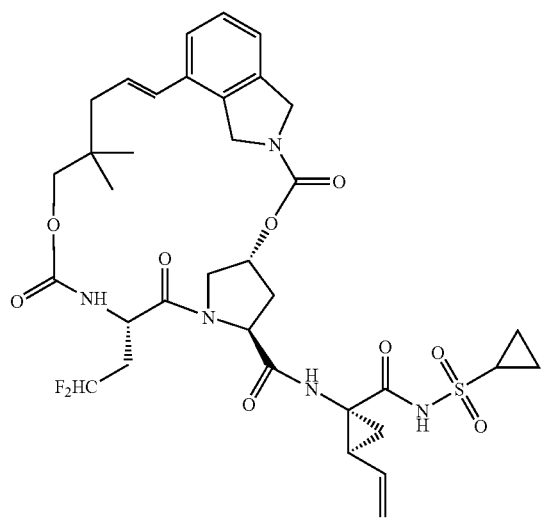
III-57
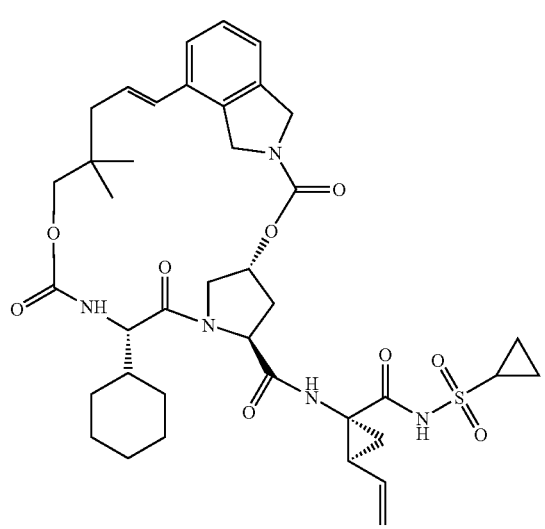
-continued
III-58
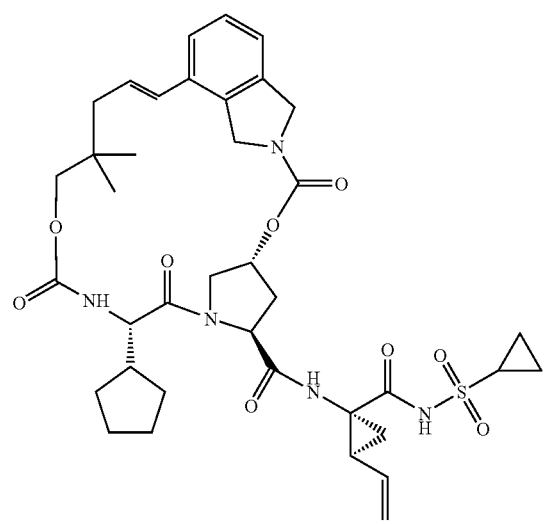
III-59
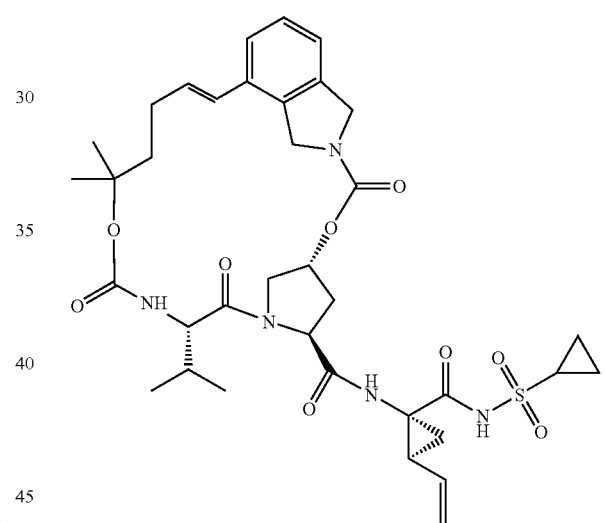
III-60
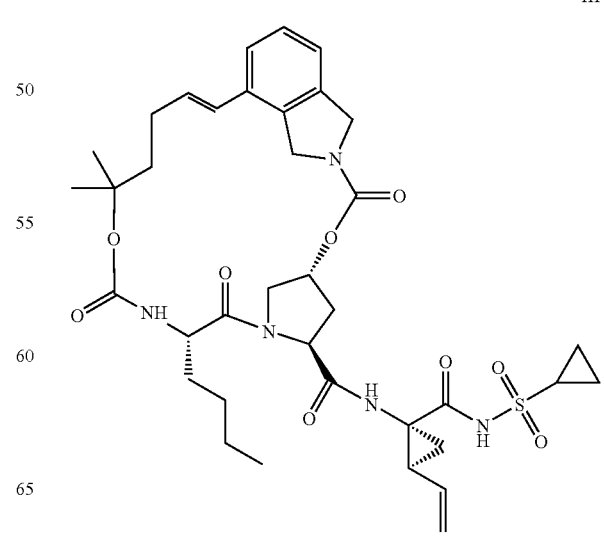

III-61
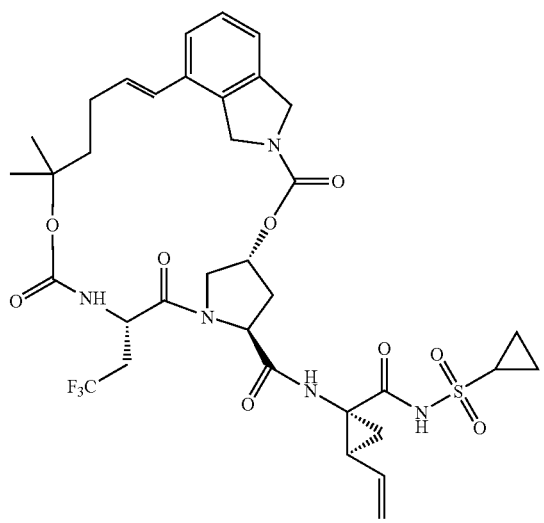
III-64
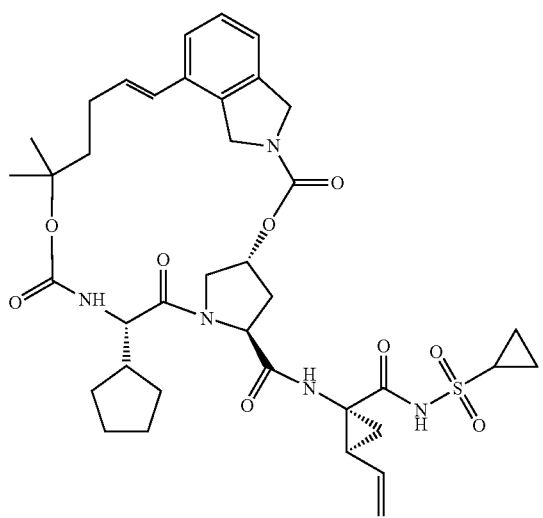
III-62
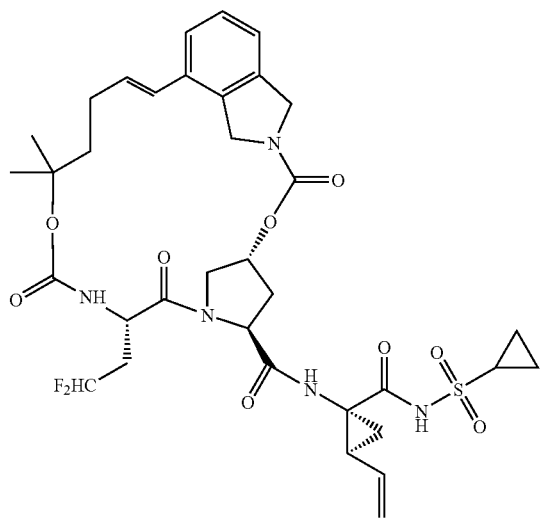
III-65
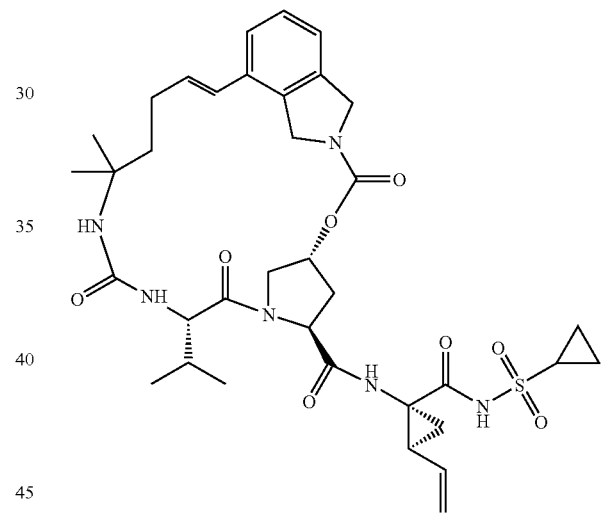
III-63
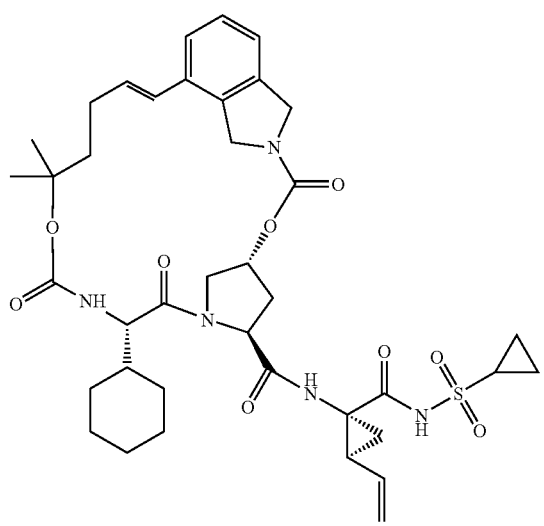
III-66
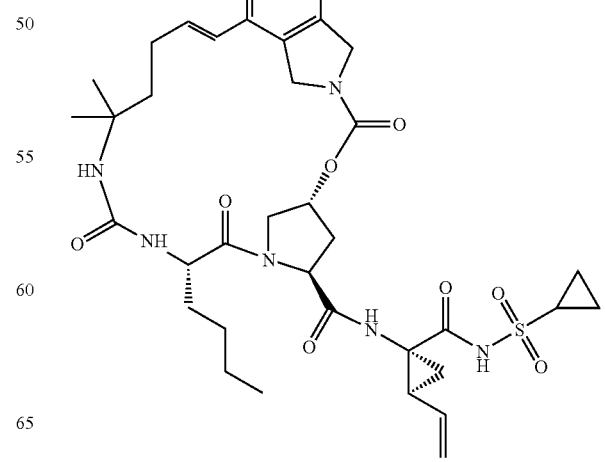

III-67
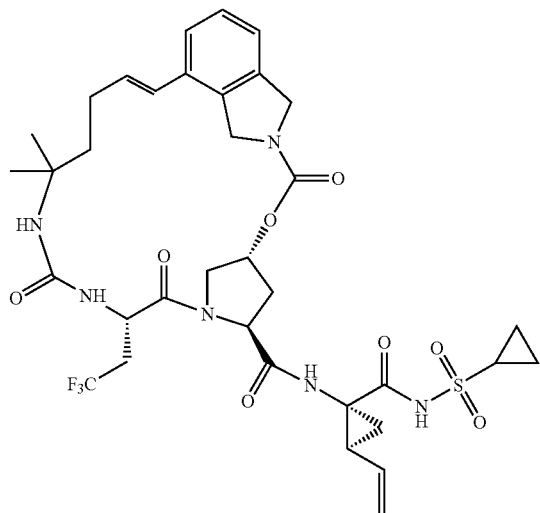
III-70
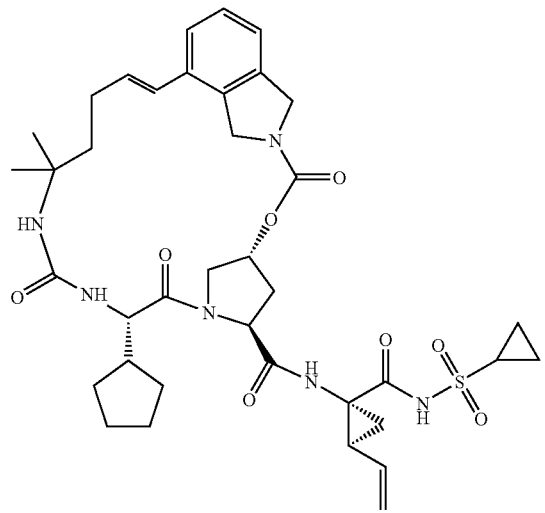
III-68
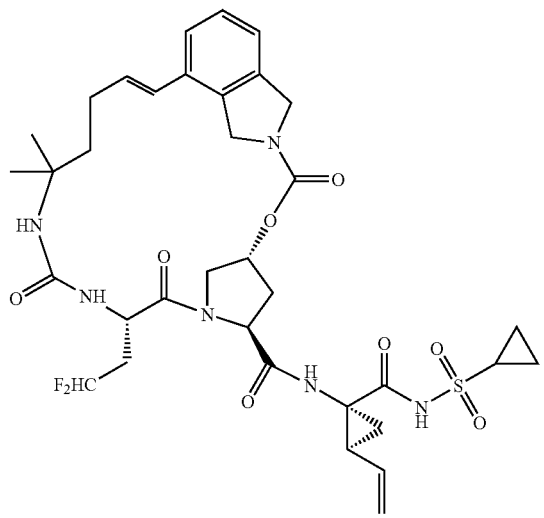
III-71
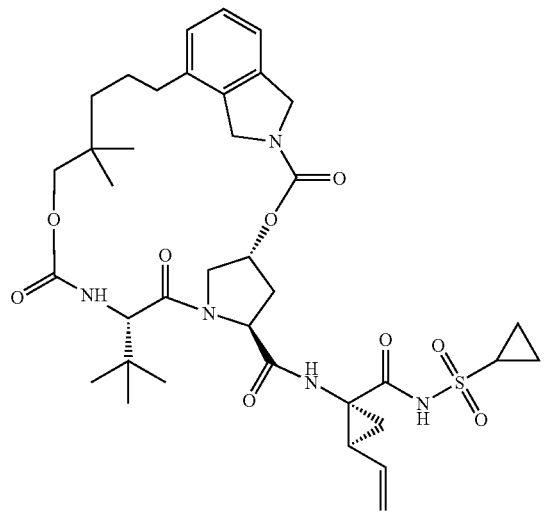
III-69
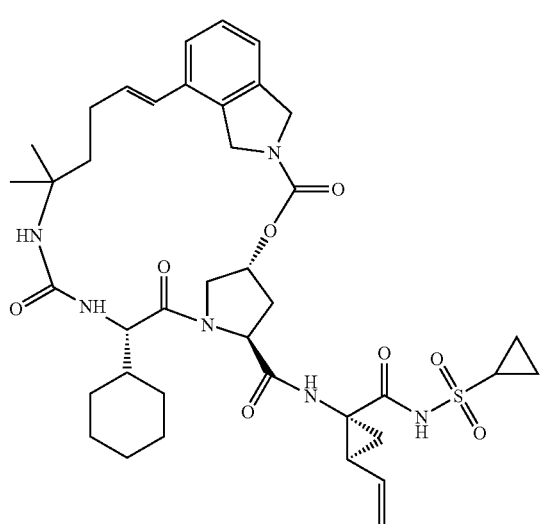
III-72
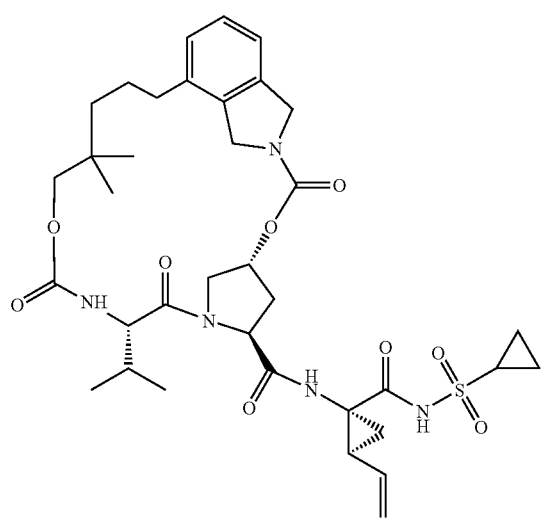

III-73
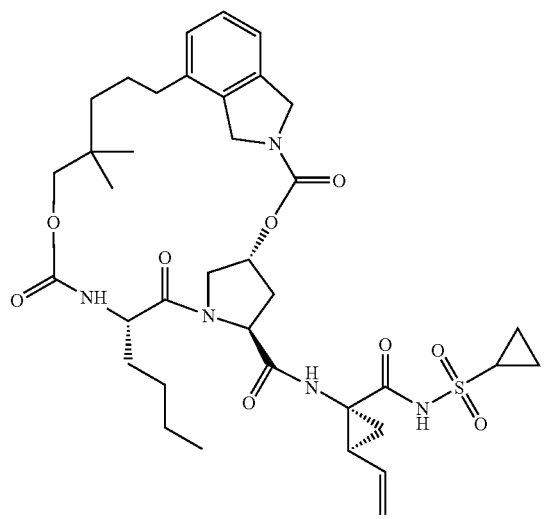
III-76
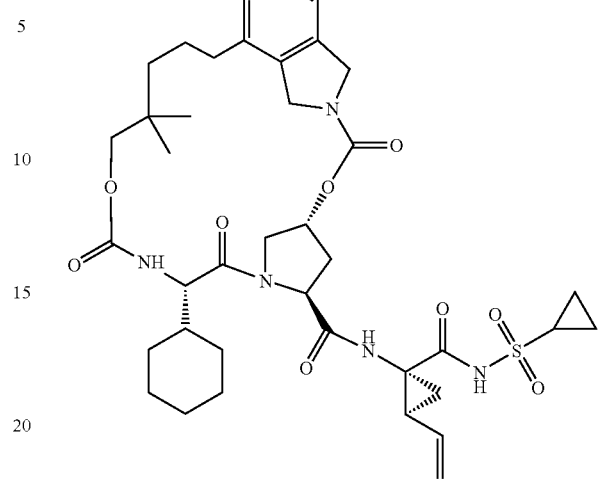
III-74
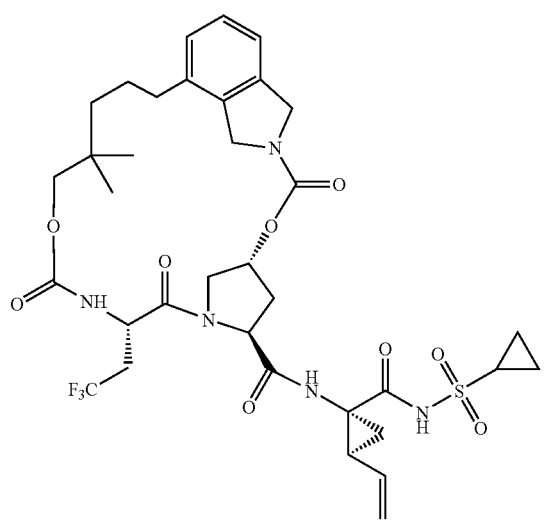
III-77
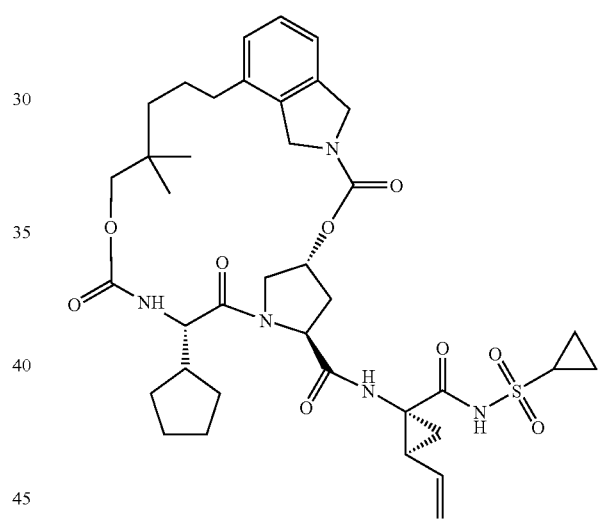
III-75
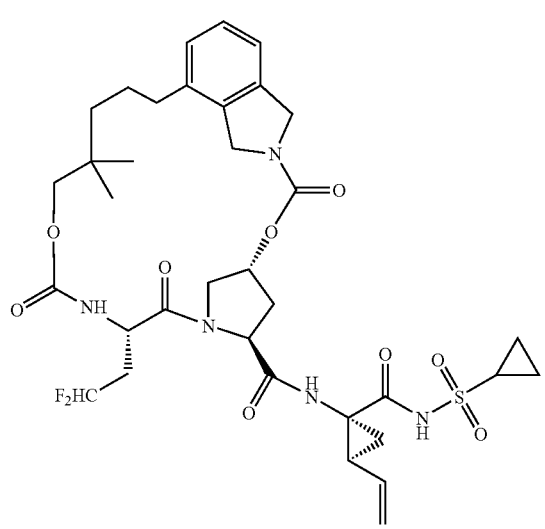
III-78
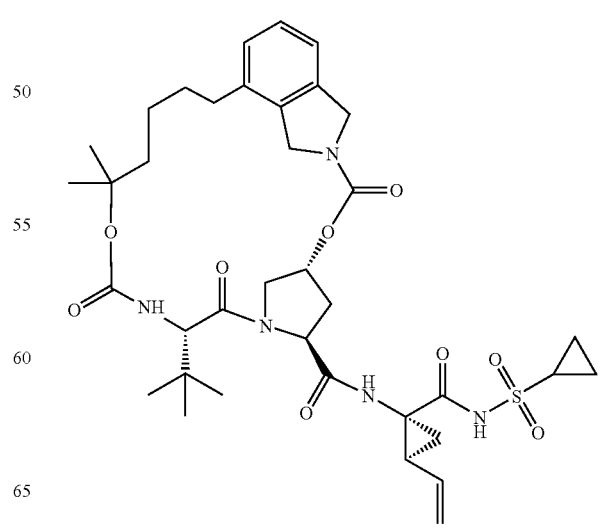

III-79
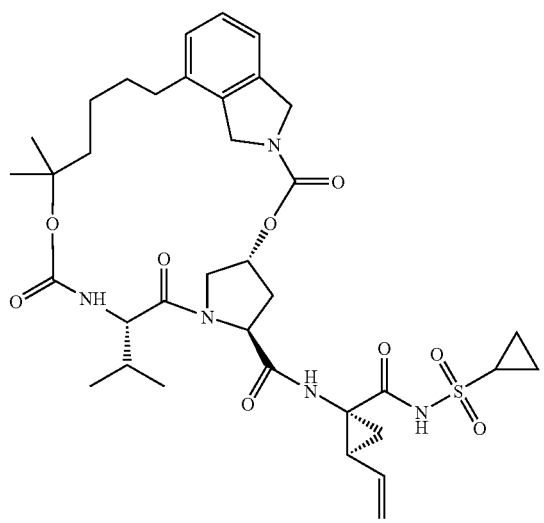
III-82
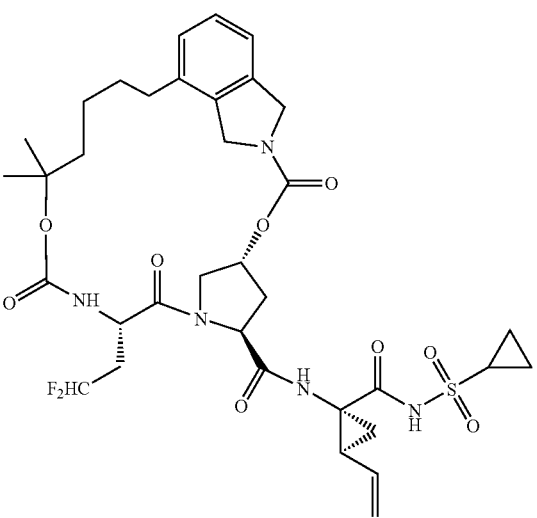
III-80
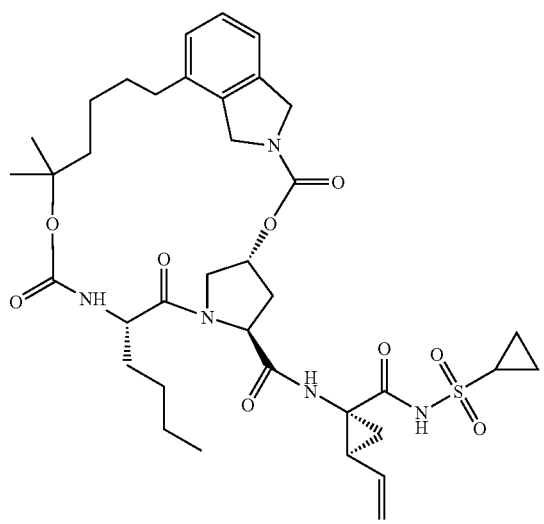
III-83
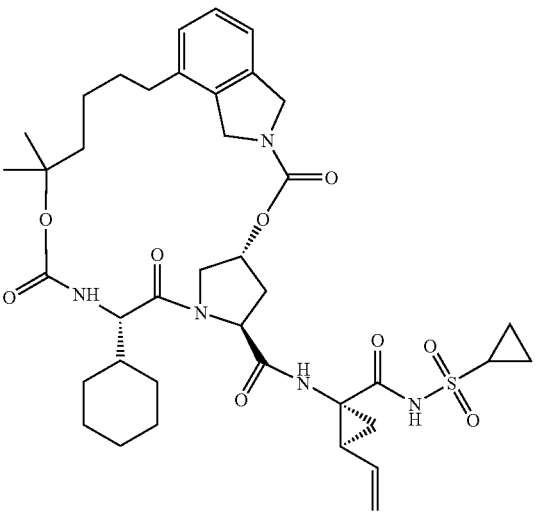
III-81
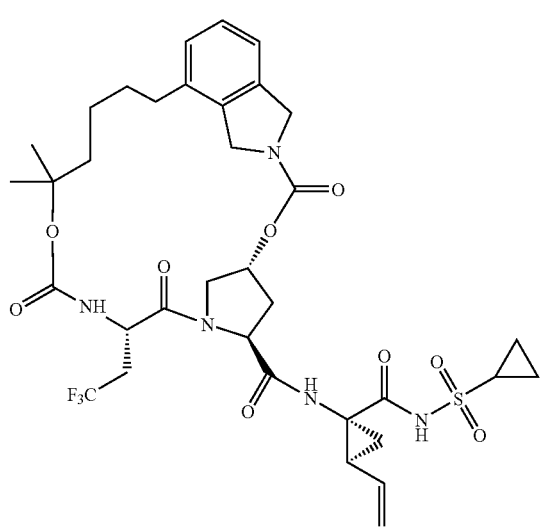
III-84
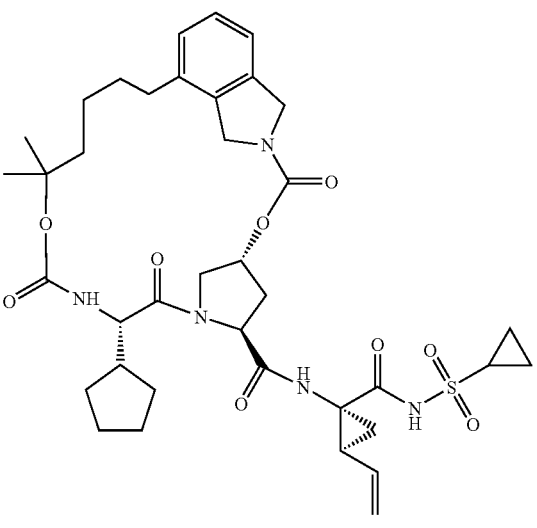

III-85
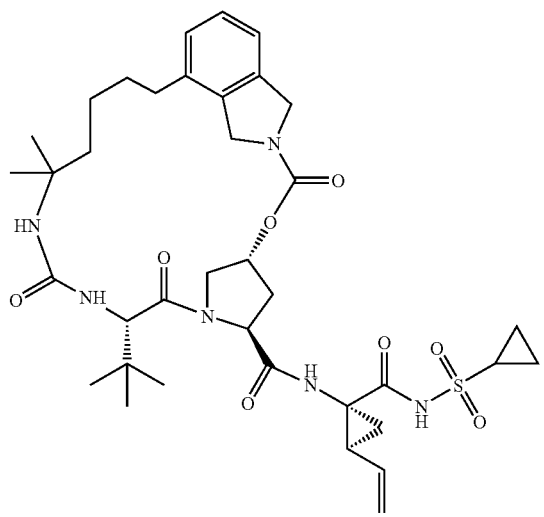
III-88
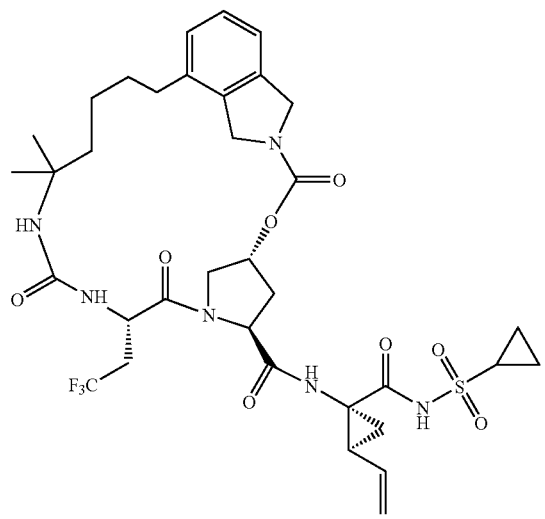
III-86
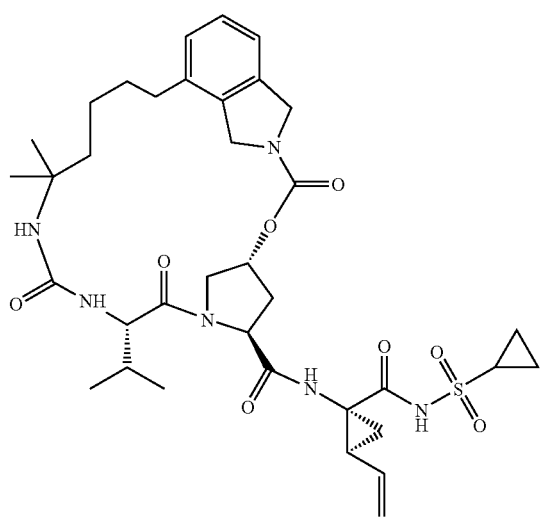
III-89
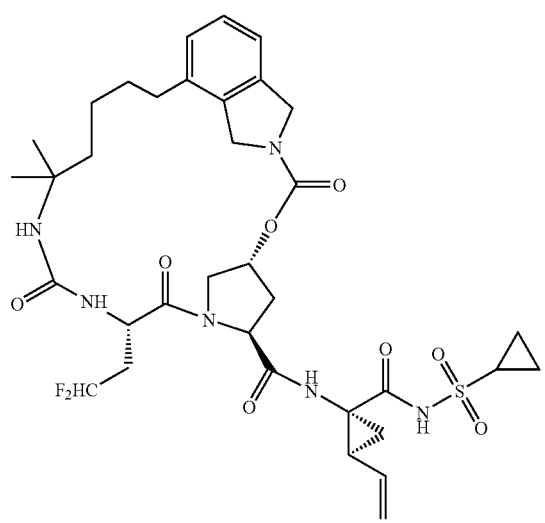
III-87
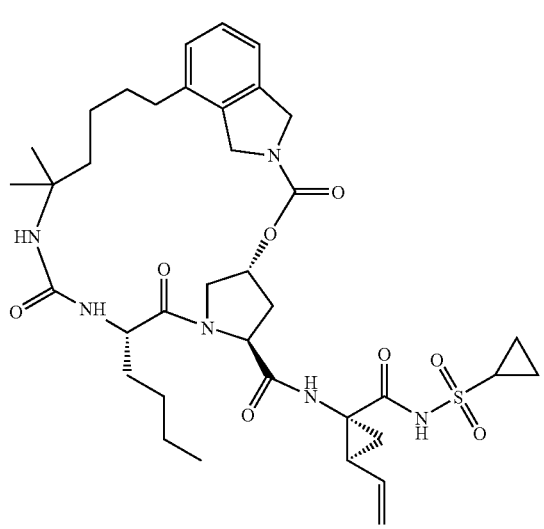
III-90
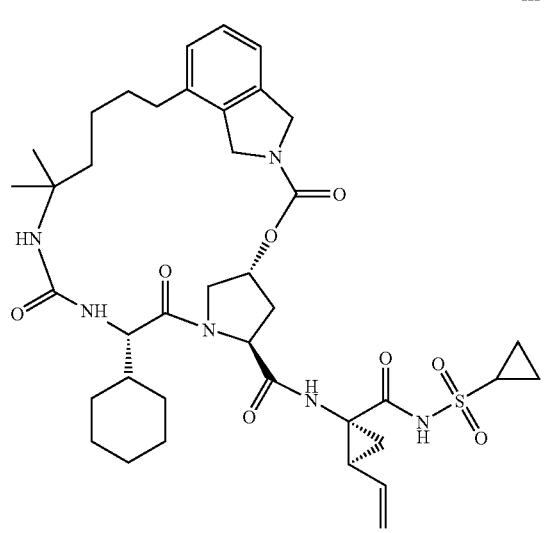

III-91
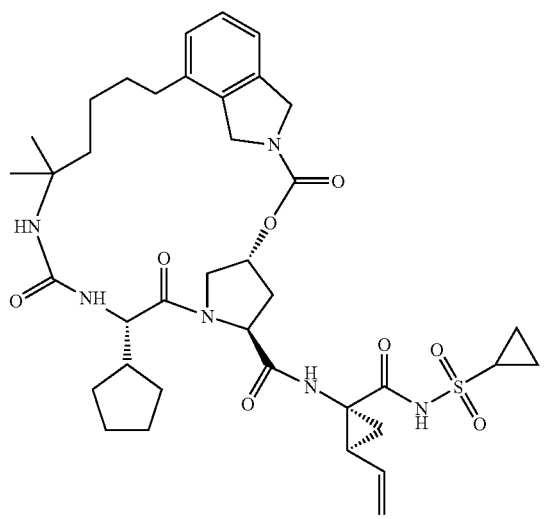
III-94
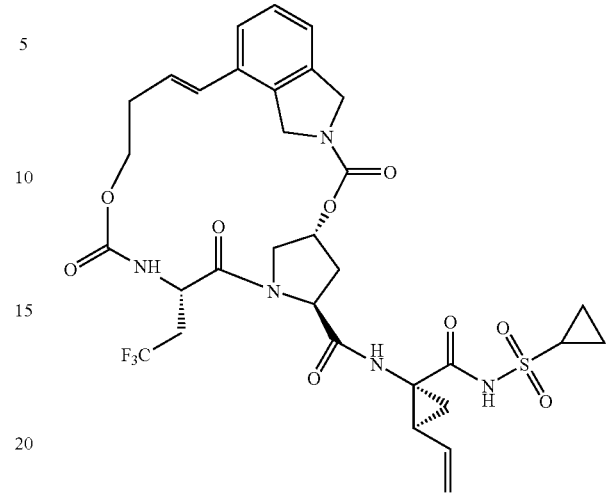
III-92
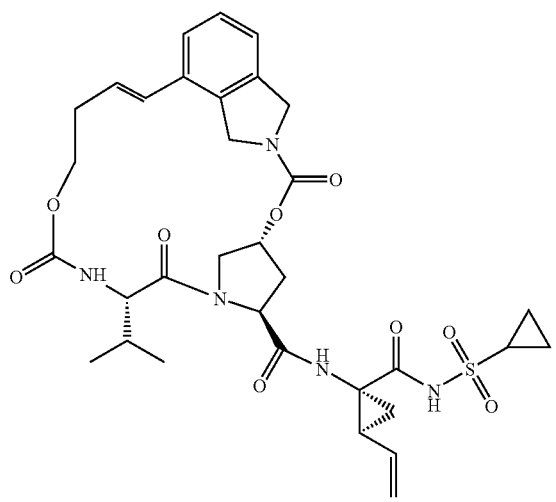
III-95
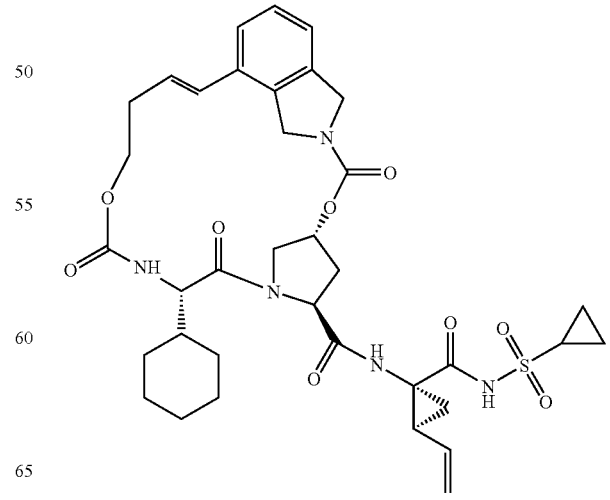
III-93
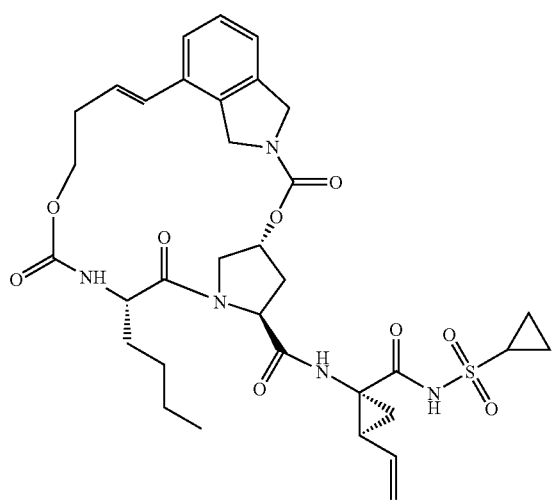
III-96

III-97
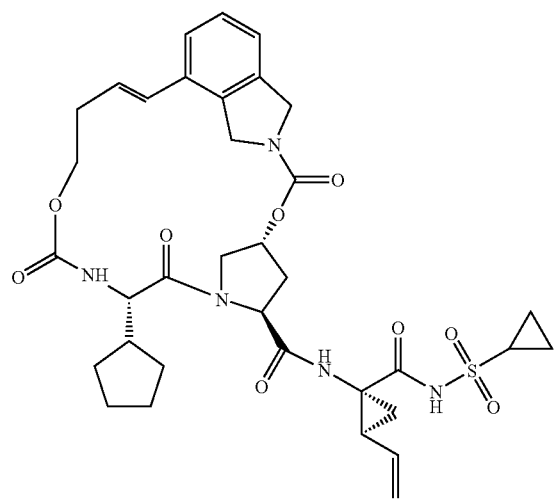
III-100
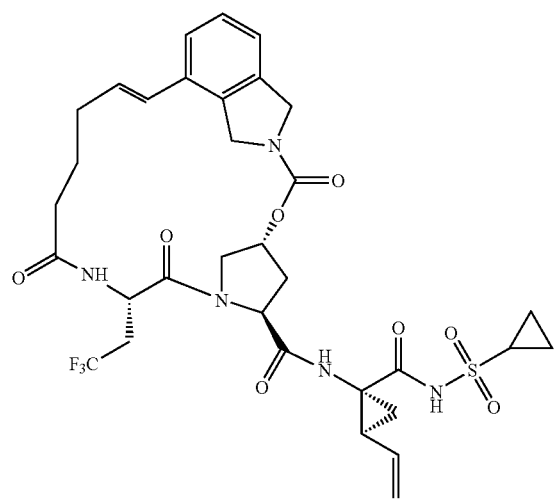
III-98
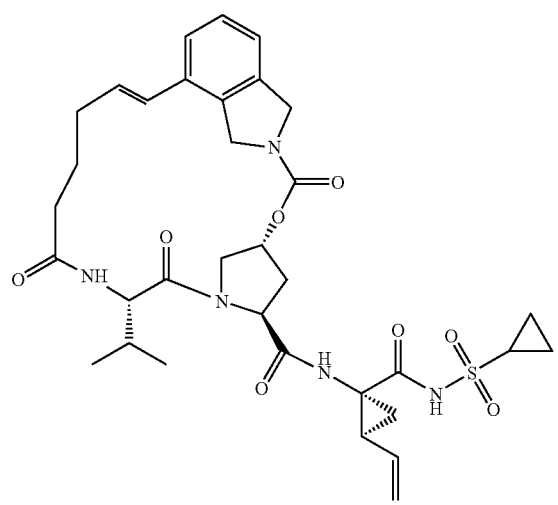
III-101
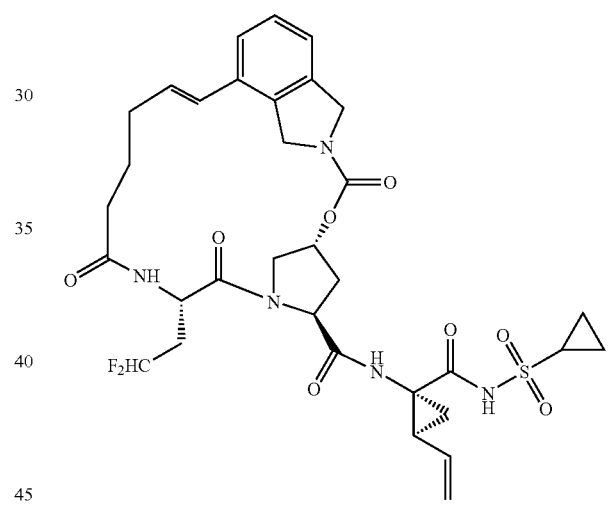
III-99
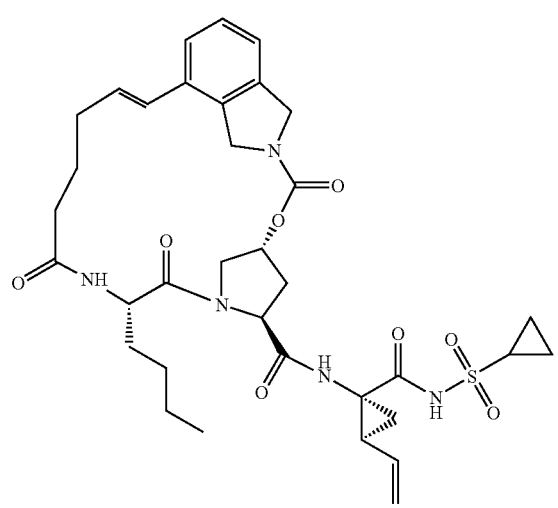
III-102
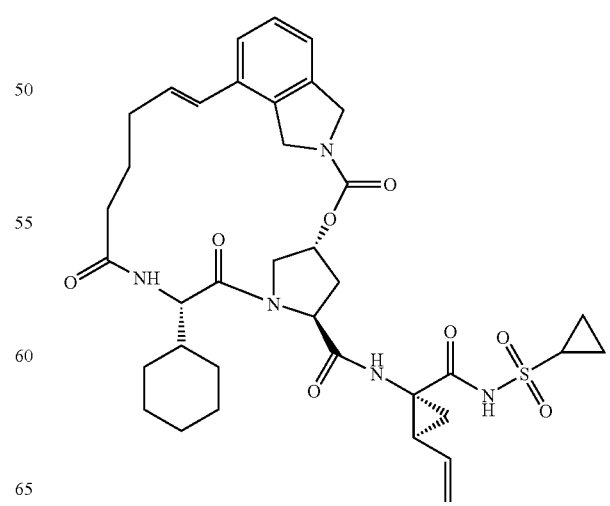

III-103
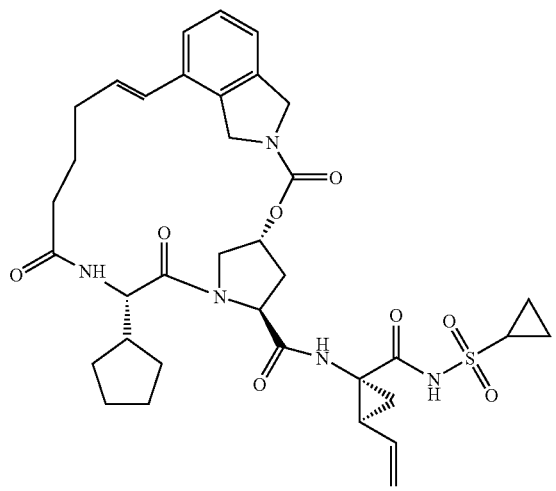
III-106
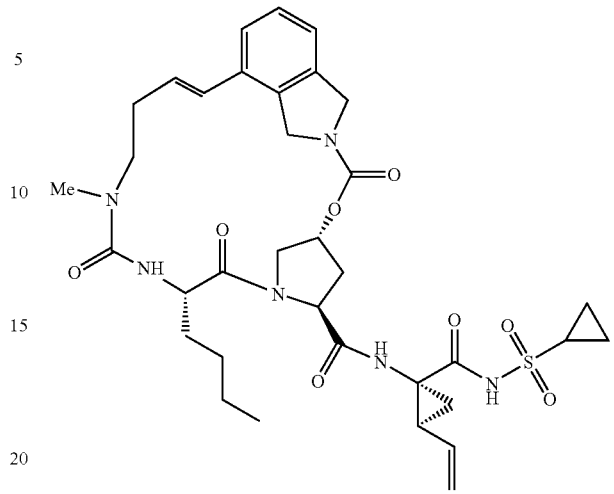
III-104
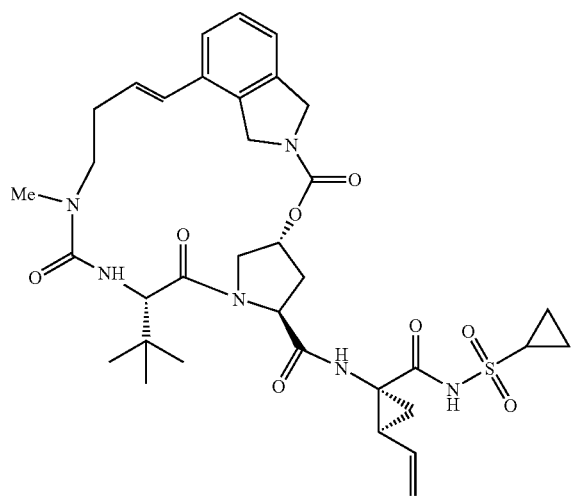
III-107
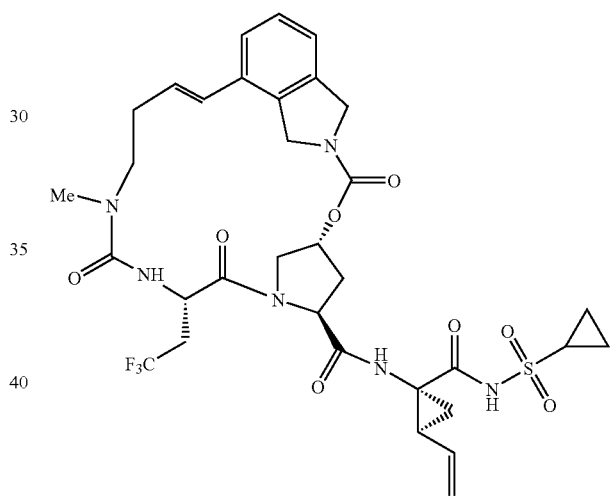
III-105
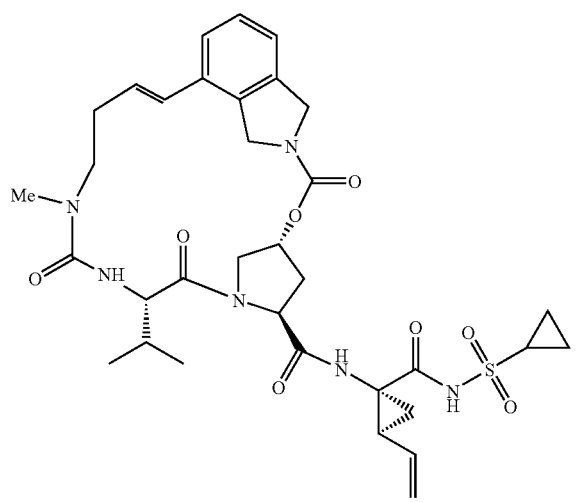
III-108
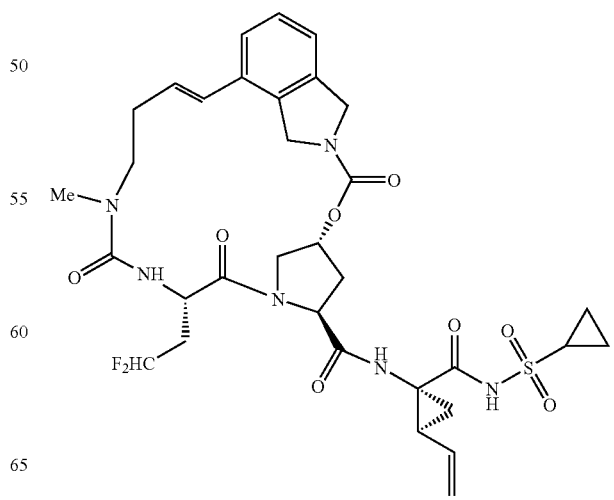

III-109
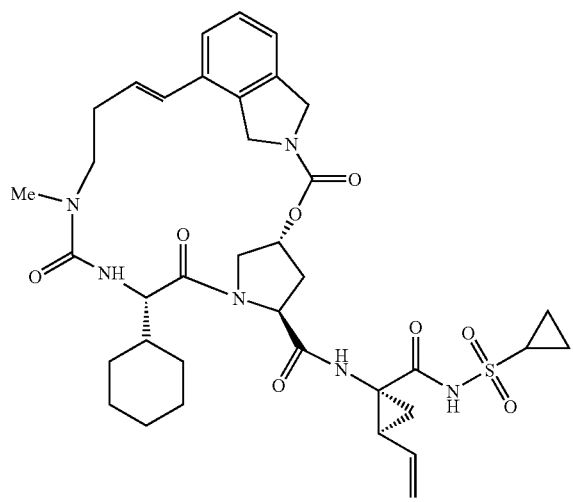
III-112
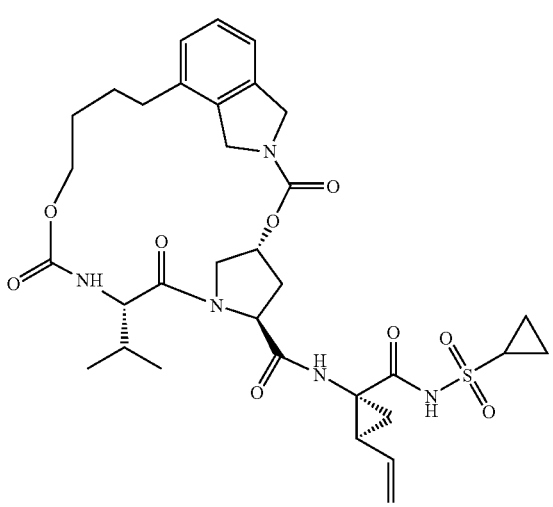
III-110
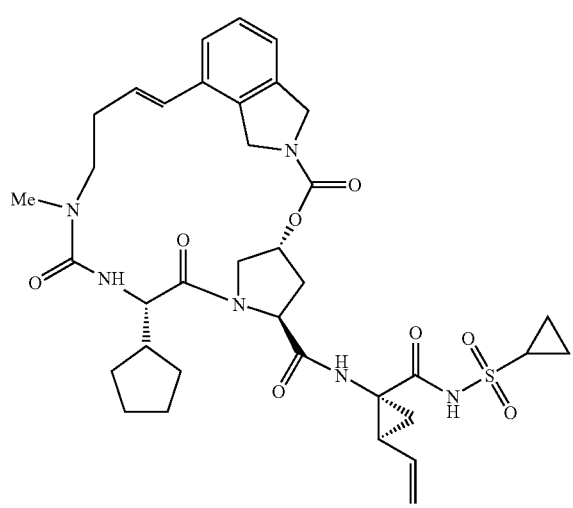
III-113
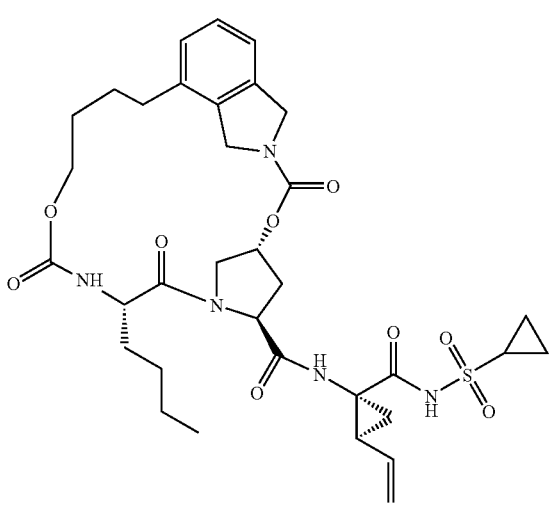
III-111
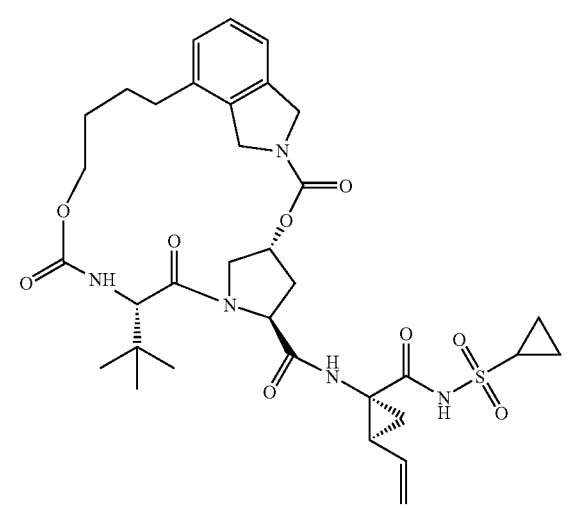
III-114
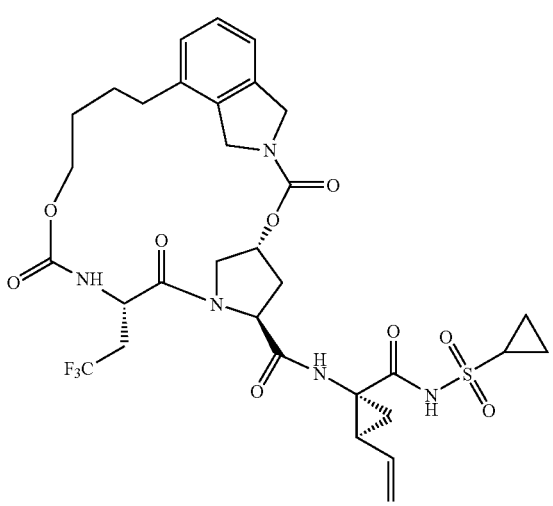

III-115
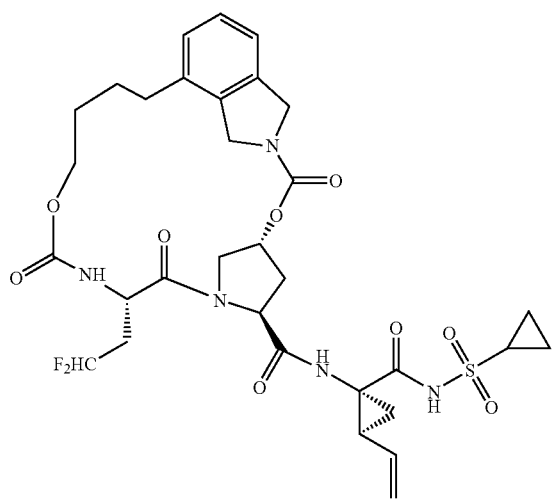
III-118
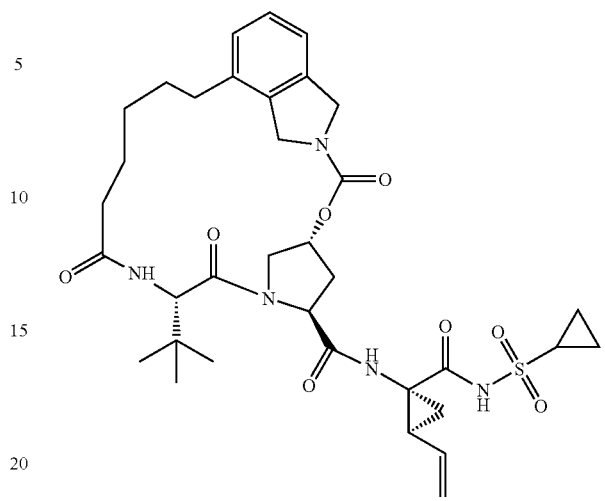
III-116
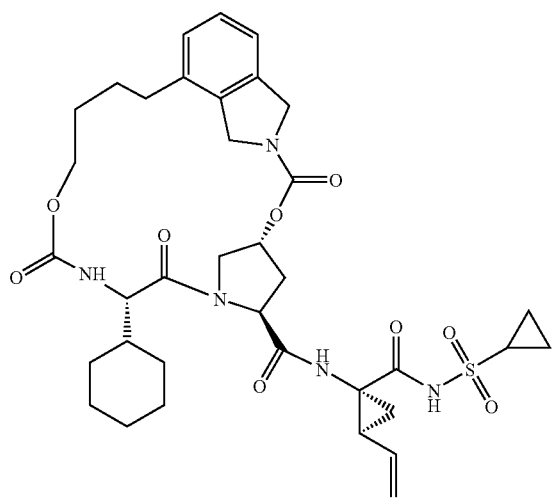
III-119
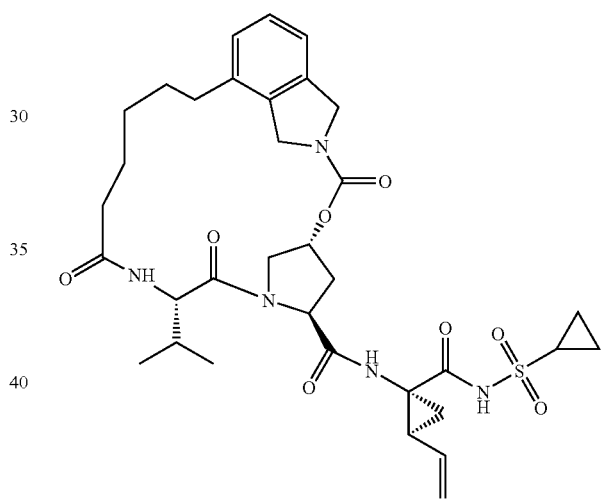
III-117
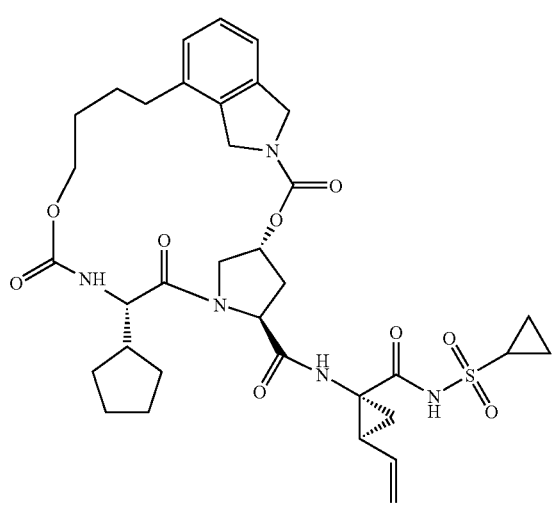
III-120
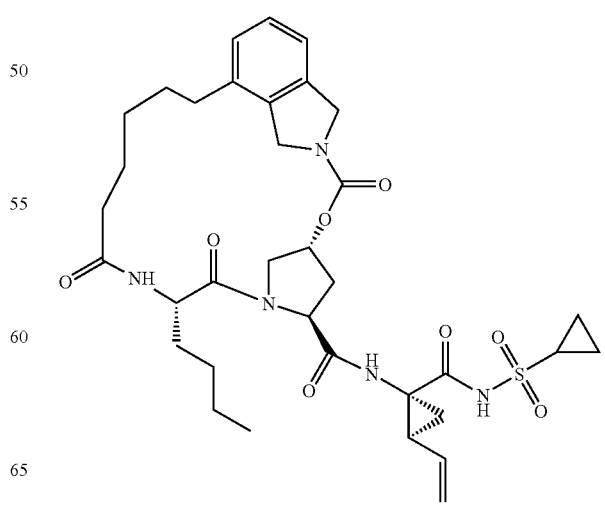

III-121
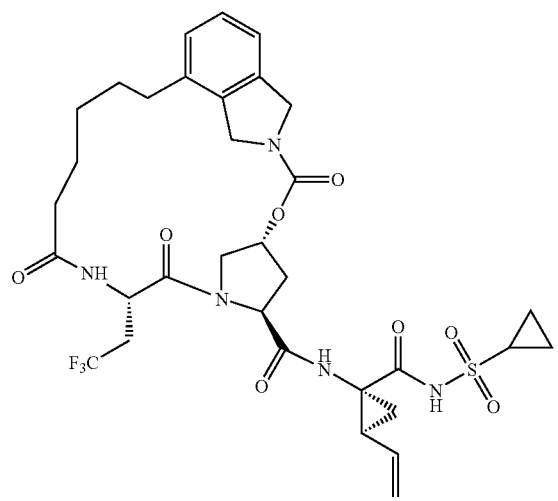
III-124
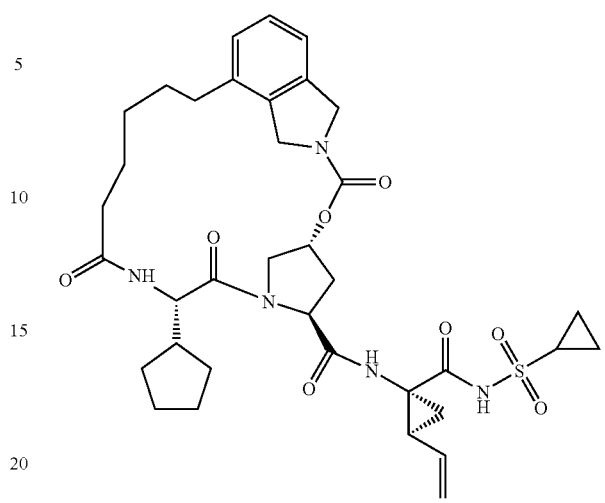
III-122
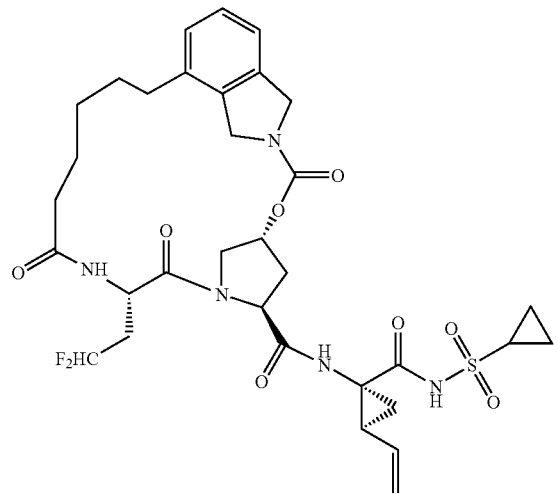
III-125
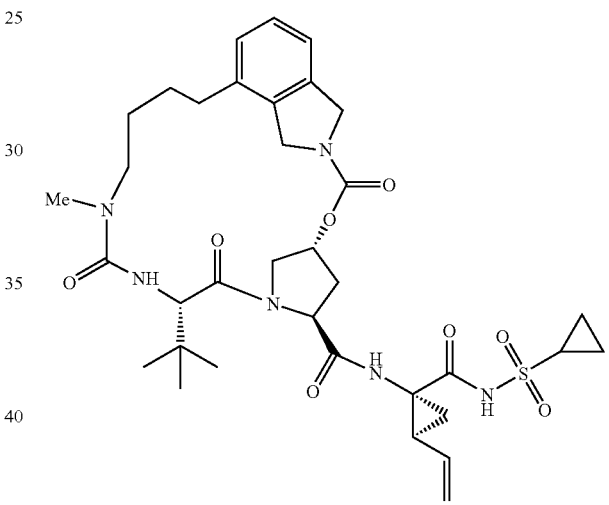
III-123
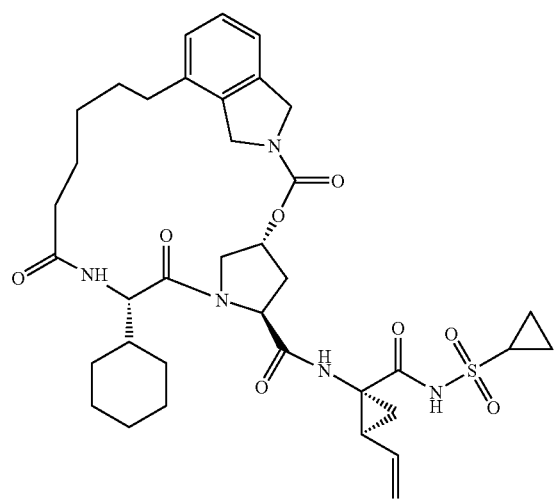
III-126
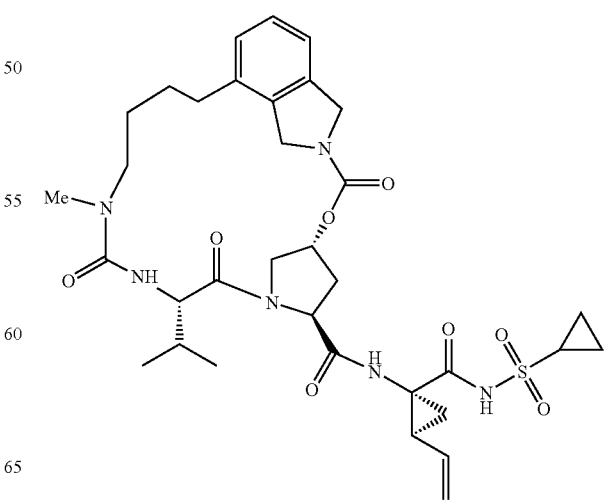

III-127
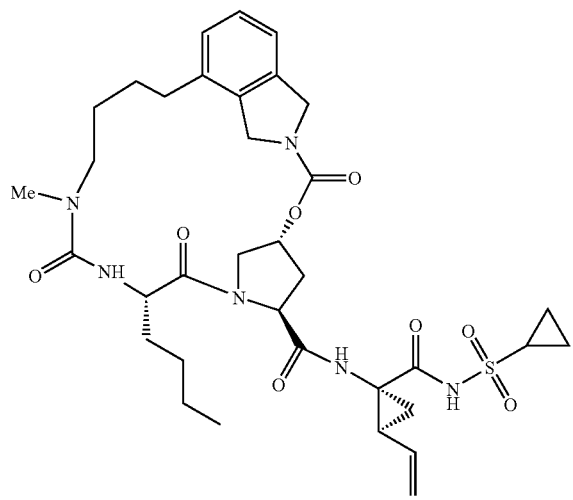
III-128
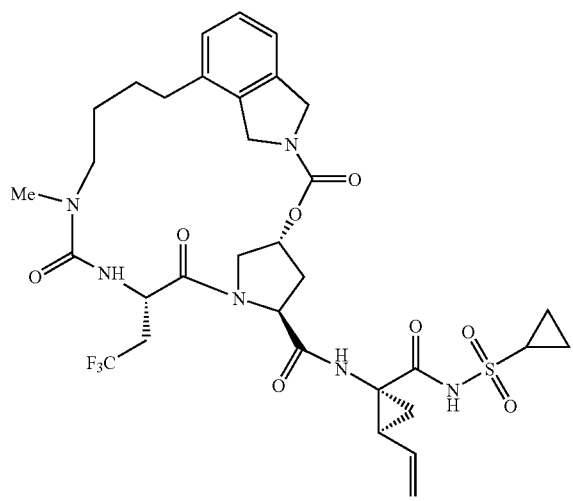
III-129
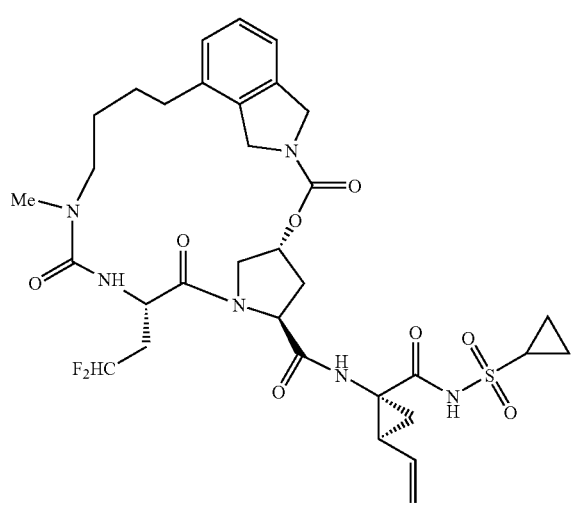
III-130
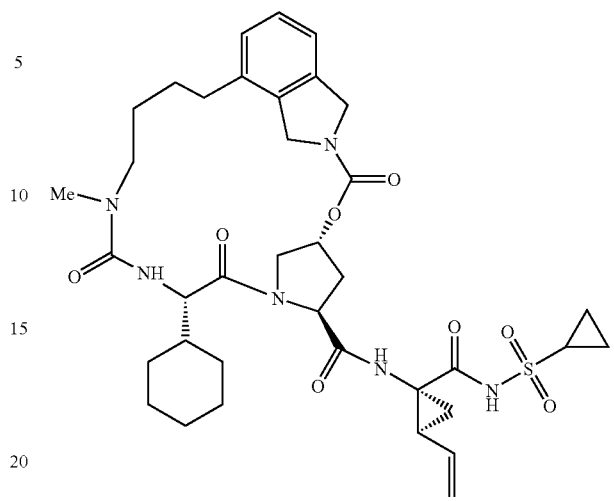
III-131
III-132

III-133
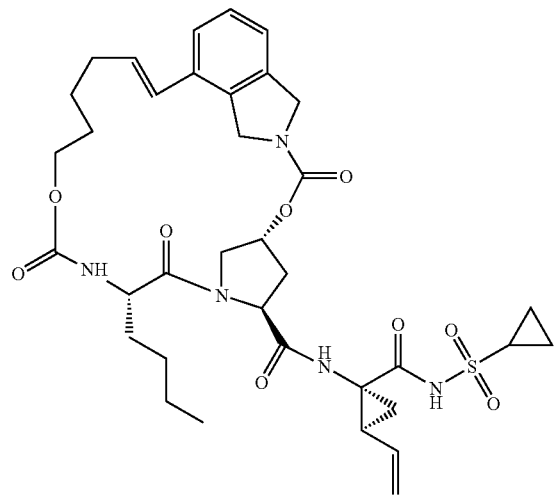
III-136
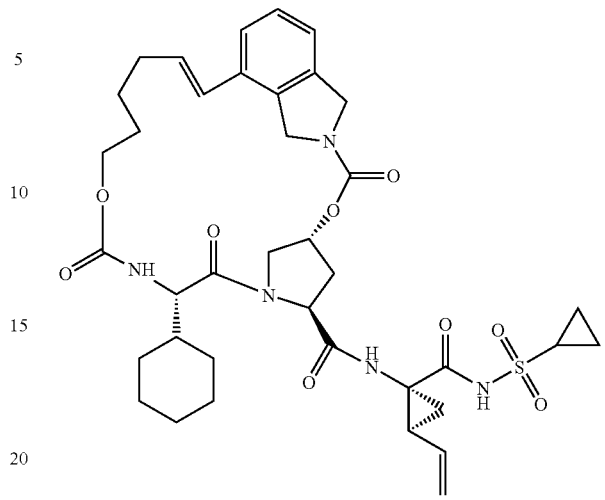
III-134
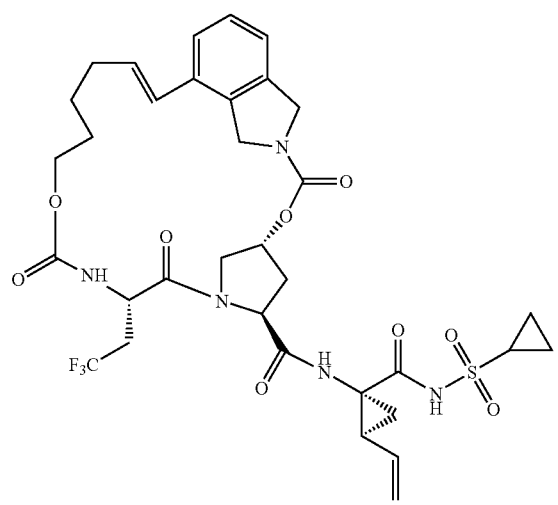
III-137
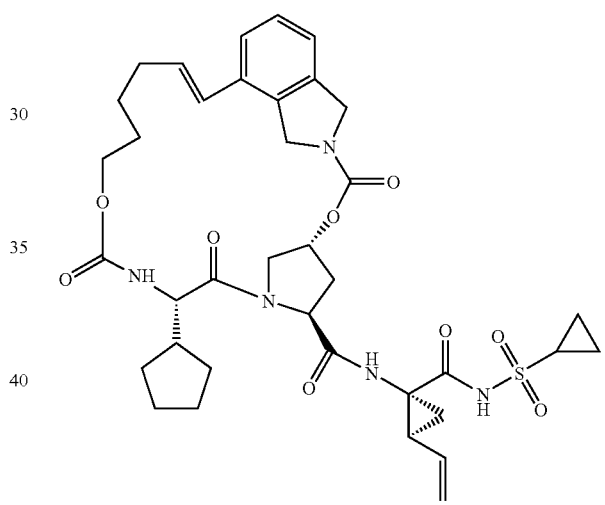
III-135
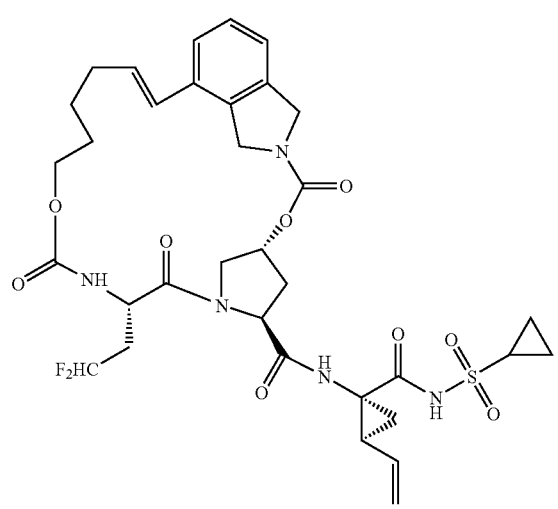
III-138
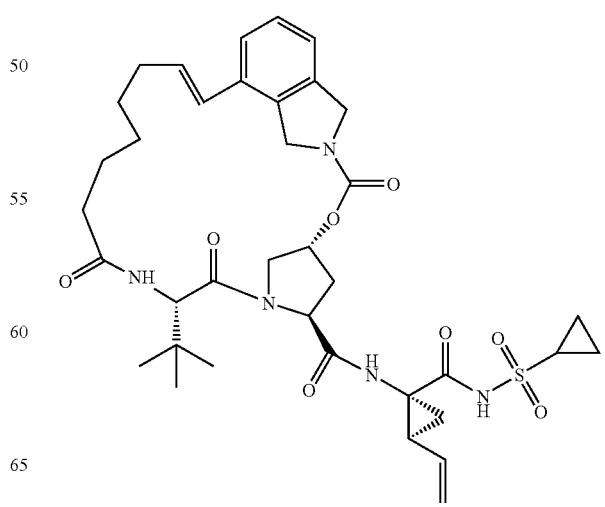

III-139
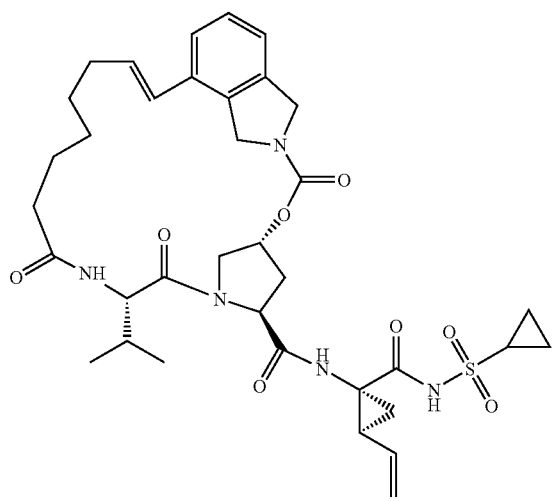
III-142
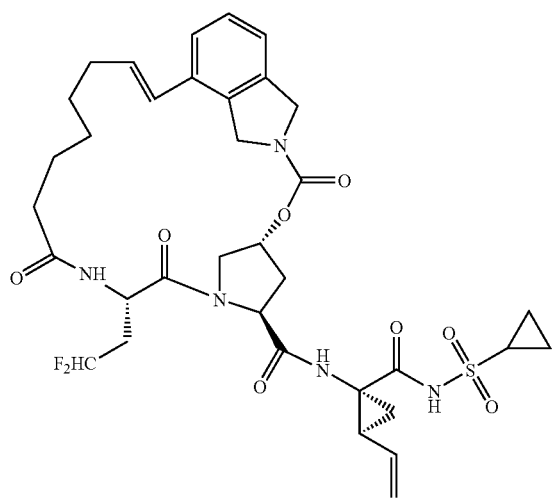
III-140
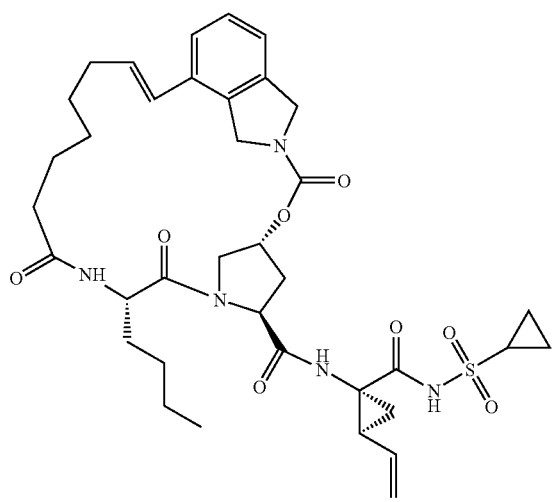
III-143
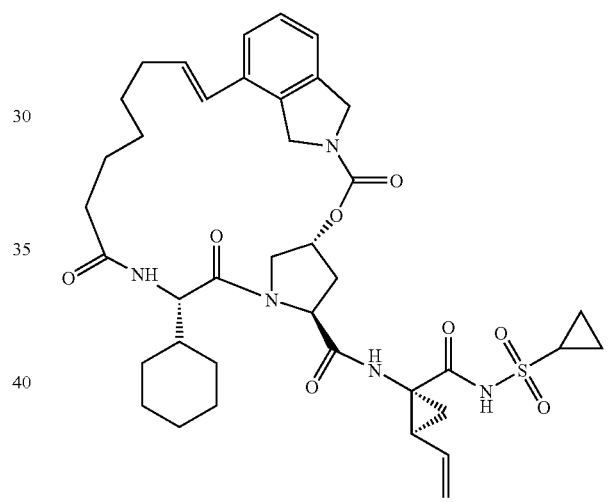
III-141
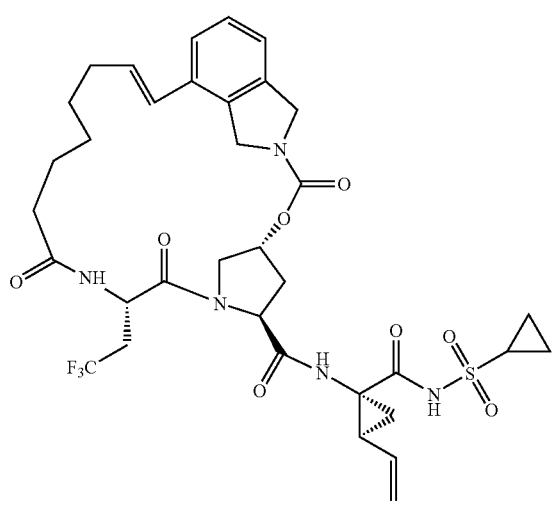
III-144
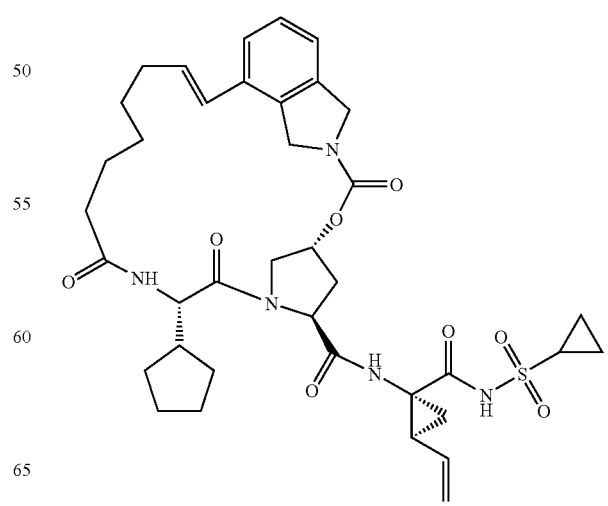

III-145
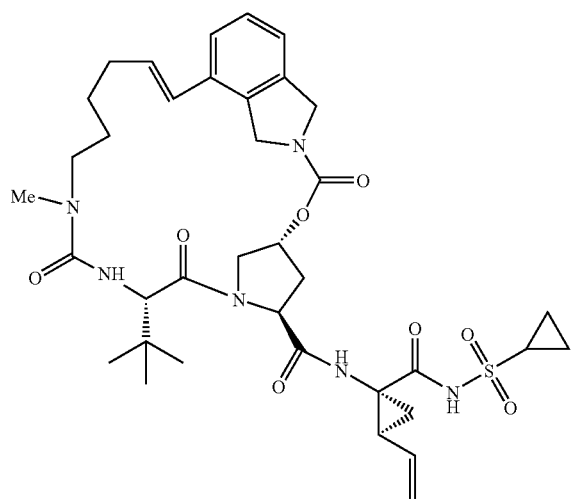
III-148
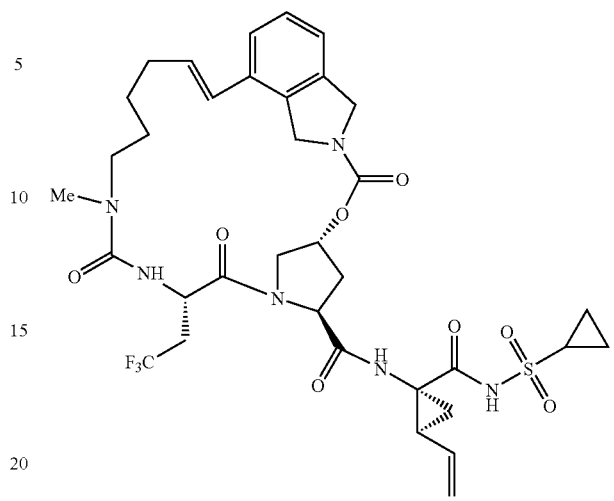
III-146
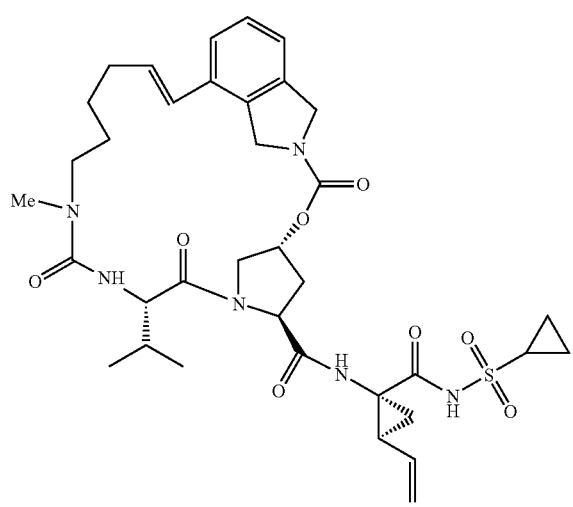
III-149
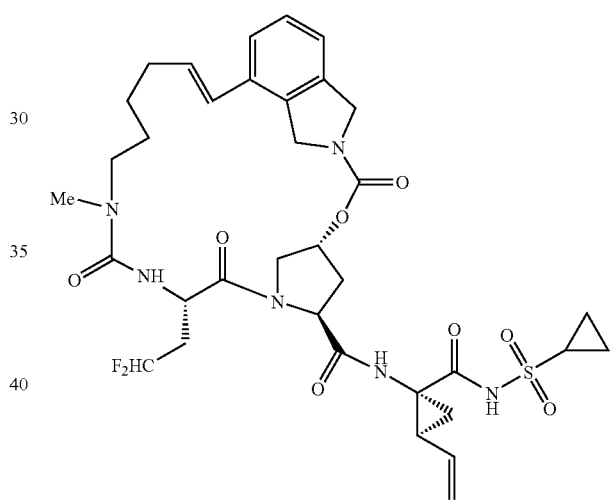
III-147
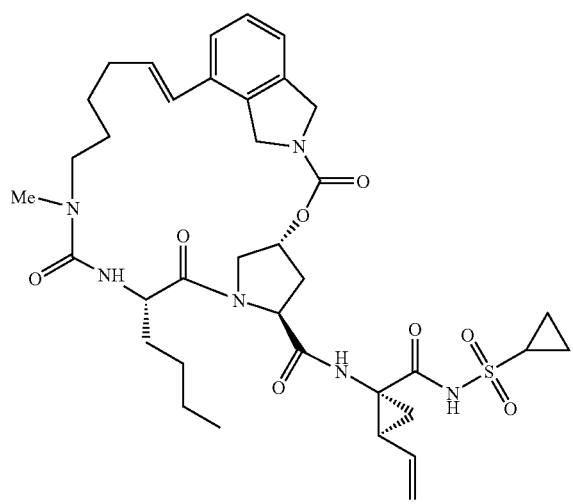
III-150
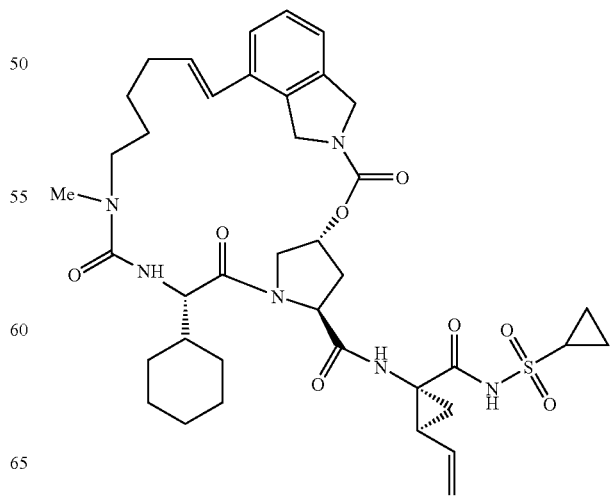

III-151
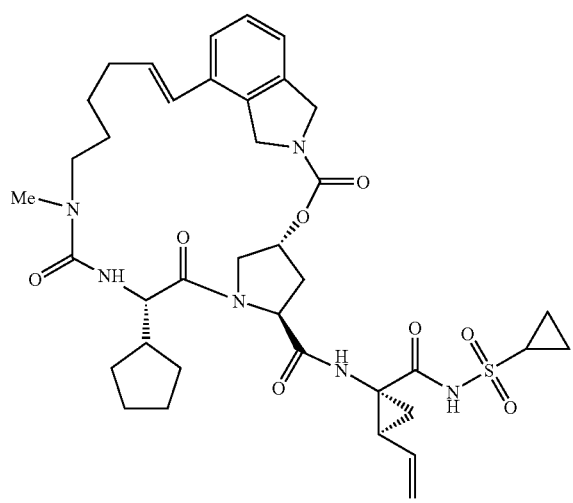
III-154
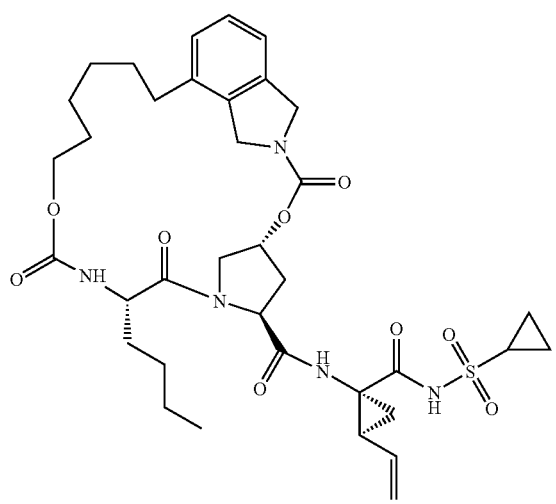
III-152
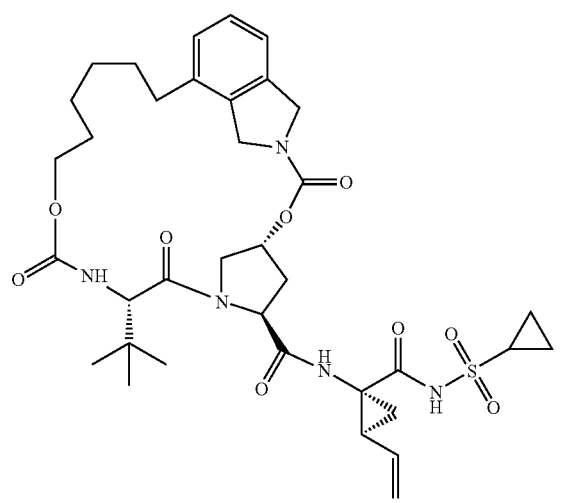
III-155
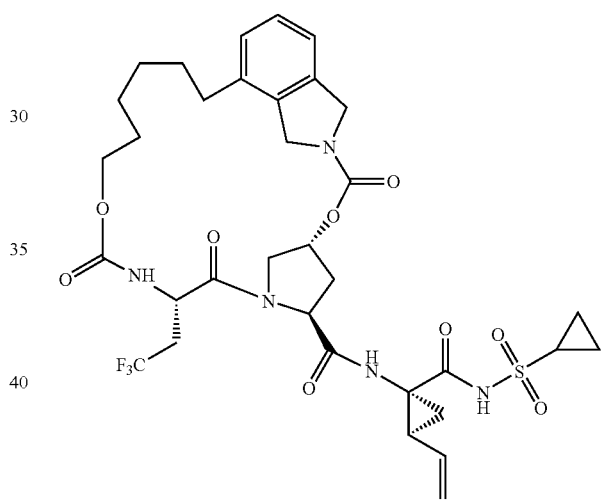
III-153
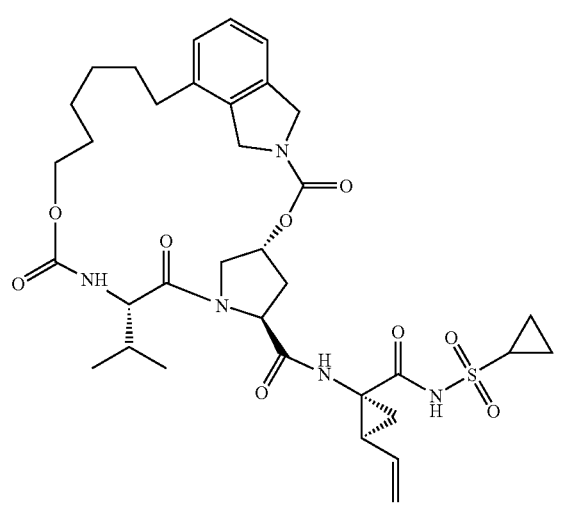
III-156
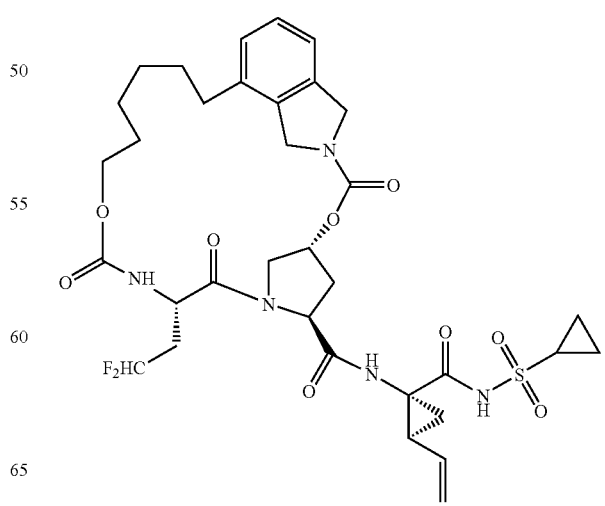

III-157
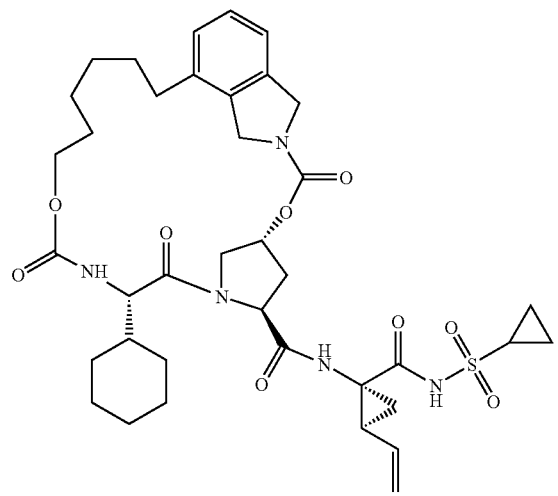
III-160
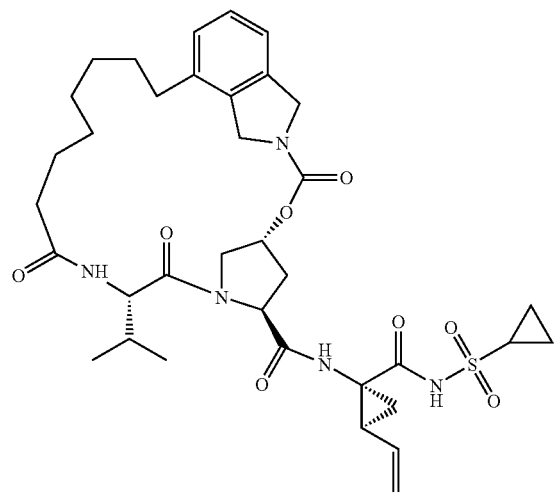
III-158
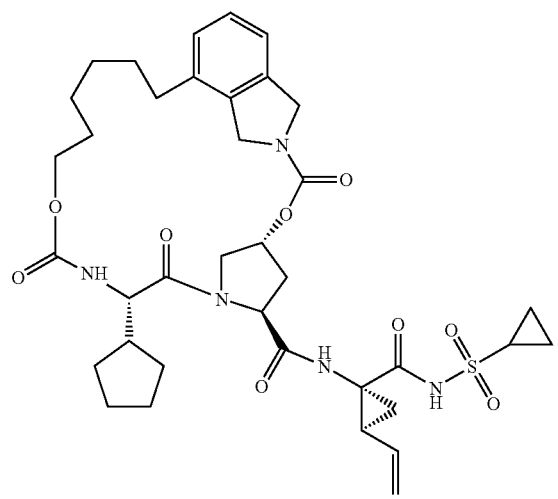
III-161
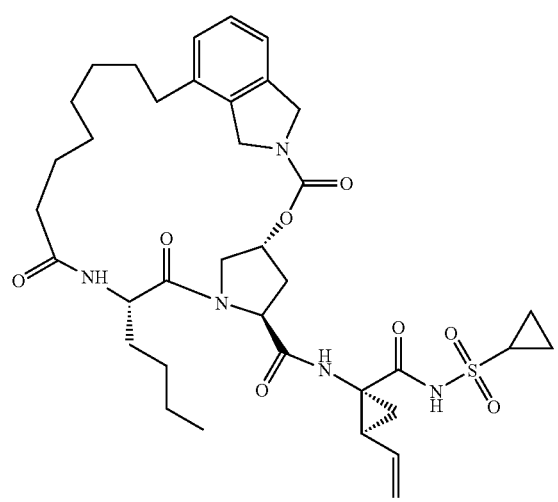
III-159
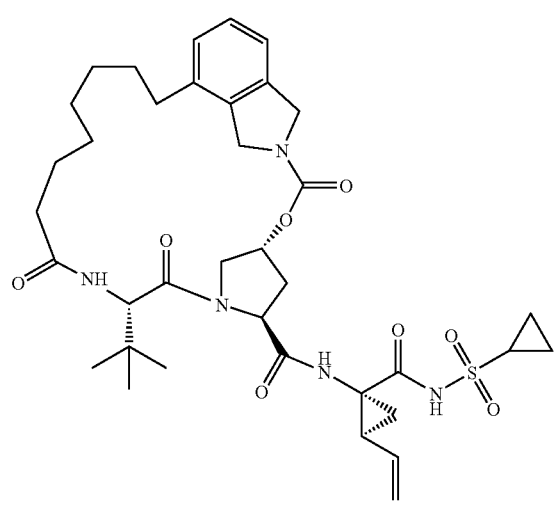
III-162
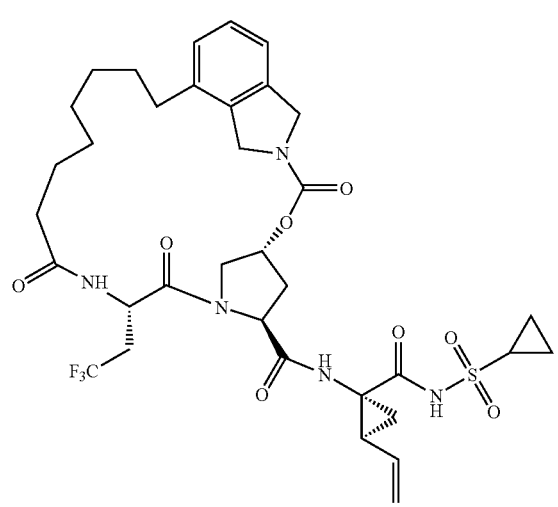

III-163
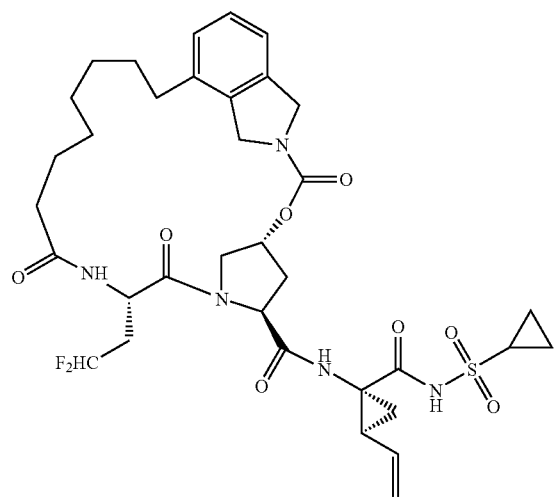
III-164
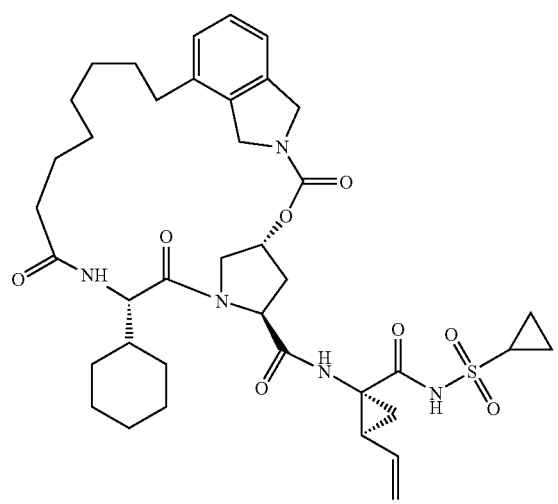
III-165
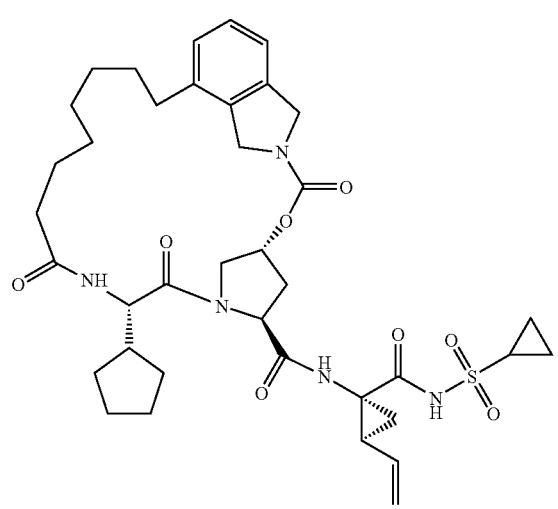
III-166
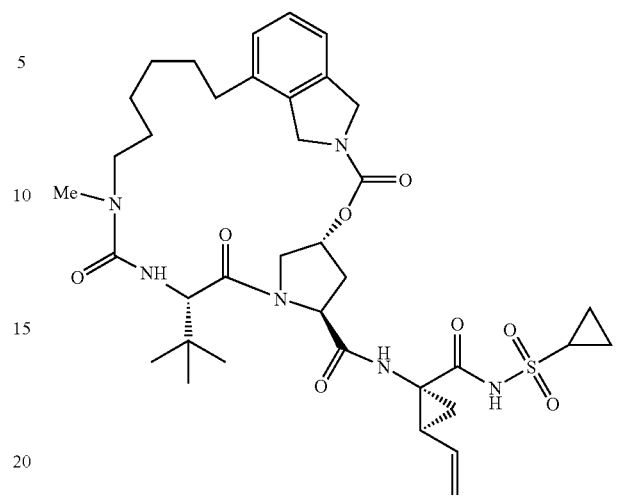
III-167
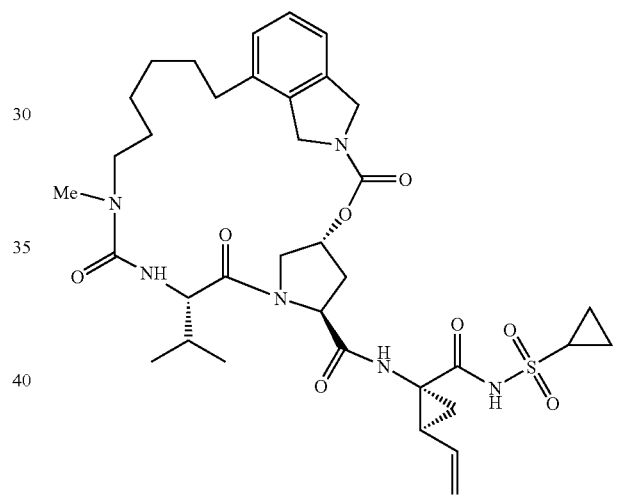
III-168
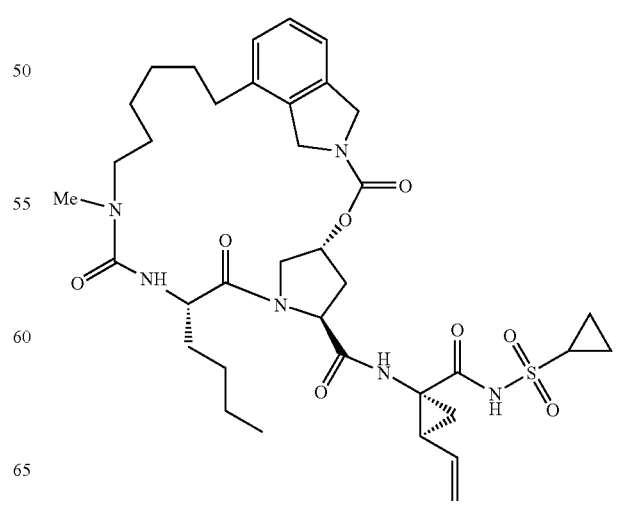

III-169
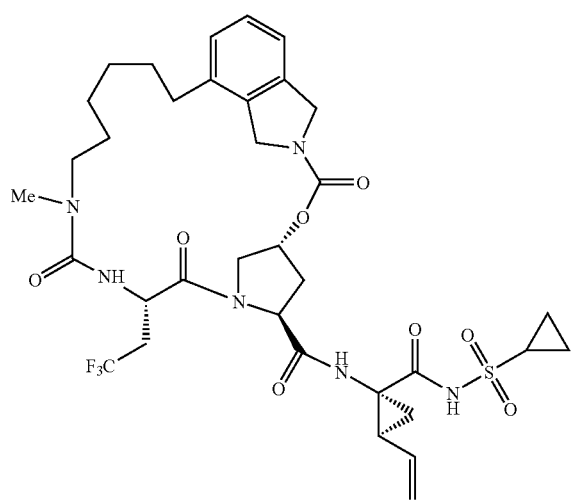
III-172
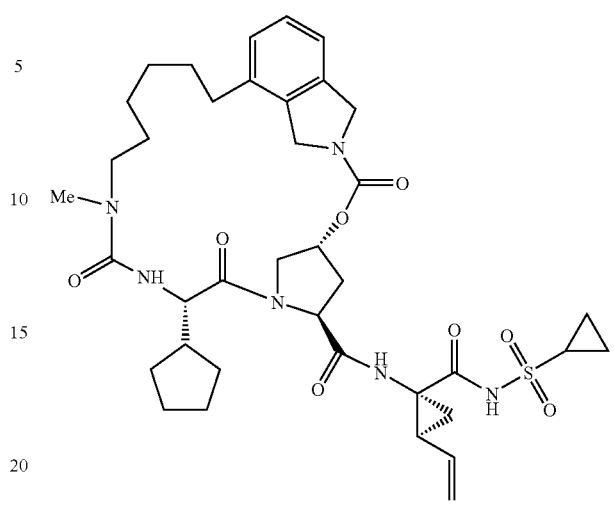
III-170
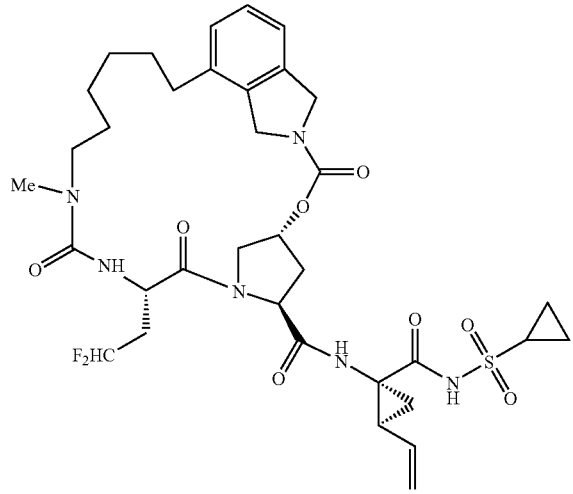
III-173
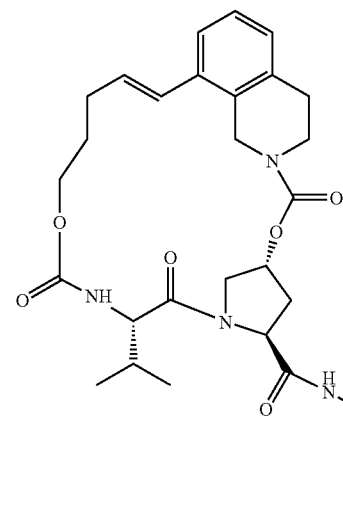
III-171
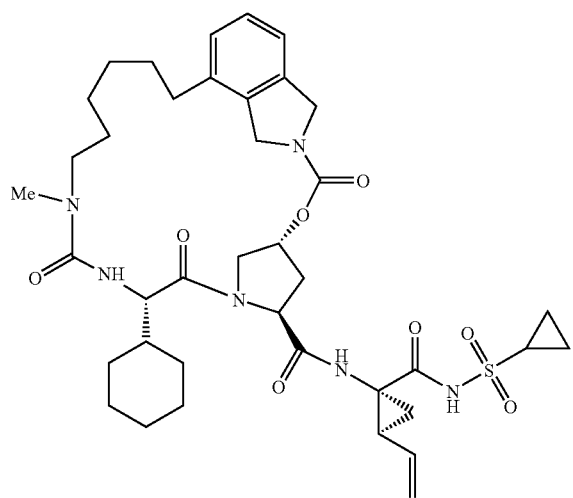
III-174
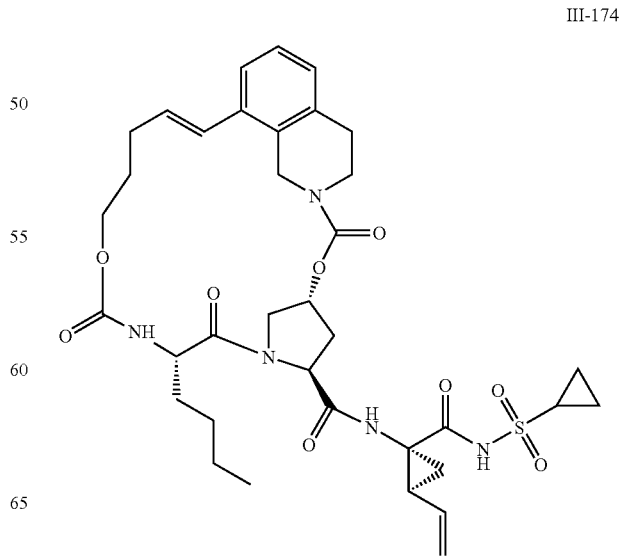

III-175
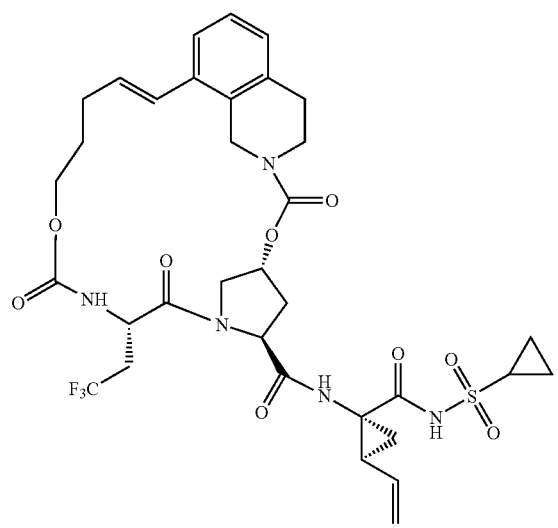
III-176
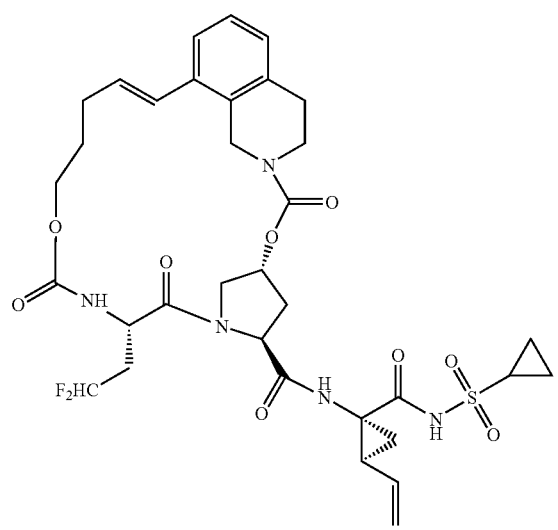
III-177
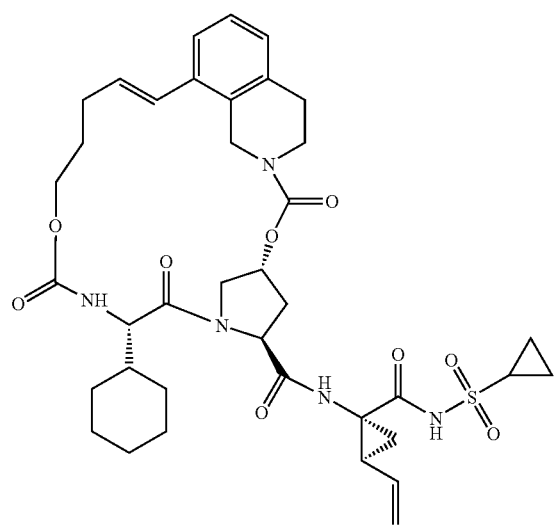
III-178
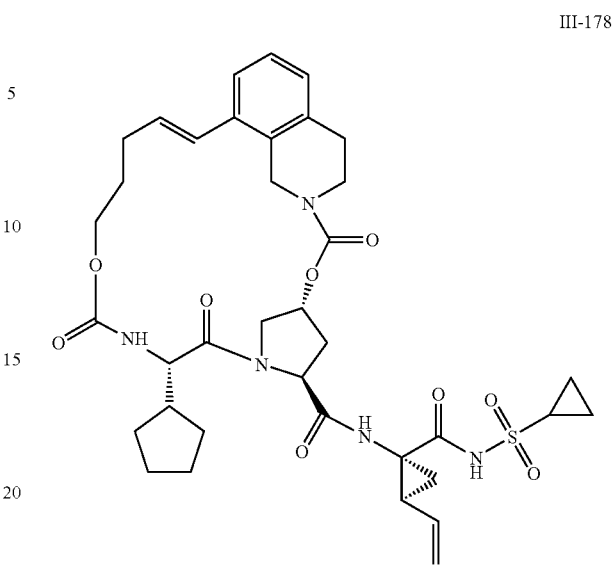
III-179
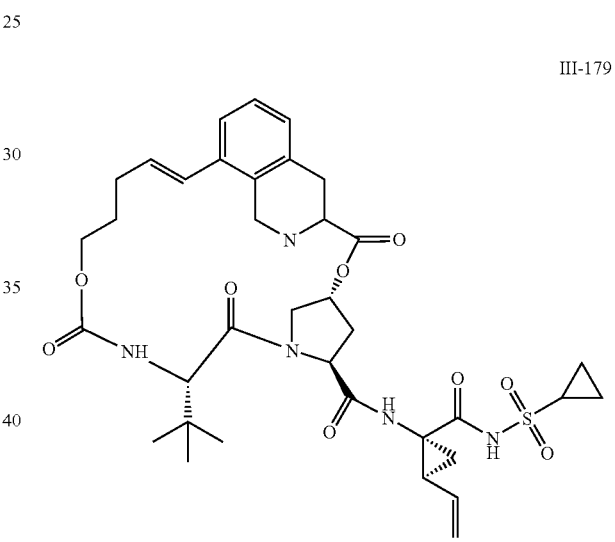
III-180
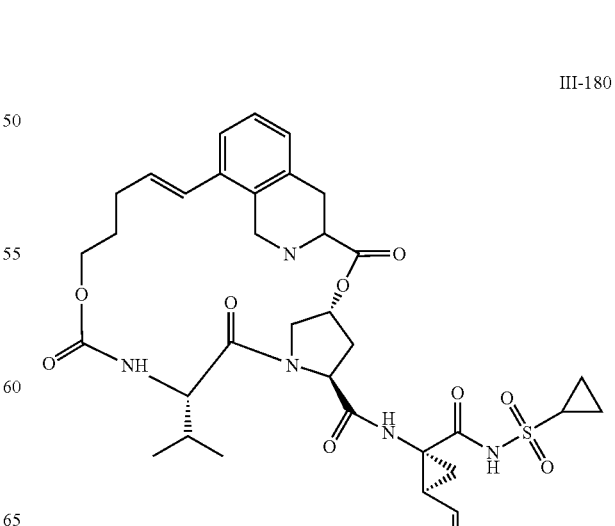

III-181
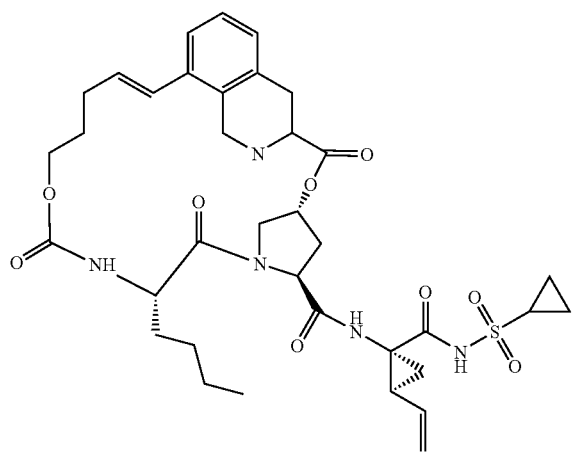
III-184
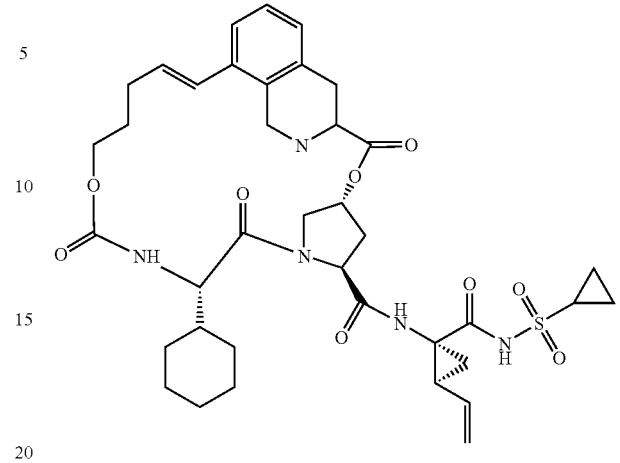
III-182
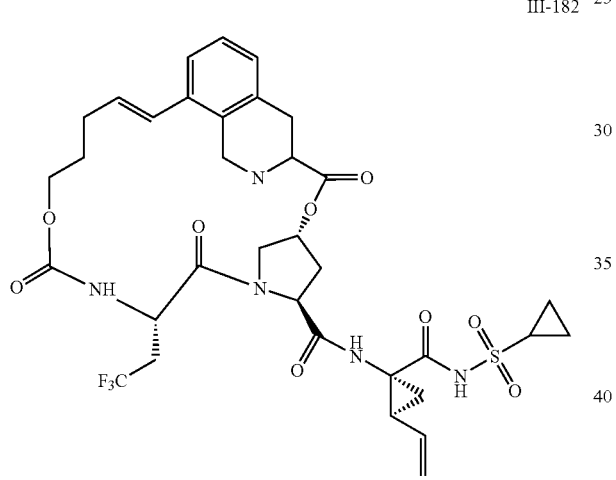
III-185
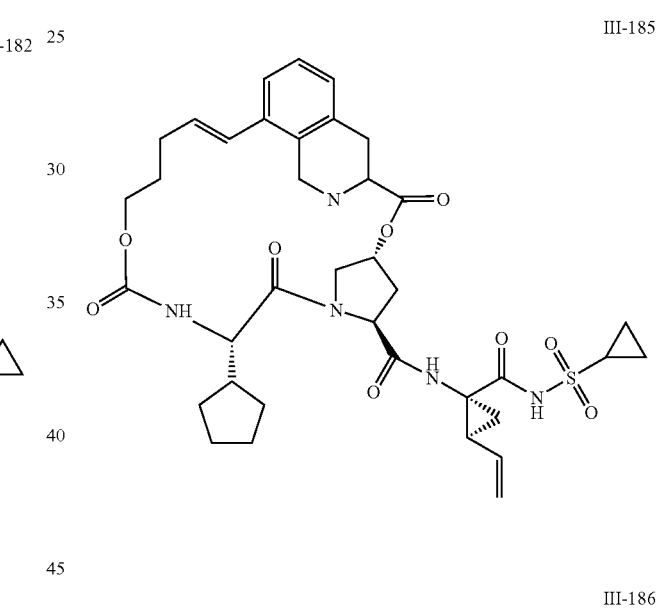
III-183
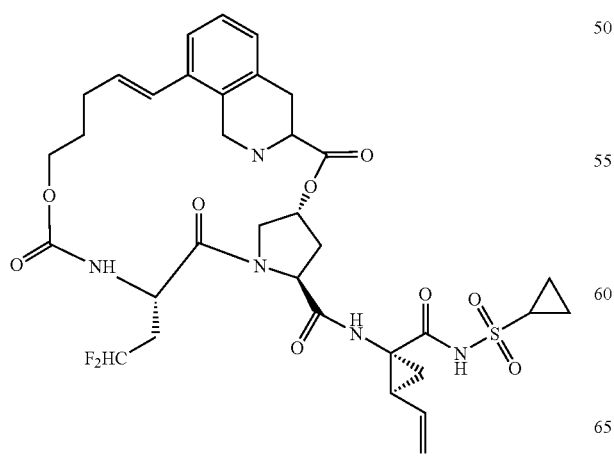
III-186
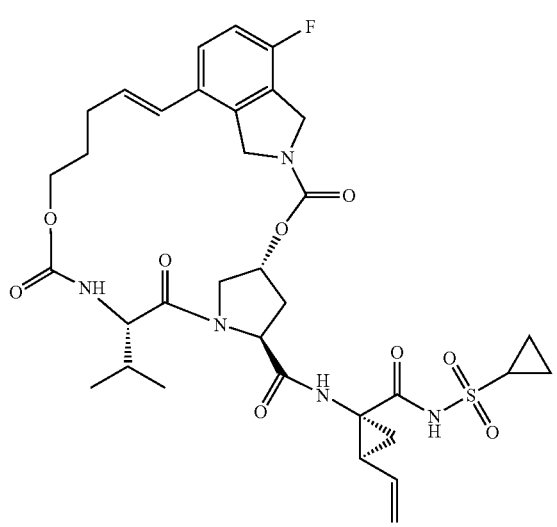

III-187
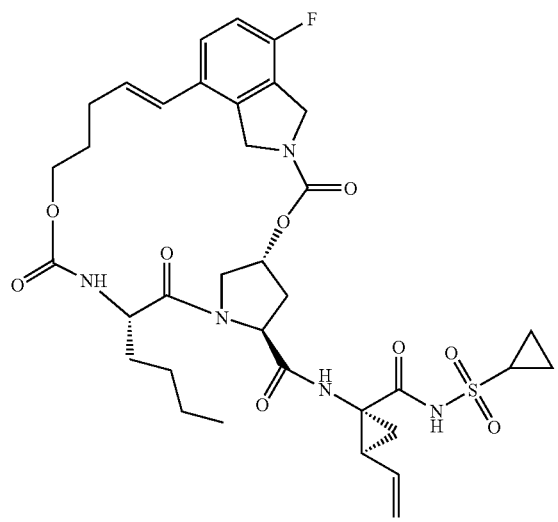
III-190
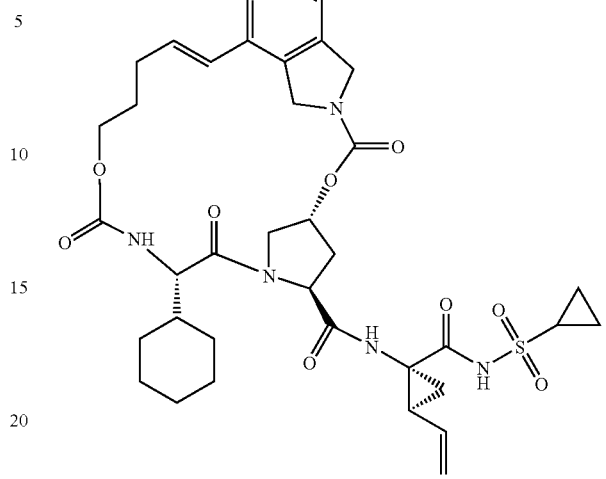
III-188
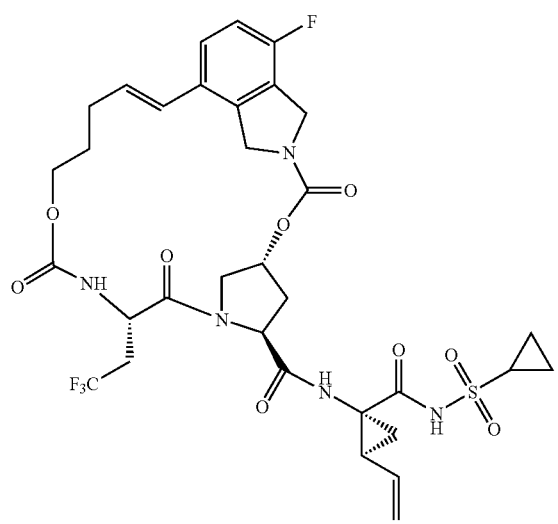
III-191
III-189
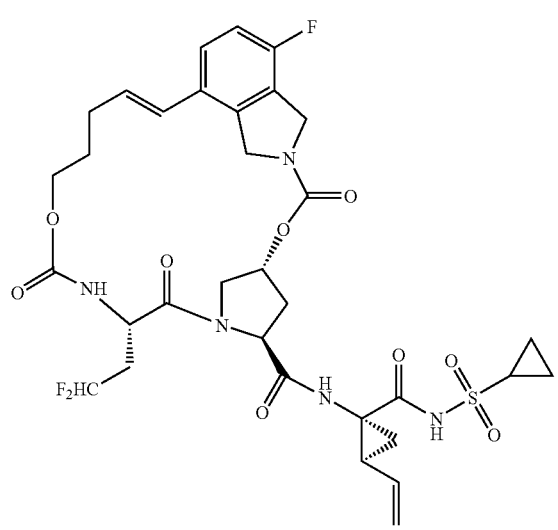
III-192

III-193
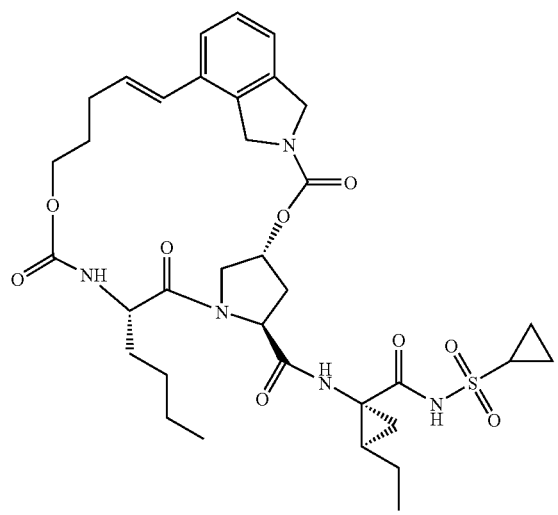
III-196
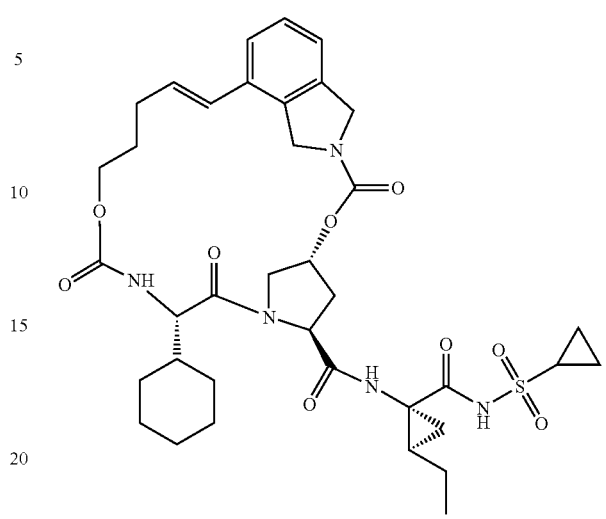
III-194
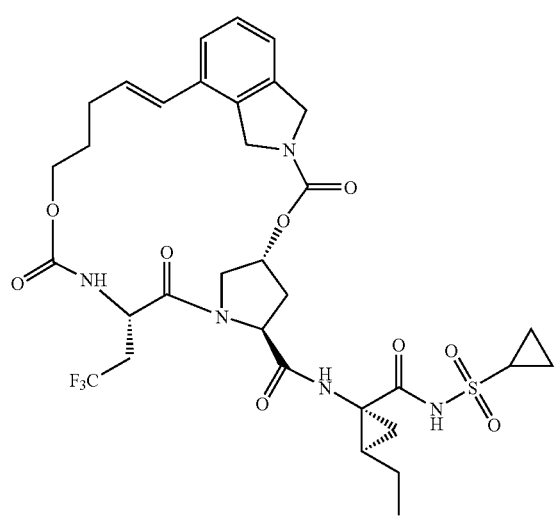
III-197
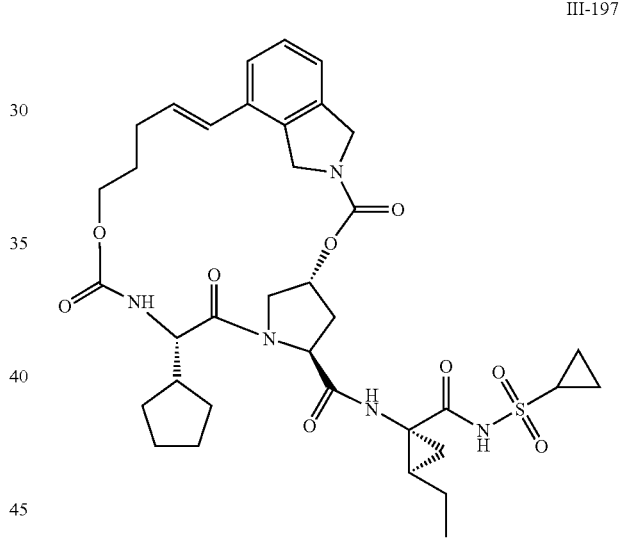
III-195
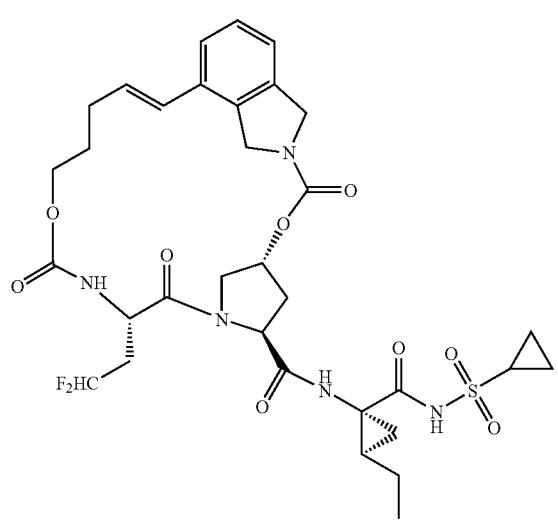
III-198
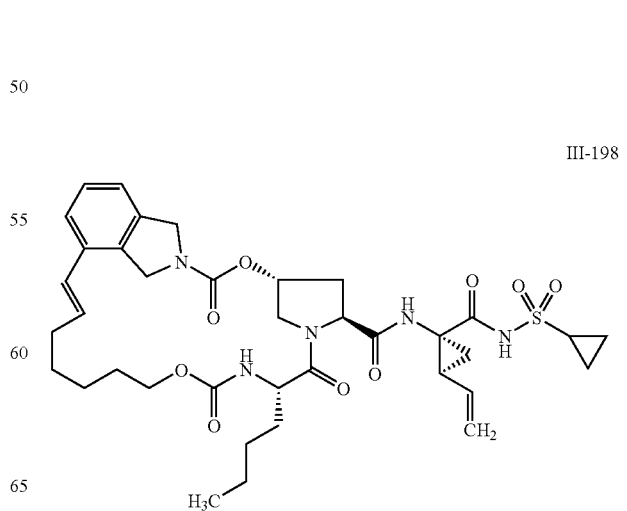

III-199
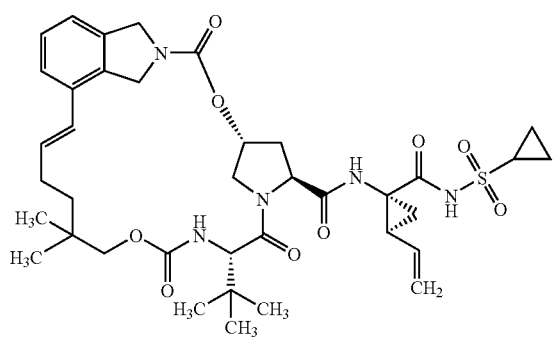
III-203
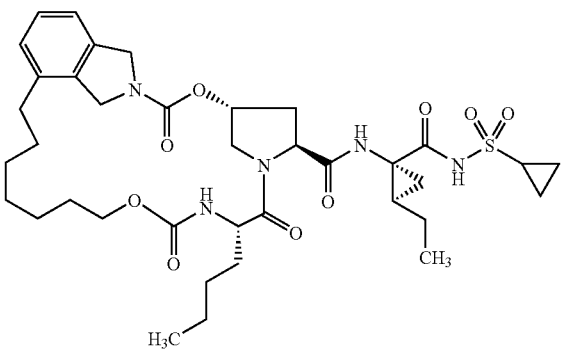
III-200
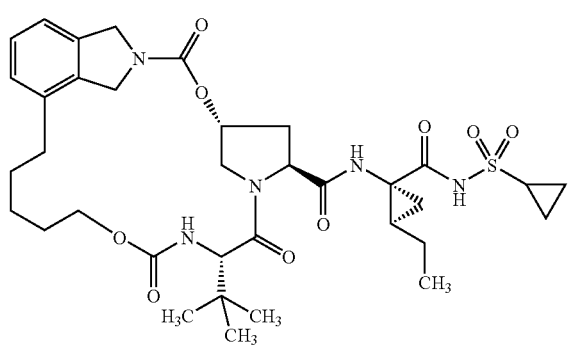
III-204
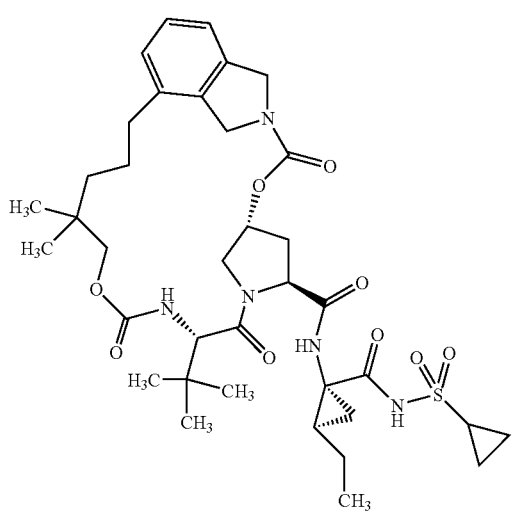
III-201
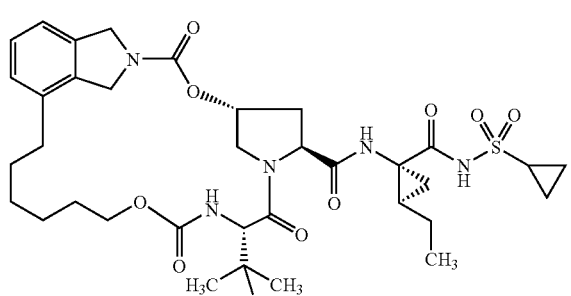
III-202
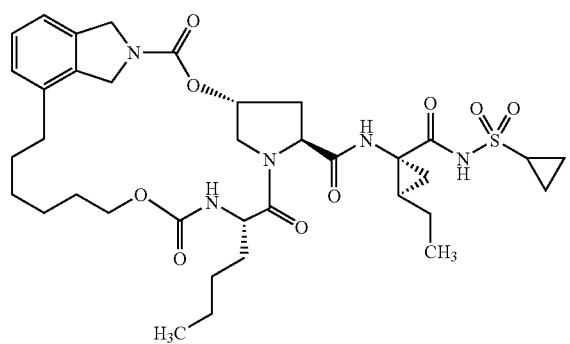
III-205

III-206
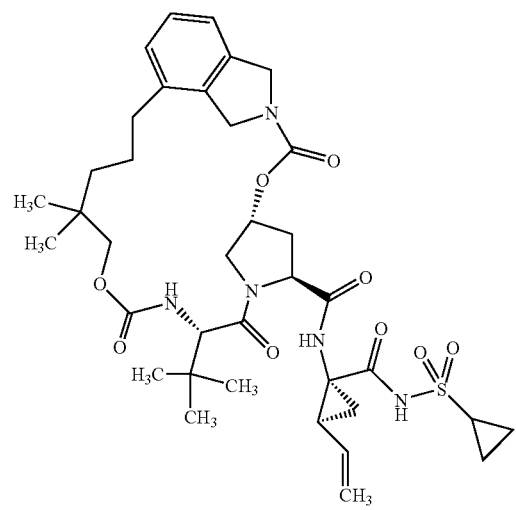
III-210
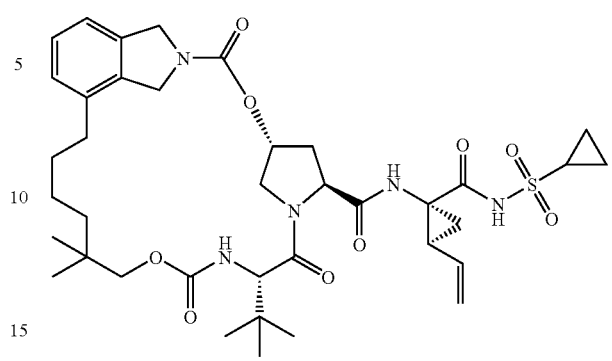
III-211
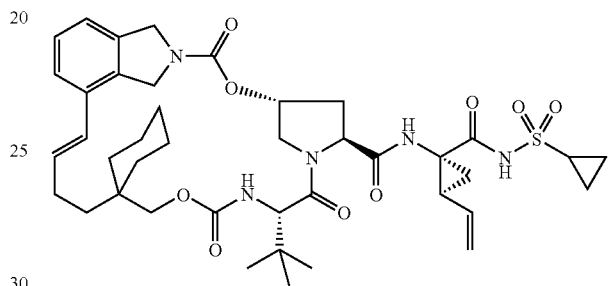
III-207
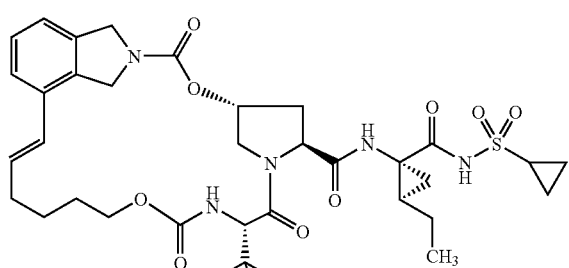
III-212
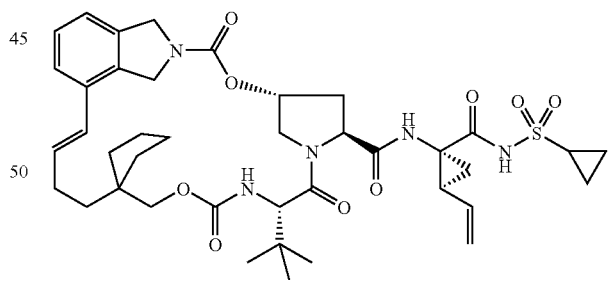
III-208
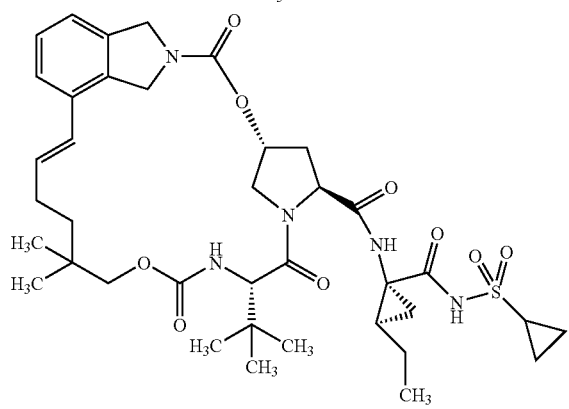
III-213
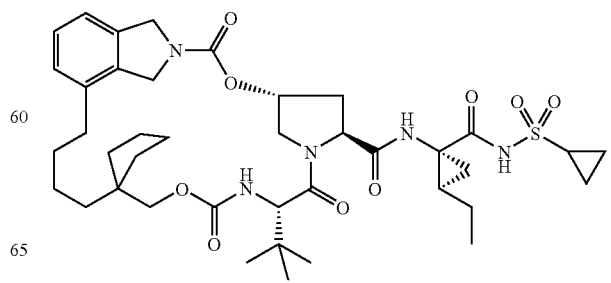
III-209
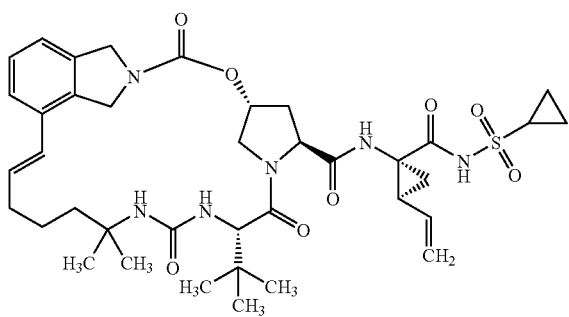
III-214

III-215
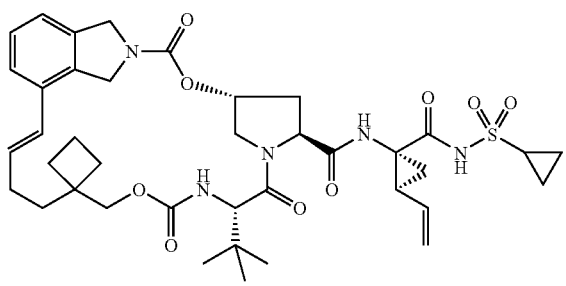
III-216
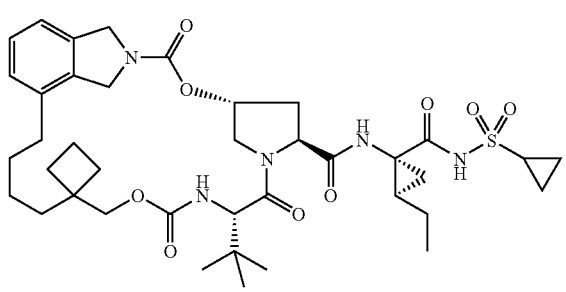
III-217
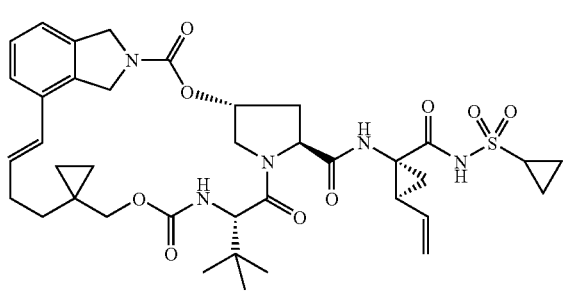
III-218
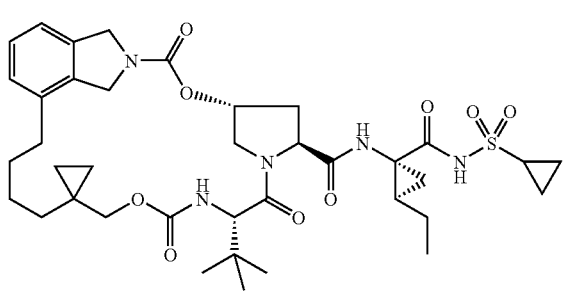
III-219
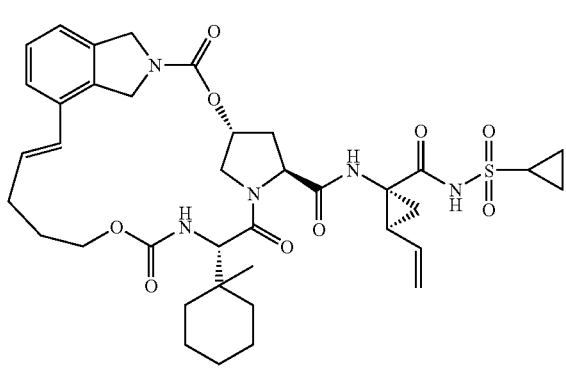
III-220
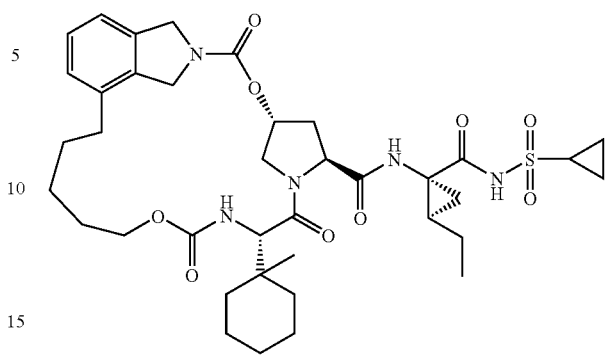
III-221
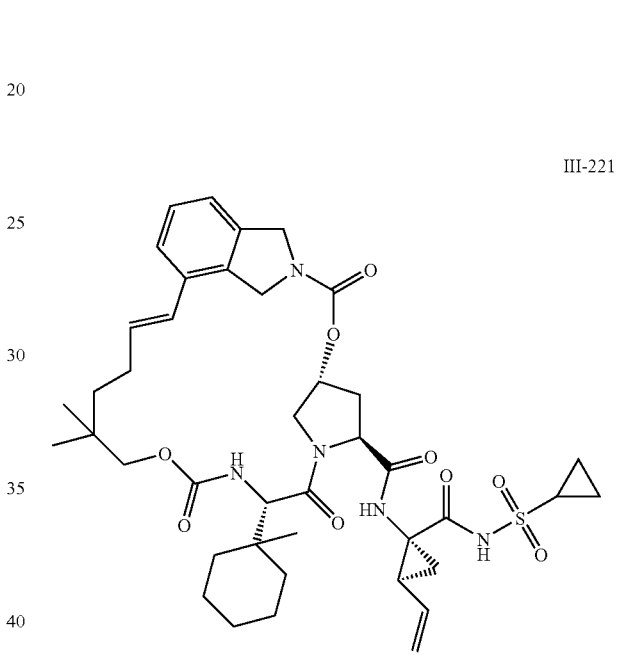
III-222
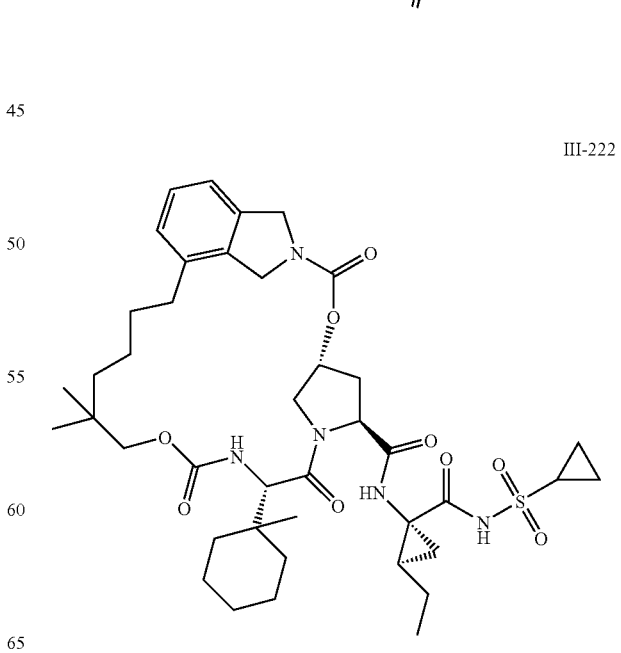

III-223
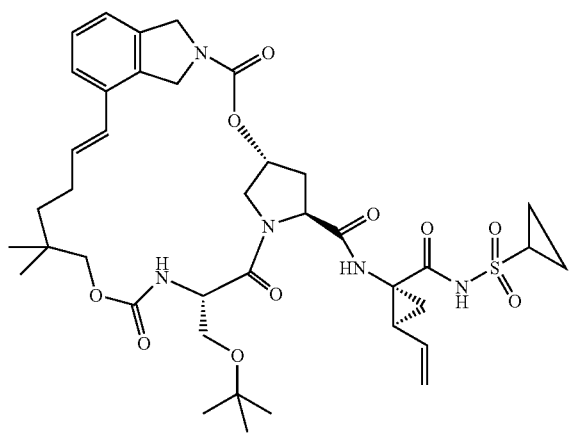
III-226
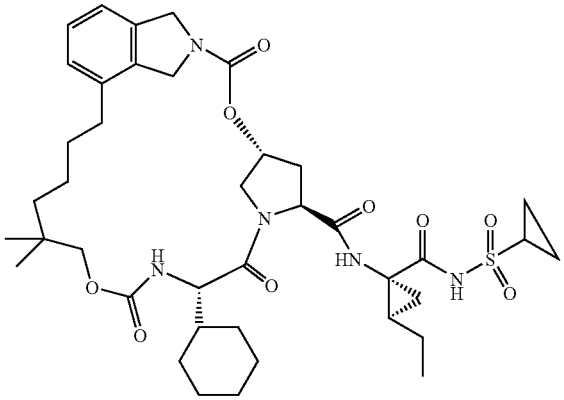
III-224
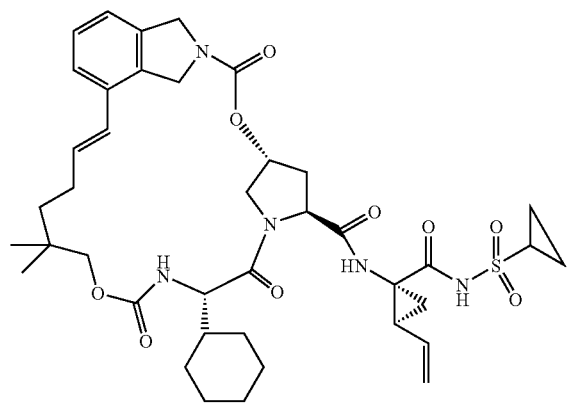
III-227
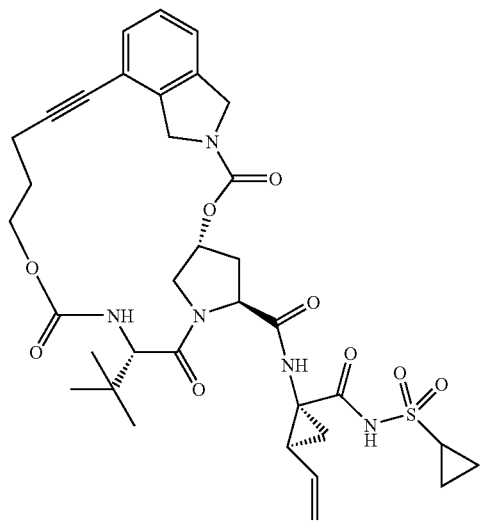
III-225
III-228
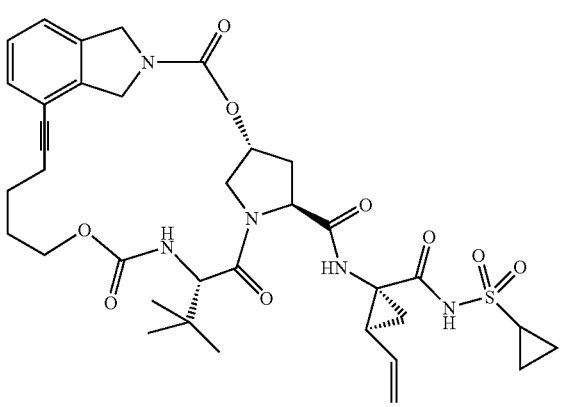

III-229
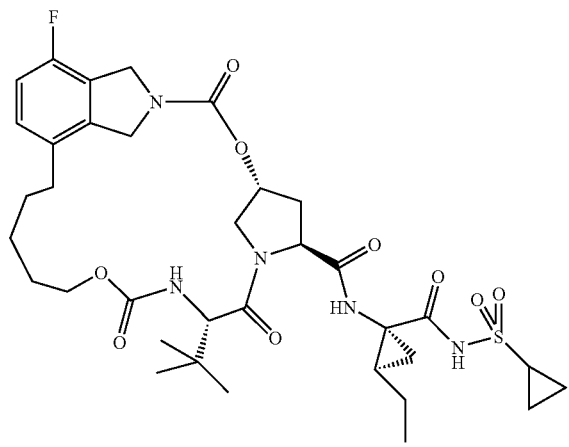
III-230
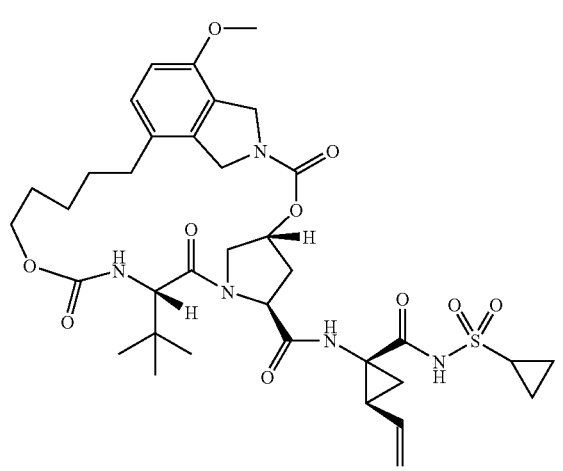
III-231
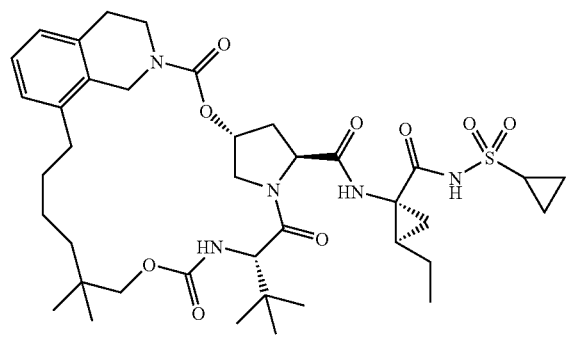
III-232
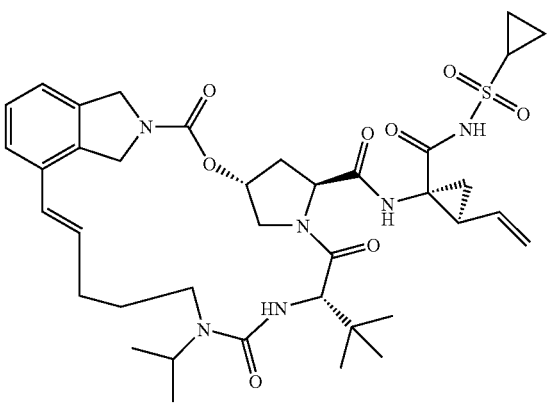
III-233
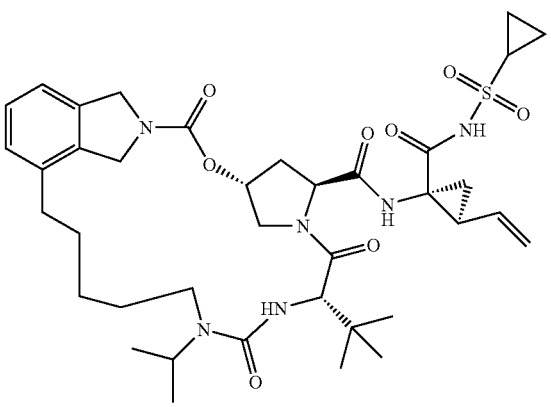
III-234
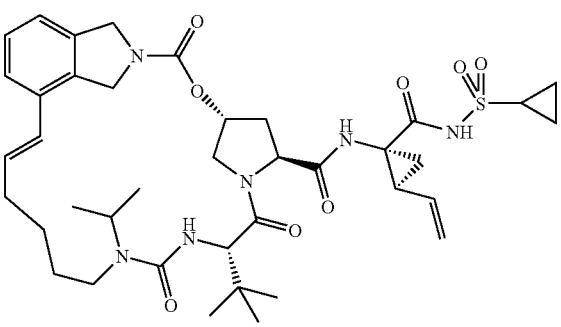
III-235
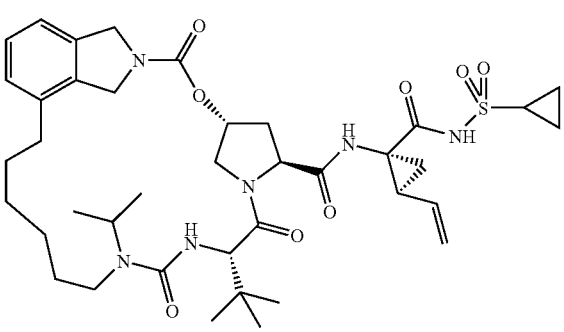

III-236
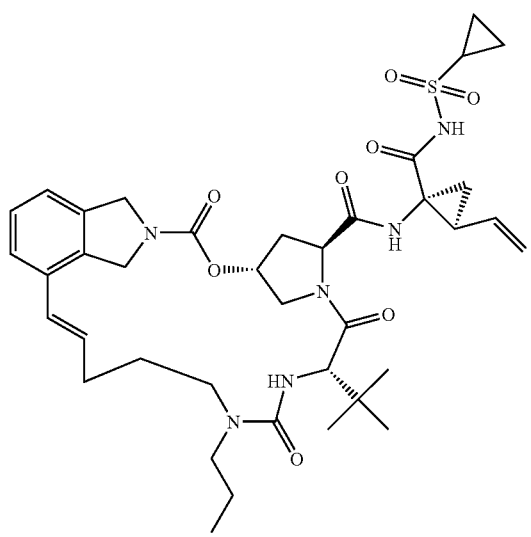

III-237
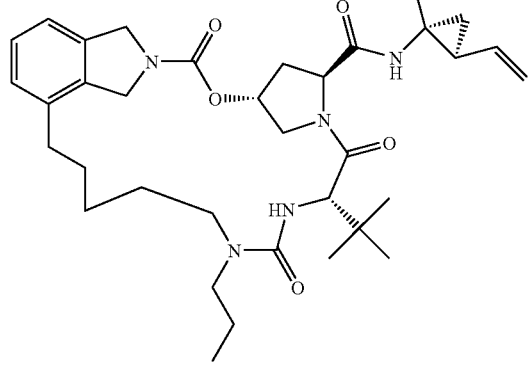

III-238
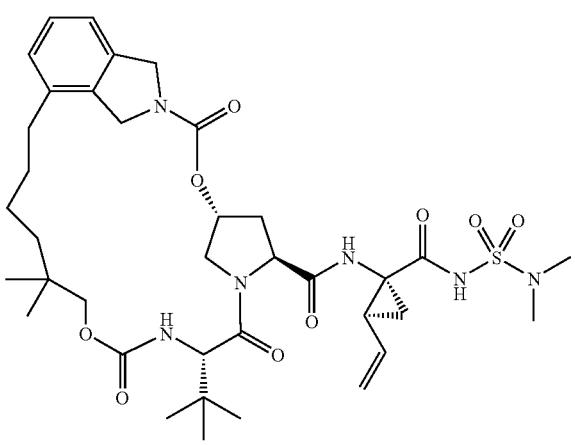

III-239
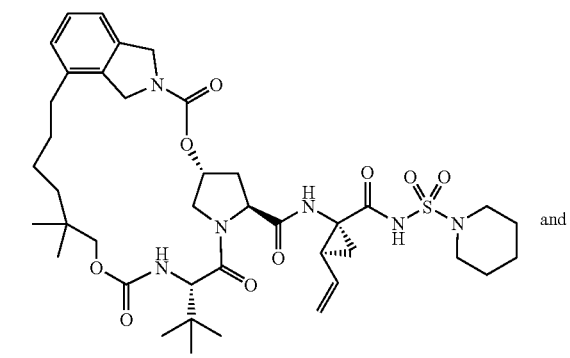

and

III-240
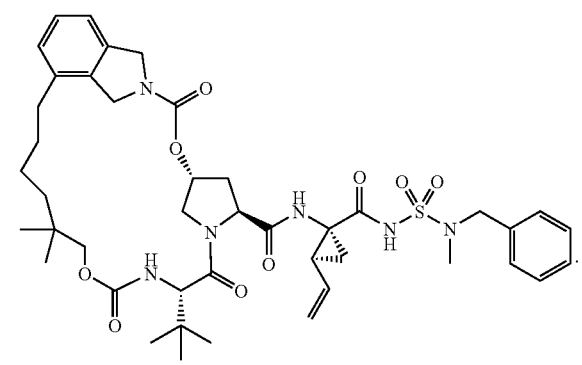

Other embodiments of the present invention include the following:

(a) A pharmaceutical composition comprising an effective amount of a compound of formula I, II, II-a, II-b, II-c, II-d, III, III-a, III-b, III-c, or III-d and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula I, II, II-a, II-b, II-c, II-d, III, III-a, III-b, III-c, or III-d and (ii) a second therapeutic agent selected from the group consisting of a HCV antiviral agent, an immunomodulator, and an anti-infective agent; wherein the compound of formula I, II, II-a, II-b, II-c, II-d, III, III-a, III-b, III-c, or III-d and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula I, II, II-a, II-b, II-c, II-d, III, III-a, III-b, III-c, or III-d.

(g) A method of preventing or treating infection by HCV in a subject in need thereof which comprises administering to the subject an effective amount of a compound of formula I, II, II-a, II-b, II-c, II-d, III, III-a, III-b, III-c, or III-d.

(h) The method of (g), wherein the compound of formula I, II, II-a, II-b, II-c, II-d, III, III-a, III-b, III-c, or III-d is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

The present invention also includes a compound of the present invention (i) for use in, (ii) for use as a medicament for, or (iii) for use in the preparation of a medicament for: (a) inhibiting HCV NS3 protease, or (b) preventing or treating infection by HCV. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group.

The term "halogen" (or "halo") refers to fluorine, chlorine, bromine and iodine (alternatively referred to as fluoro, chloro, bromo, and iodo).

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula I, II, II-a, II-b, II-c, II-d, III, III-a, III-b, III-c, or III-d or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I, II, II-a, II-b, II-c, II-d, III, III-a, III-b, III-c, or III-d is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences,* $18^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil (see A. C. Allison and E. M. Eugui, *Agents Action*, 44 (Suppl.): 165 (1993)).

For the treatment of HCV infection, the compounds of the present invention may also be administered in combination with the antiviral agent amantadine (1-aminoadamantane) (for a comprehensive description of this agent, see J. Kirschbaum, *Anal. Profiles Drug Subs.* 12: 1-36 (1983)).

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru et al., *J. Org. Chem.*, 62: 1754-1759 (1997); M. S. Wolfe et al., *Tetrahedron Lett.*, 36: 7611-7614 (1995); U.S. Pat. No. 3,480,613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, WO 02/48165 (20 Jun. 2002), and WO2005003147 (13 Jan. 2005)(including R1656, (2'R)-2'-deoxy-2'-fluoro-2'-C-methylcytidine, shown as compounds 3-6 on page 77) assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), US2005/0038240 (Feb. 17, 2005) and WO2006021341 (2 Mar. 2006), including 4'-azido nucleosides such as R1626, 4'-azidocytidine, assigned to Hoffmann-LaRoche; US 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003); US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004); the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methyl-cytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H- pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S.P.A.; WO 02/20497 (3 Mar. 2002); WO 2005/016927 (in particular JTK003), assigned to Japan Tobacco, Inc.; the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-α][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-α][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-α][2,5]benzodiazocine-1,1-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-α][2,5]benzodiazocine-11-carboxylic acid; 14-cyclohexyl-6-[2-(diethylamino)ethyl]-7-oxo-5,6,7,8-tetrahydroindolo[2,1-α][2,5]benzodiazocine-11-carboxylic acid; 14-cyclohexyl-6-(1-methylpiperidin-4-yl)-7-oxo-5,6,7,8-tetrahydroindolo[2,1-α][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-α][2,5]benzodiazocine-11-carboxamide; 14-cyclopentyl-6-[2-(dimethylamino)ethyl]-7-oxo-5,6,7,8-tetrahydroindolo[2,1-α][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-α][2,5]benzodiazocine-11-carboxylic acid; 14-cyclohexyl-6-[2-(dimethylamino)ethyl]-5,6,7,8-tetrahydroindolo[2,1-α][2,5]benzodiazocine-11-carboxylic acid; 13-cyclohexyl-5-methyl-4,5,6,7-tetrahydrofuro[3',2':6,7][1,4]diazocino[1,8-α]indole-10-carboxylic acid; 15-cyclohexyl-6-[2-(dimethylamino)ethyl]-7-oxo-6,7,8,9-tetrahydro-5H-indolo[2,1-α][2,6]benzodiazonine-12-carboxylic acid; 15-cyclohexyl-8-oxo-6,7,8,9-tetrahydro-5H-indolo[2,1-α][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The above tetracyclic indole-based HCV NS5B polymerase inhibitors may be obtained following methods A-E as outlined below, wherein different variables may be selected in accordance with the specific tetracyclic indole compound to be prepared:

Method A:

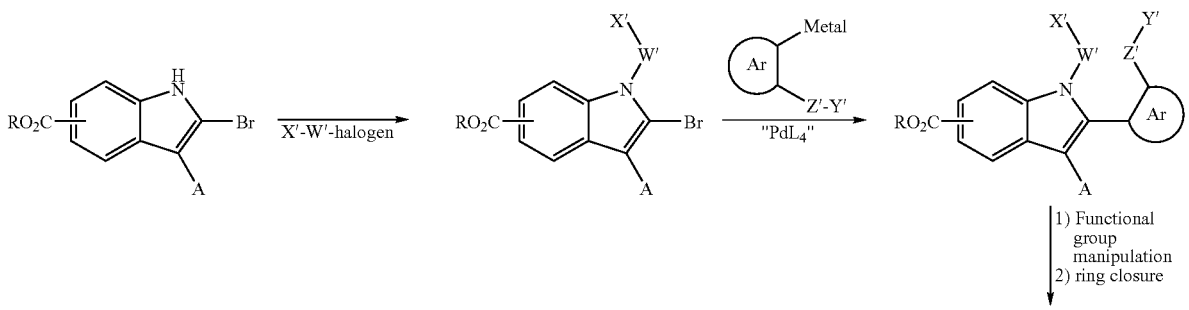

-continued

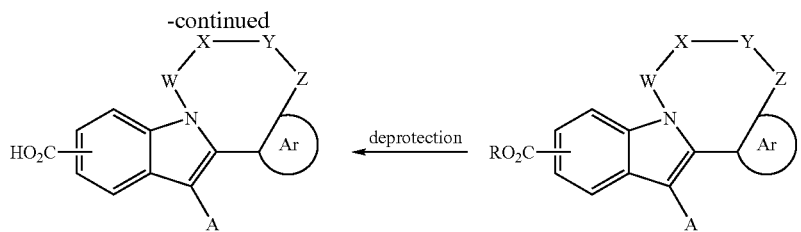

2-Bromoindole intermediate (prepared as described in International Patent Application Publication WO 2004/087714) was functionalized on the indole nitrogen to introduce pre-cursor functionality W'/X' to either or both of the elements W/X of the tether. Pd-mediated cross-coupling methodology (e.g., Suzuki, Stille etc.) then brought in the C2 aromatic bearing pre-cursor functionality Z'/Y' to either or both of the elements Z/Y of the tether. Functional group manipulation followed by ring closure afforded the tetracyclic system. Ester deprotection then yielded the target indole carboxylic acids, with the C2 aromatic tethered to the indole nitrogen.

Method B:

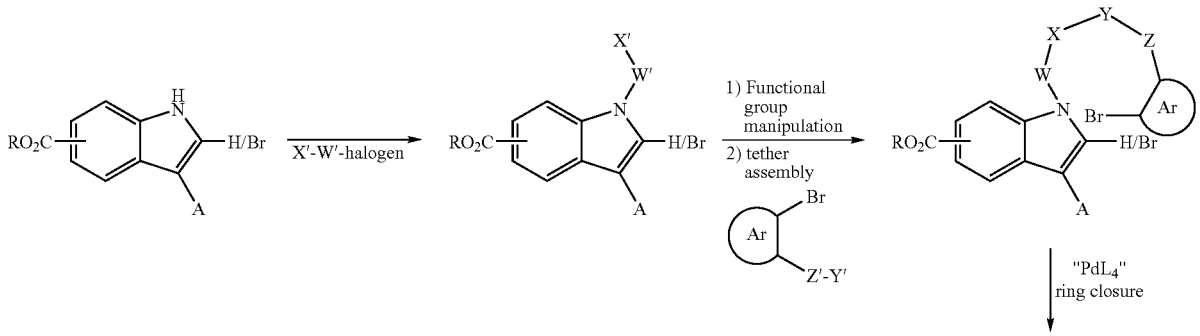

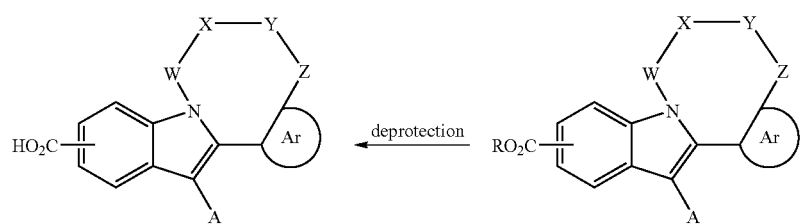

Following tether assembly out to the appropriate 2-haloaromatic, Pd-mediated ring closure afforded the fused tetracyclic system. Ester deprotection then yielded the target indole carboxylic acids, with the C2 aromatic tethered to the indole nitrogen.

Method C:

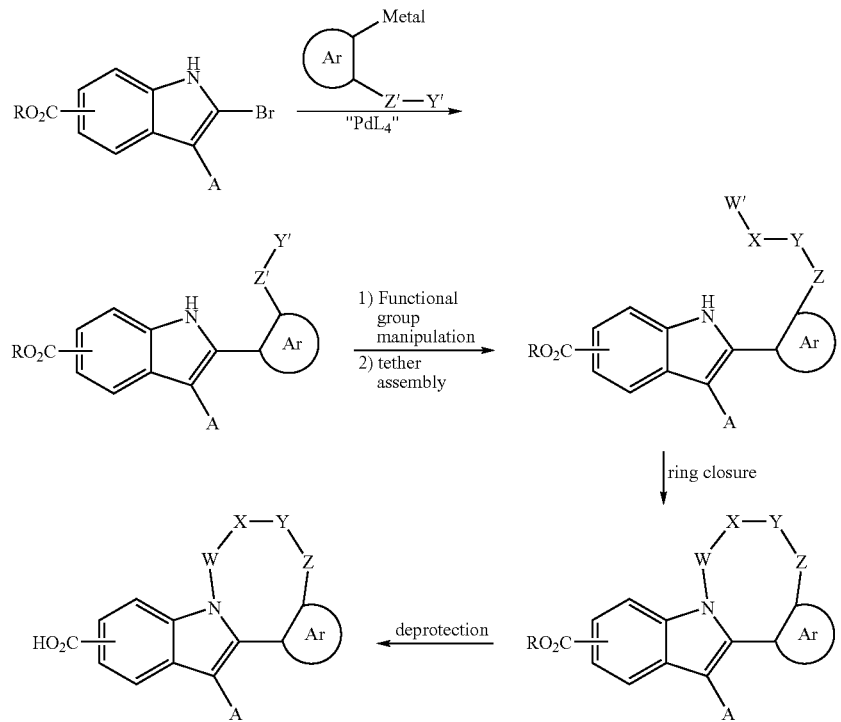

The C2 aromatic was introduced at the outset via Pd-mediated cross-coupling methodology (Suzuki, Stille etc). The tether was then built up, with cyclisation onto the indole nitrogen finally closing the ring. Ester deprotection then yielded the target indole carboxylic acids, with the C2 aromatic tethered to the indole nitrogen.

Method D:

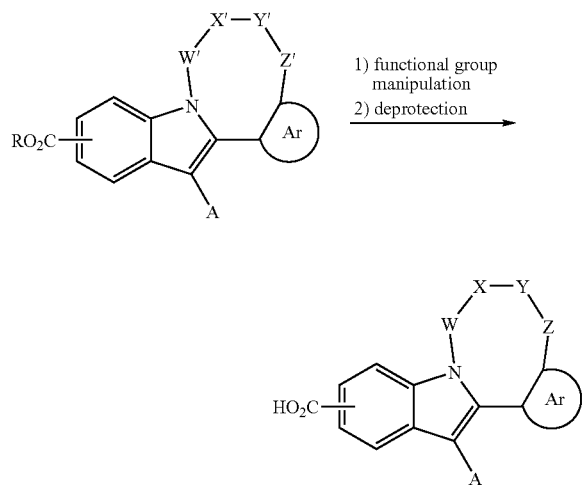

Fused tetracyclic intermediates arising from Methods A-C underwent manipulation of the functionality in the tether prior to ester deprotection to yield the target C2-tethered indole carboxylic acids.

Method E:

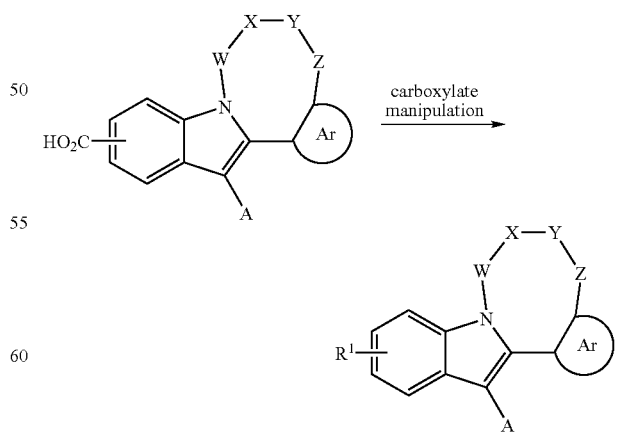

C2-tethered indole carboxylic acids arising from Methods A-D were further derivatised through manipulation of the carboxylate functionality to give compounds bearing a carboxylate replacement or carboxamide. During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The HCV NS3 protease inhibitory activity of the present compounds may be tested using assays known in the art. One such assay is HCV NS3 protease time-resolved fluorescence (TRF) assay as described in Example 56. Other examples of such assays are described in e.g., International Patent Application Publication WO 2005/046712. Compounds useful as HCV NS3 protease inhibitors would have a Ki less than 50 μM, more preferably less than 10 μM, and even more preferably less than 100 nM.

The present invention also includes processes for making compounds of formula I, II, II-a, I-b, II-c, II-d, III, III-a, II-b, III-c, or III-d. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

General Description of Synthesis:

The compounds of the present invention may be synthesized as outlined in the general Schemes 1 and 2.

SCHEME 1:

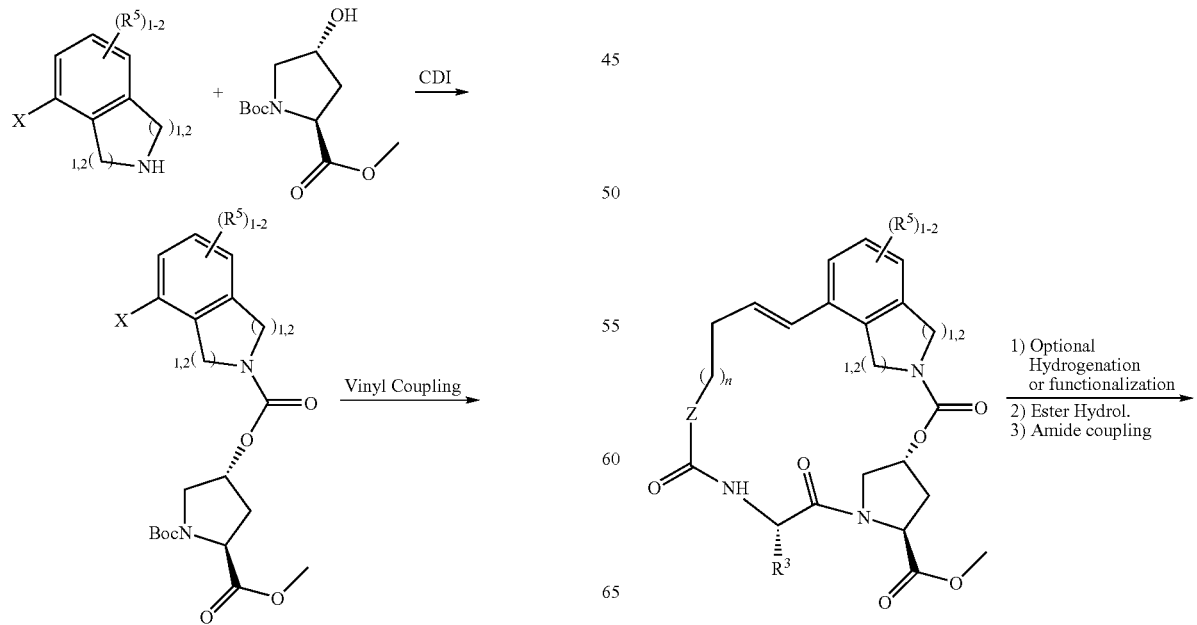

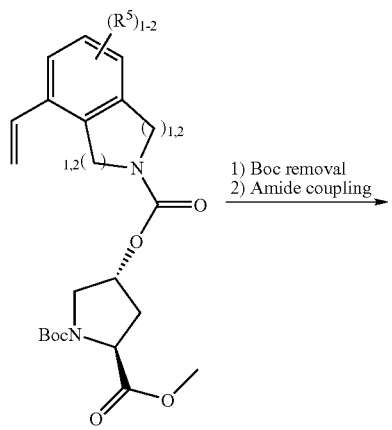

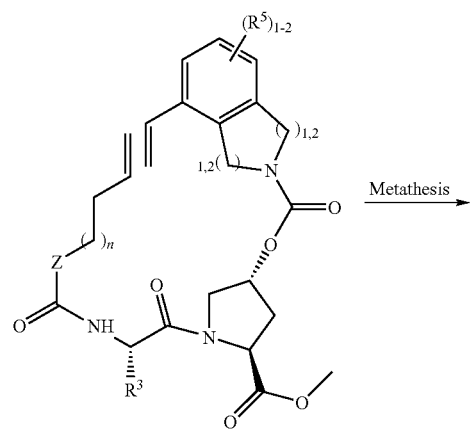

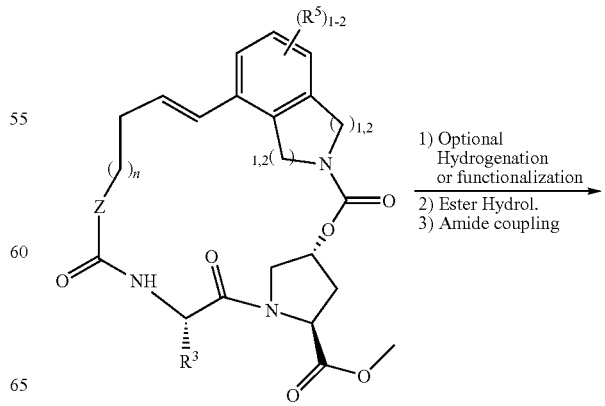

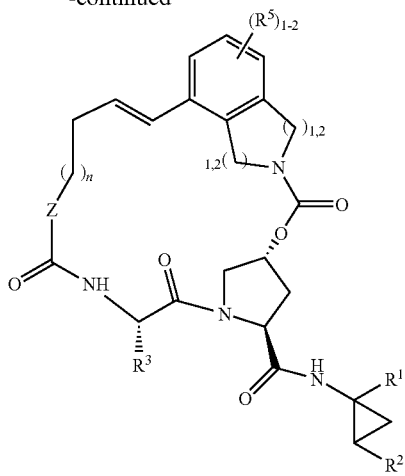

Scheme 1 (n=0-9) outlines the synthesis of a representative molecule. An appropriately protected 4-hydroxyproline derivative (for example, a carbamate protected nitrogen and an ester protected acid can be reacted with carbonyldiimidazole or equivalent reagent and then reacted with an appropriately substituted isoindoline or tetrahydroisoquinoline. The alkenyl functionality may be introduced at this or a later stage by palladium catalyzed reaction of a halide substituent such as chloride, bromide and iodide, or other functionality such as a triflate with an organometallic reagent such as a vinyl or allyltrialkyltin. Alternatively, the alkenyl functionality may be introduced prior to the reaction with protected prolinol.

Scheme 2 describes the synthesis of the olefin containing amino acid portion. An amino acid (either commercially available or may be prepared readily using known methods in the art) in which the acid functionality is protected as an ester (for example, R=methyl) can be converted to amides A by coupling an olefinic carboxylic acid utilizing a wide range of peptide coupling agents known to those skilled in the art such as DCC, EDC, BOP, TBTU, etc. Preparation of the Sulfonamides B can be Accomplished by Reaction with the Appropriate Sulfonyl chloride in an organic solvent (e.g., THF) with an amine base as scavenger. Urea derivatives C may be prepared by reacting the aminoester with a reagent such as carbonyldiimidazole, to form an intermediate isocyanate (Catalano et al., WO 03/062192) followed by addition of a second olefin containing amine. Alternatively, phosgene, diphosgene or triphosgene may be used in place of carbonyldiimidazole. Cyanoguanidine derivatives D can be prepared by reaction of the amino acid ester with diphenyl C-cyanocarbonimidate in an organic solvent, followed by addition of a second olefin containing amine. Carbamate derivatives E may be prepared by reacting an olefin containing alcohol with carbonyldiimidazole (or phosgene, triphosgene or diphosgene) in an organic solvent, followed by addition of the amino ester.

SCHEME 2:

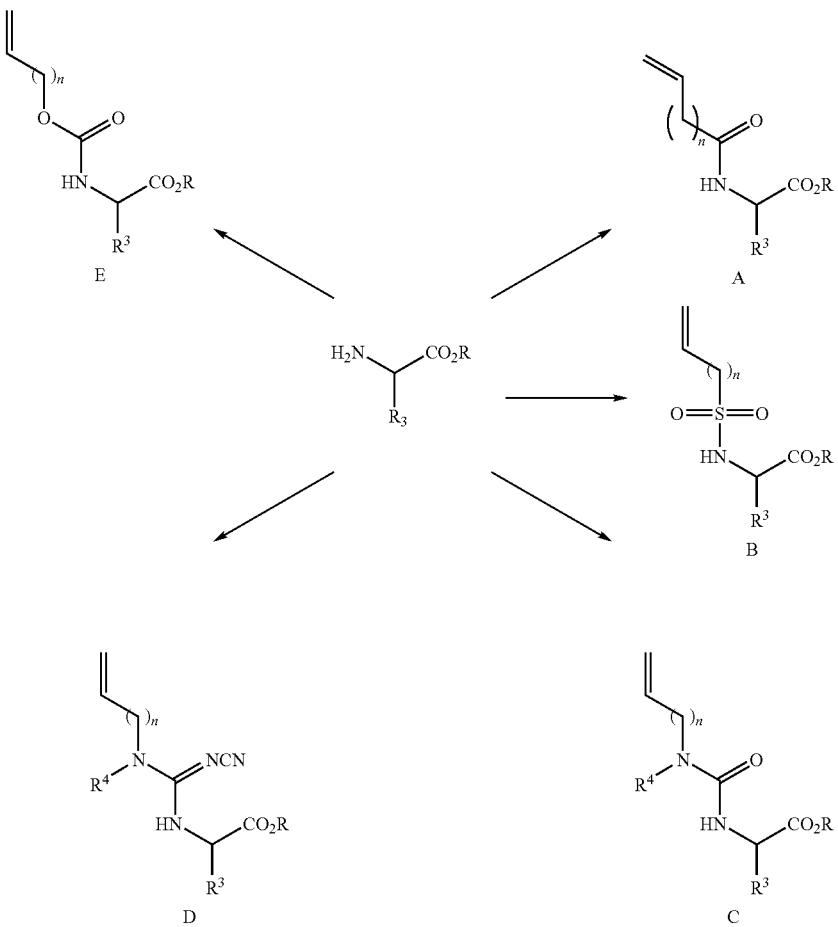

Following functionalization of the amine, the ester can be hydrolyzed under a range of basic conditions known to those skilled in the art (Theodora W. Greene, Protective Groups in Organic Synthesis, Third Edition, John Wiley and Sons, 1999).

Deprotection of the carbamate protecting group on the proline portion may be carried out by a variety of methods known to persons skilled in the art (Theodora W. Greene, Protective Groups in Organic Synthesis, Third Edition, John Wiley and Sons, 1999).

To complete the synthesis of the compounds of this invention, the amino acid derivative can be coupled to the proline derivative via a wide range of peptide coupling reagents such as DCC, EDC, BOP, TBTU etc (see Scheme 1). Macrocyclization is then achieved by an olefin metathesis using a range of catalysts that have been described in the literature for this purpose. At this stage the olefinic bond produced in the ring closing metathesis may be optionally hydrogenated to give a saturated linkage or functionalized in alternative ways such as cyclopropanation. The proline ester is then hydrolyzed under basic conditions and coupled with the cyclopropylamino acid ester (the appropriate alkenyl or alkylcyclopropane portion of the molecule can be prepared as described previously (Llinas-Brunet et al., U.S. Pat. No. 6,323,180) and subjected to an additional basic hydrolysis step to provide the final compounds. The proline ester can also be hydrolyzed and directly coupled to an appropriately functionalized cyclopropylamino acid acyl sulfonamide (which can be prepared according to Wang X. A. et al. WO 2003/099274) to provide the final compounds.

Olefin metathesis catalysts include the following Ruthenium based species: F: Miller et al., *J. Am. Chem. Soc* 1996, 118, 9606; G: Kingsbury et al., *J. Am. Chem. Soc* 1999, 121, 791; H: Scholl et al., Org. Lett. 1999, 1, 953; Hoveyda et al., US 2002/0107138; K: Furstner et al., J. Org. Chem. 1999, 64, 8275. The utility of these catalysts in ring closing metathesis is well known in the literature (e.g. Trnka and Grubbs, *Acc. Chem. Res.* 2001, 34, 18).

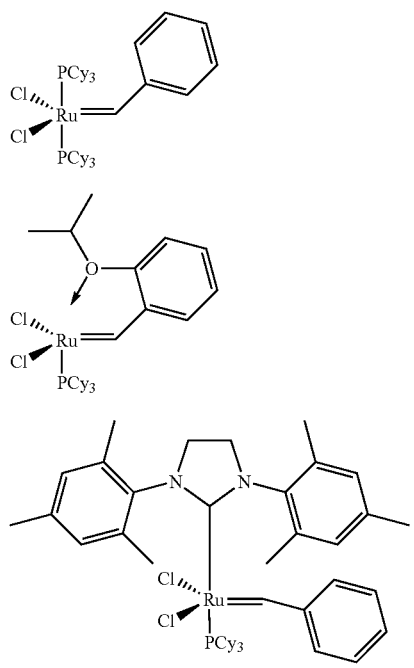

F

G

H

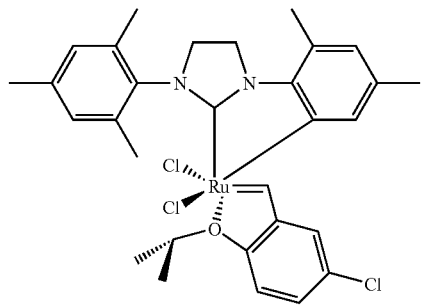

J

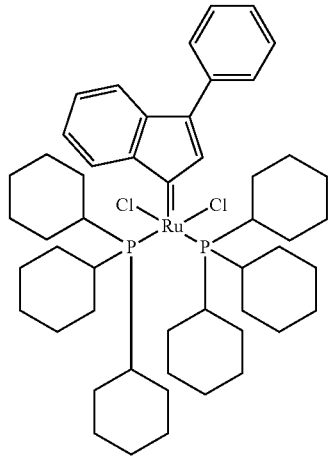

K

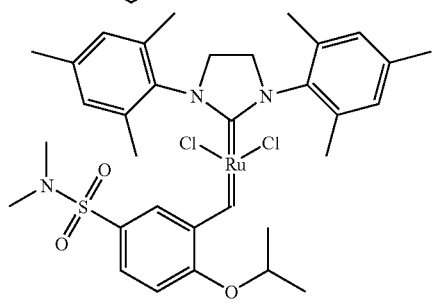

Zhan ruthenium metathesis catalyst RC-303
(Zhan catalyst 1B, RC-303, Zannan Pharma Ltd.)

List of Abbreviations

BOP Benzotriazole-1-yl-oxy-tris-(dimethylamino)-phosphonium hexafluorophosphate
$CH_3CN$ Acetonitrile
DBU 1,8-Diazabicyclo[5.4.0]undec-7-ene
DCC Dicyclohexylcarbodiimide
DCE Dichloroethane
DCM Dichloromethane
DIPEA Diisoproylethylamine
DMAP 4-Dimethylamino pyridine
DMF Dimethylformamide
DMSO Dimethyl sulfoxide
EDC N-(3-Dimethylaminopropyl)-N'-ethylcarbodiimide
$Et_3N$ Triethylamine
$Et_2O$ Diethyl ether
EtOAc Ethyl acetate
EtOH Ethanol
HATU O-(7-Azabenzotriazol-1-yl)-N,N,N',N'-tetramethyluronium hexafluorophosphate HBr Hydrobromic acid
HCl Hydrochloric acid
HOAc Acetic acid
HOAt 1-Hydroxy-7-azabenzotriazole
LiOH Lithium hydroxide
MeOH Methanol
MgSO$_4$ Magnesium Sulfate
MTBE methyl t-butyl ether
Na$_2$SO$_4$ Sodium sulfate
NaHCO$_3$ Sodium bicarbonate
NaOH Sodium hydroxide
NH$_4$Cl Ammonium chloride
NH$_4$OH Ammonium hydroxide
Pd/C Palladium on carbon
Pd(PPh$_3$)$_4$ tetrakis(triphenylphosphine)palladium (0)
PhMe Toluene
PPh$_3$ Triphenylphosphine
RT room temperature
TBTU O-Benzotriazol-1-yl-N,N,N',N'-tetramethyluronium tetrafluoroborate
THF Tetrahydrofuran

EXAMPLE 1

(5R,7S,10S)-10-Butyl-N-((1R,2S)-1-{[(cyclopropyl-sulfonyl)amino]carbonyl}-2-vinylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide (III-1)

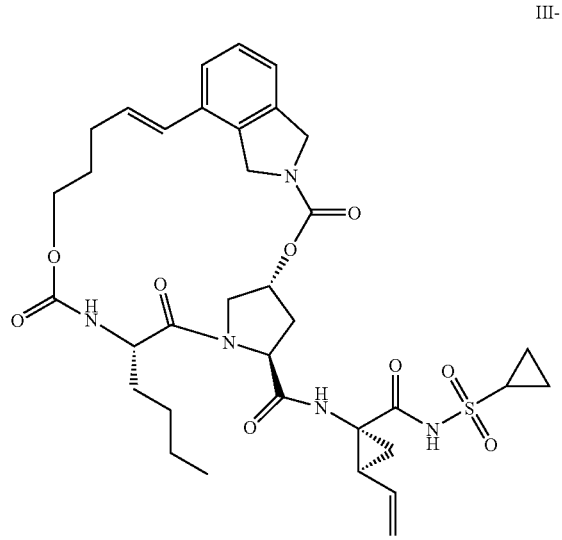

Step 1: 4-Chloroisoindoline

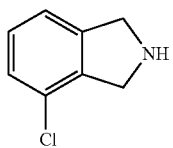

A mixture of 3-chlorophthalic acid anhydride (9 g, 49.2 mmol) and formamide (100 mL) was heated to 125° C. and stirred for 3 h. Water (300 mL) was then added and the mixture was cooled to room temperature. The mixture was filtered and the resulting white solid was washed with water and dried to give 4-chloro-1H-isoindole-1,3(2H)-dione (7.7 g, 86% yield).

To solid 4-chloro-1H-isoindole-1,3(2H)-dione (4.0 g, 22.0 mmol) was added borane-THF complex (1 M/THF, 88.1 mL, 88.1 mmol) dropwise with stirring. When the addition was complete, the reaction mixture was heated to reflux (80° C.) and stirred for 6 h. The reaction mixture was then cooled to 0° C., methanol (2.8 mL, 88.1 mmol) was carefully added dropwise and the reaction mixture was warmed to room temperature. HCl (6 N) was added until the mixture was acidic and then the mixture was concentrated. The crude product was dissolved in 1 M HCl and extracted twice with ethyl ether and twice with dichloromethane. The pH of the aqueous layer was adjusted to pH=11 with solid NaOH and extracted three times with ethyl acetate. The combined ethyl acetate extracts were dried over Na$_2$SO$_4$, filtered and concentrated to give 4-chloroisoindoline (1.8 g, 53% yield). LRMS (ESI) m/z 154 [(M+H)$^+$; calcd for C$_8$H$_9$ClN: 154].

Step 2: 1-tert-Butyl 2-methyl (2S,4R)-4-{[(4-chloro-1,3-dihydro-2H-isoindol-2-yl)carbonyl]oxy}pyrrolidine-1,2-dicarboxylate

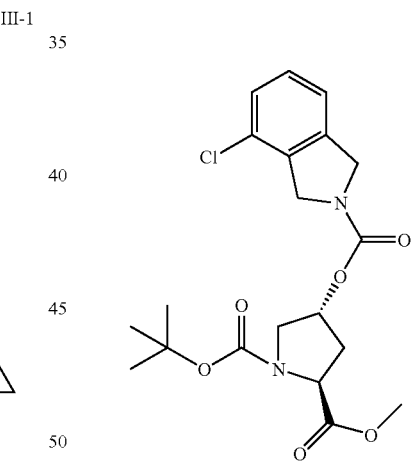

To a solution of N-Boc proline methyl ester (2.87 g, 11.7 mmol) in DMF (15 mL) at 0° C. was added carbonyldiimidazole (1.9 g, 11.7 mmol). The reaction was warmed to room temperature and stirred for 30 min. A solution of 4-chloroisoindoline (1.8 g, 11.7 mmol) in DMF (10 mL) was then added and the reaction mixture was heated to 50° C. and stirred for 2 h. The reaction mixture was poured onto ethyl ether and 0.5 M HCl and the layers were separated. The organic layer was washed with water, dried over Na$_2$SO$_4$, filtered and concentrated. The crude product was purified on silica gel (gradient elution 10% to 90% ethyl acetate in hexanes) to give 1-tert-butyl 2-methyl (2S,4R)-4-{[(4-chloro-1,3-dihydro-2H-isoindol-2-yl)carbonyl]oxy}pyrrolidine-1,2- dicarboxylate (3.3 g, 66% yield). LRMS (ESI) m/z 325 [(M+H-Boc)$^+$; calcd for $C_{15}H_{18}ClN_2O_4$: 325].

Step 3: 1-tert-Butyl 2-methyl (2S,4R)-4-{[(4-vinyl-1,3-dihydro-2H-isoindol-2-yl)carbonyl]oxy}pyrrolidine-1,2-dicarboxylate

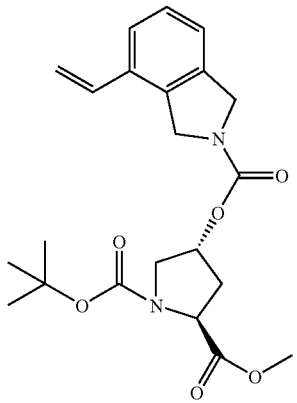

A solution of 1-tert-butyl 2-methyl (2S,4R)-4-{[(4-vinyl-1,3-dihydro-2H-isoindol-2-yl)carbonyl]oxy}pyrrolidine-1,2-dicarboxylate (40 mg, 0.09 mmol), vinyl tributylstannane (36 mg, 0.11 mmol) and cesium fluoride (31 mg, 0.21 mmol) in dioxane (0.5 mL) was degassed with $N_2$ for 15 min. Bis(tributylphospine)palladium(0) (2 mg, 0.005 mmol) was then added and the reaction vessel was sealed and heated to 100° C. for 18 h. After cooling, the reaction mixture was concentrated and purified by silica gel chromatography (10% to 90% ethyl acetate in hexanes) to give 1-tert-butyl 2-methyl (2S,4R)-4-{[(4-vinyl-1,3-dihydro-2H-isoindol-2-yl)carbonyl]oxy}pyrrolidine-1,2-dicarboxylate (10 mg, 25% yield). LRMS (ESI) m/z 317 [(M+H-Boc)$^+$; calcd for $C_{17}H_{21}N_2O_4$: 317].

Step 4: Methyl N-[(pent-4-enyloxy)carbonyl]-L-norleucyl-(4R)-4-{[(4-vinyl-1,3-dihydro-2H-isoindol-2-yl)carbonyl]oxy}L-prolinate

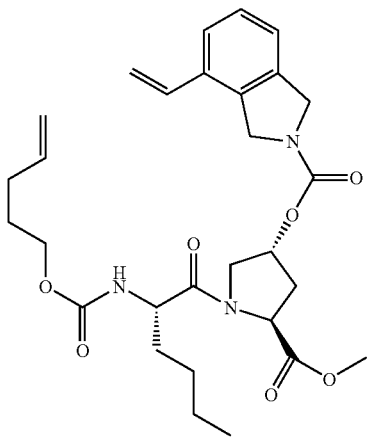

To a flask containing 1-tert-butyl 2-methyl (2S,4R)-4-{[(4-vinyl-1,3-dihydro-2H-isoindol-2-yl)carbonyl]oxy}pyrrolidine-1,2-dicarboxylate (60 mg, 0.14 mmol) was added a 4 M solution of HCl in dioxane (2 mL). After 1 h, LC-MS analysis indicated complete consumption of the starting material and formation of the desired Boc product. The volatile components were then removed in vacuo, and the crude material was taken up in DMF (2 mL).

To this mixture was added N-[(pent-4-en-1-yloxy)carbonyl]-L-norleucine (41 mg, 0.17 mmol) (prepared according to the procedure below), DIPEA (0.076 mL, 0.43 mmol), EDC (54 mg, 0.28 mmol) and HOAt (44 mg, 0.28 mmol). After stirring at r.t. for 30 min, complete consumption of the amine was evidenced via LC-MS. The reaction mixture was then worked-up with 0.5 N HCl and EtOAc. The organic layer was washed with brine and dried over $MgSO_4$. The solvent was then removed in vacuo and the crude product was purified on silica (10-90% EtOAc/hexanes) to yield 60 mg (79% yield) of methyl N-[(pent-4-enyloxy)carbonyl]-L-norleucyl-(4R)-4-{[(4-vinyl-1,3-dihydro-2H-isoindol-2-yl)carbonyl]oxy}-L-prolinate. LRMS (ESI) m/z 542 [(M+H)$^+$; calcd for $C_{29}H_{40}N_3O_7$: 542].

Step 5: Methyl (5R,7S,10S)-10-butyl-3,9,12-trioxo-1,6,7,9,10,11,12,14,15,16-decahydro-5H-2,22:5,8-dimethano-4,13,2,8,11-benzodioxatriazacycloicosine-7-carboxylate

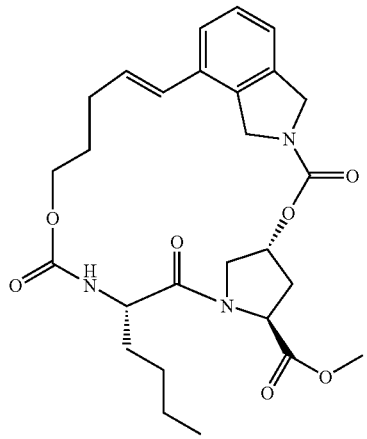

A solution of methyl N-[(pent-4-enyloxy)carbonyl]-L-norleucyl-(4R)-4-{[(4-vinyl-1,3-dihydro-2H-isoindol-2-yl)carbonyl]oxy}-L-prolinate (60 mg, 0.11 mmol) in DCE (20 mL) was degassed with $N_2$ for 15 min. The Zhan ruthenium metathesis catalyst RC-301 (Zhan Catalyst I (depicted as J on page 43), RC-301, Zannan Pharma Ltd.) (7 mg, 0.01 mmol) was then added. The solution was then heated to 100° C. for 1 h. At this time, LC-MS and TLC analysis indicated complete consumption of the starting material and formation of nearly a single product which had the desired mass. The solvent was then removed in vacuo, and the crude product was purified on silica (5-70% EtOAc/hexane) to yield 45 mg (79% yield) of methyl (5R,7S,10S)-10-butyl-3,9,12-trioxo-1,6,7,9,10,11,12,14,15,16-decahydro-5H-2,22:5,8-dimethano-4,13,2,8,11-benzodioxatriazacycloicosine-7-carboxylate. LRMS (ESI) m/z 514 [(M+H)$^+$; calcd for $C_{27}H_{36}N_3O_7$: 514].

Step 6: (5R,7S,10S)-10-Butyl-N-((1R,2S)-1-{[(cyclopropylsulfonyl)amino]carbonyl}-2-vinylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide To a solution of methyl (5R,7S,10S)-10-butyl-3,9,12-trioxo-1,6,7,9,10,11,12,14,15,16-decahydro-5H-2,22:5,8-dimethano-4,13,2,8,11-benzodioxatriazacycloicosine-7-carboxylate (45 mg, 0.09 mmol) in THF (2 mL), MeOH (0.5 mL), and water (1 mL) was added LiOH (21 mg, 0.87 mmol). The reaction mixture was heated to 40° C. and stirred for 1 h, at which time complete consumption of the methyl ester starting material was observed by LC-MS. The mixture was then worked-up with 0.5 N HCl and EtOAc. The organic layer was then dried over $K_2CO_3$, and solvent was removed in vacuo. The crude product was taken up in DMF (1 mL).

To the above solution was added (1R,2S)-1-{[(cyclopropylsulfonyl)amino]carbonyl}-2-vinylcyclopropanaminium chloride (Llinas-Brunet et al., US03/15755 and Wang et al., WO 03/099274) (32 mg, 0.12 mmol), TBTU (51 mg, 0.16 mmol) and DIPEA (0.071 mL, 0.40 mmol) and the reaction mixture was stirred at room temperature for 2 h. The reaction mixture was directly purified by reverse phase HPLC to give (5R,7S,10S)-10-butyl-N-((1R,2S)-1-{[(cyclopropylsulfonyl)amino]carbonyl}-2-vinylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide (27 mg, 47% yield). $^1$H NMR (500 MHz, ppm, CDCl$_3$) δ 10.01 (s, 1H), 7.27 (m, 2H), 7.12 (d, 1H), 7.04 (s, 1H), 6.40 (d, J=16.1 Hz, 1H), 6.08 (m, 1H), 5.76 (m, 1H), 5.44 (s, 1H), 5.36 (d, 1H), 5.25 (d, 1H), 5.14 (d, 1H), 4.80-4.68 (m, 3H), 4.59 (d, 1H), 4.44 (m, 2H), 4.38 (m, 1H), 4.28 (m, 1H), 3.95 (m, 1H), 3.77 (dd, 1H), 2.94 (m, 1H), 2.43 (m, 2H), 2.29 (d, 2H), 2.06 (m, 2H), 1.94 (m, 1H), 1.78 (m, 4H), 1.45 (m, 1H), 1.38-1.06 (m, 5H), 1.04 (d, 2H), 0.92 (t, 3H) ppm. LRMS (ESI) m/z 712 [(M+H)$^+$; calcd for C$_{35}$H$_{46}$N$_5$O$_9$S: 712].

EXAMPLE 2

(5R,7S,10S)-10-tert-Butyl-N-((1R,2S)-1-{[(cyclopropylsulfonyl)amino]carbonyl}-2-vinylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide (III-2)

III-2

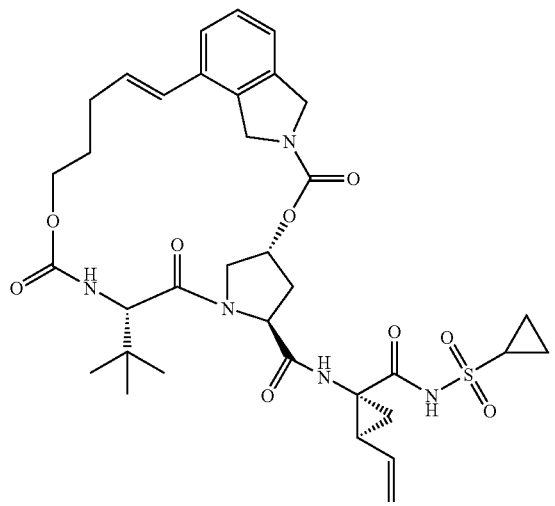

EXAMPLE 2 was prepared according to the procedure used for EXAMPLE 1 except that 3-methyl-N-[(pent-4-enyloxy)carbonyl]-L-valine (prepared according to the procedure below) was used in place of N-[(pent-4-en-1-yloxy)carbonyl]-L-norleucine in Step 4.
$^1$H NMR (500 MHz, ppm, CDCl$_3$) δ 9.90 (s, 1H), 7.28 (m, 2H), 7.13 (m, 2H), 6.31 (d, J=15.9 Hz, 1H), 6.04 (m, 1H), 5.74 (m, 1H), 5.45 (m, 2H), 5.27 (d, 1H), 5.16 (d, 1H), 4.77-4.66 (m, 3H), 4.55 (d, 1H), 4.48 (t, 1H), 4.41-4.35 (m, 2H), 4.27 (m, 1H), 3.93 (m, 1H), 3.74 (dd, 1 H), 2.93 (m, 1H), 2.45 (d, 2H), 2.32 (m, 2H), 2.10-1.95 (m, 2H), 1.74 (m, 1H), 1.47 (m, 1H), 1.37 (m, 2H), 1.07 (s, 9H) ppm. LRMS (ESI) m/z 712 [(M+H)$^+$; calcd for C$_{35}$H$_{46}$N$_5$O$_9$S: 712].

EXAMPLE 3

(5R,7S,10S)-10-tert-Butyl-N-((1R,2S)-1-{[(cyclopropylsulfonyl)amino]carbonyl}-2-vinylcyclopropyl)-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxamide (III-8)

III-8

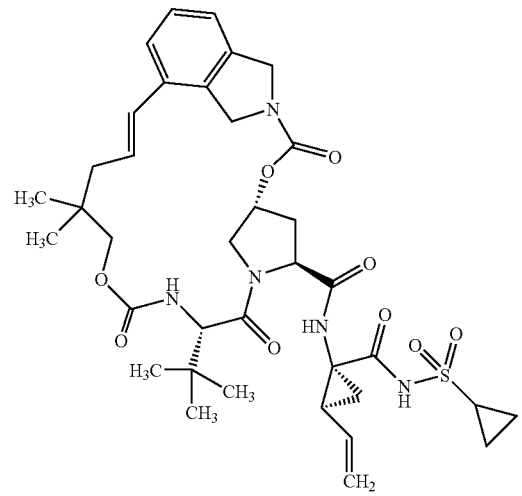

Step 1: 1-Bromo-2,3-bis(bromomethyl)benzene

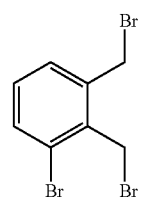

A suspension of 3-bromo-o-xylene (196 g, 1.06 mol), N-bromosuccinimide (377 g, 2.15 mol) and benzoyl peroxide (0.26 g, 1.0 mmol) in carbon tetrachloride (1800 mL) was heated to reflux under nitrogen for 15 h. The contents of the reaction flask were cooled, filtered, and the filtrate evaporated. Distilled crude material under high vacuum. Major fractions distilled between 88° C. and 152° C. Recovered 108 g pure material. Recovered 182 g slightly crude material which could be used in the following reaction. ¹H NMR (CDCl₃) δ (ppm) 7.56 (d, J=8.0 Hz, 1H), 7.31 (d, J=8.0 Hz, 1H), 7.26 (s, 1H), 7.16 (t, J=8.0 Hz, 1H), 4.84 (s, 2H), 4.64 (s, 2H).

Step 2: 2-Benzyl-4-bromoisoindoline

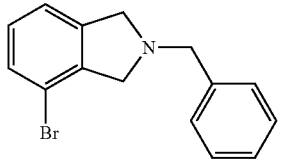

Potassium bicarbonate (204 g, 2.04 mol) was suspended in acetonitrile (12 L) and the mixture was heated to 80° C. Solutions of 1-bromo-2,3-bis(bromomethyl)benzene (280 g, 0.82 mol in 500 mL acetonitrile) and benzylamine (87.5 g, 0.82 mol in 500 mL acetonitrile) were added concurrently via addition funnels over 1 h. The reaction mixture was stirred at 77° C. for 16 h. The contents of the reaction flask were cooled, filtered and the solvent removed by evaporation. The reaction was partitioned between 1M K₂CO₃ and EtOAc. The organics were washed with brine, dried with anhydrous Na₂SO₄, filtered, and evaporated. Flash column chromatography (gradient elution: heptane to 10% EtOAc in heptane) gave after evaporation the title compound as a pale oil. ¹H NMR (CDCl₃) δ (ppm) 7.41-7.39 (m, 2H), 7.37-7.34 (m, 2H), 7.32-7.27 (m, 2H), 7.10-7.03 (m, 2H), 4.02 (s, 2H), 3.97 (s, 2H), 3.91 (s, 2H). LRMS (ESI) m/z 289 [(M+H)⁺; calcd for C₁₅H₁₅BrN: 289].

Converted to HCl salt in HCl/MeOH. Added MTBE and filtered solid to give 118 g of product as the HCl salt.

Step 3: 2-Benzyl-4-vinylisoindoline

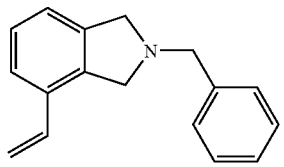

A solution of 2-benzyl-4-bromoisoindoline (16.7 g, 58.0 mmol) and tributyl(vinyl)tin (20.3 mL, 69.6 mmol) in toluene (400 mL) was degassed by bubbling nitrogen gas through the solution for 0.25 h. Tetrakis(triphenylphosphine)palladium (0) (1.30 g, 1.16 mmol) was added and the resulting solution heated in a 100° C. oil bath under nitrogen for 24 h. The contents of the reaction flask were cooled, evaporated and subjected to flash column chromatography eluting with hexane/ethyl acetate 95/5 to give after evaporation the title compound as a pale oil that turned pink on standing. LRMS (ESI) m/z 236 [(M+H)⁺; calcd for C₁₇H₁₈N: 236].

Step 4: 4-Vinylisoindoline

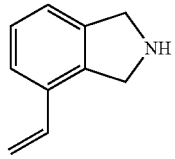

A solution of 2-benzyl-4-vinylisoindoline (58 mmol) in 1,2-dichloroethane (150 mL) was placed in a 1 L round bottom flask under nitrogen. To this was attached an addition funnel containing a solution of 1-chloroethyl chloroformate (7.51 mL, 69.6 mmol) in 1,2-dichloroethane. The reaction flask was cooled in an ice bath and the contents of the addition funnel were added dropwise over 20 min keeping the internal reaction temperature<5° C. After the addition was complete the reaction flask was allowed to warm to room temperature then heated to reflux for 45 min. The contents of the reaction flask were cooled to room temperature then the solvent removed by evaporation. Methanol (200 mL) was added and the contents of the reaction flask were heated to reflux for 30 min. The reaction flask was cooled and the solvent removed by evaporation. Water (200 mL) was added and the resulting mixture washed with ethyl acetate (2×250 mL). The aqueous layer was made basic with 2N sodium hydroxide then extracted with methylene chloride (4×250 mL). The combined organic extracts were dried with anhydrous sodium sulfate, filtered and the filtrate evaporated. The remaining residue was subjected to flash column chromatography eluting with methylene chloride/methanol/ammonium hydroxide 97/3/0.3 to 95/5/0.5. Evaporation of fractions gave the title compound as a brown oil, 6.00 g (41.4 mmol, 71% yield for two steps). LRMS (ESI) m/z 146 [(M+H)⁺; calcd for C₁₀H₁₂N: 146].

Step 5: 1-tert-Butyl 2-methyl (2S,4R)-4-{[(4-vinyl-1, 3-dihydro-2H-isoindol-2-yl)carbonyl] oxy}pyrrolidine-1,2-dicarboxylate

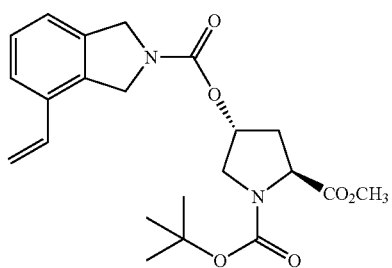

A solution of 1-tert-butyl 2-methyl (2S,4R)-4-hydroxypyrrolidine-1,2-dicarboxylate (10.1 g, 41.4 mmol) in DMF (90 mL) under nitrogen was cooled to 0° C. Solid 1,1'-carbonyldiimidazole (6.70 g, 41.4 mmol) was added to the reaction. The contents of the reaction flask were warmed to room temperature and after 2 h a solution of 4-vinylisoindoline (6.00 g, 41.4 mmol) in DMF (10 mL) was added. The reaction was heated in a 60° C. oil bath for 2 h then cooled and poured into water and 5% potassium bisulfate. The resulting mixture was extracted with ethyl acetate (4×250 mL). Combined organics were washed with brine, dried with anhydrous sodium sulfate, filtered and evaporated. Flash column chromatography eluting with hexane/ethyl acetate 70/30 gave the title compound as a white foam, 13.9 g (33.4 mmol, 81% yield). LRMS (ESI) m/z 417 [(M+H)$^+$; calcd for C$_{22}$H$_{29}$N$_2$O$_6$: 417].

Step 6: (3R,5S)-5-(Methoxycarbonyl)pyrrolidin-3-yl 4-vinyl-1,3-dihydro-2H-isoindole-2-carboxylate Hydrochloride

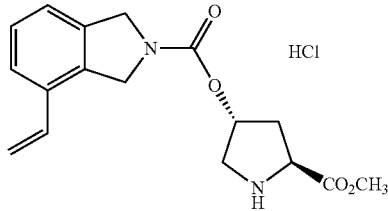

A solution of 1-tert-Butyl 2-methyl (2S,4R)-4-{[(4-vinyl-1,3-dihydro-2H-isoindol-2-yl)carbonyl]oxy}pyrrolidine-1,2-dicarboxylate (13.9 g, 33.4 mmol) in ethyl acetate (700 mL) was cooled in an ice bath the saturated with hydrogen chloride gas. The reaction flask was sealed and allowed to warm to room temperature. After 3.5 h the solvent was removed by evaporation to give the title compound as a gray solid, 11.2 g, 95% yield). $^1$H NMR (500 MHz, ppm, CD$_3$OD) δ 7.47-7.45 (m, 1H), 7.32-7.31 (m, 1H), 7.26-7.21 (m, 1H), 6.79-6.73 (m, 1H), 5.79-5.73 (m, 1H), 5.46 (s, 1H), 5.41-5.38 (m, 1H), 4.80-4.72 (m, 4H), 3.91 (s, 3H), 3.74-3.63 (m, 2H), 2.77-2.71 (m, 1H), 2.51-2.46 (m, 1H). LRMS (ESI) m/z 317 [(M+H)$^+$; calcd for C$_{17}$H$_{21}$N$_2$O$_4$: 317].

Step 7: Methyl N-{[(2,2-dimethylpent-4-enyl)oxy]carbonyl}-3-methyl-L-valyl-(4R)-4-{[(4-vinyl-1,3-dihydro-2H-isoindol-2-yl)carbonyl]oxy}-L-prolinate

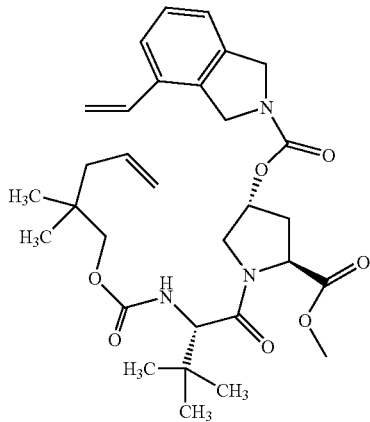

To a solution of (3R,5S)-5-(methoxycarbonyl)pyrrolidin-3-yl 4-vinyl-1,3-dihydro-2H-isoindole-2-carboxylate hydrochloride (2.00 g, 5.67 mmol) and N-{[(2,2-dimethylpent-4-enyl)oxy]carbonyl}-3-methyl-L-valine (1.54 g, 5.67 mmol) in DMF (100 mL) was added EDC (1.41 g, 7.37 mmol), HOBt (1.00 g, 7.37 mmol) and DIPEA (3.16 mL, 22.8 mmol). The reaction mixture was stirred at RT for 18 h and then diluted with ethyl acetate and aqueous NaHCO$_3$. The layers were separated and the organic layer was washed with water and brine, dried over Na$_2$SO$_4$, filtered and concentrated. The crude residue was purified on silica gel (gradient elution 5% to 50% ethyl acetate in hexanes) to give methyl N-{[(2,2-dimethylpent-4-enyl)oxy]carbonyl}-3-methyl-L-valyl-(4R)-4-{[(4-vinyl-1,3-dihydro-2H-isoindol-2-yl)carbonyl]oxy}-L-prolinate (2.75 g, 85% yield) as a white foam. LRMS (ESI) m/z 570 [(M+H)$^+$; calcd for C$_{31}$H$_{44}$N$_3$O$_7$: 570].

Step 8: Methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate

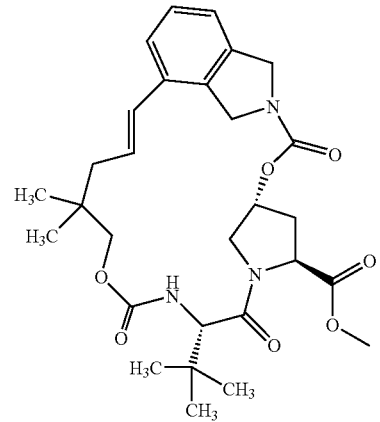

A solution of methyl N-{[(2,2-dimethylpent-4-enyl)oxy]carbonyl}-3-methyl-L-valyl-(4R)-4-{[(4-vinyl-1,3-dihydro-2H-isoindol-2-yl)carbonyl]oxy}-L-prolinate (2.46 g, 4.32 mmol) in anhydrous dichloromethane (450 mL) was purged with nitrogen for 15 min. A solution of bis(tricyclohexylphosphine)-3-phenyl-1H-indene-1-ylideneruthenium dichloride (Neolyst M1 catalyst purchased from Strem) (0.40 g, 0.43 mmol) in degassed, anhydrous dichloromethane (50 mL) was then added dropwise over 30 min. The reaction mixture was stirred at RT, during which time 0.2 g portions of the catalyst were added approximately every 8-12 h. Reaction progress was monitored by HPLC until the reaction was complete at 48 h. The residue was purified by flash chromatography on silica gel, eluting with 10-70% EtOAc/Hexane, to give methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (1.85 g, 76% yield). LRMS (ESI) m/z 542 [(M+H)$^+$; calcd for C$_{29}$H$_{40}$N$_3$O$_7$: 542].

Step 9: (5R,7S,10S)-10-tert-Butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylic Acid

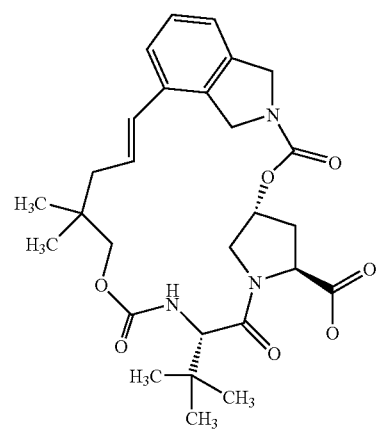

To a solution of methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (0.9 g, 1.67 mmol) in THF:H2O (2:1, 45 mL) was added LiOH (0.40, 16.7 mmol). The reaction mixture was heated to 40° C. and stirred for 1 h. The reaction mixture was diluted with aqueous HCl, and extracted with EtOAc. The combined EtOAc layer was washed with water, brine, dried over $Na_2SO_4$, filtered and concentrated. The product was used with no further purification. LRMS (ESI) m/z 528 [(M+H)$^+$; calcd for $C_{28}H_{38}N_3O_7$: 528].

Step 10: (5R,7S,10S)-10-tert-Butyl-N-((1R,2S)-1-{[(cyclopropylsulfonyl)amino]carbonyl}-2-vinylcyclopropyl)-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxamide A solution of (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylic acid (100 mg, 0.19 mmol), (1R,2S)-1-{[(cyclopropylsulfonyl)amino]carbonyl}-2-vinylcyclopropanaminium chloride (Llinas-Brunet et al., US03/15755 and Wang et al., WO 03/099274) (76 mg, 0.28 mmol), O-(7-azabenzotriazol-1-yl)-N,N,N',N'-tetramethyluronium phosphorushexafluoride (HATU, 108 mg, 0.28 mmol), DIPEA (0.073 mL, 0.42 mmol) and 4-dimethylaminopyridine (2 mg) in dichloromethane (5 mL) was stirred at 40° C. for 1 h. The reaction solution was diluted with aqueous saturated $NaHCO_3$, and extracted with EtOAc. The combined EtOAc layer was washed with water, brine, dried over Na2SO4, filtered and concentrated. The residue was purified by flash chromatography eluting with 3% MeOH/$CH_2Cl_2$, to give (5R,7S,10S)-10-tert-butyl-N-((1R,2S)-1-{[(cyclopropylsulfonyl)amino]carbonyl}-2-vinylcyclopropyl)-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxamide (80 mg, 57% yield). $^1$H NMR (400 MHz, ppm, DCl$_3$) δ 7.48 (s, 1H), 7.23 (s, 1H), 7.12 (d, 1H), 6.23 (d, J=15.9 Hz, 1H), 5.94 (m, 1H), 5.76 (m, 1H), 5.50 (m, 2H), 5.43 (s, 1H), 5.24 (d, J=16.6 Hz, 1H), 5.11 (d, 1H), 4.70 (s, 2H), 4.61 (d, 1H), 4.48 (m, 3H), 4.35 (d, 1H), 4.14 (d, 1H), 3.74 (d, 1H), 3.34 (d, 1H), 2.89 (m, 1 H), 2.43 (dd, 2H), 2.06 (m, 1H), 1.93 (m, 1H), 1.89 (dd, 1H), 1.43 (d, 1H), 1.25 (m, 3H), 1.09 (s, 3H), 1.06 (s, 9H), 0.86 (s, 3H). LRMS (ESI) m/z 740 [(M+H)$^+$; calcd for $C_{37}H_{50}N_5O_9S$: 740].

EXAMPLE 4

(5R,7S,10S)-10-tert-Butyl-N-((1R,2S)-1-{[(cyclopropylsulfonyl)amino]carbonyl}-2-vinylcyclopropyl)-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide
(III-12)

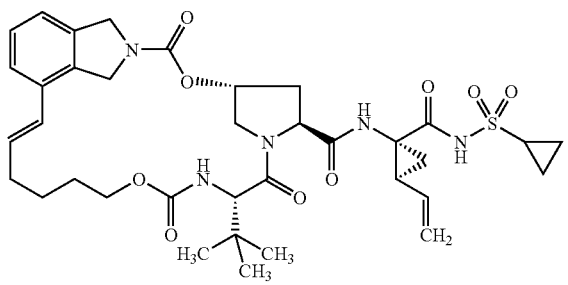

III-12

The title compound was prepared according to the procedure used for EXAMPLE 3 except that 3-methyl-N-[(hex-5-enyloxy)carbonyl]-L-valine (prepared according to the procedure below) was used in place of N-{[(2,2-dimethylpent-4-enyl)oxy]carbonyl}-3-methyl-L-valine in Step 7. $^1$H NMR (500 MHz, ppm, CD$_3$OD) δ 9.13 (s, 1H), 7.26 (t, 1H), 7.23 (d, 1H), 7.16 (d, 1H), 6.39 (d, J=16.4 Hz, 1H), 6.08 (m, 1H), 5.76 (m, 1H), 5.38 (s, 1H), 5.29 (d, 1 H), 5.12 (d, 1H), 4.79 (d, 1H), 4.73-4.63 (m, 4H), 4.41 (s, 1H), 4.37 (q, 1H), 4.24 (d, 1H), 3.96 (dd, 1H), 3.77 (quin, 1H), 2.94 (m, 1H), 2.51 (q, 1H), 2.29-2.13 (m, 4H), 1.87 (dd, 1 H), 1.68 (m, 2H), 1.53 (quin, 2H), 1.44 (dd, 1H), 1.25 (m, 2H), 1.05 (s, 9H). LRMS (ESI) m/z 726 [(M+H)$^+$; calcd for $C_{36}H_{48}N_5O_9S$: 726].

EXAMPLE 5

(5R,7S,10S)-10-Butyl-N-((1R,2S)-1-{[(cyclopropylsulfonyl)amino]carbonyl}-2-vinylcyclopropyl)-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide
(III-133)

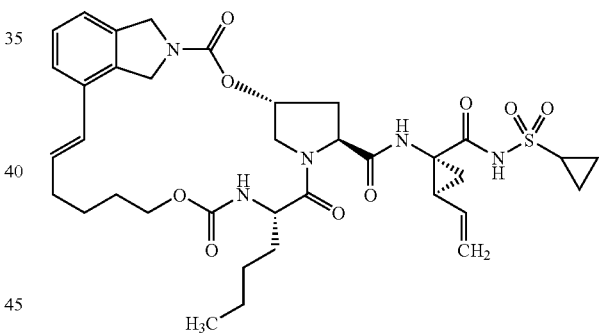

III-133

The title compound was prepared according to the procedure used for EXAMPLE 3 except that 3-methyl-N-[(hex-5-enyloxy)carbonyl]-L-norleucine (prepared according to the procedure below) was used in place of N-{[(2,2-dimethylpent-4-enyl)oxy]carbonyl}-3-methyl-L-valine in Step 7. $^1$H NMR (500 MHz, ppm, CD$_3$OD) δ 7.24 (t, 1H), 7.23 (d, 1H), 7.15 (d, 1H), 6.91 (d, 1H), 6.37 (d, J=16.1 Hz, 1H), 6.07 (m, 1H), 5.75 (m, 1H), 5.39 (s, 1H), 5.29 (d, 1 H), 5.12 (d, 1H), 4.77 (d, 1H), 4.66 (m, 3H), 4.57 (m, 1H), 4.47 (q, 1H), 4.39 (q, 1H), 4.27 (d, 1H), 3.90 (dd, 1H), 3.77 (quin, 1H), 2.96 (m, 1H), 2.49 (q, 1H), 2.29 (m, 1H), 2.22 (m, 3 H), 1.88 (dd, 1H), 1.75 (m, 2H), 1.64 (m, 2H), 1.52 (m, 2H), 1.39 (m, 5H), 1.27 (m, 1H), 1.18 (m, 1H), 1.09 (m, 2H), 0.94 (t, 3H). LRMS (ESI) m/z 726 [(M+H)$^+$; calcd for $C_{36}H_{48}N_5O_9S$: 726].

EXAMPLE 6

(5R,7S,10S)-10-Butyl-N-((1R,2S)-1-{[(cyclopropylsulfonyl)amino]carbonyl}-2-vinylcyclopropyl)-3,9,12-trioxo-1,6,7,9,10,11,12,14,15,16,17,18-dodecahydro-5H-2,24:5,8-dimethano-4,13,2,8,11-benzodioxatriazacyclodocosine-7-carboxamide (III-198)

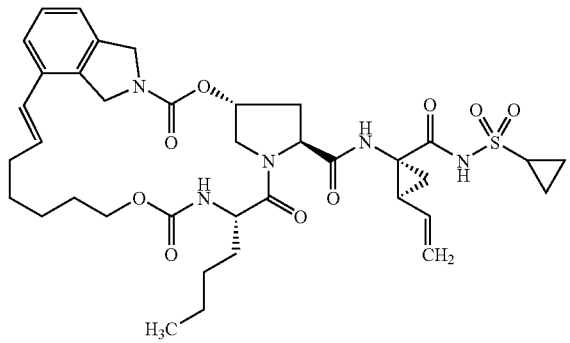

III-198

The title compound was prepared according to the procedure used for EXAMPLE 3 except that N-[(hept-6-en-1-yloxy)carbonyl]-L-norleucine (prepared according to the procedure below) was used in place of N-{[(2,2-dimethylpent-4-enyl)oxy]carbonyl}-3-methyl-L-valine in Step 7. $^1$H NMR (500 MHz, ppm, CD$_3$OD) δ 9.26 (s, 1H), 7.39 (d, 1H), 7.24 (t, 1H), 7.15 (d, 1H), 6.30 (d, J=15.9 Hz, 1H), 6.20 (m, 1H), 5.75 (m, 1H), 5.53 (s, 1H), 5.31 (d, 1H), 5.12 (d, 1H), 4.70 (m, 4H), 4.43 (dd, 1H), 4.34 (m, 2H), 4.27 (q, 1H), 3.91 (dd, 1H), 3.79 (quin, 1H), 3.31 (m, 1H), 2.97 (m, 1H), 2.31 (m, 1H), 2.22 (m, 3H), 1.89 (dd, 1H), 1.74 (m, 2H), 1.66 (m, 1H), 1.56 (m, 3H), 1.38 (m, 8H), 1.19 (m, 1H), 1.09 (m, 2H), 0.94 (t, 3H). LRMS (ESI) m/z 740 [(M+H)$^+$; calcd for C$_{37}$H$_{50}$N$_5$O$_9$S: 740].

EXAMPLE 7

(5R,7S,10S)-10-tert-Butyl-N-((1R,2S)-1-{[(cyclopropylsulfonyl)amino]carbonyl}-2-vinylcyclopropyl)-15,15-dimethyl-3,9,12-trioxo-6,7,9,10,11,12,14,15,16,17-decahydro-1H,5H-2,23:5,8-dimethano-4,13,28,11-benzodioxatriazacyclohenicosine-7-carboxamide (III-199)

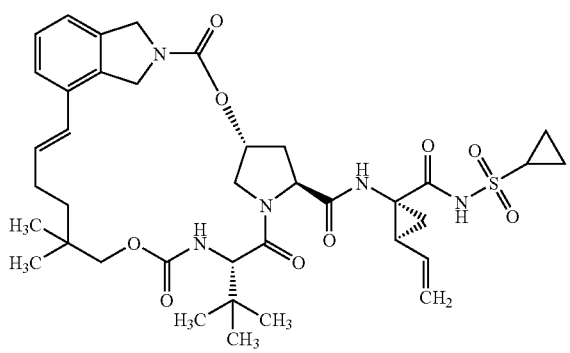

III-199

The title compound was prepared according to the procedure used for EXAMPLE 3 except that N-{[(2,2-dimethylhex-5-enyl)oxy]carbonyl}-3-methyl-L-valine (prepared according to the procedure below) was used in place of N-{[(2,2-dimethylpent-4-enyl)oxy]carbonyl}-3-methyl-L-valine in Step 7. $^1$H NMR (500 MHz, ppm, CD$_3$OD) δ 9.17 (s, 1H), 7.27 (t, J=7.5 Hz, 1H), 7.21 (t, J=7.5 Hz, 2H), 7.16 (d, J=7.5 Hz, 1H), 6.38 (d, J=16 Hz, 1H), 6.03 (m, 1H), 5.79 (m, 1H), 5.32 (m, 2H), 5.13 (m, 1H), 4.82-4.77 (m, 1H), 4.73-4.61 (m, 4H), 4.48 (s, 1H), 4.39 (m, 1H), 4.19 (d, J=12 Hz, 1H), 3.96 (m, 1H), 2.96 (m, 1 H), 2.59-2.55 (m, 1H), 2.35-2.12 (m, 4H), 1.89 (m, 1H), 1.49-1.23 (m, 6H), 1.51-0.98 (m, 14 H), 0.95-0.85 (m, 4H). LRMS (ESI) m/z 754 [(M+H)$^+$; calcd for C$_{38}$H$_{52}$N$_5$O$_9$S: 754].

EXAMPLE 8

5R,7S,10S)-10-tert-Butyl-N-((1R,2R)-1-{[(cyclopropylsulfonyl)amino]carbonyl}-2-ethylcyclopropyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-200)

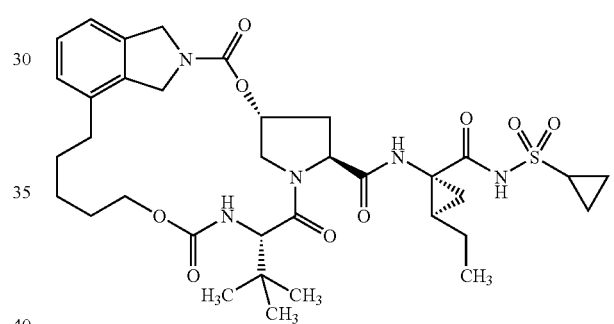

III-200

A solution of EXAMPLE 2 (0.32 mg, 0.45 mmol) and palladium on carbon (10% wt., 0.03 g) in EtOAc (10 mL) was vigorously stirred under a hydrogen balloon for 1 h. The reaction mixture was filtered and concentrated. The residue was purified by reverse-phase HPLC (DELTAPAK C18 column), running 40-65% CH$_3$CN in water (with NH$_4$OAc 1 g/L). The fractions were concentrated, diluted with aqueous saturated NaHCO$_3$ (20 mL) and extracted with CH$_2$Cl$_2$ (3×70 mL). The combined CH$_2$Cl$_2$ layers were washed with water (50 mL), dried over Na2SO4, filtered and concentrated to give (5R,7S,10S)-10-tert-butyl-N-((1R,2R)-1-{[(cyclopropylsulfonyl)amino]carbonyl}-2-ethylcyclopropyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (0.31 g, 97% yield). $^1$H NMR (CD$_3$OD, ppm) δ 7.23 (t, 1H), 7.14 (d, 1H), 7.10 (d, 1H), 7.02 (d, 1H), 5.52 (s, 1H), 4.74-4.60 (m, 4H), 4.48-4.30 (m, 4H), 3.88 (d, 1H), 3.75 (s, 1H), 2.99 (m, 1H), 2.62 (m, 1H), 2.41 (m, 2H), 2.14 (m, 1H), 1.79 (m, 1H), 1.65-1.51 (m, 6H), 1.47-1.19 (m, 5H), 1.07 (s, 9H), 0.99 (t, 3H).

LRMS (ESI) m/z 716 [(M+H)⁺; calcd for $C_{35}H_{50}N_5O_9S$: 716].

EXAMPLE 9

(5R,7S,10S)-10-tert-Butyl-N-((1R,2R)-1-{[(cyclopropylsulfonyl)amino]carbonyl}-2-ethylcyclopropyl)-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-201)

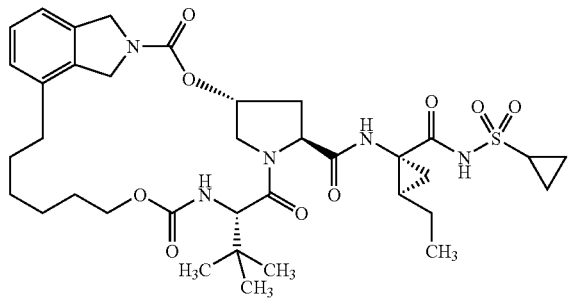

III-201

The title compound was prepared from EXAMPLE 4 using the procedure described for EXAMPLE 8. ¹H NMR (500 MHz, ppm, CD₃OD) δ 7.23 (t, 1H), 7.14 (d, 1H), 7.10 (d, 1H), 7.02 (d, 1H), 5.36 (s, 1H), 4.71 (m, 3H), 4.64 (t, 1H), 4.56 (m, 1H), 4.40 (m, 2H), 4.24 (d, 1H), 3.96 (dd, 1H), 3.72 (quin, 1H), 2.98 (m, 1H), 2.58 (m, 1H), 2.49 (m, 2H), 2.15 (t, 1H), 1.69-1.19 (m, 15H), 1.09 (m, 1H), 1.06 (s, 9H), 0.98 (t, 3H). LRMS (ESI) m/z 730 [(M+H)⁺; calcd for $C_{36}H_{52}N_5O_9S$: 730].

EXAMPLE 10

(5R,7S,10S)-10-Butyl-N-((1R,2R)-1-{[(cyclopropylsulfonyl)amino]carbonyl}-2-ethylcyclopropyl)-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-202)

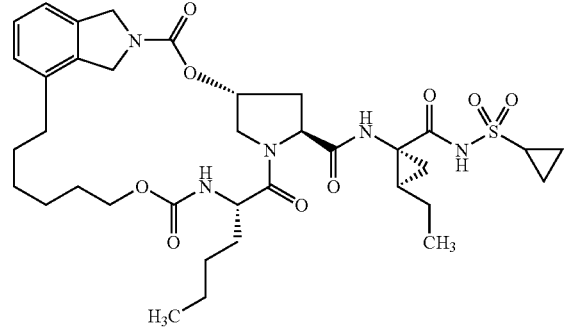

III-202

The title compound was prepared from EXAMPLE 5 using the procedure described for EXAMPLE 8. ¹H NMR (500 MHz, ppm, CD₃OD) δ 7.23 (t, 1H), 7.14 (d, 1H), 7.09 (d, 1H), 6.99 (d, 1H), 5.39 (s, 1H), 4.76-4.61 (m, 4H), 4.43 (m, 3H), 4.29 (d, 1H), 3.92 (dd, 1H), 3.69 (quin, 1H), 2.99 (m, 1H), 2.57 (m, 1H), 2.51 (m, 2H), 2.19 (tt, 1H), 1.77 (m, 1H), 1.70-1.30 (m, 20H), 1.17 (m, 2H), 1.10 (m, 2H), 0.99 (t, 3H), 0.95 (t, 3H). LRMS (ESI) m/z 730 [(M+H)⁺; calcd for $C_{36}H_{52}N_5O_9S$: 730].

EXAMPLE 11

(5R,7S,10S)-10-Butyl-N-((1R,2R)-1-{[(cyclopropylsulfonyl)amino]carbonyl}-2-ethylcyclopropyl)-3,9,12-trioxo-1,6,7,9,10,11,12,14,15,16,17,18,19,20-tetradecahydro-5H-2,24:5,8-dimethano-4,13,2,8,11-benzodioxatriazacyclodocosine-7-carboxamide (III-203)

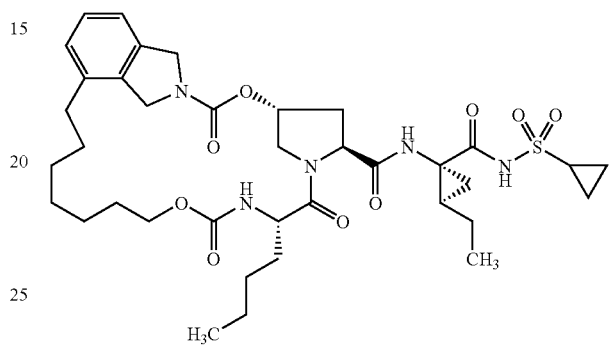

III-203

The title compound was prepared from EXAMPLE 6 using the procedure described for EXAMPLE 8. ¹H NMR (500 MHz, ppm, CD₃OD) δ 7.25 (t, 1H), 7.15 (d, 1H), 7.11 (d, 1H), 5.55 (s, 1H), 4.70 (m, 4H), 4.49 (m, 1H), 4.38 (t, 1H), 4.29 (m, 2H), 3.94 (dd, 1H), 3.73 (quin, 1H), 3.00 (m, 1H), 2.63 (quin, 1H), 2.51 (m, 1H), 2.38 (m, 1H), 2.20 (tt, 1H), 1.76 (quin, 1H), 1.68-1.07 (m, 24H), 1.00 (t, 3H), 0.95 (t, 3H). LRMS (ESI) m/z 744 [(M+H)⁺; calcd for $C_{37}H_{54}N_5O_9S$: 744].

EXAMPLE 12

(5R,7S,10S)-10-tert-Butyl-N-((1R,2R)-1-{[(cyclopropylsulfonyl)amino]carbonyl}-2-ethylcyclopropyl)-15,15-dimethyl-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-204)

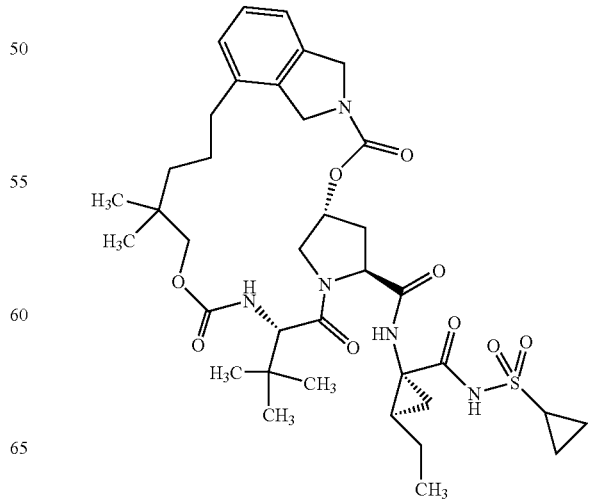

III-204

The title compound was prepared from EXAMPLE 3 using the procedure described for EXAMPLE 8. $^1$H NMR (400 MHz, ppm, CD$_3$OD) δ 9.06 (s, 1H), 7.22 (dd, 1H), 7.13 (d, 1H), 7.07 (d, 1H), 5.51 (s, 1H), 4.72 (d, 2H), 4.68 (d, 2H), 4.44 (d, 2H), 4.28 (m, 2 H), 3.87 (dd, 1H), 3.28 (m, 1H), 2.98 (d, 1H), 2.85 (m, 3H), 2.52 (m, 1H), 2.43 (m, 2H), 2.15 (m, 1H), 1.15-1.17 (m, 3H), 1.41 (m, 2H), 1.30 (m, 1H), 1.21 (m, 4H), 1.08 (m, 1H), 1.06 (s, 3H), 1.05 (s, 9H), 0.98 (t, 3H), 0.81 (s, 3H). LRMS (ESI) m/z 744 [(M+H)$^+$; calcd for C$_{37}$H$_{54}$N$_5$O$_9$S: 744].

EXAMPLE 13

(5R,7S,10S)-10-tert-Butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-205)

III-205

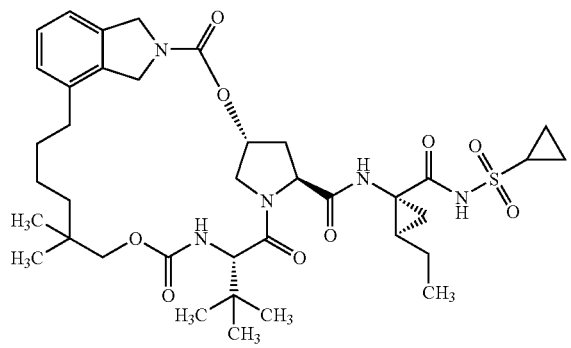

The title compound was prepared from EXAMPLE 7 using the procedure described for EXAMPLE 8. $^1$H NMR (500 MHz, ppm, CD$_3$OD) δ 9.09 (s, 1H), 7.24 (t, J=7.5 Hz, 1H), 7.15 (d, J=7.5 Hz, 1H), 7.10 (d, J=7.5 Hz, 1H), 5.53 (s, 1H), 4.75-4.59 (m, 4H), 4.44-4.37 (m, 3H), 4.20 (d, J=12 Hz, 1H), 3.95-3.91 (m, 1H), 3.31 (m, 2H), 2.99-2.96 (m, 1H), 2.62-2.46 (m, 3H), 2.17-2.13 (m, 1H), 1.67-1.50 (m, 6H), 1.37-1.18 (m, 7H), 1.15-0.96 (m, 16H), 0.80 (s, 3H). LRMS (ESI) m/z 758 [(M+H)$^+$; calcd for C$_{38}$H$_{56}$N$_5$O$_9$S: 758].

Alternative Preparation:

Step 1: 1-Bromo-2,3-bis(bromomethyl)benzene

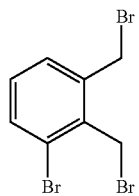

To a suspension of 3-bromo-o-xylene (999 g, 5.40 mol) in chlorobenzene (9 L) at RT was added N-bromosuccinimide (1620 g, 9.1 mol) and benzoyl peroxide (2.6 g, 10.8 mmol). The reaction mixture was heated to 80° C. and stirred under nitrogen for 18 h. The reaction mixture was cooled to 70° C. and an additional portion of NBS (302 g, 1.7 mol) was added. The reaction mixture was heated to 80° C. and stirred under nitrogen for 22 h. The reaction mixture was cooled to RT, diluted with heptane (6 L) and filtered. The filter cake was washed with heptane (4 L) and the combined filtrates were evaporated. The crude product was dissolved in heptane (2 L) and chloroform (200 mL) and filtered through basic alumina (500 g). The alumina pad was washed with heptane (4 L) and the combined filtrates were evaporated to give 1-bromo-2,3-bis(bromomethyl)benzene (1760 g, crude weight) which was used without further purification. $^1$H NMR (CDCl$_3$) δ (ppm) 7.56 (d, J=8.0 Hz, 1H), 7.31 (d, J=8.0 Hz, 1H), 7.26 (s, 1H), 7.16 (t, J=8.0 Hz, 1H), 4.84 (s, 2H), 4.64 (s, 2H).

Step 2: 2-Benzyl-4-bromoisoindoline Hydrochloride

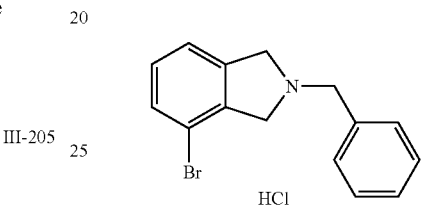

Potassium bicarbonate (657 g, 6.56 mol) was suspended in MeCN (17 L) and the mixture was heated to 80° C. Solutions of crude 1-bromo-2,3-bis(bromomethyl)benzene (900 g, 2.63 mol in 1 L MeCN) and benzylamine (281 g, 2.63 mol in 1 L MeCN) were added concurrently via addition funnels over 2 h. The reaction mixture was stirred at 77° C. for 2 h and then cooled to RT and stirred for 16 h. The contents of the reaction flask were cooled, filtered and the solvent removed by evaporation. The reaction was partitioned between water (6 L) and EtOAc (2 L). The pH was adjusted to >9 by the addition of 1M K$_2$CO$_3$, the layers were separated and the aqueous phase extracted with an additional portion of EtOAc (2 L). The combined organics were washed with brine, dried with anhydrous Na$_2$SO$_4$, filtered, and evaporated. The crude oil was diluted with EtOH (300 mL) and cooled to 0° C. Methanolic HCl was added until the mixture was acidic, followed by MTBE (700 mL) and the mixture sonicated, then stirred for 15 h. MTBE (1 L) was added and the mixture was filtered and washed with 20% EtOH in MTBE followed by MTBE. The solid was air dried to give 2-benzyl-4-bromoisoindoline hydrochloride (211 g). An additional portion of product (86 g) was isolated by concentration of the mother liquors. LRMS (ESI) m/z 289 [(M+H)$^+$; calcd for C$_{15}$H$_{15}$BrN: 289].

Step 3: 4-Bromoisoindoline

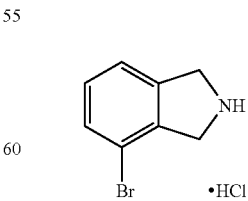

To a solution of 2-benzyl-4-bromoisoindoline hydrochloride (11 g, 30.96 mmol) in 200 mL EtOAc was added 1M NaOH (100 mL) and the mixture stirred for 30 min. The organic layer was separated, washed with brine, dried over anhydrous Na₂SO₄ and solvent evaporated to an oil which was azeotroped once with toluene (50 mL). The oil was dissolved in chlorobenzene (50 mL) and 4A molecular sieves (5 g) added to the stirred solution. After 10 min, 1-chloroethylchloroformate (5.6 mL, 51 mmol) was added dropwise over 5 min. The reaction mixture was then heated to 90° C. for 2 h, cooled to room temperature and filtered. The solids were washed with chlorobenzene (5 mL) and methanol (40 mL). The filtrate was heated to 70° C. for 1 h., allowed to cool and stirred at room temperature overnight. The solids were filtered, washed with chlorobenzene (2 mL) and hexane and dried to give 6.84 g of title compound. LRMS (ESI) m/z 198.1 [(M+H)⁺; calcd for C₈H₉BrN: 198.0].

Step 4: 1-t-Butyl 2-methyl (2S,4R)-4-{[(4-bromo-1,3-dihydro-2H-isoindol-2-yl)carbonyl]oxy}pyrrolidine-1,2-dicarboxylate

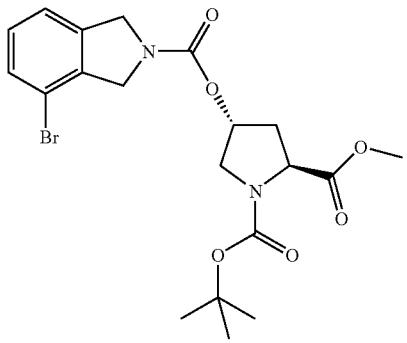

To a solution of (2S,4R)—BOC-4-hydroxyproline methyl ester (126.3 g, 515 mmol) in DMF (960 mL) at 0° C. was added N,N'-carbonyldiimidazole (83.51 g, 515 mmol). The reaction mixture was stirred at room temperature for 3 h. 4-Bromoisoindoline hydrochloride (120 g, 515 mmol) and diisopropylethylamine (96.3 mL, 540 mmol) were added and the reaction mixture heated to 50° C. for 6 h then allowed to cool to room temperature and stirred overnight. The reaction mixture was partitioned between EtOAc (3 L) and 10% aqueous KHSO₄ (6 L), the aqueous re-extracted with EtOAc (2 L) and the combined organic phases washed with 10% aqueous NaHCO₃, brine, dried over Na₂SO₄ and solvent evaporated to a foam (239 g). LRMS (ESI) m/z 471.0 [(M+H)⁺; calcd for C₂₀H₂₆BrN₂O₆: 471.1].

Step 5: 1-t-Butyl 2-methyl (2S,4R)-4-{[(4-vinyl-1,3-dihydro-2H-isoindol-2-yl)carbonyl]oxy}pyrrolidine-1,2-dicarboxylate

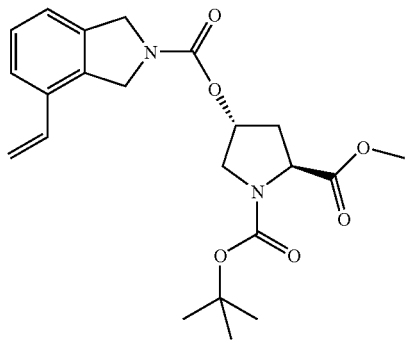

To a solution of 1-t-butyl 2-methyl (2S,4R)-4-{[(4-bromo-1,3-dihydro-2H-isoindol-2-yl)carbonyl]oxy}pyrrolidine-1,2-dicarboxylate (10.0 g, 21.3 mmol) in ethanol (200 mL) was added potassium vinyltrifluoroborate (4.28 g, 32 mmol) and triethylamine (4.5 mL, 32 mmol) followed by dichloro[1,1-bis(diphenylphosphino)ferrocene]palladium (II) chloride dichloromethane adduct (175 mg, 0.21 mmol). The reaction mixture was heated to reflux for 6 h, cooled to room temperature, diluted with 10% aqueous KHSO₄ and the ethanol removed by evaporation in vacuo. The aqueous residue was extracted with EtOAc and the organic phase washed with brine, dried over Na₂SO₄, solvent evaporated and crude product purified by chromatography on silica eluting with 40-60% EtOAc/hexane to give, after evaporation, the title compound (8.18 g). LRMS (ESI) m/z 417.2 [(M+H)⁺; calcd for C₂₂H₂₉N₂O₆: 417.2].

Step 6: (3R,5S)-5-(Methoxycarbonyl)pyrrolidin-3-yl 4-vinyl-1,3-dihydro-2H-isoindole-2-carboxylate Hydrochloride

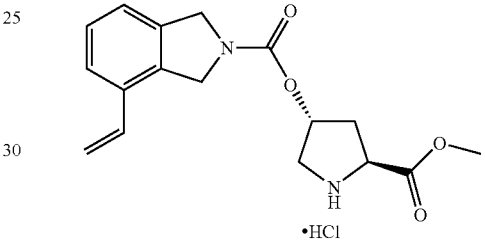

A mixture of 1-t-butyl 2-methyl (2S,4R)-4-{[(4-vinyl-1,3-dihydro-2H-isoindol-2-yl)carbonyl]oxy}pyrrolidine-1,2-dicarboxylate (18.0 g, 43.2 mmol) and HCl/dioxane (4 M) (43.2 mL, 173 mmol) was stirred at RT for 2 h. The reaction mixture was concentrated to remove the dioxane followed by concentration from Et₂O to give (3R,5S)-5-(methoxycarbonyl)pyrrolidin-3-yl 4-vinyl-1,3-dihydro-2H-isoindole-2-carboxylate hydrochloride as an off-white solid (15 g) which was used without further purification. LRMS (ESI) m/z 317 [(M+H)⁺; calcd for C₁₇H₂₁N₂O₄: 317].

Step 7: Methyl N-{[(2,2-dimethylhex-5-en-1-yl)oxy]carbonyl}-3-methyl-L-valyl-(4R)-4-{[(4-vinyl-1,3-dihydro-2H-isoindol-2-yl)carbonyl]oxy}-L-prolinate

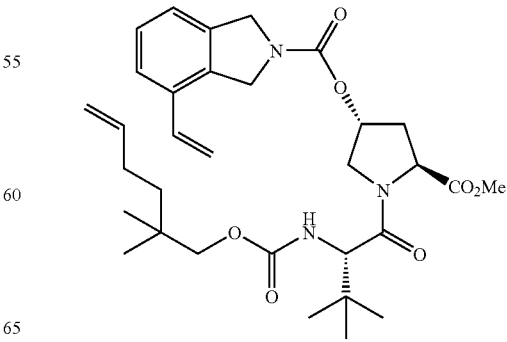

To a solution of (3R,5S)-5-(methoxycarbonyl)pyrrolidin-3-yl 4-vinyl-1,3-dihydro-2H-isoindole-2-carboxylate hydrochloride (5.0 g, 14.2 mmol) and N-{[(2,2-dimethylhex-5-enyl)oxy]carbonyl}-3-methyl-L-valine (4.0 g, 14.2 mmol) in DMF (20 ml) at RT was added DIPEA (2.5 mL, 14.2 mmol), EDC (5.5 g, 28.4 mmol), and HOAt (1.9 g, 14.2 mmol). After 18 h the reaction mixture was poured into Et$_2$O, and extracted with 1 N HCl. The aqueous layer was extracted with EtOAc, and the combined organic layers were washed with 1 N HCl, water, NaHCO$_3$, and brine. The organic layer was dried over MgSO$_4$ and the solvent was removed in vacuo. The crude product was purified on silica (30% EtOAc in hexanes) to yield 4.2 g of the title compound as a thick oil. LRMS (ESI) m/z 584.4 [(M+H)$^+$; calcd for C$_{32}$H$_{46}$N$_3$O$_7$: 584.3].

Step 8: Methyl (5R,7S,10S,18E)-10-tert-butyl-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate

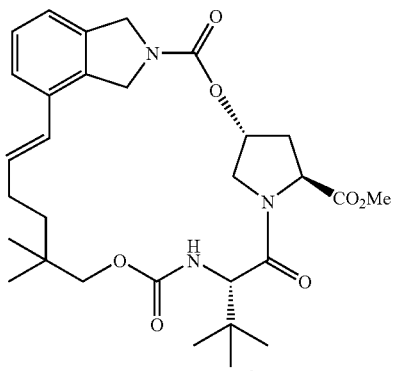

To a solution of methyl N-{[(2,2-dimethylhex-5-en-1-yl)oxy]carbonyl}-3-methyl-L-valyl-(4R)-4-{[(4-vinyl-1,3-dihydro-2H-isoindol-2-yl)carbonyl]oxy}-L-prolinate (4.7 g, 8.05 mmol) in degassed (nitrogen bubbling for 30 min) DCM (1410 mL) was added Zhan 1B catalyst (Zhan catalyst 1B, RC-303, Zannan Pharma Ltd.) (0.591 g, 0.805 mmol). The mixture was then stirred at RT under an N$_2$ atmosphere. After 19 h, the reaction was complete and DMSO (57 μL, 0.805 mmol) was added. The mixture was stirred for 2 h and the mixture was concentrated in vacuo to ~70 mL. The crude product was then directly purified on silica (gradient elution, 0-50% EtOAc in hexanes) to yield 4.4 g of the title compound as an oil. LRMS (ESI) m/z 556.3 [(M+H)$^+$; calcd for C$_{30}$H$_{42}$N$_3$O$_7$: 556.3].

Step 9: Methyl (5R,7S,10S)-10-tert-butyl-15,15-dimethyl-3,9,12-trioxo-6,7,9,10,11,12,14,15,16,17,18,19-dodecahydro-1H,5H-2,23:58-dimethano-4,13,2,8,11-benzodioxatriazacyclohenicosine-7-carboxylate

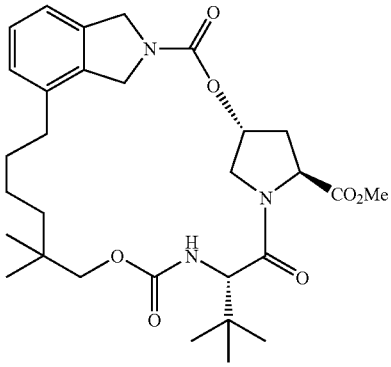

To a solution of methyl (5R,7S,10S,18E)-10-tert-butyl-15,15-dimethyl-3,9,12-trioxo-6,7,9,10,11,12,14,15,16,17-decahydro-1H,5H-2,23:5,8-dimethano-4,13,2,8,11-benzodioxatriaza-cyclohenicosine-7-carboxylate (4.4 g, 7.92 mmol) in EtOAc (79 mL) was added Pd/C (0.421 g, 0.396 mmol). A H$_2$ balloon was then placed on the reaction flask. The flask was evacuated quickly and filled with H$_2$. After 17 h, the reaction was complete as determined by LC-MS. The Pd/C was filtered through glass wool, and the crude product was purified on silica (gradient elution, 0-60% EtOAc in hexanes) to yield 4.01 g of the title compound as a white powder. LRMS (ESI) m/z 558.4 [(M+H)$^+$; calcd for C$_{30}$H$_{44}$N$_3$O$_7$: 558.3].

Step 10: (5R,7S,10S)-10-tert-Butyl-15,15-dimethyl-3,9,12-trioxo-6,7,9,10,11,12,14,15,16,17,18,19-dodecahydro-1H,5H-223:5,8-dimethano-4,13,2,8,11-benzodioxatriazacyclohenicosine-7-carboxylic acid

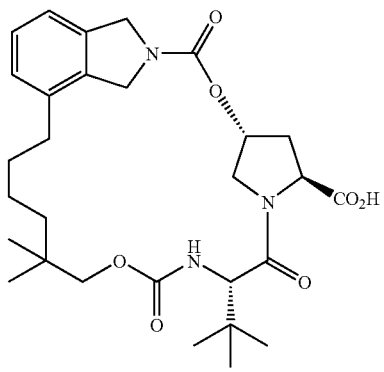

To a solution of methyl (5R,7S,10S)-10-tert-butyl-15,15-dimethyl-3,9,12-trioxo-6,7,9,10,11,12,14,15,16,17,18,19-dodecahydro-1H,5H-2,23:5,8-dimethano-4,13,2,8,1-benzo-dioxatriazacyclohenicosine-7-carboxylate (5.76 g, 10.33 mmol) in THF (41.3 mL), MeOH (41.3 mL), and water (20.7 mL) at RT was added LiOH (4.33 g, 103 mmol). After full conversion (45 min), as judged by LC-MS, the reaction was worked up by partitioning between Et$_2$O and 1N HCl. The aqueous layer was then extracted with EtOAc. The combined organic layers were dried over MgSO$_4$ and the solvent was removed in vacuo to yield 5.53 g of the title compound, which was used without further purification. LRMS (ESI) m/z 544.4 [(M+H)$^+$; calcd for C$_{29}$H$_{42}$N$_3$O$_7$: 544.3].

Step 11: (5R,7S,10S)-10-tert-Butyl-N-((1R,2R)-1-{[(cyclopropylsulfonyl)amino]carbonyl}-2-ethyl-cyclopropyl)-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-205)

To a solution of (5R,7S,10S)-10-tert-Butyl-15,15-dimethyl-3,9,12-trioxo-6,7,9,10,11,12,14,15,16,17,18,19-dodecahydro-1H,5H-2,23:5,8-dimethano-4,13,2,8,11-benzodioxatriaza-cyclohenicosine-7-carboxylic acid (5.53 g, 10.17 mmol) and (1R,2R)-1-amino-N-(cyclopropylsulfonyl)-2-ethylcyclopropanecarboxamide hydrochloride (3.28 g, 12.21 mmol) in DMF (50.9 mL) was added DIPEA (7.11 ml, 40.7 mmol) and HATU (5.03 g, 13.22 mmol). After full conversion (1 h), the reaction mixture was partitioned between EtOAc and 1N HCl. The organic layer was washed with brine three times, dried over MgSO$_4$, and the solvent was removed in vacuo. The crude material was then purified on silica (gradient elution, 20-80% EtOAc in hexanes) to yield 5.8 g of the title compound as a white powder.

EXAMPLE 14

(5R,7S,10S)-10-tert-Butyl-N-((1R,2S)-1-{[(cyclopropylsulfonyl)amino]carbonyl}-2-vinylcyclopropyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-5)

III-5

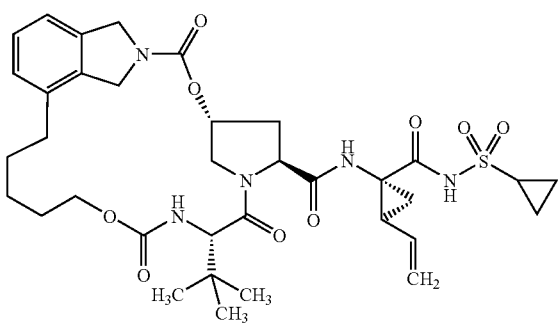

Step 1: Methyl (5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate

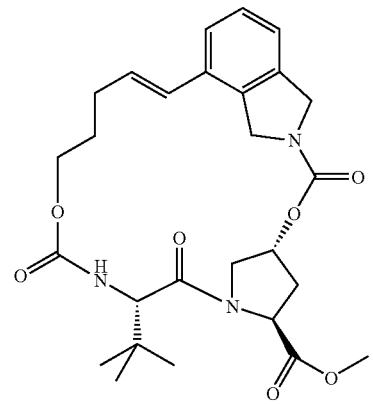

Methyl (5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate was prepared according to the procedure used for methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 3, Step 8) except that 3-methyl-N-[(pent-4-enyloxy)carbonyl]-L-valine (prepared according to the procedure below) was used in place of N-{[(2,2-dimethylpent-4-enyl)oxy]carbonyl}-3-methyl-L-valine in Step 7. LRMS (ESI) m/z 514 [(M+H)$^+$; calcd for C$_{27}$H$_{36}$N$_3$O$_7$: 514].

Step 2: Methyl (5R,7S,10S)-10-tert-butyl-3,9,12-trioxo-1,6,7,9,10,11,12,14,15,16,17,18-dodecahydro-5H-2,22:5,8-dimethano-4,13,28,11-benzodioxatriazacycloicosine-7-carboxylate

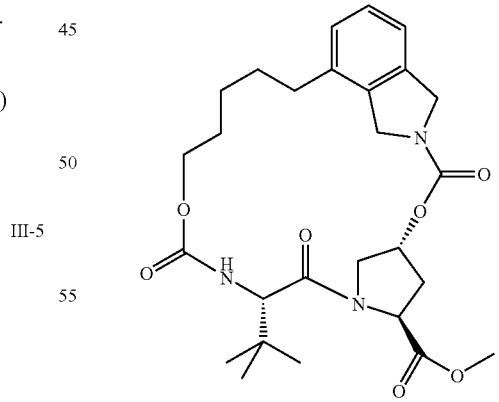

To a solution of methyl (5R,7S,10S)-10-tert-butyl-3,9,12-trioxo-1,6,7,9,10,11,12,14,15,16,17,18-dodecahydro-5H-2,22:5,8-dimethano-4,13,2,8,11-benzodioxatriazacycloicosine-7-carboxylate (0.10 g, 0.20 mmol) in ethyl acetate (7 mL) was added 10% palladium on carbon (0.01 g). The reaction mixture was stirred under a balloon of hydrogen for 5 h at room temperature. Contents of the reaction flask were filtered through CELITE and the filtrate evaporated. The crude product was used with no further purification (0.09 g, 90% yield). LRMS (ESI) m/z 516 [(M+H)$^+$; calcd for $C_{27}H_{38}N_3O_7$: 516].

Step 3: (5R,7S,10S)-10-tert-Butyl-N-((1R,2S)-1-{[(cyclopropylsulfonyl)amino]carbonyl}-2-vinylcyclopropyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide To a solution of methyl (5R,7S,10S)-10-tert-butyl-3,9,12-trioxo-1,6,7,9,10,11,12,14,15,16,17,18-dodecahydro-5H-2,22:5,8-dimethano-4,13,2,8,11-benzodioxatriazacycloicosine-7-carboxylate (90 mg, 0.18 mmol) in THF (2 mL) and MeOH (0.5 mL), was added LiOH (1N 1.75 mL, 1.75 mmol). The reaction mixture was heated to 40° C. and stirred for 1 h, at which time complete consumption of the methyl ester starting material was observed by LC-MS. The mixture was then worked-up with 0.5 N HCl and EtOAc. The organic layer was then dried over $K_2CO_3$, and solvent was removed in vacuo. The crude product was taken up in DMF (1 mL).

To the above solution was added (1R,2S)-1-{[(cyclopropylsulfonyl)amino]carbonyl}-2-vinylcyclopropanaminium chloride (51 mg, 0.19 mmol), TBTU (77 mg, 0.24 mmol) and DIPEA (0.07 mL, 0.40 mmol) and the reaction mixture was stirred at room temperature for 2 h. The reaction mixture was directly purified by reverse phase HPLC to give (5R,7S,10S)-10-tert-butyl-N-((1R,2S)-1-{[(cyclopropylsulfonyl)amino]carbonyl}-2-vinylcyclopropyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (34 mg, 28% yield). $^1$H NMR (500 MHz, ppm, $CD_3OD$) δ 9.14 (s, 1H), 7.23 (t, 1H), 7.13 (d, 1H), 7.10 (d, 1H), 5.75 (quin, 1H), 5.53 (s, 1H), 5.29 (d, 1H), 5.12 (d, 1H), 4.75-4.59 (m, 5H), 4.42 (m, 2H), 4.34 (s, 1H), 4.30 (d, 1H), 3.88 (dd, 1H), 3.75 (m, 1H), 3.60 (q, 2H), 2.95 (m, 1H), 2.63 (m, 1H), 2.41 (m, 2H), 2.26-2.12 (m, 2H), 1.88 (dd, 1H), 1.79 (m, 1H), 1.56 (m, 3H), 1.41 (m, 3H), 1.25 (m, 2H), 1.17 (t, 2H), 1.06 (s, 9H). LRMS (ESI) m/z 714 [(M+H)$^+$; calcd for $C_{35}H_{48}N_5O_9S$: 714].

EXAMPLE 15

(5R,7S,10S)-10-tert-Butyl-N-((1R,2S)-1-{[(cyclopropylsulfonyl)amino]carbonyl}-2-vinylcyclopropyl)-15,15-dimethyl-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-206)

III-206

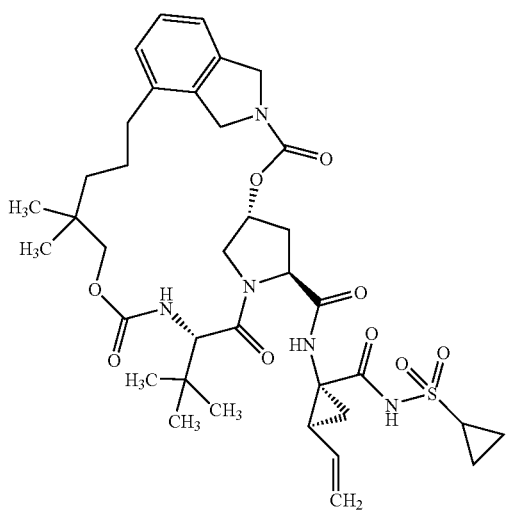

The title compound was prepared according to the procedure used for EXAMPLE 14 (using steps 2 and 3) except that methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 3, Step 1) was used in place of methyl (5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate in Step 2. $^1$H NMR (400 MHz, ppm, $CDCl_3$) δ 9.91 (s, 1H), 7.22 (t, 1H), 7.09 (d, 2H), 7.05 (d, 1H), 5.77 (m, 1H), 5.60 (s, 1H), 5.45 (d, 1H), 5.29 (s, 1H), 5.15 (d, 1H), 4.72 (q, 2H), 4.40-4.55 (m, 4H), 4.30 (d, 1H), 4.25 (d, 1H), 3.78 (dd, 1H), 3.26 (d, 1H), 2.91 (m, 1H), 2.50 (m, 3H), 2.39 (m, 3H), 2.11 (m, 1H), 1.98 (m, 2H), 1.51 (m, 2H), 1.38 (m, 4H), 1.18 (m, 1H), 1.04 (s, 9H), 1.01 (t, 3H), 0.79 (s, 3H). LRMS (ESI) m/z 742 [(M+H)$^+$; calcd for $C_{37}H_{52}N_5O_9S$: 742].

EXAMPLE 16

(5R,7S,10S)-10-tert-Butyl-N-((1R,2R)-1-{[(cyclopropylsulfonyl)amino]carbonyl}-2-ethylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide (III-16)

III-16

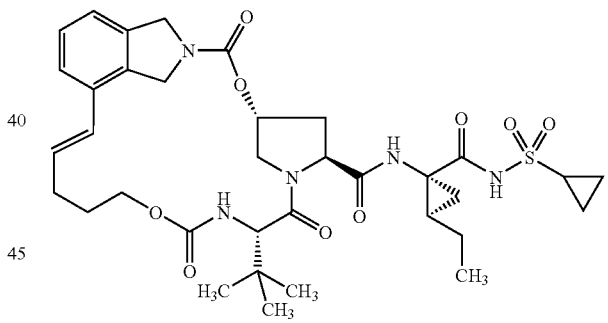

To a solution of methyl (5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 14, Step 1) (60 mg, 0.12 mmol) in THF (1 mL) and MeOH (0.5 mL) was added LiOH (1N 1.17 mL, 1.17 mmol). The reaction mixture was heated to 40° C. and stirred for 1 h, at which time complete consumption of the methyl ester starting material was observed by LC-MS. The mixture was then worked-up with 0.5 N HCl and EtOAc. The organic layer was then dried over $K_2CO_3$, and solvent was removed in vacuo. The crude product was taken up in DMF (1 mL).

To the above solution was added (1R,2R)-1-{[(cyclopropylsulfonyl)amino]carbonyl}-2-ethylcyclopropanaminium chloride (32 mg, 0.12 mmol), TBTU (48 mg, 0.15 mmol) and DIPEA (0.044 mL, 0.25 mmol) and the reaction mixture was stirred at room temperature for 2 h. The reaction mixture was directly purified by reverse phase HPLC to give (5R,7S,10S)-10-tert-butyl-N-((1R,2R)-1-{[(cyclopropylsulfonyl)amino]carbonyl}-2-ethylcyclopropyl)-3,9,12-trioxo-1,6,7,9,10,11,12,14,15,16-decahydro-5H-2,22:5,8-dimethano-4,13,2,8,11-benzodioxatriazacycloicosine-7-carboxamide (55 mg, 67% yield). $^1$H NMR (500 MHz, ppm, CD$_3$OD) δ 7.33 (d, 1H), 7.26 (t, 1H), 7.16 (d, 1H), 6.39 (d, J=15.7 Hz, 1H), 6.13 (m, 1H), 5.37 (s, 1H), 4.69 (m, 4H), 4.47-4.28 (m, 4H), 3.89 (m, 1H), 3.83 (d, 1H), 2.98 (m, 1H), 2.40 (m, 2H), 2.31 (m, 1H), 2.11 (t, 1H), 1.99 (s, 1H), 1.73 (s, 1H), 1.60 (m, 2H), 1.52 (m, 1 H), 1.29-1.15 (m, 3H), 1.08 (s, 9H), 0.98 (t, 3H). LRMS (ESI) m/z 714 [(M+H)$^+$; calcd for C$_{35}$H$_{48}$N$_5$O$_9$S: 714].

EXAMPLE 17

(5R,7S,10S)-10-tert-Butyl-N-((1R,2R)-1-{[(cyclopropylsulfonyl)amino]carbonyl}-2-ethylcyclopropyl)-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide (III-207)

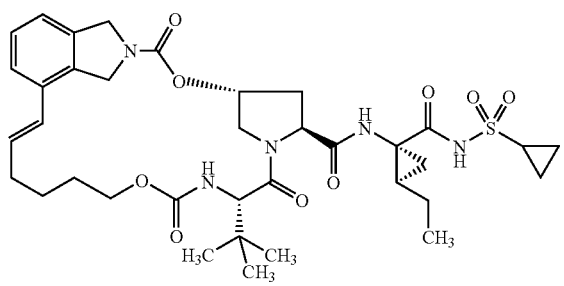
III-207

Step 1: Methyl (5R,7S,10S)-10-tert-butyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate

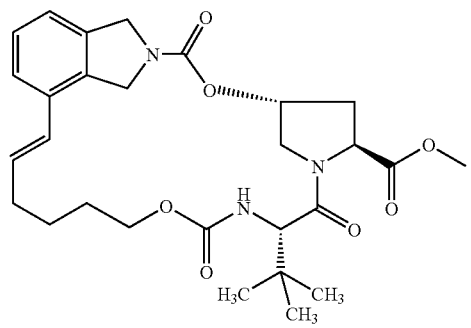

Methyl (5R,7S,10S)-10-tert-butyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate was prepared according to the procedure used for methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 3, Step 8) except that 3-methyl-N-[(hex-5-enyloxy)carbonyl]-L-valine (prepared according to the procedure below) was used in place of N-{[(2,2-dimethylpent-4-enyl)oxy]carbonyl}-3-methyl-L-valine in Step 7.

LRMS (ESI) m/z 528 [(M+H)$^+$; calcd for C$_{28}$H$_{38}$N$_3$O$_7$: 528].

Step 2: (5R,7S,10S)-10-tert-Butyl-N-((1R,2R)-1-{[(cyclopropylsulfonyl)amino]carbonyl}-2-ethylcyclopropyl)-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide EXAMPLE 17 was prepared according to the procedure used for EXAMPLE 16 except using methyl (5R,7S,10S)-10-tert-butyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate in place of methyl-(5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 14, Step 1). $^1$H NMR (500 MHz, ppm, CD$_3$OD) δ 9.06 (s, 1H), 7.27 (t, 1H), 7.24 (d, 1H), 7.18 (d, 1H), 6.40 (d, J=16.4 Hz, 1H), 6.11 (m, 1H), 5.39 (t, 1H), 4.80 (d, 1H), 4.69 (m, 4H), 4.42 (s, 1H), 4.25 (d, 1H), 3.97 (dd, 1 H), 3.79 (quin, 1H), 2.98 (m, 1H), 2.50 (q, 1H), 2.78 (m, 2H), 2.15 (m, 1H), 1.77-1.54 (m, 8 H), 1.32-1.19 (m, 4H), 1.11 (m, 1H), 1.07 (s, 9H), 0.98 (t, 3H). LRMS (ESI) m/z 728 [(M+H)$^+$; calcd for C$_{36}$H$_{50}$N$_5$O$_9$S: 728].

EXAMPLE 18

(5R,7S,10S)-10-tert-Butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17-decahydro-1H,5H-2,23:5,8-dimethano-4,13,28,11-benzodioxatriazacyclohenicosine-7-carboxamide (III-208)

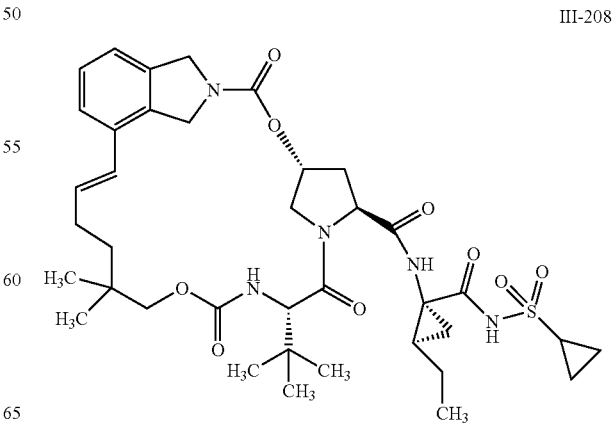
III-208

Step 1: Methyl (5R,7S,10S)-10-tert-butyl-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate

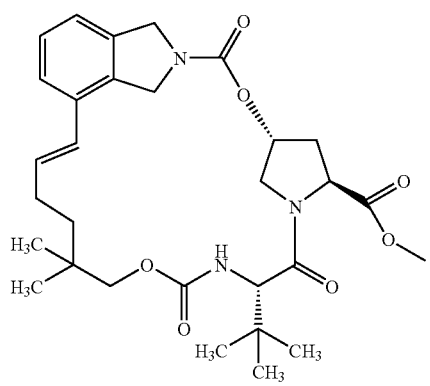

Methyl (5R,7S,10S)-10-tert-butyl-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate was prepared according to the procedure used for methyl (5R,7S,10S)-10-tert-butyl-15,15-dimethyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 3, Step 8) except that N-{[(2,2-dimethylhex-5-enyl)oxy]carbonyl}-3-methyl-L-valine (prepared according to the procedure below) was used in place of N-{[(2,2-dimethylpent-4-enyl)oxy]carbonyl}-3-methyl-L-valine in Step 7. LRMS (ESI) m/z 556 [(M+H)$^+$; calcd for $C_{30}H_{42}N_3O_7$: 556].

Step 2: (5R,7S,10S)-10-tert-Butyl-N-((1R,2R)-1-{[(cyclopropylsulfonyl)amino]carbonyl}-2-ethylcyclopropyl)-15,15-dimethyl-3,9,12-trioxo-6,7,9,10,11,12,13,14,15,16,17-decahydro-1H,5H-2,23:5,8-dimethano-4,13,2,8,11-benzodioxatriazacyclohenicosine-7-carboxamide EXAMPLE 18 was prepared according to the procedure used for EXAMPLE 16 except using methyl (5R,7S,10S)-10-tert-butyl-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxylate in place of methyl-(5R,7S,10S)-10-tert-butyl-3,9,12-trioxo-1,6,7,9,10,11,12,14,15,16-decahydro-5H-2,22:5,8-dimethano-4,13,2,8,11-benzodioxatriazacycloicosine-7-carboxylate (EXAMPLE 14, Step 1). $^1$H NMR (500 MHz, ppm, CD$_3$OD) δ 10.05 (s, 1H), 7.24 (m, 2H), 7.17 (d, 1H), 7.11 (d, 1H), 6.61 (s, 1H), 6.28 (d, J=16.4 Hz, 1H), 5.95 (m, 1H), 5.58 (m, 1H), 5.31 (s, 1H), 4.71 (m, 2H), 4.55 (m, 2H), 4.46 (d, 2 H), 4.29 (dd, 1H), 4.17 (d, 1H), 3.89 (d, 1H), 3.32 (d, 1H), 2.92 (m, 1H), 2.59 (m, 1H), 2.21-2.30 (m, 2H), 2.08 (m, 1H), 1.60-1.78 (m, 6H), 1.22-1.31 (m, 5H), 1.06 (s, 9H), 1.04 (t, 3H), 0.093 (t, 3H), 0.87 (s, 3H). LRMS (ESI) m/z 756 [(M+H)$^+$; calcd for $C_{38}H_{54}N_5O_9S$: 756].

EXAMPLE 19

(5R,7S,10S)-10-tert-Butyl-N-((1R,2S)-1-{[(cyclopropylsulfonyl)amino]carbonyl}-2-vinylcyclopropyl)-13-methyl-3,9,12-trioxo-6,7,9,10,11,12,13,14,15,16-decahydro-1H,5H-2,22:5,8-dimethano-4,2,8,11,13-benzoxatetraazacycloicosine-7-carboxamide (III-4)

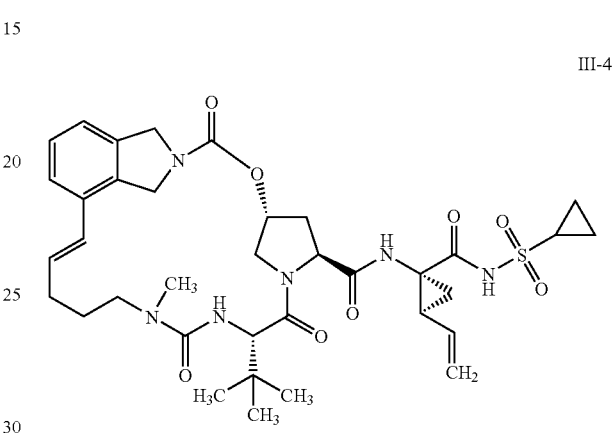

III-4

The title compound was prepared according to the procedure used for EXAMPLE 3 except that 3-methyl-N-{[methyl(pent-4-enyl)amino]carbonyl}-L-valine (prepared according to the procedure below) was used in place of N-{[(2,2-dimethylpent-4-enyl)oxy]carbonyl}-3-methyl-L-valine in Step 7. LRMS (ESI) m/z 725 [(M+H)$^+$; calcd for $C_{36}H_{49}N_6O_8S$: 725].

EXAMPLE 20

(5R,7S,10S)-10-tert-Butyl-N-((1R,2S)-1-{[(cyclopropylsulfonyl)amino]carbonyl}-2-vinylcyclopropyl)-13-methyl-3,9,12-trioxo-1,6,7,9,10,11,12,13,14,15,16,17-dodecahydro-5H-2,23:5,8-dimethano-4,2,8,11,13-benzoxatetraazacyclohenicosine-7-carboxamide (III-145)

III-145

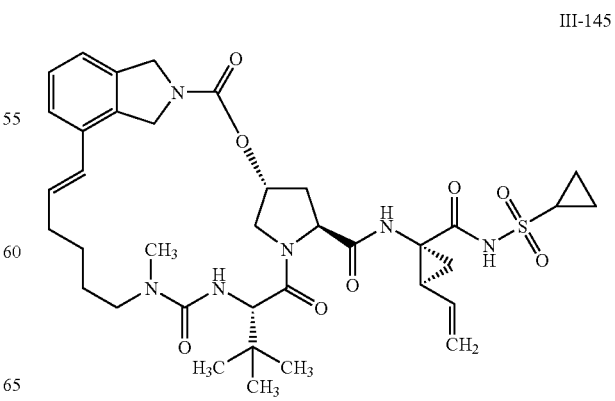

The title compound was prepared according to the procedure used for EXAMPLE 3 except that 3-methyl-N-{[methyl(hex-5-enyl)amino]carbonyl}-L-valine (prepared according to the procedure below) was used in place of N-{[(2,2-dimethylpent-4-enyl)oxy]carbonyl}-3-methyl-L-valine in Step 7. ¹H NMR (500 MHz, ppm, CD₃OD) δ 9.21 (s, 1H), 7.26-7.21 (m, 2 H), 7.16-7.14 (m, 1H), 6.37 (d, J=15 Hz, 1H), 6.13-6.09 (m, 1H), 5.83-5.77 (m, 1H), 5.35-5.26 (m, 3H), 5.12-5.09 (m, 2H), 4.72-4.58 (m, 4H), 4.40-4.36 (m, 1H), 4.23 (d, J=12 Hz, 1 H), 4.10-4.00 (m, 1H), 3.98-3.95 (m, 1H), 2.95-2.80 (m, 5H), 2.51-2.47 (m, 1H), 2.28-2.13 (m, 3H), 1.88-1.84 (m, 1H), 1.72-1.65 (m, 1H), 1.55-1.40 (m, 4H), 1.30-1.20 (m, 2H), 1.15-0.98 (m, 11H). LRMS (ESI) m/z 739 [(M+H)⁺; calcd for $C_{37}H_{51}N_6O_8S$: 739].

EXAMPLE 21

(5R,7S,10S)-10-tert-Butyl-N-((1R,2S)-1-{[(cyclopropylsulfonyl)amino]carbonyl}-2-vinylcyclopropyl)-14,14-dimethyl-3,9,12-trioxo-1,6,7,9,10,11,12,13,14,15,16,17-dodecahydro-5H-2,23:5,8-dimethano-4,2,8,11,13-benzoxatetraazacyclohenicosine-7-carboxamide (III-209)

III-209

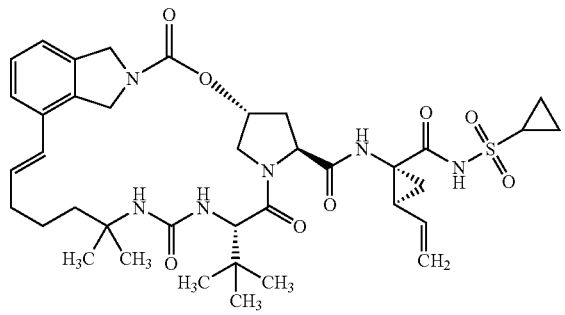

The title compound was prepared according to the procedure used for EXAMPLE 3 except that N-{[(1,1-dimethylhex-5-enyl)amino]carbonyl}-3-methyl-L-valine (prepared according to the procedure below) was used in place of N-{[(2,2-dimethylpent-4-enyl)oxy]carbonyl}-3-methyl-L-valine in Step 7. ¹H NMR (500 MHz, ppm, CD₃OD) δ 7.25 (t, J=7.5 Hz, 1H), 7.15 (t, J=8.4 Hz, 2H), 6.42 (d, J=16 Hz, 1H), 6.01-5.98 (m, 2H), 5.93-5.87 (m, 1H), 5.78-5.72 (m, 1H), 5.54-5.53 (m, 1H), 5.26 (d, J=18 Hz, 1H), 5.10 (d, J=11 Hz, 1 H), 4.76-4.65 (m, 3H), 4.43 (m, 1H), 4.31-4.26 (m, 2H), 3.96-3.92 (m, 1H), 2.93 (m, 1H), 2.42-2.37 (m, 2H), 2.21-2.11 (m, 4H), 1.87-1.84 (m, 1H), 1.52-1.44 (m, 2H), 1.42-1.39 (m, 1 H), 1.36-1.28 (m, 4H), 1.26-1.15 (m, 6H), 1.06 (s, 9H). LRMS (ESI) m/z 753 [(M+H)⁺; calcd for $C_{38}H_{53}N_6O_8S$: 753].

EXAMPLE 22

(6R,8S,11S)-11-tert-Butyl-N-((1R,2S)-1-{[(cyclopropylsulfonyl)amino]carbonyl}-2-vinylcyclopropyl)-4,10,13-trioxo-1,7,8,10,11,12,13,15,16,17-decahydro-2H,6H-3,23:6,9-dimethano-5,1,4,3,9,12-benzodioxatriazacyclohenicosine-8-carboxamide (III-13)

III-13

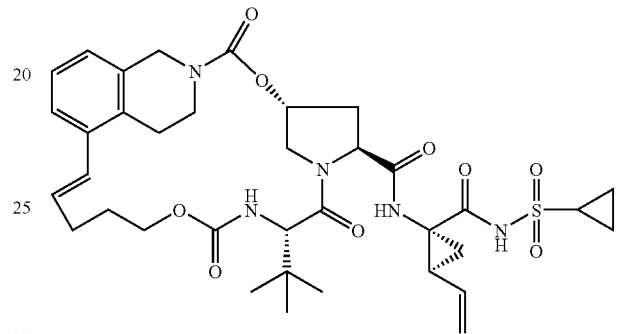

Prepared according to the procedure used for EXAMPLE 1 using 5-bromo-1,2,3,4-tetrahydroisoquinoline hydrochloride in place of 4-chloroisoindoline in Step 1. ¹H NMR (500 MHz, ppm, CDCl₃) δ 7.35 (d, J=8 Hz, 1H), 7.11 (t, J=7.5 Hz, 1H), 7.01 (br d, J=9 Hz, 1H), 6.97 (d, J=7.5 Hz, 1H), 6.50 (d, J=15.5 Hz, 1H), 6.03 (m, 1H), 5.78 (m, 1H), 5.54 (br s, 1H), 5.34 (d, J=17 Hz, 1H), 5.14 (d, J=10 Hz, 1H), 4.95 (d, J=17 Hz, 1H), 4.50 (dd, J=12 Hz, 6.5 Hz, 1H), 4.29 (d, J=16 Hz, 1H), 3.90 (m, 3H), 3.15 (m, 1H), 2.94 (m, 1H), 2.74 (m, 2H), 2.38-2.1 (m, 5H), 2.00 (m, 1H), 1.85 (m, 1H), 1.68 (m, 1H), 1.48 (m, 1H), 1.26 (m, 2H), 1.08 (m, 2H), 0.99 (s, 9H). LRMS (ESI) m/z 726 [(M+H)⁺; calcd for $C_{36}H_{48}N_5O_9S$: 726].

Preparation of
N-[(Pent-4-eN-1-yloxy)carbonyl]-L-norleucine

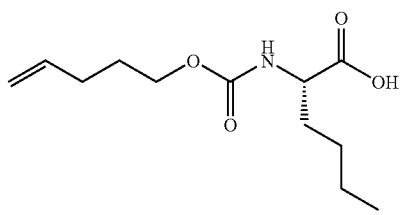

To a solution of 1-penten-4-ol (0.95 g, 11.0 mmol) in DMF (15 mL) at 0° C. was added carbonyldiimidazole (1.79 g, 11.0 mmol). The reaction mixture was warmed to room temperature and stirred for 30 min. L-norleucine methyl ester hydrochloride (2.0 g, 11.0 mmol) was then added, the reaction mixture was heated to 50° C. and stirred for 15 min. Upon cooling, the reaction mixture was diluted with ethyl ether and washed twice with water. The organic layer was dried over sodium sulfate, filtered and concentrated. The crude product was purified by silica gel chromatography (gradient elution 10 to 90% ethyl acetate in hexanes) to afford 2.1 g (74% yield) methyl N-[(pent-4-en-1-yloxy)carbonyl]-L-norleucinate as a clear oil.

To a stirred solution of methyl N-[(pent-4-enyloxy)carbonyl]-L-norleucinate (8.50 g, 33.03 mmol) in THF (20 mL) was added 1N NaOH (20 mL). This reaction solution was stirred at room temperature for 3 h, then acidified to pH 3 with 1N HCl and extracted with (3×250 mL) EtOAc. The combined EtOAc layer was washed with 50 mL water, 50 mL brine, dried over sodium sulfate, filtered and concentrated to give 7.09 g (88% yield) of the title product as clear oil. LRMS (ESI) m/z 244 [(M+H)$^+$; calcd for $C_{12}H_{22}NO_4$: 244].

Preparation of
3-Methyl-N-[(pent-4-enyloxy)carbonyl]-L-valine

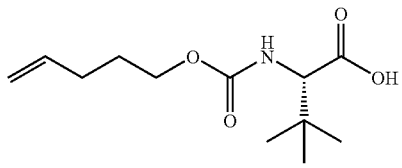

A solution of 4-pentenol (7.22 g, 83.8 mmol) and triphosgene (11.3 g, 38.1 mmol) in dioxane (160 mL) was cooled to 0° C. followed by a dropwise addition of DIPEA (9.85 g, 76.2 mL). The white suspension was stirred vigorously for 1 h at 25° C., then cooled to 0° C. A 1 N solution of NaOH (76.2 mL) and t-butylglycine (10.0 g, 76.2 mmol) were added. The resulting suspension was warmed to 25° C. and stirred for 18 h. Approximately half of the dioxane was removed in vacuo, the solution was poured into 1 N NaOH (100 mL) and washed with dichloromethane (3×150 mL). The aqueous layer was acidified with 6 N HCl and the desired product was extracted with dichloromethane (3×150 mL). The combined organics were dried over MgSO$_4$ and concentrated to give 13.7 g (73.9% yield) of 3-methyl-N-[(pent-4-enyloxy)carbonyl]-L-valine as a colorless oil. LRMS (ESI) m/z 244 [(M+H)$^+$; calcd for $C_{12}H_{22}NO_4$: 244].

Preparation of
N-[(Hex-5-en-1-yloxy)carbonyl]-L-norleucine

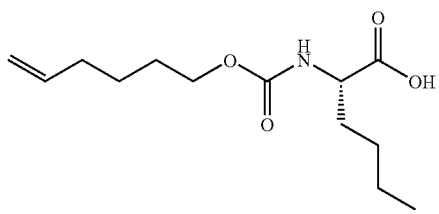

N-[(Hex-5-en-1-yloxy)carbonyl]-L-norleucine was prepared according to the procedure for N-[(pent-4-en-1-yloxy) carbonyl]-L-norleucine by using 5-hexenol instead of 4-pentenol. LRMS (ESI) m/z 258 [(M+H)$^+$; calcd for $C_{13}H_{24}NO_4$: 258].

Preparation of
3-Methyl-N-[(hex-5-enyloxy)carbonyl]-L-valine

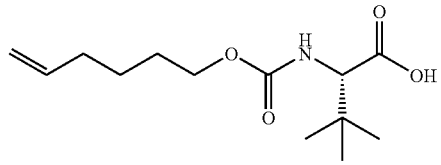

3-Methyl-N-[(hex-5-enyloxy)carbonyl]-L-valine was prepared according to the procedure for 3-methyl-N-[(pent-4-enyloxy)carbonyl]-L-valine by using 5-hexenol instead of 4-pentenol. LRMS (ESI) m/z 258 [(M+H)$^+$; calcd for $C_{13}H_{24}NO_4$: 258].

Preparation of
N-[(Hept-6-en-1-yloxy)carbonyl]-L-norleucine

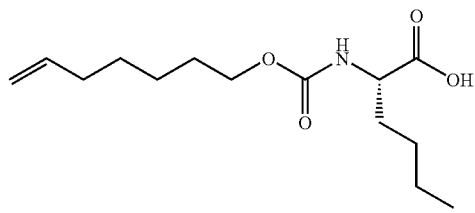

N-[(Hept-6-en-1-yloxy)carbonyl]-L-norleucine was prepared according to the procedure for N-[(pent-4-en-1-yloxy) carbonyl]-L-norleucine by using 6-heptenol instead of 4-pentenol. LRMS (ESI) m/z 272 [(M+H)$^+$; calcd for $C_{14}H_{26}NO_4$: 272].

Preparation of N-{[(2,2-Dimethylpent-4-enyl)oxy] carbonyl}-3-methyl-L-valine

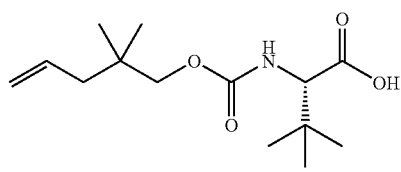

Step 1: 2,2-Dimethylpent-4-en-1-ol

A solution of 2,2-dimethyl 4-pentenoic acid (6.0 g, 46.8 mmol) in anhydrous THF was cooled in an ice bath to 0° C. A slow stream of 1M lithium aluminum hydride in THF (56.2 mL, 56.2 mmol) was added and the reaction was allowed to warm to 25° C. The reaction mixture was stirred for 1 h before pouring into 1N HCl and diethyl ether. The organic layer was separated, dried over MgSO₄ and concentrated to provide 2,2-dimethylpent-4-en-1-ol as a clear oil (4.7 g, 87.9% yield).

Step 2: N-{[(2,2-Dimethylpent-4-enyl)oxy]carbonyl}-3-methyl-L-valine

DIPEA (2.48 g, 19.2 mmol) was added dropwise to a 0° C. solution of 2,2-dimethylpent-4-en-1-ol (2.24 g, 19.6 mmol) and triphosgene (2.56 g, 8.64 mmol) in 60 mL dioxane. The resulting white suspension was stirred for 5 min at 0° C., then allowed to warm to 25° C. over 1 h. The suspension was cooled to 0° C. with an ice bath, followed by addition of 1 N NaOH (19.2 mL) and L-tert-butylglycine (2.52 g, 19.2 mmol). The reaction mixture was warmed to 25° C. and stirred for 72 h. The dioxane was removed in vacuo and the reaction mixture was basified to pH 12 with 1 N NaOH. The aqueous layer was extracted with dichloromethane (3×150 mL), then acidified to pH~1 with 6 N HCl. The aqueous layer was extracted with dichloromethane (3×150 mL). The combined organic layers were dried over MgSO₄ and concentrated to give N-{[(2,2-dimethylpent-4-enyl)oxy]carbonyl}-3-methyl-L-valine as a white powder (4.26 g, 827% yield). LRMS (ESI) m/z 272 [(M+H)⁺; calcd for $C_{14}H_{26}NO_4$: 272].

Preparation of N-{[(2,2-Dimethylhex-5-enyl)oxy]carbonyl}-3-methyl-L-valine

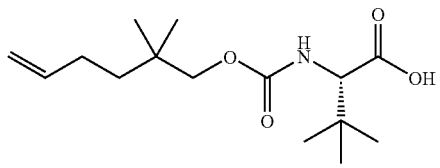

Step 1: Ethyl 2,2-dimethylhex-5-enoate

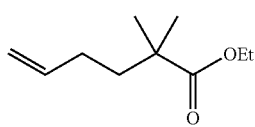

To a stirred solution of diisopropylamine (13.38 mL, 94.70 mmol) in anhydrous THF (50 mL), at −70° C. and under nitrogen, was slowly added 2.5 M n-BuLi in ether (36.50 mL, 91.25 mmol). Stirred for 15 minutes, to this reaction solution was then added dropwise ethyl isobutyrate (11.51 mL, 86.09 mmol) in THF (50 mL), stirred for 20 minutes before added dropwise 4-bromo-1-butene (9.79 mL, 96.42 mmol) in HMPA (20 mL). The reaction solution was then stirred to −50° C. in 5 hours, quenched with 1M HCl (10 mL) and water (100 mL), then extracted with (3×125 mL) ether. The combined ether layer was washed with water (4×70 mL), aqueous saturated NaHCO₃ (2×70 mL), dried over Na₂SO4, filtered and concentrated. The crude product was flash chromatographed on 120 g silica gel 60, eluting with 1-20% EtOAc/Hexane to give the title product as clear oil (11.01 g, 75% yield). LRMS (ESI) m/z 171 [(M+H)⁺; calcd for $C_{10}H_{19}O_2$: 171].

Step 2: 2,2-Dimethylhex-5-en-1-ol

To a stirred solution of 1M LAH in ether (142.14 mL, 142.14 mmol), at 0° C. and under nitrogen, was added dropwise ethyl 2,2-dimethylhex-5-enoate (11.00 g, 64.61 mmol) dissolved in 100 mL anhydrous ether over 1 hour. This reaction solution was stirred at 22° C. for 20 hours, then quenched with water (3 mL), 1M NaOH (11 mL) and water (9 mL), dried over Na2SO4, filtered and concentrated to give the title product (7.22 g, 87.09%). ¹H NMR (500 MHz, CDCl₃) δ 5.85-5.77 (m, 1H); 5.01 (d, 1H); 4.93 (d, 1H); 3.33 (d, 2H); 2.03 (m, 2H); 1.34 (m, 2H); 0.89 (m, 6H) ppm.

Step 3: N-{[(2,2-Dimethylhex-5-enyl)oxy]carbonyl}-3-methyl-L-valine

To a stirred solution of 2,2-dimethylhex-5-en-1-ol (10.75 g, 83.85 mmol) in anhydrous 1,4-dioxane (100 mL), at 0° C. and under nitrogen, was added triphosgene (13.69 g, 46.12 mmol) and then DIPEA (14.61 mL, 83.85 mmol) cautiously. This reaction solution was stirred at 22° C. for 1 hour, cooled to 0° C. and added slowly 1N NaOH (83.85 mL, 83.85 mmol) and L-tert-leucine (11.00 g, 83.85 mmol), then stirred at 22° C. for 20 hours. The reaction solution was basified to pH 10 with 1N NaOH, washed with CH₂Cl₂ (3×100 mL), acidified to pH 5 with 1N HCl and extracted with CH₂Cl₂ (3×150 mL). The combined CH₂Cl₂ layer was washed with water (100 mL), dried over Na2SO4, filtered and concentrated to give the title product (20.26 g, 84.66%). ¹H NMR (500 MHz, CDCl₃) δ 5.85-5.77 (m, 1H); 5.24 (d, 1H); 5.01 (d, 1H); 4.93 (d, 1H); 4.20 (d, 1H); 3.86 (d, 1H); 3.79 (d, 1H); 2.01 (m, 2H); 1.36 (m, 2 H); 1.04 (s, 9H); 0.92 (m, 6H) ppm. LRMS (ESI) m/z 286 [(M+H)⁺; calcd for $C_{15}H_{28}NO_4$: 286].

Preparation of 3-Methyl-N-{[methyl(pent-4-enyl)amino]carbonyl}-L-valine

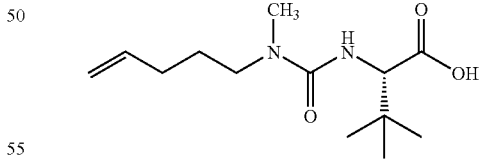

Step 1: N-Methylpent-4-enamide

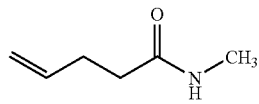

A solution of DIPEA (14.7 mL, 84.7 mmol) in methylenechloride (400 mL) was cooled using an ice bath then saturated with methylamine gas. A solution of 4-pentenoyl chloride (10.0 g, 84.7 mmol) in methylenechloride (100 mL) was added to the reaction flask dropwise via an addition funnel. Contents of the reaction flask were stirred with cooling 2 h then washed with 5% potassium bisulfate. The organic layer was dried with sodium sulfate (anh.), filtered and evaporated. Flash column chromatography eluting with ethyl acetate/hexane 60/40 gave after evaporation N-methylpent-4-enamide as a colorless oil, 8.65 g (90% yield).

Step 2: N-Methylpent-4-en-1-amine

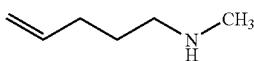

A solution of N-methylpent-4-enamide (8.20 g, 72.3 mmol) in tetrahydrofuran (200 mL) was cooled to −70° C. under nitrogen. Lithium aluminum hydride solution (1.0 M in ether, 200 mL, 200 mmol) was added in a stream. Contents of the reaction flask were first warmed to 0° C. and placed in a freezer for 18 h then heated to 50° C. for 5 h. The reaction was cooled to −70° C. and quenched by dropwise addition of water (8 mL), 2N sodium hydroxide (8 mL), then water (10 mL). Contents of the reaction flask were warmed to room temperature, filtered, and the filtrate dried with anhydrous magnesium sulfate. Filtration and concentration afforded the N-methylpent-4-en-1-amine as a colorless oil, 3.16 g (44% yield).

Step 3: Methyl 3-methyl-N-(oxomethylene)-L-valinate

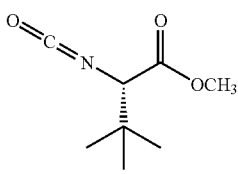

A solution of methyl 3-methyl-L-valinate hydrochloride (10.0 g, 54.9 mmol) and pyridine (22.3 mL, 276 mmol) in methylenechloride (300 mL) was cooled in an ice bath under nitrogen. Phosgene (20% in toluene, 41.1 mL, 83.0 mmol) was added dropwise over 0.5 h using an addition funnel. The resulting mixture was stirred 1 h then poured into cold 1M hydrochloric acid and extracted with methylenechloride (3×100 mL). The combined organic extracts were washed with brine, dried with anhydrous magnesium sulfate, filtered and concentrated. Flash column chromatography eluting with hexane/ethyl acetate 90/10 gave methyl 3-methyl-N-(oxomethylene)-L-valinate as an orange oil, 6.99 g (74% yield).

Step 4: Methyl 3-methyl-N-{[methyl(pent-4-enyl)amino]carbonyl}-L-valinate

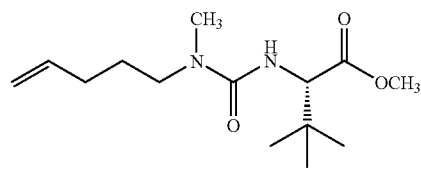

A solution of N-methylpent-4-en-1-amine (2.0 g, 20.2 mmol) in tetrahydrofuran (20 mL) was stirred at room temperature under nitrogen. To this was added methyl 3-methyl-N-(oxomethylene)-L-valinate (3.5 g, 20.2 mmol) and the resulting solution stirred 2 h. Contents of the reaction flask were evaporated and subjected to flash column chromatography eluting with hexane/ethyl acetate 60/40 to give methyl 3-Methyl-N-{[methyl(pent-4-enyl)amino]carbonyl}-L-valinate as an orange oil, 3.02 g (55% yield).

Step 5: 3-Methyl-N-{[methyl(pent-4-enyl)amino]carbonyl}-L-valine

A solution of methyl 3-methyl-N-{[methyl(pent-4-enyl)amino]carbonyl}-L-valinate (3.00 g, 11.2 mmol), lithium hydroxide (1M, 56.0 mL, 56.0 mmol) in tetrahydrofuran (40 mL) was heated to 50° C. for 1 h. Contents of the reaction flask were cooled and evaporated to remove tetrahydrofuran. The remaining mixture was poured into 5% potassium bisulfate and extracted with methylene chloride (3×10 mL). The combined organic extracts were dried with anhydrous sodium sulfate, filtered and evaporated to give the title compound as a colorless oil, 2.87 g (100% yield). LRMS (ESI) m/z 257 [(M+H)$^+$; calcd for $C_{13}H_{25}N_2O_3$: 257].

Preparation of 3-Methyl-N-{[methyl(hex-5-enyl)amino]carbonyl}-L-valine

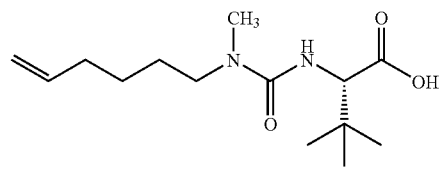

Step 1: 5-Hexenoyl Chloride

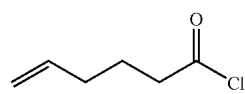

A solution of hex-5-enoic acid (10.0 g, 87.7 mmol) in methylenechloride (250 mL) was cooled in an ice bath under nitrogen. To this was added oxalyl chloride (9.40 mL, 105 mmol) followed by DMF (0.5 mL). The reaction was warmed to room temperature and stirred 18 h. Solvent was removed by evaporation to afford the title compound as a colorless oil.

3-Methyl-N-{[methyl(hex-5-enyl)amino]carbonyl}-L-valine

3-Methyl-N-{[methyl(hex-5-enyl)amino]carbonyl}-L-valine was prepared according to the procedure for 3-methyl-N-{[methyl(pent-4-enyl)amino]carbonyl}-L-valine (Steps 1-5) by using 5-hexenoyl chloride instead of 4-pentenoyl chloride in Step 1. LRMS (ESI) m/z 271 [(M+H)$^+$; calcd for $C_{14}H_{27}N_2O_3$: 271].

Preparation of N-{[(1,1-Dimethylhex-5-enyl)amino]carbonyl}-3-methyl-L-valine

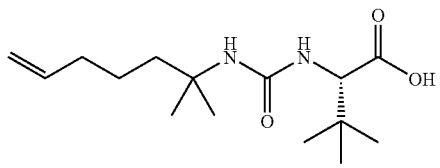

Step 1: 2-Methylhept-6-en-2-amine

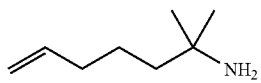

Cerium chloride (25.0 g, 102 mmol) was dried in a 1 L round bottom flask under vacuum for 24 h at 125° C. The flask was cooled to room temperature and tetrahydrofuran (200 mL) was added and the resulting mixture stirred 24 h. The reaction flask was cooled to −70° C. and methyl lithium (1.6M, 100 mL, 160 mmol) was added via cannula. The reaction was stirred 0.5 h with cooling then warmed to 25° C. over 20 min. The reaction was cooled to −70° C. and hex-5-enenitrile (5.0 mL, 44.1 mmol) in tetrahydrofuran (5 mL) was added to give a red-orange suspension. After stirring 20 min the reaction was quenched by slow addition of ammonium hydroxide (10 mL) and warmed to room temperature. The reaction was filtered through CELITE and the filtrate concentrated. Flash column chromatography methylenechloride/methanol/ammonium hydroxide 90/10/1 gave after evaporation of fractions the title compound as a colorless oil, 1.15 g (21% yield). LRMS (ESI) m/z 285 [(M+H)$^+$; calcd for $C_{15}H_{29}N_2O_3$: 285].

N-{[(1,1-Dimethylhex-5-enyl)amino]carbonyl}-3-methyl-L-valine

N-{[(1,1-Dimethylhex-5-enyl)amino]carbonyl}-3-methyl-L-valine was prepared according to the procedure for 3-methyl-N-{[methyl(pent-4-enyl)amino]carbonyl}-L-valine (Steps 4-5) by using 2-methylhept-6-en-2-amine instead of N-methylpent-4-en-1-amine in Step 4.

Preparation of (1R,2R)-1-{[(cyclopropylsulfonyl)amino]carbonyl}-2-ethylcyclopropanaminium Chloride

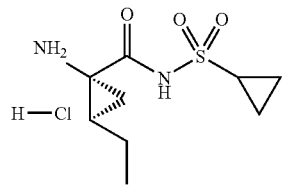

A mixture of (1R,2S)-1-{[(cyclopropylsulfonyl)amino]carbonyl}-2-vinylcyclopropanaminium chloride (Llinas-Brunet et al., US 03/15755 and Wang et al., WO 03/099274) (0.05 g, 0.187 mmol) and palladium on carbon (10% wt., 0.01 g) in EtOAc (5 mL) was vigorously stirred under hydrogen atmosphere provided by a hydrogen balloon for 1 hour. The reaction mixture was filtered and concentrated to give (1R,2R)-1-{[(cyclopropylsulfonyl)amino]carbonyl}-2-ethylcyclopropanaminium chloride (0.045 g, 89% yield).

EXAMPLE 23

(5R,7S,10S)-10-tert-Butyl-N-((1R,2S)-1-{[(cyclopropylsulfonyl)amino]carbonyl}-2-vinylcyclopropyl)-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-210)

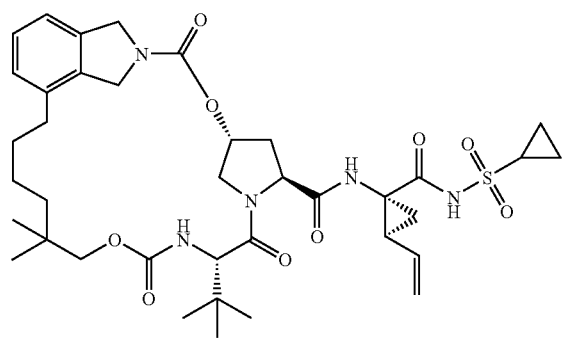

III-210

EXAMPLE 23 was prepared from (5R,7S,10S)-10-tert-butyl-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxylic acid (EXAMPLE 13 Alternative Preparation, Step 10) using the procedure for EXAMPLE 3, Step 10. $^1$H NMR (500 MHz, CD$_3$OD, ppm) δ 7.25-7.09 (m, 3H), 5.82-5.74 (m, 1H), 5.35-5.29 (m, 2H), 5.15-5.12 (m, 1H), 4.75-4.59 (m, 3H), 4.45-4.38 (m, 2H), 4.21-4.12 (m, 1H), 4.13-4.09 (m, 1H), 3.95-3.92 (m, 1 H), 2.98-2.94 (m, 1H), 2.62-2.54 (m, 1H), 2.49-2.46 (m, 2H), 2.25-2.21 (m, 1H), 2.19-2.13 (m, 1H), 1.90-1.88 (m, 1H), 1.52 (m, 2H), 1.48-1.45 (m, 1H), 1.40-1.18 (m, 6H), 1.15-1.00 (m, 14 H), and 0.81 (m, 4H). LRMS (ESI) m/z 756.4 [(M+H)⁺; calcd for $C_{38}H_{53}N_5O_9S$: 755.9].

EXAMPLE 24

(5'R,7'S,10'S,18'E)-10'-tert-Butyl-N-((1R,2S)-1-{[(cyclopropylsulfonyl)amino]carbonyl}-2-vinyl-cyclopropyl)-3',9'12'-trioxo-6',7',9',10',11',12'16',17'-octahydro-1'H,5'H-spiro[cyclohexane-1,15'-[4,13]dioxa[2,8,11]triaza[2,23:5,8]dimethano[4,13,2,8,11]benzodioxatriazacyclo-henicosine]-7'-carboxamide (III-211)

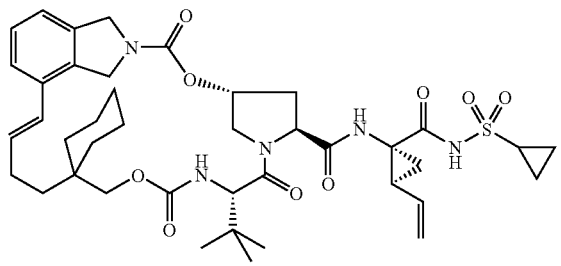

III-211

EXAMPLE 24 was prepared using the procedures from EXAMPLE 13 Alternate Preparation, Steps 7, 8, 10 and 11 using N-{[(1-but-3-en-1-ylcyclohexyl)methoxy]carbonyl}-3-methyl-L-valine in Step 7 and (1R,2S)-1-{[(cyclopropylsulfonyl)amino]carbonyl}-2-vinylcyclopropanaminium chloride in Step 11. ¹H NMR (500 MHz, CD₃OD, ppm) δ 7.27 (t, J=7.6 Hz, 1H), 7.17 (m, 2H), 7.08 (d, J=9.8 Hz, 1H), 6.42 (d, J=16.4 Hz, 1H), 5.95-5.89 (m, 1H), 5.83-5.75 (m, 1H), 5.33-5.28 (m, 1H), 5.13 (d, J=10.3 Hz, 1H), 4.83 (d, J=16.6 Hz, 1 H), 4.73-4.65 (m, 3H), 4.61 (d, J=11.2 Hz, 1H), 4.49 (d, J=9.8 Hz, 1H), 4.41-4.38 (m, 1H), 4.23 (d, J=11.0 Hz, 1H), 3.94 (dd, J=12.0 & 3.4 Hz, 1H), 3.62 (d, J=11.0 Hz, 1H), 2.98-2.93 (m, 1H), 2.62 (q, J=6.6 Hz, 1H), 2.31-2.02 (m, 4H), 1.88 (m, 1H), 1.59-1.41 (m, 10H), 1.31-1.19 (m, 4H), and 1.12-1.06 (m, 10H). LRMS (ESI) m/z 794.6 [(M+H)⁺; calcd for $C_{41}H_{56}N_5O_9S$: 794.4].

EXAMPLE 25

(5'R,7'S,10'S)-10'-tert-Butyl-N-((1R,2R)-1-{[(cyclopropylsulfonyl)amino]carbonyl}-2-ethylcyclopropyl)-3',9',12'-trioxo-6',7',9',10',11',12',16',17',18',19'-decahydro-1'H,5'H-spiro[cyclohexane-1,15'-[4,13]dioxa[2,8,11]triaza[2,23:5,8]dimethano[4,13,2,8,11]benzodioxatriazacyclohenicosine]-7'-carboxamide (III-212)

III-212

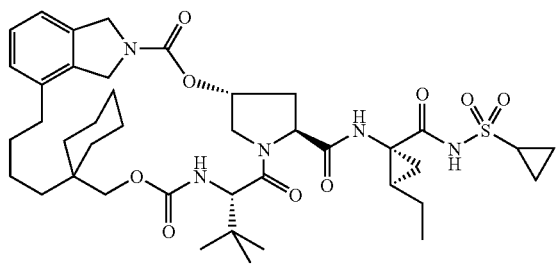

EXAMPLE 25 was prepared from EXAMPLE 24 using the procedure described for EXAMPLE 8. ¹H NMR (500 MHz, CD₃OD, ppm) δ 7.22 (t, J=7.4 Hz, 1H), 7.14 (d, J=7.6 Hz, 1H), 7.08 (d, J=8.1 Hz, 1H), 5.34 (s, 1H), 4.74-4.57 (m, 4H), 4.43 (m, 2H), 4.26-4.18 (m, 2H), 3.90 (d, J=9.3 Hz, 1H), 3.53 (d, J=10.8 Hz, 1H), 2.98 (m, 1H), 2.62-2.46 (m, 3 H), 2.13 (m, 1H), and 1.68-0.92 (m, 39H). LRMS (ESI) m/z 798.6 [(M+H)⁺; calcd for $C_{41}H_{60}N_5O_9S$: 798.4].

EXAMPLE 26

(5'R,7'S,10'S,18'E)-10'-tert-Butyl-N-((1R,2S)-1-{[(cyclopropylsulfonyl)amino]carbonyl}-2-vinyl-cyclopropyl)-3',9',12'-trioxo-6',7',9',10',11',12',16',17'-octahydro-1'H,5'H-spiro[cyclopentane-1,15'-[4,13]dioxa[2,8,11]triaza[2,23:5,8]-dimethano[4,13,2,8,11]benzodioxatriazacyclohenicosine]-7'-carboxamide (III-213)

III-213

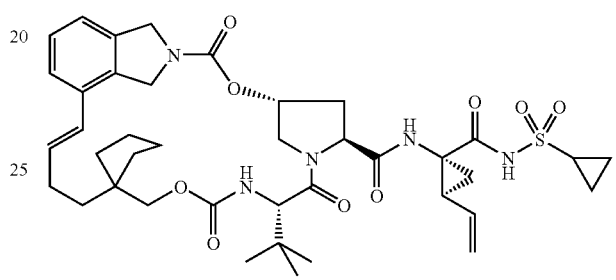

EXAMPLE 26 was prepared using the procedures from EXAMPLE 13 Alternate Preparation, Steps 7, 8, 10 and 11 using N-{[(1-but-3-en-1-ylcyclopentyl)methoxy]carbonyl}-3-methyl-L-valine in Step 7 and (1R,2S)-1-{[(cyclopropylsulfonyl)amino]carbonyl}-2-vinylcyclopropanaminium chloride in Step 11. ¹H NMR (500 MHz, CD₃OD, ppm) δ 7.27 (t, J=7.6 Hz, 1H), 7.20 (d, J=7.6 Hz, 1H), 7.17 (d, J=7.6 Hz, 1H), 7.06 (d, J=9.8 Hz, 1H), 6.41 (d, J=16.1 Hz, 1H), 6.02-5.96 (m, 1H), 5.82-5.75 (m, 1H), 5.31 (m, 2H), 5.13 (d, J=10.3 Hz, 1H), 4.82 (d, J=14.9 Hz, 1H), 4.73-4.65 (m, 4H), 4.48 (d, J=9.8 Hz, 1H), 4.41-4.38 (m, 1 H), 4.22 (d, J=11.2 Hz, 1H), 3.95 (dd, J=12.0 & 3.4 Hz, 1H), 3.45 (d, J=11.0 Hz, 1H), 2.96 (m, 1H), 2.60 (q, J=6.8 Hz, 1H), 2.33 (m, 4H), 2.25 (q, J=9.0 Hz, 1H), 2.17 (m, 2H), 1.90-1.83 (m, 2H), 1.68 (m, 4H), 1.60-1.41 (m, 4H), 1.28 (m, 3H), and 1.13-1.06 (m, 10H). LRMS (ESI) m/z 780.4 [(M+H)⁺; calcd for $C_{40}H_{54}N_5O_9S$: 780.4].

EXAMPLE 27

(5'R,7'S,10'S)-10'-tert-Butyl-N-((1R,2R)-1-{[(cyclopropylsulfonyl)amino]carbonyl}-2-ethylcyclopropyl)-3',9',12'-trioxo-6',7',9',10',11',12',16',17',18',19'-decahydro-1'H,5'H-spiro[cyclopentane-1,15'-[4,13]dioxa[2,8,11]triaza[2,23:5,8]-dimethano[4,13,2,8,11]benzodioxatriazacyclohenicosine]-7'-carboxamide (III-214)

III-214

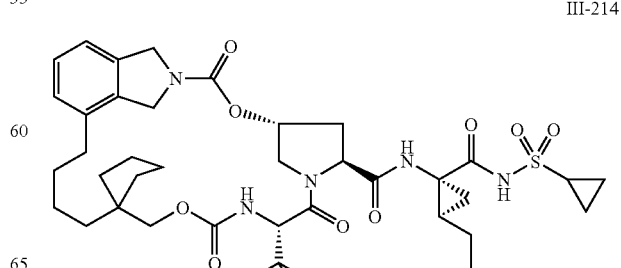

EXAMPLE 27 was prepared from EXAMPLE 26 using the procedure described for EXAMPLE 8. ¹H NMR (500 MHz, CD₃OD, ppm) δ 9.08 (s, 1H), 7.23 (t, J=7.3 Hz, 1H), 7.15 (d, J=7.3 Hz, 1H), 7.09 (d, J=7.1 Hz, 1H), 5.36 (s, 1H), 4.75-4.58 (m, 4H), 4.43 (m, 2 H), 4.34 (d, J=10.5 Hz, 1H), 4.21 (d, J=11.7 Hz, 1H), 3.91 (d, J=10.0 Hz, 1H), 2.98 (brs, 1 H), 2.59-2.49 (m, 3H), 2.14 (m, 1H), 1.82 (m, 1H), and 1.62-0.94 (m, 34H). LRMS (ESI) m/z 784.5 [(M+H)⁺; calcd for C₄₀H₅₈N₅O₉S: 784.4].

EXAMPLE 28

(5'R,7'S,10'S,18'E)-10'-tert-Butyl-N-((1R,2S)-1-{[(cyclopropylsulfonyl)amino]carbonyl}-2-vinyl-cyclopropyl)-3',9',12'-trioxo-6',7',9',10',11',12',16',17'-octahydro-1'H,5'H-spiro[cyclobutane-1,15'-[4,13]dioxa[2,8,11]triaza[2,23:5,8]dimethano[4,13,2,8,11]benzodioxatriazacyclo-henicosine]-7'-carboxamide (III-215)

III-215

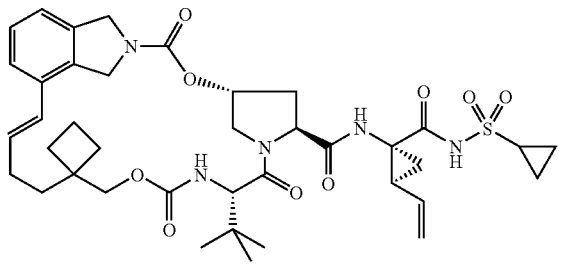

EXAMPLE 28 was prepared using the procedures from EXAMPLE 13 Alternate Preparation, Steps 7, 8, 10 and 11 using N-{[(1-but-3-en-1-ylcyclobutyl)methoxy]carbonyl}-3-methyl-L-valine in Step 7 and (1R,2S)-1-{[(cyclopropylsulfonyl)amino]carbonyl}-2-vinylcyclopropanaminium chloride in Step 11. ¹H NMR (500 MHz, CD₃OD, ppm) δ 7.25 (t, J=7.6 Hz, 1H), 7.20 (d, J=7.6 Hz, 1H), 7.16 (d, J=7.6 Hz, 1H), 7.02 (d, J=9.3 Hz, 1H), 6.40 (d, J=16.1 Hz, 1H), 6.04-5.98 (m, 1H), 5.81-5.73 (m, 1H), 5.31 (m, 2H), 5.11 (d, J=11.5 Hz, 1H), 4.80 (m, 1H), 4.72-4.62 (m, 4H), 4.43 (d, J=9.5 Hz, 1H), 4.40-4.36 (m, 1H), 4.22 (d, J=11.5 Hz, 1H), 3.93 (dd, J=12.0 & 3.7 Hz, 1H), 3.78 (d, J=11.0 Hz, 1H), 2.93 (sep, J=4.2 Hz, 1H), 2.58 (q, J=7.4 Hz, 1H), 2.32 (m, 1H), 2.23-2.11 (m, 4H), 1.98-1.84 (m, 5H), 1.73 (m, 1H), 1.55 (m, 2H), 1.44 (m, 1H), 1.24 (m, 2H), and 1.06 (s, 9H). LRMS (ESI) m/z 766.4 [(M+H)⁺; calcd for C₃₉H₅₂N₅O₉S: 766.3].

EXAMPLE 29

(5'R,7'S,10'S)-10'-tert-Butyl-N-((1R,2R)-1-{[(cyclo-propylsulfonyl)amino]carbonyl}-2-ethylcyclopro-pyl)-3',9',12'-trioxo-6',7',9',10',11',12',16',17',18',19'-decahydro-1'H,5'H-spiro[cyclobutane-1,15'-[4,13]dioxa[2,8,11]triaza[2,23:5,8]dimethano[4,13,2,8,11]benzodioxatriazacyclohenicosine]-7'-carboxamide (III-216)

III-216

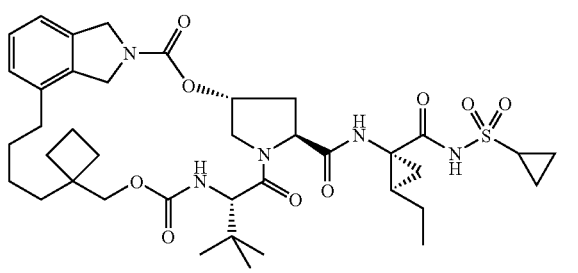

EXAMPLE 29 was prepared from EXAMPLE 28 using the procedure described for EXAMPLE 8. ¹H NMR (500 MHz, CD₃OD, ppm) δ 7.21 (t, J=7.5 Hz, 1H), 7.13 (d, J=7.3 Hz, 1H), 7.07 (d, J=7.1 Hz, 1H), 7.06 (d, J=10.3 Hz, 1H), 5.35 (m, 1H), 4.71 (m, 1H), 4.66-4.57 (m, 3H), 4.44-4.33 (m, 3H), 4.21 (d, J=11.0 Hz, 1H), 3.89 (dd, J=11.7 & 3.2 Hz, 1H), 3.68 (d, J=10.7 Hz, 1H), 2.96 (sep, J=4.3 Hz, 1H), 2.54 (m, 3H), 2.13 (m, 1H), 2.04 (m, 1H), 1.85 (m, 2H), 1.76 (q, J=8.8 Hz, 2H), 1.65-1.39 (m, 9H), 1.32-1.16 (m, 5H), and 1.12-0.87 (m, 14H). LRMS (ESI) m/z 770.6 [(M+H)⁺; calcd for C₃₉H₅₆N₅O₉S: 770.4].

EXAMPLE 30

(5'R,7'S,10'S,18'E)-10'-tert-Butyl-N-((1R,2S)-1-{[(cyclopropylsulfonyl)amino]carbonyl}-2-vinyl-cyclopropyl)-3',9',12'-trioxo-6',7',9',10',11',12',16',17'-octahydro-1'H,5'H-spiro[cyclopropane-1,15'-[4,13]dioxa[2,8,11]triaza[2,23:5,8]dimethano[4,13,2,8,11]benzo-dioxatriazacyclohenicosine]-7'-carboxamide (III-217)

III-217

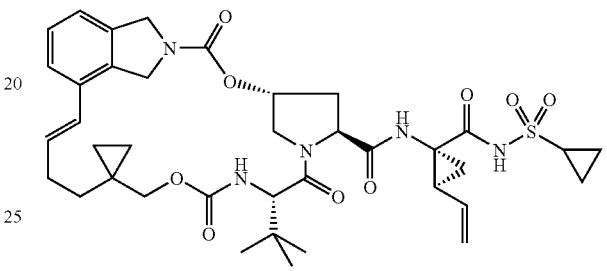

EXAMPLE 30 was prepared using the procedures from EXAMPLE 13 Alternate Preparation, Steps 7, 8, 10 and 11 using N-{[(1-but-3-en-1-ylcyclopropyl)methoxy]carbonyl}-3-methyl-L-valine in Step 7 and (1R,2S)-1-{[(cyclopropylsulfonyl)amino]carbonyl}-2-vinylcyclopropanaminium chloride in Step 11. ¹H NMR (500 MHz, CD₃OD, ppm) δ 7.25 (t, J=7.6 Hz, 1H), 7.17 (d, J=6.6 Hz, 1H), 7.15 (d, J=6.8 Hz, 1H), 7.04 (d, J=8.8 Hz, 1H), 6.41 (d, J=16.1 Hz, 1H), 6.02 (m, 1H), 5.77 (m, 1H), 5.34 (m, 1H), 5.29 (d, J=17.1 Hz, 1H), 5.11 (d, J=11.2 Hz, 1H), 4.87 (m, 1H), 4.67 (m, 3H), 4.42 (m, 2H), 4.24 (d, J=11.0 Hz, 1 H), 3.94 (dd, J=11.7 & 3.7 Hz, 1H), 3.01 (d, J=11.7 Hz, 1H), 2.94 (sep, J=4.2 Hz, 1H), 2.58 (q, J=5.3 Hz, 1H), 2.40 (m, 1H), 2.18 (m, 3H), 1.87 (m, 2H), 1.43 (m, 1H), 1.24 (m, 2 H), 1.05 (m, 11H), 0.58 (m, 1H), and 0.44 (m, 3H). LRMS (ESI) m/z 752.3 [(M+H)⁺; calcd for C₃₈H₅₀N₅O₉S: 752.3].

EXAMPLE 31

(5'R,7'S,10'S)-10'-tert-Butyl-N-((1R,2R)-1-{[(cyclo-propylsulfonyl)amino]carbonyl}-2-ethylcyclopro-pyl)-3',9',12'-trioxo-6',7',9',10',11',12',16',17',18',19'-decahydro-1'H,5'H-spiro[cyclopropane-1,15'-[4,13]dioxa[2,8,11]triaza[2,23:58]dimethano[4,13,2,8,11]benzo-dioxatriazacyclohenicosine]-7'-carboxamide (III-218)

III-218

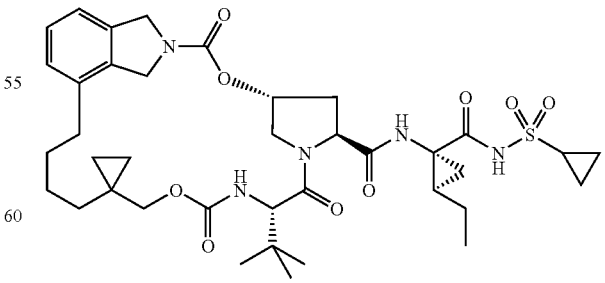

EXAMPLE 31 was prepared from EXAMPLE 30 using the procedure described for EXAMPLE 8. ¹H NMR (500 MHz, CD₃OD, ppm) δ 7.21 (t, J=7.5 Hz, 1H), 7.14 (d, J=7.6 Hz, 1H), 7.06 (d, J=7.6 Hz, 1H), 7.05 (d, J=9.8 Hz, 1H), 5.36

(m, 1H), 4.86 (m, 1H), 4.75-4.59 (m, 4H), 4.45 (m, 1H), 4.36 (d, J=9.5 Hz, 1H), 4.22 (d, J=11.2 Hz, 1H), 3.90 (dd, J=12.0 & 3.4 Hz, 1H), 2.97 (sep, J=4.0 Hz, 1H), 2.86 (d, J=11.5 Hz, 1H), 2.54 (m, 3H), 2.14 (m, 1H), 1.74 (m, 1H), 1.64-1.52 (m, 6H), 1.45-1.19 (m, 6H), 1.11-0.89 (m, 14H), 0.55 (m, 1H), 0.36 (m, 1H), and 0.30 (m, 2H). LRMS (ESI) m/z 756.3 [(M+H)$^+$; calcd for $C_{38}H_{54}N_5O_9S$: 756.4].

EXAMPLE 32

(5R,7S,10S,17E)-N-((1R,2S)-1-{[(Cyclopropylsulfonyl)amino]carbonyl}-2-vinylcyclopropyl)-10-(1-methylcyclohexyl)-3,9,12-trioxo-1,6,7,9,10,11,12,14,15,16-decahydro-5H-2,22:5,8-dimethano-4,13,2,8,11-benzodioxatriazacycloicosine-7-carboxamide (III-219)

III-219

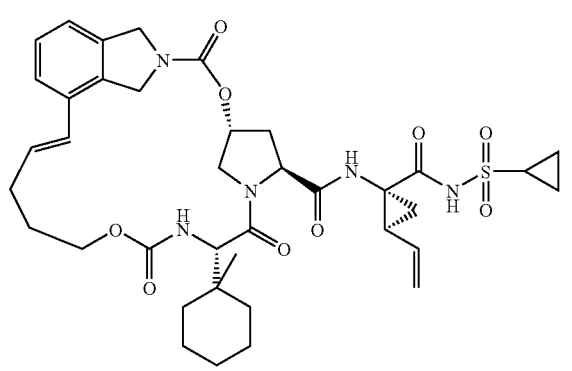

EXAMPLE 32 was prepared using the procedures from EXAMPLE 13 Alternate Preparation, Steps 7, 8, 10 and 11 using (2S)-(1-methylcyclohexyl){[(pent-4-en-1-yloxy)carbonyl]amino}acetic acid in Step 7 and (1R,2S)-1-{[(cyclopropylsulfonyl)amino]carbonyl}-2-vinylcyclopropanaminium chloride in Step 11. $^1$H NMR (500 MHz, CD$_3$OD, ppm) δ 7.32 (d, J=7.5 Hz, 1H), 7.25 (t, J=8.0 Hz, 1H), 7.17 (d, J=7.5 Hz, 1H), 7.15 (d, J=9.5 Hz, 1H), 6.37 (d, J=16.0 Hz, 1H), 6.10 (m, 1H), 5.72 (m, 1H), 5.37 (s, 1H), 5.28 (dd, J=17.0 and 1.5 Hz, 1H), 5.12 (dd, J=10.0 and 1.5 Hz, 1H), 4.67 (m, 4H), 4.42 (m, 3H), 4.28 (m, 1H), 3.87 (m, 2H), 2.93 (m, 1H), 2.40 (m, 2H), 2.31 (m, 1H), 2.22 (m, 1H), 2.12 (m, 1H), 2.0 (m, 1H), 1.88 (dd, J=8.25 and 5.5 Hz, 1H), 1.71 (m, 1H), 1.63-1.36 (m, 10H), 1.30-1.19 (m, 4H), 1.09 (s, 3H), and 1.08 (m, 2H). LRMS (ESI) m/z 752.3 [(M+H)$^+$; calcd for $C_{38}H_{50}N_5O_9S$: 752.3].

EXAMPLE 33

(5R,7S,10S)—N-((1R,2R)-1-{[(Cyclopropylsulfonyl)amino]carbonyl}-2-ethylcyclopropyl)-10-(1-methylcyclohexyl)-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-220)

III-220

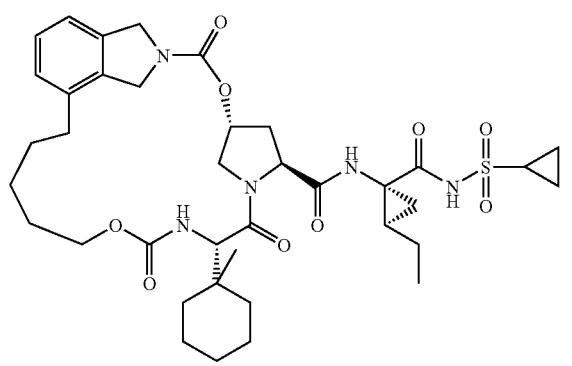

EXAMPLE 33 was prepared from EXAMPLE 32 using the procedure described for EXAMPLE 8. $^1$H NMR (500 MHz, CD$_3$OD, ppm) δ 7.23 (t, J=7.5 Hz, 1H), 7.13 (d, J=7.5 Hz, 1H), 7.09 (d, J=7.5 Hz, 1H), 7.04 (d, J=9.5 Hz, 1H), 5.52 (t, J=3.0 Hz, 1H), 4.67 (m, 4H), 4.45-4.29 (m, 4H), 3.90 (dd, J=12.0 and 3.0 Hz, 1H), 3.74 (m, 1H), 2.96 (m, 1H), 2.62 (m, 1H). 2.44 (m, 1H), 2.40 (m, 1H), 2.15 9m, 1H), 1.87 (m, 1H), 1.64-1.15 (m, 24H), 1.07 (m, 2H), 1.06 (s, 3H), and 0.97 (t, J=7.5 Hz, 1H). LRMS (ESI) m/z 756.4 [(M+H)$^+$; calcd for $C_{38}H_{54}N_5O_9S$: 756.4].

EXAMPLE 34

(5R,7S,10S,18E)-N-((1R,2S)-1-{[(Cyclopropylsulfonyl)amino]carbonyl}-2-vinylcyclopropyl)-15,15-dimethyl-10-(1-methylcyclohexyl)-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide (III-221)

III-221

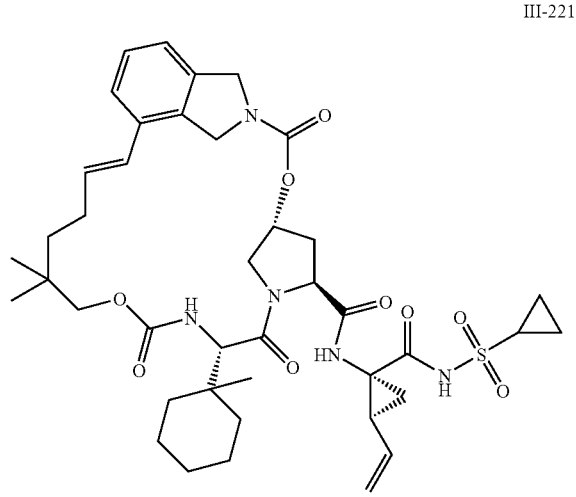

EXAMPLE 34 was prepared using the procedures from EXAMPLE 13 Alternate Preparation, Steps 7, 8, 10 and 11 using (2S)-({[(2,2-dimethylhex-5-en-1-yl)oxy]carbonyl}amino)(1-methylcyclohexyl)acetic acid in Step 7 and (1R,2S)-1-{[(cyclopropylsulfonyl)amino]carbonyl}-2-vinylcyclopropanaminium chloride in Step 11. $^1$H NMR (400 MHz, CDCl$_3$, ppm) δ 10.11 (s, 1H), 7.23 (t, J=9.7 Hz, 1H), 7.16 (d, J=7.3 Hz, 1 H), 7.10 (d, J=7.4 Hz, 1H), 6.69 (s, 1H), 6.28 (d, J=16.1 Hz, 1H), 5.93 (m, 1H), 5.86-5.77 (m, 1H), 5.54 (d, J=9.6 Hz, 1H), 5.33 (s, 1H), 5.23 (d, J=17.2 Hz, 1H), 5.13 (d, J=11.4 Hz, 1H), 4.77-4.62 (m, 3H), 4.69-4.52 (m, 2H), 4.42 (d, J=9.8 Hz, 1H), 4.29 (dd, J=10.6, 6.7 Hz, 1H), 4.12 (m, 1H), 3.91 (dd, J=11.6, 3.8 Hz, 1H), 3.48 (q, J=7.0 Hz, 1H), 3.31 (d, J=10.8 Hz, 1H), 2.88 (m, 1H), 2.62-2.57 (m, 1H), 2.38-2.17 (m, 2H), 2.17-1.97 (m, 3H), 1.63-1.52 (m, 4H), 1.52-1.26 (m, 9H), 1.22-1.11 (m, 3H), 1.05 (s, 3H), 0.99 (s, 3H), and 0.86 (s, 3 H). LRMS (ESI) m/z 794.4 [(M+H)$^+$; calcd for $C_{41}H_{56}N_5O_9S$: 795.0].

EXAMPLE 35

(5R,7S,10S)—N-((1R,2R)-1-{[(Cyclopropylsulfonyl)amino]carbonyl}-2-ethylcyclopropyl)-15,15-dimethyl-10-(1-methylcyclohexyl)-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-222)

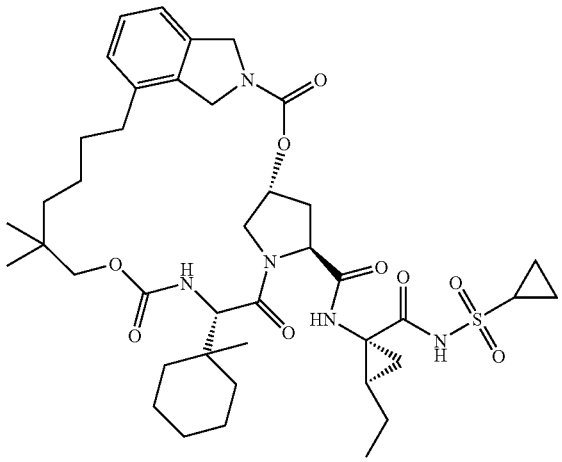

III-222

EXAMPLE 35 was prepared from EXAMPLE 34 using the procedure described for EXAMPLE 8. $^1$H NMR (400 MHz, CDCl$_3$, ppm) δ 9.97 (s, 1H), 7.22 (m, 1H), 7.09 (d, J=7.5 Hz, 1H), 7.06 (d, J=7.3 Hz, 1H), 6.70 (s, 1H), 5.52 (d, J=9.7 Hz, 1H), 5.34 (m, 1H), 4.72 (m, 2H), 4.51-4.38 (m, 3H), 4.31 (m, 1H), 4.18 (d, J=12.0 Hz, 1H), 3.87 (dd, J=11.8, 3.4 Hz, 1H), 3.48 (q, J=7.0 Hz, 2H), 3.25 (d, J=10.7 Hz, 1H), 2.93 (m, 1H), 2.63-2.50 (m, 2H), 2.47-2.28 (m, 2H), 1.64-1.33 (m, 13H), 1.32-1.14 (m, 3H), 1.11-1.08 (m, 11H), 1.06 (s, 3 H), 0.96 (s, 3H), and 0.79 (s, 3H). LRMS (ESI) m/z 798.6 [(M+H)$^+$; calcd for C$_{41}$H$_{60}$N$_5$O$_9$S: 799.0].

EXAMPLE 36

(5R,7S,10S,18E)-N-((1R,2S)-1-{[(Cyclopropylsulfonyl)amino]carbonyl}-2-vinylcyclopropyl)-3,9,12-trioxo-10-(2,22-trifluoroethyl)-6,7,9,10,11,12,14,15,16,17-decahydro-1H,5H-2,23:5,8-dimethano-4,13,2,8,11-benzodioxatriazacyclohenicosine-7-carboxamide (III-134)

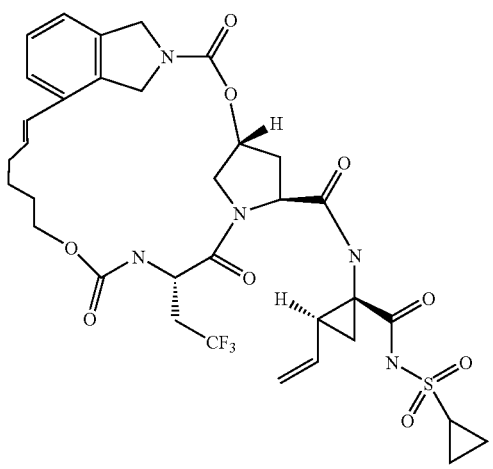

III-134

EXAMPLE 36 was prepared using the procedures from EXAMPLE 13 Alternate Preparation, Steps 7, 8, 10 and 11 using (2S)-4,4,4-trifluoro-2-{[(hex-5-en-1-yloxy)carbonyl]amino}butanoic acid in Step 7 and (1R,2S)-1-{[(cyclopropylsulfonyl)amino]carbonyl}-2-vinylcyclo-propanaminium chloride in Step 11.

LRMS (ESI) m/z 752.3 [(M+H)$^+$; calcd for C$_{34}$H$_{40}$N$_5$O$_9$S: 752.3].

EXAMPLE 37

(5R,7S,10S,18E)-10-(tert-Butoxymethyl)-N-((1R,2S)-1-{[(cyclopropylsulfonyl)amino]carbonyl}-2-vinylcyclopropyl)-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide (III-223)

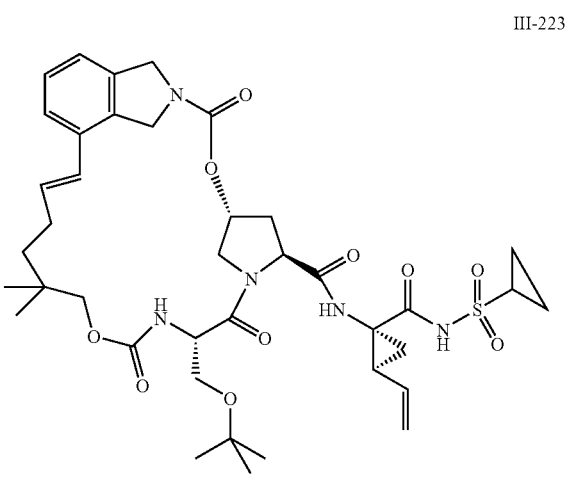

III-223

EXAMPLE 37 was prepared using the procedures from EXAMPLE 13 Alternate Preparation, Steps 7, 8, 10 and 11 using O-(tert-butyl)-N-{[(2,2-dimethylhex-5-en-1-yl)oxy]carbonyl}-L-serine in Step 7 and (1R,2S)-1-{[(cyclopropylsulfonyl)amino]carbonyl}-2-vinylcyclopropanaminium chloride in Step 11. $^1$H NMR (500 MHz, CDCl$_3$, ppm) δ 10.00 (s, 1 H), 7.27 (t, J=7.0 Hz, 1H), 7.20 (d, J=7.0 Hz, 1H), 7.10 (d, J=7.0 Hz, 1H), 6.90 (s, 1H), 6.25 (d, J=16.0 Hz, 1H), 6.00 (m, 1H), 5.85 (m, 1H), 5.60 (d, J=9.0 Hz, 1H), 5.31 (m, 2H), 5.17 (d, J=10.0 Hz, 1H), 4.81-4.85 (m, 1H), 4.65-4.75 (m, 3H), 4.60 (d, J=11.0 Hz, 1H), 4.47-4.54 (m, 2H), 4.15 (d, J=13.5 Hz, 1H), 3.82 (m, 1H), 3.70 (m, 1H), 3.57 (t, J=9.0 Hz, 1H), 3.30 (d, J=11.0 Hz, 1H), 2.91-2.95 (m, 1H), 2.18-2.29 (m, 3H), 1.95-1.97 (m, 1H), 1.54 (s, 6H), 1.42-1.46 (m, 1H), 1.38-1.40 (m, 1H), 1.26-1.34 (m, 3H), 1.21 (s, 9H), 0.99 (s, 3H), and 0.87 (br s, 3H). LRMS (ESI) m/z 784.4 [(M+H)$^+$; calcd for C$_{39}$H$_{53}$N$_5$O$_{10}$S: 784.4].

EXAMPLE 38

(5R,7S,10S)-10-(tert-Butoxymethyl)-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide
(III-224)

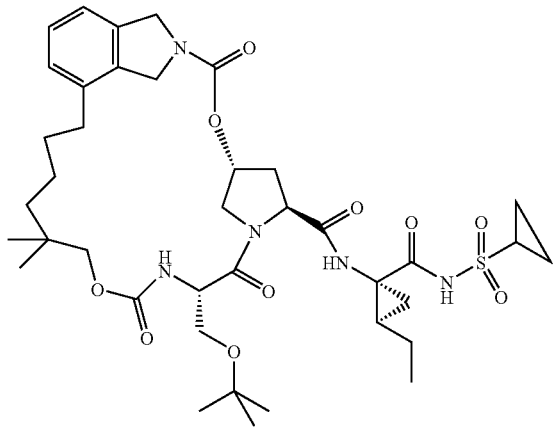

III-224

EXAMPLE 38 was prepared from EXAMPLE 37 using the procedure described for EXAMPLE 8. $^1$H NMR (500 MHz, CDCl$_3$, ppm) δ 10.00 (s, 1H), 7.20 (t, J=7.5 Hz, 1H), 7.10 (d, J=8.0 Hz, 1H), 7.05 (d, J=8.5 Hz, 1H), 6.82 (s, 1H), 5.54 (d, J=9.5 Hz, 1H), 5.31 (m, 1H), 4.80 (m, 1H), 4.68-7.76 (m, 2H), 4.45-4.56 (m, 4H), 4.17 (d, J=11.5 Hz, 1H), 3.78 (m, 1H), 3.68-3.70 (m, 1H), 3.58 (t, J=9.0 Hz, 1H), 3.25 (d, J=11.0 Hz, 1H), 2.95-2.98 (m, 1H), 2.71-2.75 (m, 1H), 2.49-2.51 (m, 1H), 2.37-2.42 (m, 1H), 1.64-1.71 (m, 3H), 1.54 (s, 9H), 1.45-1.33 (m, 3H), 1.26-1.33 (m, 5H), 1.20 (s, 6H), 1.00 (t, J=7.0 Hz, 2H), 0.96 (s, 2 H), and 0.80 (br s, 2H). LRMS (ESI) m/z 788.4 [(M+H)$^+$; calcd for C$_{39}$H$_{57}$N$_5$O$_{10}$S: 788.4].

EXAMPLE 39

(5R,7S,10S,18E)-10-Cyclohexyl-N-((1R,2S)-1-{[(cyclopropylsulfonyl)amino]carbonyl}-2-vinylcyclo propyl)-15,15-dimethyl-3,9,12-trioxo-6,7,9,10,11,12,14,15,16,17-decahydro-1H,5H-2,23:5,8-dimethano-4,13,2,8,11-benzodioxatriazacyclohenicosine-7-carboxamide
(III-225)

III-225

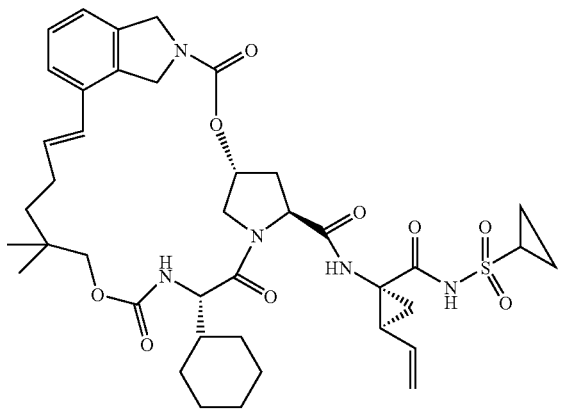

EXAMPLE 39 was prepared using the procedures from EXAMPLE 13 Alternate Preparation, Steps 7, 8, 10 and 11 using (2S)-cyclohexyl({[(2,2-dimethylhex-5-en-1-yl)oxy]carbonyl}amino)acetic acid in Step 7 and (1R,2S)-1-{[(cyclopropylsulfonyl)amino]carbonyl}-2-vinylcyclo-propanaminium chloride in Step 11. $^1$H NMR (500 MHz, CD$_3$OD, ppm) δ 7.26 (m, 1H), 7.20 (t, J=7.5 Hz, 1H), 7.15 (d, J=9.5 Hz, 1 H), 6.38 (d, J=9.5 Hz, 1H), 5.99-6.02 (m, 1H), 5.74-5.80 (m, 1H), 5.29-5.34 (m, 2H), 5.11-5.14 (m, 1H), 4.79-4.81 (m, 2H), 4.64-4.72 (m, 3H), 4.56 (d, J=11.5 Hz, 1H), 4.36-4.40 (m, 2H), 4.18 (d, J=11.5 Hz, 1H), 4.10 (d, J=5.5 Hz, 0.5H), 3.91-3.94 (dd, J=11.5, 3.5 Hz, 1 H), 3.34 (d, J=11.0 Hz, 1H), 2.95-2.97 (m, 1H), 2.52-2.56 (m, 1H), 2.16-2.35 (m, 5H), 1.65-1.82 (m, 8H), and 0.85-1.43 (m, 17H). LRMS (ESI) m/z 780.4 [(M+H)$^+$; calcd for C$_{40}$H$_{53}$N$_5$O$_9$S: 780.9].

EXAMPLE 40

(5R,7S,10S)-10-Cyclohexyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide
(III-226)

III-226

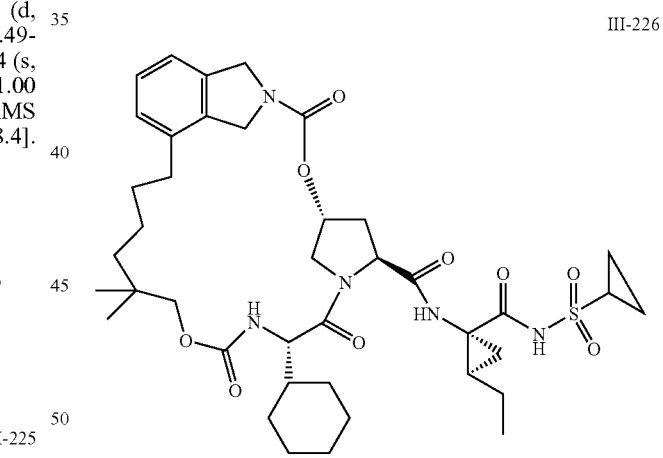

EXAMPLE 40 was prepared from EXAMPLE 39 using the procedure described for EXAMPLE 8. $^1$H NMR (500 MHz, CDCl$_3$, ppm) δ 10.13 (s, 1H), 7.22 (t, J=7.5 Hz, 1H), 7.10 (d, J=7.5 Hz, 1H), 7.05 (d, J=7.5 Hz, 1H), 6.73 (s, 1H), 5.40 (d, J=9.5 Hz, 1H), 5.36 (m, 1H), 4.67-4.76 (m, 2H), 4.55 (d, J=15.5 Hz, 1H), 4.44 (d, J=14.5 Hz, 1H), 4.41 (d, J=11.0 Hz, 1H), 4.29-4.39 (m, 2H), 4.16 (d, J=11.0 Hz, 1H), 3.82-3.85 (dd, J=11.5, 3.5 Hz, 1 H), 3.25 (d, J=11.0 Hz, 1H), 2.95 (m, 1H), 2.51-2.59 (m, 2H), 2.36-2.44 (m, 2H), 1.73-1.76 (m, 5H), and 0.79 (br s, 2H). LRMS (ESI) m/z 784.4 [(M+H)$^+$; calcd for C$_{40}$H$_{57}$N$_5$O$_9$S: 784.4].

EXAMPLE 41

(5R,7S,10S)-10-tert-Butyl-N-((1R,2S)-1-{[(cyclopropylsulfonyl)amino]carbonyl}-2-vinylcyclopropyl)-3,9,12-trioxo-17,18-didehydro-1,6,7,9,10,11,12,14,15,16-decahydro-5H-2,22:5,8-dimethano-4,13,2,8,11-benzodioxatriazacycloicosine-7-carboxamide (III-227)

III-227

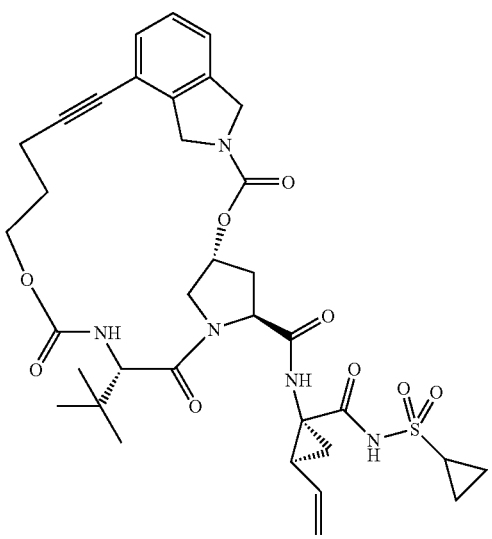

Step 1: 1-tert-Butyl 2-methyl-(2S,4R)-4-{[(4-bromo-1,3-dihydro-2H-isoindol-2-yl)carbonyl]oxy}pyrrolidine-1,2-dicarboxylate

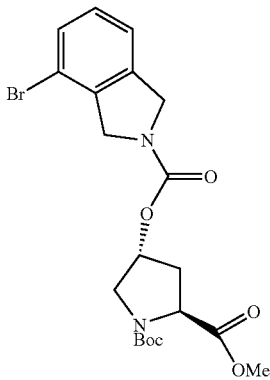

1-tert-Butyl 2-methyl-(2S,4R)-4-{[(4-bromo-1,3-dihydro-2H-isoindol-2-yl)carbonyl]oxy}pyrrolidine-1,2-dicarboxylate was prepared according to the procedure described in EXAMPLE 3, Step 5 using 4-bromoisoindoline instead of 4-vinylisoindoline.

LRMS (ESI) m/z 370.2 [(M-Boc+H); calcd for $C_{15}H_{18}BrN_2O_4$: 370.3].

Step 2: N-[({5-[2-({[(3R,5S)-1-(tert-Butoxycarbonyl)-5-(methoxycarbonyl)pyrrolidin-3-yl]oxy}carbonyl)-2,3-dihydro-1H-isoindol-4-yl]pent-4-yn-1-yl}oxy)carbonyl]-3-methyl-L-valine

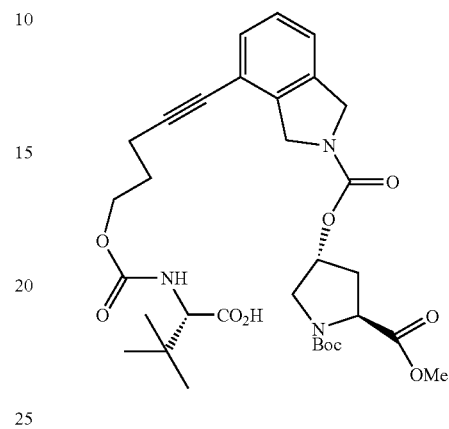

A solution of 1-tert-butyl 2-methyl-(2S,4R)-4-{[(4-bromo-1,3-dihydro-2H-isoindol-2-yl)carbonyl]oxy}pyrrolidine-1,2-dicarboxylate (100 mg, 0.21 mmol) and 3-methyl-N-[(pent-4-yn-1-yloxy)carbonyl]-L-valine (103 mg, 0.43 mmol) in THF (1 mL) and pyrrolidine (1 mL) was purged with nitrogen. Copper iodide (4 mg, 0.02 mmol) and Pd(PPh$_3$)$_4$ (25 mg, 0.02 mmol) were added and the reaction mixture was heated for 30 min at 70° C. under nitrogen. The resulting mixture was poured into saturated aqueous NaHCO$_3$ and EtOAc, the organic layer separated and washed twice with 10% citric acid solution, then brine and dried over Na$_2$SO$_4$. The residue was purified by column chromatography on silica gel (eluting with 90:10:1 DCM:MeOH:NH$_4$OH) and concentrated to give N-[({5-[2-({[(3R,5S)-1-(tert-butoxycarbonyl)-5-(methoxycarbonyl)pyrrolidin-3-yl]oxy}carbonyl)-2,3-dihydro-1H-isoindol-4-yl]pent-4-yn-1-yl}oxy)carbonyl]-3-methyl-L-valine (131 mg, 99% yield) as colorless oil. LRMS (ESI) m/z 530.5 [(M+H)$^+$; calcd for $C_{27}H_{36}N_3O_8$: 530.6].

Step 3: Methyl (5R,7S,10S)-10-tert-butyl-3,9,12-trioxo-17,18-didehydro-1,6,7,9,10,11,12,14,15,16-decahydro-5H-2,22:5,8-dimethano-4,13,2,8,11-benzodioxatriazacycloicosine-7-carboxylate

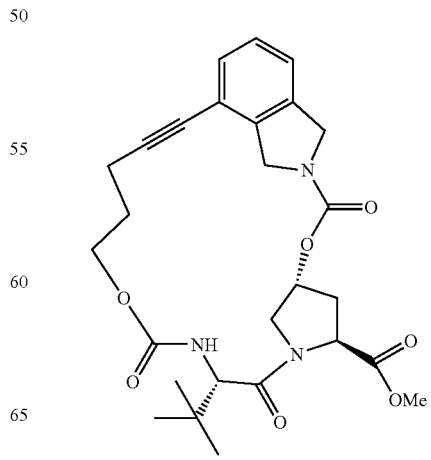

A solution of N-[({5-[2-({[(3R,5S)-1-(tert-butoxycarbonyl)-5-(methoxycarbonyl)pyrrolidin-3-yl]oxy}carbonyl)-2,3-dihydro-1H-isoindol-4-yl]pent-4-yn-1-yl}oxy)carbonyl]-3-methyl-L-valine (131 mg, 0.21 mmol) in DCM was saturated with HCl gas and stirred for 30 min. The resulting amino acid, N-[({5-[2-({[(3R,5S)-5-(methoxycarbonyl)pyrrolidinium-3-yl]oxy}carbonyl)-2,3-dihydro-1H-isoindol-4-yl]pent-4-yn-1-yl}oxy)carbonyl]-3-methyl-L-valine, was obtained through removal of the solvent.

To a solution of this crude amine (120 mg, 0.21 mmol) and Et$_3$N (86 mg, 0.85 mmol) in 5 mL of DCM was added HATU (81 mg, 0.21 mmol) and DMAP (1 mg, 0.008 mmol). The resulting solution was stirred for 2 h at 25° C., then the solvent was evaporated. The crude product was partitioned between 10% aqueous citric acid and EtOAc, the organic layer dried over Na$_2$SO$_4$ and concentrated to an oil. The residue was purified by column chromatography on silica gel (gradient elution, 10 to 70% EtOAc in hexanes) and concentrated to give methyl-(5R,7S,10S)-10-tert-butyl-3,9,12-trioxo-17,18-didehydro-1,6,7,9,10,11,12,14,15,16-decahydro-5H-2,22:5,8-dimethano-4,13,2,8,11-benzodioxatriazacycloicosine-7-carboxylate (47 mg, 43% yield) as a colorless oil. LRMS (ESI) m/z 512.5 [(M+H)$^+$; calcd for C$_{27}$H$_{34}$N$_3$O$_7$: 512.6].

Step 4: (5R,7S,10S)-10-tert-Butyl-N-((1R,2S)-1-{[(cyclopropylsulfonyl)amino]carbonyl}-2-vinylcyclo propyl)-3,9,12-trioxo-17,18-didehydro-1,6,7,9,10,11,12,14,15,16-decahydro-5H-2,22:5,8-dimethano-4,13,2,8,11-benzodioxatriazacycloicosine-7-carboxamide (III-227)

EXAMPLE 41 was prepared from methyl-(5R,7S,10S)-10-tert-butyl-3,9,12-trioxo-17,18-didehydro-1,6,7,9,10,11,12,14,15,16-decahydro-5H-2,22:5,8-dimethano-4,13,2,8,11-benzodioxa-triazacycloicosine-7-carboxylate according to the procedures given in EXAMPLE 13 Alternative Preparation, Steps 10 and 11 using (1R,2S)-1-{[(cyclopropylsulfonyl)amino]carbonyl}-2-vinylcyclo-propanaminium chloride in Step 11. $^1$H NMR (400 MHz, CDCl$_3$, ppm) δ 7.25-7.17 (m, 3H), 7.09 (br s, 1H), 5.80-5.71 (m, 1H), 5.45 (d, J=9.8 Hz, 1H), 5.41 (s, 1H), 5.23 (d, J=17.2 Hz, 1H), 5.13 (d, J=9.6 Hz, 1H), 4.82 (m, 3H), 4.69-4.44 (m, 3H), 4.38 (m, 2H), 3.99 (m, 1H), 3.81 (dd, J=11.2, 2.8 Hz, 1H), 2.89 (m, 1H), 2.80 (s, 1H), 2.69-2.58 (m, 1H), 2.53 (m, 1H), 2.48 (m, 1H), 2.33 (m, 1H), 2.15-2.08 (m, 1H) 1.94 (t, J=5.9 Hz, 2H) 1.83-1.75 (m, 1H), 1.46 (td, J=5.9, 3.3 Hz, 1H), 1.37 (m, 1H), 1.06 (s, 9H), and 1.02 (m, 3H). LRMS (ESI) m/z 710.4 [(M+H)$^+$; calcd for C$_{35}$H$_{44}$N$_5$O$_9$S: 710.8].

EXAMPLE 42

(5R,7S,10S)-10-tert-Butyl-N-((1R,2S)-1-{[(cyclopropylsulfonyl)amino]carbonyl}-2-vinylcyclopropyl)-3,9,12-trioxo-18,19-didehydro-6,7,9,10,11,12,14,15,16,17-decahydro-1H,5H-2,23:5,8-dimethano-4,13,2,8,11-benzodioxatriazacyclohenicosine-7-carboxamide (III-228)

III-228

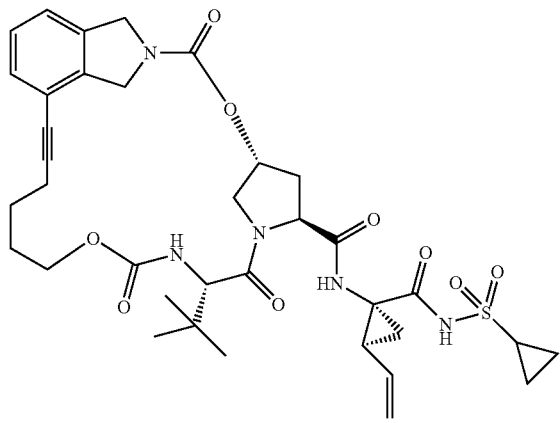

EXAMPLE 42 was prepared according to the procedure described for EXAMPLE 41 except that N-[(hex-5-yn-1-yloxy)carbonyl]-3-methyl-L-valine was used instead of 3-methyl-N-[(pent-4-yn-1-yloxy)carbonyl]-L-valine in Step 1. $^1$H NMR (400 MHz, DMSO-d$_6$, ppm) δ 7.95 (s, 1H), 7.29 (m, 2H), 6.98 (d, J=8.4 Hz, 1H), 6.02 (m, 1H), 5.23 (m, 1H), 5.10-4.92 (m, 1H), 4.84 (m, 1H), 4.66 (m, 2H), 4.57-4.40 (m, 4H), 4.26 (m, 1H), 4.19 (d, J=8.8 Hz, 1 H), 4.01 (m, 1H), 3.84 (m, 1H), 3.62 (m, 1H), 2.74-2.62 (m, 1H), 2.34-2.24 (m, 1H), 2.19 (m, 1H), 1.92 (m, 1H), 1.70-1.62 (m, 2H), 1.59-1.42 (m, 4H), 1.21 (m, 2H), 0.97 (s, 9H), and 0.79-0.58 (m, 4H). LRMS (ESI) m/z 724.3 [(M+H)$^+$; calcd for C$_{36}$H$_{46}$N$_5$O$_9$S: 724.8].

EXAMPLE 43

(5R,7S,10S,17E)-10-tert-Butyl-N-((1R,2S)-1-{[(cyclopropylsulfonyl)amino]carbonyl}-2-vinylcyclopropyl)-21-fluoro-3,9,12-trioxo-1,6,7,9,10,11,12,14,15,16-decahydro-5H-2,22:5,8-dimethano-4,13,2,8,11-benzodioxatriazacycloicosine-7-carboxamide (III-15)

III-15

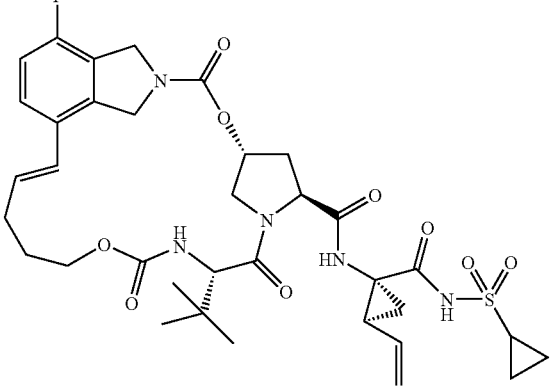

Step 1:
1-Bromo-2,3-bis(bromomethyl)-4-fluorobenzene

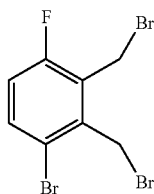

6-Bromo-3-fluoro-o-xylene (5.00 g, 24.6 mmol) was dissolved in 75 mL carbon tetrachloride. N-Bromosuccinimide (8.76 g, 49.2 mmol) and benzoyl peroxide (0.089 g, 0.37 mmol) were added and the resulting white suspension was refluxed for 18 h. The reaction mixture was filtered and the filtrate concentrated to an oily suspension. The residue was purified by column chromatography on silica gel (eluting with hexanes) and concentrated to give 1-bromo-2,3-bis(bromomethyl)-4-fluorobenzene (8.40 g, 94% yield) as a colorless oil. $^1$H NMR (400 MHz, CDCl$_3$, ppm) δ 7.55 (dd, J=8.9, 5.2 Hz, 1H), 6.97 (t, J=8.9 Hz, 1H), 4.78 (s, 3H), and 4.67 (s, 3H).

Step 2: 2-Benzyl-4-bromo-7-fluoroisoindoline

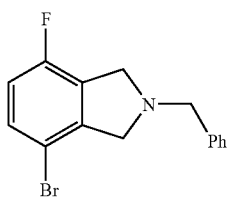

To a mixture of 1-bromo-2,3-bis(bromomethyl)-4-fluorobenzene (7.59 g, 21.0 mmol) and potassium hydrogen carbonate (5.26 g, 52.6 mmol) in 800 mL CH$_3$CN was added benzylamine (2.25 g, 21.0 mmol). The resulting suspension was refluxed for 8 h then stirred at 25° C. for 18 h. The mixture was filtered, and the residue was purified by column chromatography on silica gel (gradient elution, 10 to 60% DCM in hexanes) and concentrated to give 2-benzyl-4-bromo-7-fluoroisoindoline (3.00 g, 46% yield) as colorless oil. LRMS (ESI) m/z 306.3 [(M+H)$^+$; calcd for C$_{15}$H$_{14}$NBrF: 306.2].

Step 3: (5R,7S,10S,17E)-10-tert-Butyl-N-((1R,2S)-1-{[(cyclopropylsulfonyl)amino]carbonyl}-2-vinylcyclopropyl)-21-fluoro-3,9,12-trioxo-1,6,7,9,10,11,12,14,15,16-decahydro-5H-2,22:5,8-dimethano-4,13,2,8,11-benzodioxatriazacycloicosine-7-carboxamide (III-15)

EXAMPLE 43 was prepared from 2-benzyl-4-bromo-7-fluoroisoindoline using the procedures described in EXAMPLE 3, Steps 3-6 and EXAMPLE 13 Alternative Preparation, Steps 7, 8, 10 and 11, using 3-methyl-N-[(pent-4-enyloxy)carbonyl]-L-valine in Step 7 and (1R,2S)-1-{[(cyclopropyl-sulfonyl)amino]carbonyl}-2-vinylcyclopropan-aminium chloride in Step 11. $^1$H NMR (400 MHz, CDCl$_3$, ppm) δ 9.86 (s, 1H), 7.24 (m, 1H), 7.20 (m, 1H), 6.91 (t, J=8.6 Hz, 1H), 6.25 (d, J=16.6 Hz, 1H), 5.99-5.90 (m, 1H), 5.78-5.64 (m, 1H), 5.43 (m, 2 H), 5.25 (d, J=16.6 Hz, 1H), 5.15 (d, J=10.3 Hz, 1H), 4.74 (m, 2H), 4.67 (d, J=15.4 Hz, 1 H), 4.54 (m, 1H), 4.47 (t, J=8.8 Hz, 1H), 4.39-4.31 (m, 2H), 4.30-4.22 (m, 1H), 3.88 (m, 1 H), 3.75 (dd, 1H), 2.95-2.85 (m, 1H), 2.50-2.39 (m, 2H) 2.30-2.21 (m, 2H), 2.15 (m, 1H), 1.97-1.92 (m, 2H), 1.72 (m, 1H), 1.44 (dd, J=9.7, 5.8 Hz, 1H), 1.31 (m, 2H), and 1.08 (m, 11H). LRMS (ESI) m/z 730.4 [(M+H)$^+$; calcd for C$_{35}$H$_{45}$FN$_5$O$_9$S: 730.8].

EXAMPLE 44

(5R,7S,10S)-10-tert-Butyl-N-((1R,2R)-1-4{[(cyclopropylsulfonyl)amino]carbonyl}-2-ethylcyclopropyl)-21-fluoro-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-229)

III-229

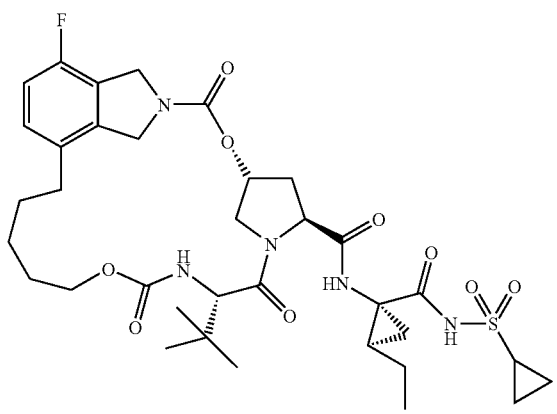

EXAMPLE 44 was prepared from EXAMPLE 43 using the procedure described for EXAMPLE 8. $^1$H NMR (400 MHz, CDCl$_3$, ppm) δ 9.88 (s, 1H), 7.03 (m, 1H), 6.92 (d, J=8.5 Hz 1H), 6.88 (d, J=7.8 Hz, 1H), 5.60 (s, 1H), 5.37 (d, J=9.7 Hz, 1H), 4.83-4.71 (m, 1 H), 4.61 (m, 2H), 4.47-4.23 (m, 4H), 3.80-3.73 (m, 2H), 2.99-2.81 (m, 1H), 2.61-2.54 (m, 1H), 2.42-2.31 (m, 3H), 1.82-1.62 (m, 9H), 1.59-1.52 (m, 2H), 1.38-1.29 (m, 5H), 1.04 (s, 9H), and 0.97 (t, J=7.4 Hz, 3H). LRMS (ESI) m/z 734.4 [(M+H)$^+$; calcd for C$_{35}$H$_{49}$FN$_5$O$_9$S: 734.8].

EXAMPLE 45

(5R,7S,10S)-10-tert-Butyl-N-((1R,2S)-1-{[(cyclopropylsulfonyl)amino]carbonyl}-2-vinylcyclopropyl)-21-methoxy-3,9,12-trioxo-1,6,7,9,1011,12,14,15,16,17,18-dodecahydro-5H-2,22:5,8-dimethano-4,13,2,8,11-benzodioxatriazacycloicosine-7-carboxamide (III-230)

III-230

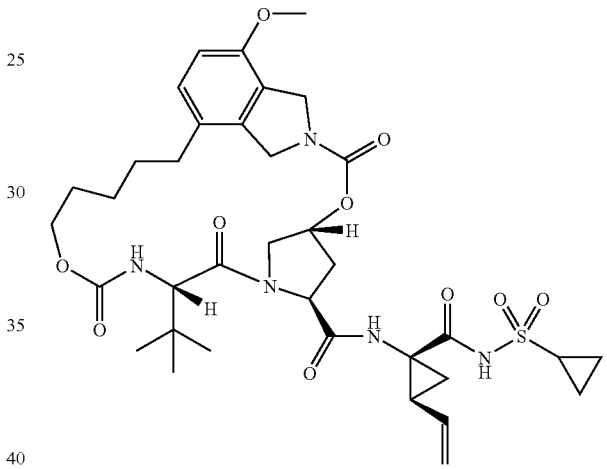

Step 1: 2-Benzyl-4-bromo-7-methoxyisoindoline

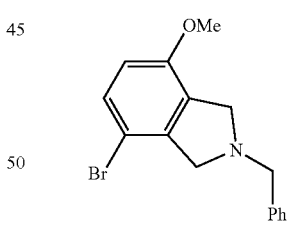

To a solution of methyl 1-bromo-2,3-bis(bromomethyl)-4-methoxybenzene (prepared as described in *J. Org. Chem.* 1992, 57, 6374, from commercially available 1-bromo-4-methoxy-2,3-dimethylbenzene) in CH$_3$CN (0.1 M) were added 2.5 eq of KHCO$_3$ and the mixture heated at 60° C. Then 1 eq. of benzylamine in CH$_3$CN (0.9 M) was added within 15 minutes and the mixture was heated to reflux for 2 h. The reaction mixture was allowed to cool, filtered over celite and concentrated in vacuo. The crude material was purified by flash chromatography on silica gel (5% EtOAc in petroleum ether, then 10%) to afford the title compound (55%). $^1$H NMR (300 MHz, CDCl$_3$, ppm) δ 3.77 (s, 3H), 3.92 (s, 2H), 3.98 (s, 2H), 4.01 (s, 2H), 6.60 (d, J 8.6, 1H), and 7.22-7.46 (m, 6H). MS (ES$^+$) m/z 318, 320 (M+H)$^+$.

Step 2: (3R,5S)-5-(Methoxycarbonyl)pyrrolidin-3-yl 4-methoxy-7-vinyl-1,3-dihydro-2H-isoindole-2-carboxylate Hydrochloride

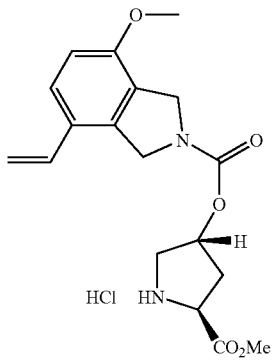

1-tert-Butyl 2-methyl (2S,4R)-4-{[(4-methoxy-7-vinyl-1,3-dihydro-2H-isoindol-2-yl)carbonyl]oxy}pyrrolidine-1,2-dicarboxylate was prepared from 2-benzyl-4-bromo-7-methoxy isoindoline using the procedures described in EXAMPLE 3, Steps 3-5 and was converted to (3R,5S)-5-(methoxycarbonyl)pyrrolidin-3-yl 4-methoxy-7-vinyl-1,3-dihydro-2H-isoindole-2-carboxylate hydrochloride using the following procedure. To a solution of 1-tert-butyl 2-methyl (2S,4R)-4-{[(4-methoxy-7-vinyl-1,3-dihydro-2H-isoindol-2-yl)carbonyl]oxy}pyrrolidine-1,2-dicarboxylate in CH$_3$OH (0.06 M) cooled at 0° C. was added acetyl chloride (70 eq). The resulting mixture was stirred at 5° C. for 4 h and then concentrated in vacuo at 0° C. affording the crude product, which was used straightaway without any further purification. MS (ES$^+$) m/z 347 (M+H)$^+$.

Step 3: (5R,7S,10S)-10-tert-Butyl-N-((1R,2S)-1-{[(cyclopropylsulfonyl)amino]carbonyl}-2-vinylcyclopropyl)-21-methoxy-3,9,12-trioxo-1,6,7,9,10,11,12,14,15,16,17,18-dodecahydro-5H-2,22:5,8-dimethano-4,13,2,8,11-benzodioxatriazacycloicosine-7-carboxamide (III-230)

EXAMPLE 45 was prepared from (3R,5S)-5-(methoxycarbonyl)pyrrolidin-3-yl 4-methoxy-7-vinyl-1,3-dihydro-2H-isoindole-2-carboxylate hydrochloride using the procedures described in EXAMPLE 13 Alternative Preparation, Steps 7 through 11, using 3-methyl-N-[(pent-4-enyloxy)carbonyl]-L-valine in Step 7 and (1R,2S)-1-{[(cyclopropylsulfonyl)amino]carbonyl}-2-vinylcyclo-propanaminium chloride in Step 11. $^1$H NMR (600 MHz, DMSO-d$_6$, ppm) δ 10.46 (s, 1H), 8.85 (s, 1H), 7.10 (d, J=8.3 Hz, 1H), 7.06 (d, J=8.0 Hz, 1H), 6.85 (d, J=8.3 Hz, 1H), 5.63-5.54 (m, 1H), 5.25 (s, 1H), 5.22 (d, J=18.2 Hz, 1H), 5.10 (d, J=11.8 Hz, 1H), 4.64 (d, J=14.2 Hz, 1H), 4.56 (d, J=13.5 Hz, 1H), 4.52 (d, J=13.5 Hz, 1H), 4.50 (d, J=14.2 Hz, 1H), 4.33 (dd, J=10.7 Hz, 6.8 Hz, 1H), 4.23-4.18 (m, 2H), 4.12-4.10 (m, 1H), 3.78 (s, 3H), 3.75-3.71 (m, 2H), 2.96-2.90 (m, 1H), 2.50 (obscured by residual DMSO, 1H), 2.33-2.23 (m, 2H), 2.18-2.11 (m, 1H), 2.06-2.01 (m, 1H), 1.71-1.69 (m, 1H), 1.68-1.62 (m, 1H), 1.53-1.43 (m, 3H), 1.37-1.22 (m, 3H), 1.10-1.07 (m, 2H), 1.05-1.02 (m, 2H), and 1.00-0.86 (m, 9H). LRMS (ESI) m/z 744 [(M+H)$^+$; calcd for C$_{36}$H$_{50}$N$_5$O$_{10}$S: 744.3].

EXAMPLE 46

(5R,7S,10S)-10-tert-Butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dodecahydro-1H,5H-2,23-ethano-5,8-methano-4,13,2,8,11-benzodioxatriazacyclohenicosine-7-carboxamide (III-231)

III-231

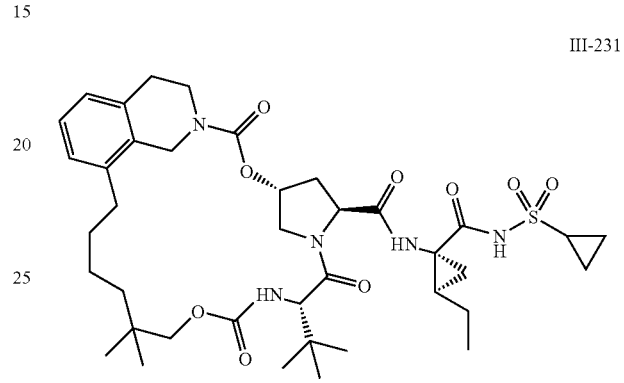

Step 1: 8-Hydroxy-1,2,3,4-tetrahydroisoquinoline Hydrobromide:

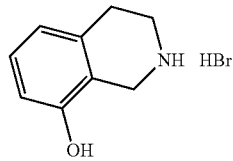

A mixture of 8-methoxy-1,2,3,4-tetrahydroisoquinoline hydrochloride [*Tetrahedron Letters*, 1991, 32(17), 1965.] (3.0 g 15.0 mmol) and 45 mL of 48% aqueous HBr was heated for 18 h at 120° C. The resulting brown suspension was filtered and dried to provide 8-hydroxy-1,2,3,4-tetrahydroisoquinoline hydrobromide (2.8 g, 81% yield). LRMS (ESI) m/z 150.1 [(M+H)$^+$; calcd for C$_9$H$_{11}$NO: 150.2].

Step 2: 1-tert-Butyl 2-methyl (2S,4R)-4-{[(8-hydroxy-3,4-dihydroisoquinolin-2(1H)-yl)carbonyl]oxy}pyrrolidine-1,2-dicarboxylate:

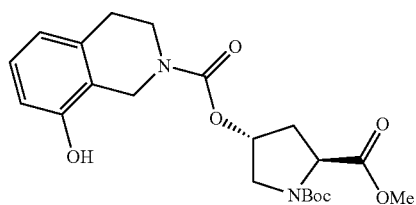

Carbonyldiimidazole (0.176 g, 1.086 mmol) was added to a stirred, room temperature solution of DMF (5 mL) and N-Boc-trans-4-hydroxy-L-proline methyl ester (0.21 g, 0.87 mmol) and the mixture was stirred 45 min. 8-Hydroxy-1,2,3,4-tetrahydroisoquinoline (0.20 g, 0.87 mmol) and Et$_3$N (0.18 g, 1.74 mmol) were added and the resulting solution was heated at 50° C. for 2 h. The reaction mixture was poured into aqueous saturated NH$_4$Cl and extracted with EtOAc, dried over Na$_2$SO$_4$ and concentrated to an oil. The residue was purified by column chromatography on silica gel (gradient elution, 10 to 80% EtOAc in hexanes) to give 1-tert-butyl 2-methyl (2S,4R)-4-{[(8-hydroxy-3,4-dihydroisoquinolin-2(1H)-yl)carbonyl]oxy}pyrrolidine-1,2-dicarboxylate (0.25 g, 0.60 mmol, 69% yield) as a colorless foam after evaporation of solvent. LRMS (ESI) m/z 321.3 [((M-Boc)+H)$^+$; calcd for C$_{16}$H$_{21}$N$_2$O$_5$: 321.4].

Step 3: 1-tert-Butyl 2-methyl (2S,4R)-4-({[8-{[(trifluoromethyl)sulfonyl]oxy}-3,4-dihydroisoquinolin-2(1H)-yl]carbonyl}oxy)pyrrolidine-1,2-dicarboxylate:

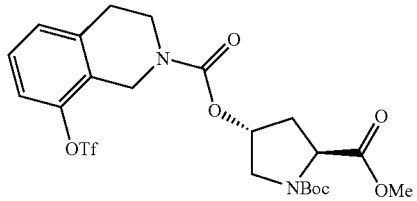

Trifluoromethanesulfonic anhydride (1.76 g, 6.24 mmol) was added to a stirred, 0° C. mixture of 1-tert-butyl 2-methyl (2S,4R)-4-{[(8-hydroxy-3,4-dihydroisoquinolin-2(1H)-yl)carbonyl]oxy}pyrrolidine-1,2-dicarboxylate (1.81 g, 4.30 mmol) and Et$_3$N (1.31 g, 12.90 mmol) in DCM (20 mL) and stirred for 18 h. The resulting mixture was poured into saturated aqueous NaHCO$_3$ and extracted into dichloromethane. The organic layer was washed with 10% citric acid solution, dried over Na$_2$SO$_4$ and concentrated to red oil. The oil was purified by column chromatography on silica gel (gradient elution, 10 to 70% EtOAc in hexanes) to give a yellow oil, 1-tert-butyl 2-methyl (2S,4R)-4-({[8-{[(trifluoro methyl)sulfonyl]oxy}-3,4-dihydroisoquinolin-2(1H)-yl]carbonyl}oxy) pyrrolidine-1,2-dicarboxylate (1.65 g, 69.4% yield).
LRMS (ESI) m/z 453.2 [((M-Boc)+H)$^+$; calcd for C$_{17}$H$_{20}$F$_3$N$_2$O$_7$S: 453.4].

Step 4: 1-tert-Butyl 2-methyl (2S,4R)-4-{[(8-vinyl-3,4-dihydroisoquinolin-2(1H)-yl)carbonyl]oxy}pyrrolidine-1,2-dicarboxylate:

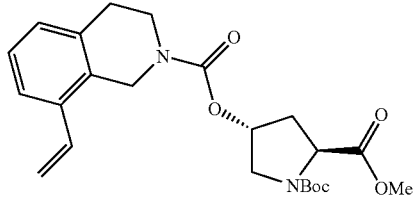

A solution of 1-tert-butyl 2-methyl (2S,4R)-4-({[8-{[(trifluoromethyl)sulfonyl]oxy}-3,4-dihydroisoquinolin-2(1H)-yl]carbonyl}oxy)pyrrolidine-1,2-dicarboxylate (1.74 g, 3.15 mmol), tri-n-butyl vinyl tin (1.10 g, 1.46 mmol) and lithium chloride (0.40 g, 9.45 mmol) in 25 mL DMF was purged with nitrogen for 10 min. Then bis(triphenylphosphine)palladium (II) chloride (0.22 g, 0.32 mmol) was added, and the mixture stirred at 25° C. under nitrogen for 18 h. The mixture was partitioned between EtOAc and saturated NaHCO$_3$, the organic layer separated and washed with water then brine, dried over anhydrous sodium sulfate and concentrated to an oil. The oil was purified by column chromatography on silica gel (gradient elution, 10 to 65% EtOAc in hexanes) to give a colorless oil, 1-tert-butyl 2-methyl (2S,4R)-4-{[(8-vinyl-3,4-dihydroisoquinolin-2(1H)-yl)carbonyl]oxy}pyrrolidine-1,2-dicarboxylate (1.00 g, 74% yield). LRMS (ESI) m/z 453.2 [(M+Na)$^+$; calcd for C$_{23}$H$_{30}$N$_2$O$_6$Na: 453.5].

Step 5: (5R,7S,10S)-10-tert-Butyl-N-((1R,2R)-1-{[(cyclopropylsulfonyl)amino]carbonyl}-2-ethyl-cyclo-propyl)-15,15-dimethyl-3,9,12-trioxo-6,7,9,10,11,12,14,15,16,17,18,19-dodecahydro-1H,5H-2,23-ethano-5,8-methano-4,13,2,8,11-benzodioxatriazacyclohenicosine-7-carboxamide (III-231)

EXAMPLE 46 was prepared from 1-tert-butyl 2-methyl (2S,4R)-4-{[(8-vinyl-3,4-dihydroisoquinolin-2(1H)-yl)carbonyl]oxy}pyrrolidine-1,2-dicarboxylate using the procedures described in EXAMPLE 3, Step 6 followed by EXAMPLE 13 Alternative Preparation, Steps 7 through 11.
$^1$H NMR (400 MHz, CDCl$_3$, ppm) δ 9.02 (s, 1H), 7.13 (m, 1H), 7.08 (d, J=7.7 Hz, 1H), 7.02 (d, J=7.3 Hz, 1H), 6.97 (d, J=7.7 Hz, 1H), 6.96 (m, 1H), 5.36 (s, 1H), 4.68 (d, J=16.3 Hz, 1H), 4.60-4.31 (m, 3H), 4.25 (m, 1H), 4.18 (m, 1H), 4.11-3.94 (m, 2H), 3.47 (q, J=7.0 Hz, 2H), 2.91 (m, 1H), 2.80 (m, 2H), 2.52 (m, 1H), 2.41-2.28 (m, 2H), 2.11 (td, 1H), 1.60-1.52 (m, 3H), 1.51 (m, 4H), 1.32 (m, 3H), 1.24 (m, 3H), 1.21 (t, J=7.0 Hz, 3H), 1.09 (m, 2H), 1.03 (s, 9H), 0.93 (s, 3H), and 0.82 (s, 3H). LRMS (ESI) m/z 772.5 [(M+H)$^+$; calcd for C$_{39}$H$_{58}$N$_5$O$_9$S: 773.0].

EXAMPLE 47

(5R,7S,10S,17E)-10-tert-Butyl-N-((1R,2S)-1-{[(cyclopropylsulfonyl)amino]carbonyl}-2-vinylcyclopropyl)-13-isopropyl-3,9,12-trioxo-6,7,9,10,11,12,13,14,15,16-decahydro-1H,5H-2,22:5,8-dimethano-4,2,8,11,13-benzoxatetraazacycloicosine-7-carboxamide
(III-232)

III-232

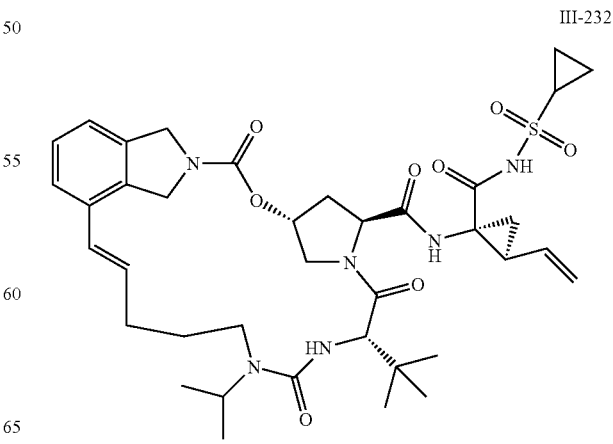

EXAMPLE 47 was prepared using the procedures from EXAMPLE 13 Alternate Preparation, Steps 7, 8, 10 and 11 using N-{[isopropyl(pent-4-en-1-yl)amino]carbonyl}-3-methyl-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO, ppm) δ 10.48 (s, 1H), 9.05 (s, 1H), 7.35 (d, J=7.7 Hz, 1H), 7.36 (t, J=6.7 Hz, 1H), 7.18 (d, J=7.7 Hz, 1H), 6.58 (d, J=16.1 Hz, 1H), 6.35-6.27 (m, 1H), 6.68-5.57 (m, 1H), 5.25-5.18 (m, 2H), 5.09 (dd, J=12.0 Hz, 1H), 4.98 (d, J=12.0 Hz, 1H), 4.90-4.84 (m, 1H), 4.68-4.57 (m, 3H), 4.30-4.24 (m, 3H), 4.13 (d, J=8.8 Hz, 1H), 4.07-3.95 (m, 1H), 3.70 (d, J=12.8 Hz, 1H), 3.38-3.27 (m, 1H), 2.94-2.87 (m, 1H), 2.37-1.99 (m, 5H), 1.97-1.88 (m, 1H), 1.70 (dd, J=9.6 Hz, $J_2$=4.0 Hz, 1H), 1.58-1.52 (m, 1H), 1.47 (dd, J=9.6 Hz, $J_2$=4.0 Hz, 1H), 1.20-1.13 (m, 6H), and 1.07-0.98 (m, 13H). LRMS (ESI) m/z 753 [(M+H)$^+$; calcd for $C_{38}H_{53}N_6O_8S$: 753.4].

EXAMPLE 48

(5R,7S,10S)-10-tert-Butyl-N-((1R,2S)-1-{[(cyclopropylsulfonyl)amino]carbonyl}-2-vinylcyclopropyl)-13-isopropyl-3,9,12-trioxo-6,7,9,10,11,12,13,14,15,16,17,18-dodecahydro-1H,5H-2,22:5,8-dimethano-4,2,8,11,13-benzoxatetraazacycloicosine-7-carboxamide (III-233)

III-233

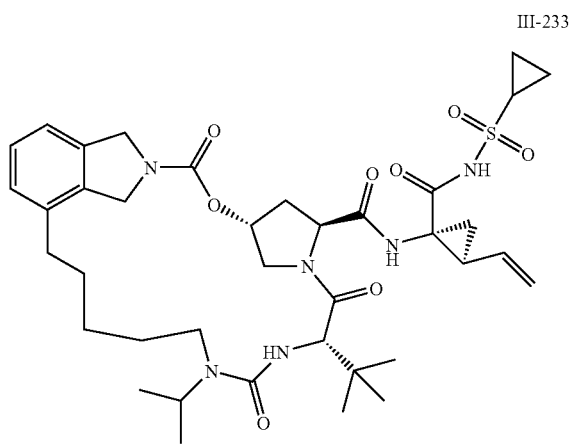

EXAMPLE 48 was prepared using the procedures from EXAMPLE 13 Alternate Preparation, Steps 7 through 11 using N-{[isopropyl(pent-4-en-1-yl)amino]carbonyl}-3-methyl-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO, ppm) δ 10.50 (s, 1H), 9.06 (s, 1H), 7.26-7.22 (m, 1H), 7.16-7.11 (m, 2H), 5.68-5.59 (m, 1H), 5.34 (bs, 1H), 5.22 (d, J=17.3 Hz, 1H), 5.11-5.08 (m, 2H), 4.73-4.54 (m, 5H), 4.33 (dd, J=10.9 Hz, $J_2$=6.6 Hz, 1H), 4.16 (d, J=9.4 Hz, 2), 3.95-3.90 (m, 1H), 3.73-3.71 (m, 1H), 3.08-3.04 (m, 1H), 2.95-2.86 (m, 2H), 2.66-2.58 (m, 1H), 2.35-2.28 (m, 2H), 2.16-2.09 (m, 2H), 1.70 (dd, J=7.9 Hz, $J_2$=5.2 Hz, 1H), 1.58-1.45 (m, 3H), 1.39-1.36 (m, 2H), 1.31-1.21 (m, 1H), 1.16-1.10 (m, 6H), 1.09-1.01 (m, 4H), and 0.98 (s, 9H). LRMS (ESI) m/z 755 [(M+H)$^+$; calcd for $C_{38}H_{55}N_6O_8S$: 755.4].

EXAMPLE 49

(5R,7S,10S,18E)-10-tert-Butyl-N-((1R,2S)-1-{[(cyclopropylsulfonyl)amino]carbonyl}-2-vinylcyclopropyl)-13-isopropyl-3,9,12-trioxo-1,6,7,9,10,11,12,13,14,15,16,17-dodecahydro-5H-2,23:5,8-dimethano-4,2,8,11,13-benzoxatetraazacyclohenicosine-7-carboxamide (III-234)

III-234

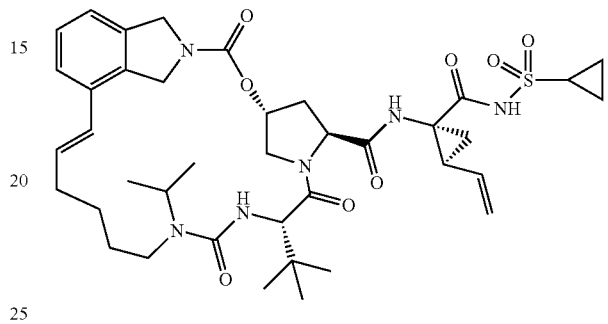

EXAMPLE 49 was prepared using the procedures from EXAMPLE 13 Alternate Preparation, Steps 7, 8, 10 and 11 using N-{[hex-5-en-1-yl(isopropyl)amino]carbonyl}-3-methyl-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO, ppm) δ 10.55 (s, 1H), 9.06 (s, 1H), 7.30-7.20 (m, 3H), 6.36 (d, J=16.4 Hz, 1H), 6.04 (m, 1H), 5.72-5.63 (m, 1H), 5.30-5.21 (m, 3H), 5.09 (d, J=11.9 Hz, 1H), 4.70-4.57 (m, 4H), 4.34 (d, J=9.1 Hz, 1H), 4.29 (dd, J=11.1, 6.4 Hz, 1H), 4.09 (d, J=11.9 Hz, 1H), 3.97-3.84 (m, 2H), 3.47-3.42 (m, 1H), 2.92-2.87 (m, 2H), 2.35-2.20 (m, 2H), 2.17-2.02 (m, 3H), 1.69 (dd, J=8.08, 5.2 Hz, 1H), 1.58 (m, 1H), 1.48-1.39 (m, 4H), 1.18 (d, J=6.6 Hz, 3H), 1.14 (d, J=6.6 Hz, 3H), 1.11-1.02 (m, 3H), and 0.99 (s, 9H). LRMS (ESI) m/z 767 [(M+H)$^+$; calcd for $C_{39}H_{55}N_6O_8S$: 767.4].

EXAMPLE 50

(5R,7S,10S)-10-tert-Butyl-N-((1R,2S)-1-{[(cyclopropylsulfonyl)amino]carbonyl}-2-vinylcyclopropyl)-13-isopropyl-3,9,12-trioxo-1,6,7,9,10,11,12,13,14,15,16,17,18,19-tetradecahydro-5H-2,23:5,8-dimethano-4,2,8,11,13-benzoxatetraazacyclohenicosine-7-carboxamide (III-235)

III-235

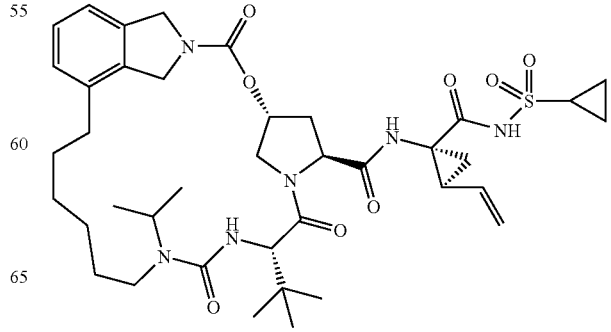

175

EXAMPLE 50 was prepared using the procedures from EXAMPLE 13 Alternate Preparation, Steps 7 through 11 using N-{[hex-5-en-1-yl(isopropyl)amino]carbonyl}-3-methyl-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO+TFA, ppm) δ 10.52 (s, 1H), 9.02 (s, 1H), 7.14 (m, 1H), 7.06 (d, J=7.6 Hz, 1H), 7.01 (d, J=7.1 Hz, 1H), 5.7-5.59 (m, 1H), 5.26-5.16 (m, 3H), 5.02 (d, J=10.8 Hz, 1H), 4.62-4.48 (m, 4H), 4.28 (m, 2H), 4.08 (d, J=11.9 Hz, 1H), 3.89-3.76 (m, 2H), 3.42-3.31 (m, 1H), 2.89-2.75 (m, 2H), 2.6-2.29 (m, 5H), 2.12-1.98 (m, 2H), 1.7 (m, 1H), 1.52-1.16 (m, 6H), and 1.13-0.95 (m, 19H). LRMS (ESI) m/z 769 [(M+H)$^+$; calcd for $C_{39}H_{57}N_6O_8S$: 769.4].

EXAMPLE 51

(5R,7S,10S,17E)-10-tert-Butyl-N-((1R,2S)-1-{[(cyclopropylsulfonyl)amino]carbonyl}-2-vinylcyclopropyl)-3,9,12-trioxo-13-propyl-6,7,9,10,11,12,13,14,15,16-decahydro-1H,5H-2,22:5,8-dimethano-4,2,8,11,13-benzoxatetraazacycloicosine-7-carboxamide (III-236)

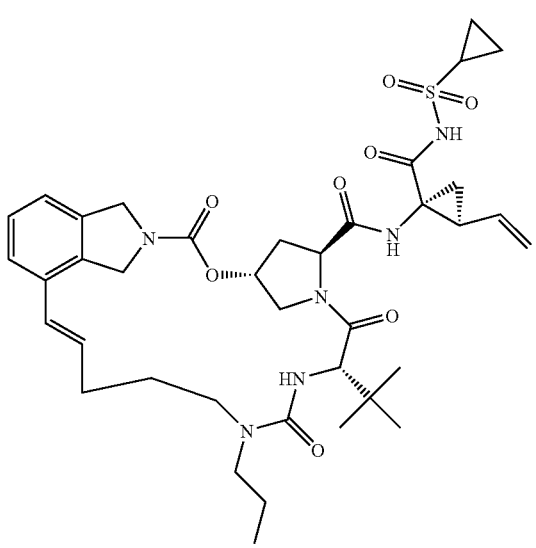

III-236

EXAMPLE 51 was prepared using the procedures from EXAMPLE 13 Alternate Preparation, Steps 7, 8, 10 and 11 using 3-methyl-N-{[pent-4-en-1-yl(propyl)amino]carbonyl}-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO, ppm) δ 10.50 (s, 1H), 9.01 (s, 1H), 7.35 (d, J=8.4 Hz, 1H), 7.26 (t, J=8.6 Hz, 1H), 7.17 (d, J=8.4 Hz, 1H), 6.53 (d, J=20.0 Hz, 1H)), 6.31 (dd, J$_1$=20 Hz, J$_2$=5.6 Hz, 1H), 5.67-5.56 (m, 1H), 5.25-5.20 (m, 2H), 5.09 (dd, J=15.0 Hz, 1H), 4.97-4.83 (m, 4H), 4.67-4.55 (m, 4H), 4.43-4.37 (m, 2H), 4.14 (d, J=10.7 Hz, 1H), 3.68 (dd, J=12.0 Hz, J$_2$=4.0 Hz, 1H), 3.38-3.32 (m, 1H), 3.23-3.05 (m, 3H), 2.95-2.87 (m, 1H), 2.34-1.97 (m, 4H), 1.85-1.52 (m, 4H), 1.38-1.33 (m, 1H), 1.09-0.97 (m, 12H), and 0.98 (t, J=10.0 Hz, 3H). LRMS (ESI) m/z 753 [(M+H)$^+$; calcd for $C_{38}H_{53}N_6O_8S$: 753.4].

176

EXAMPLE 52

(5R,7S,10S)-10-tert-Butyl-N-((1R,2S)-1-{[(cyclopropylsulfonyl)amino]carbonyl}-2-vinylcyclopropyl)-3,9,12-trioxo-13-propyl-6,7,9,10,11,12,13,14,15,16,17,18-dodecahydro-1H,5H-2,22:5,8-dimethano-4,2,8,11,13-benzoxatetraazacycloicosine-7-carboxamide (III-237)

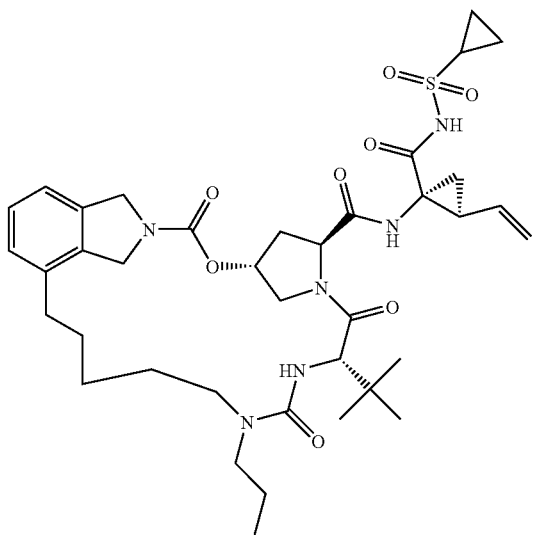

III-237

EXAMPLE 52 was prepared using the procedures from EXAMPLE 13 Alternate Preparation, Steps 7 through 11 using 3-methyl-N-{[pent-4-en-1-yl(propyl)amino]carbonyl}-L-valine in Step 7 and (1R,2S)-1-{[(cyclopropylsulfonyl)amino]carbonyl}-2-vinylcyclopropanaminium chloride in Step 11. $^1$H-NMR (400 MHz, DMSO, ppm) δ 10.51 (s, 1H), 9.09 (s, 1H), 7.27-7.22 (m, 1H), 7.18-7.10 (m, 2H), 5.20-5.10 (m, 1H), 5.38 (bs, 1H), 5.25 (d, J=13 Hz, 1H), 5.05-5.12 (m, 2H), 4.52-4.68 (m, 4H), 4.34 (dd, J=14 Hz, J$_2$=5 Hz, 1H), 4.20 (d, J=8 Hz, 1H), 4.12 (d, J=11 Hz, 1H), 3.74 (dd, J=12 Hz, J$_2$=5 Hz, 1H), 3.42-3.34 (m, 1H), 3.11 (t, J=12 Hz, 2H), 2.92-2.83 (m, 2H), 2.63-2.56 (m, 1H), 2.37-2.25 (m, 2H), 2.18-2.05 (m, 2H), 1.76-1.70 (m, 1H), 1.60-1.45 (m, 5H), 1.42-1.36 (m, 2H), 1.24-1.12 (m, 2H), 1.10-1.03 (m, 4H), 0.88 (s, 9H), and 0.87 (t, J=7 Hz, 3H). LRMS (ESI) m/z 755 [(M+H)$^+$; calcd for $C_{38}H_{55}N_6O_8S$: 755.4].

EXAMPLE 53

(5R,7S,10S)-10-tert-Butyl-N-[(1R,2S)-1-({[(dimethylamino)sulfonyl]amino}carbonyl)-2-vinylcyclopropyl]-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacycloheni-cosine-7-carboxamide (III-238)

III-238

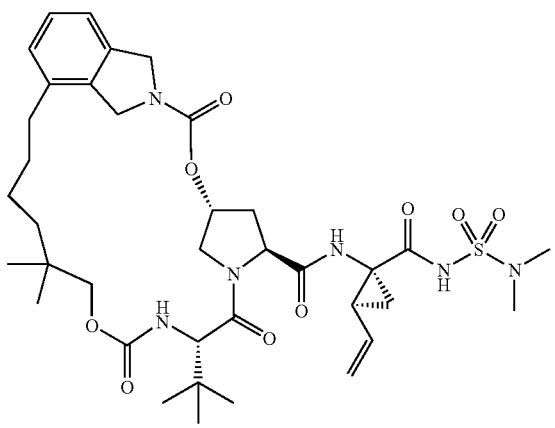

To a solution of (5R,7S,10S)-10-tert-butyl-15,15-dimethyl-3,9,12-trioxo-6,7,9,10,11,12,14,15,16,17,18,19-dodecahydro-1H,5H-2,23:5,8-dimethano-4,13,2,8,1-benzodioxatriazacyclohenicosine-7-carboxylic acid (EXAMPLE 13 Alternative Preparation, Step 10) (200 mg, 0.306 mmol), N,N-dimethylsulfamide (TCI Industries, 152 mg, 1.226 mmol), DIPEA (0.268 mL, 1.532 mmol), and DMAP (150 mg, 1.226 mmol) in DMF (6 mL) was added DBU (0.208 mL, 1.379 mmol) and the mixture was stirred for 5 min. HATU (128 mg, 0.337 mmol) was added and the mixture was stirred for 18 h. Additional HATU (40 mg, 0.150 mmol) was added and the reaction was stirred an additional 24 h. The reaction mixture was purified by reverse phase chromatography to give EXAMPLE 53 (130 mg) as a white foam. $^1$H NMR (500 MHz, CDCl$_3$, ppm) δ 9.77 (s, 1H), 7.22 (t, J=7.6 Hz, 1H), 7.09 (d, J=7.6 Hz, 1H), 7.05 (d, J=7.3 Hz, 1H), 6.86 (s, 1H), 5.74 (m, 1H), 5.57 (d, J=13.7 Hz, 1H), 5.34 (m, 1H), 5.24 (dd, J=0.7 and 17.2 Hz, 1H), 5.15 (dd, J=1.5 and 10.3 Hz, 1H), 4.72 (q, J=14.7 Hz, 2H), 4.3-4.6 (m, 6H), 4.18 (d, J=10.7 Hz, 1H), 3.84 (dd, J=3.4 and 11.7 Hz, 1H), 3.26 (d, J=10.7 Hz, 1 H), 2.90 (s, 6H), 2.70-1.70 (m, 6H), 1.60-1.20 (m, 5H), 1.30 (m, 1H), 1.05 (m, 9H), 0.96 (s, 3H), and 0.79 (s, 3H). LRMS (ESI) m/z 759.6 [(M+H)$^+$; calcd for C$_{37}$H$_{55}$N$_6$O$_9$S: 759.4].

EXAMPLE 54

(5R,7S,10S)-10-tert-Butyl-15,15-dimethyl-3,9,12-trioxo-N-((1R,2S)-1-{[(piperidin-1-ylsulfonyl)amino]carbonyl}-2-vinylcyclopropyl)-6,7,9,10,11,12,14,15,16,17,18,19-dodecahydro-1H,5H-2,23:5,8-dimethano-4,13,2,8,11-benzodioxatriazacyclohenicosine-7-carboxamide (III-239)

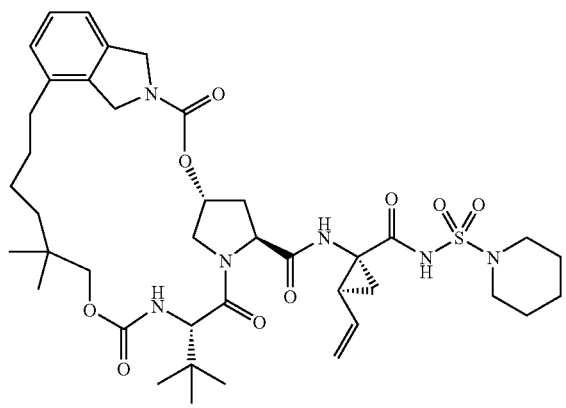

III-239

EXAMPLE 54 was prepared according to the procedure used for EXAMPLE 53 except that piperidine-1-sulfonamide (*Bioorg. Med. Chem. Lett.*, 2003, (13), 837.) was used in place of N,N-dimethylsulfamide. $^1$H NMR (500 MHz, CDCl$_3$, ppm) δ 9.72 (s, 1H), 7.21 (t, J=7.6 Hz, 1H), 7.09 (d, J=7.6 Hz, 1H), 7.05 (d, J=7.3 Hz, 1H), 6.78 (s, 1H), 5.75 (m, 1H), 5.50 (d, J=13.7 Hz, 1H), 5.32 (m, 1H), 5.22 (dd, J=0.7 and 17.2 Hz, 1H), 5.14 (dd, J=1.5 and 10.3 Hz, 1H), 4.72 (q, J=14.7 Hz, 2H), 4.6-4.3 (m, 6H), 4.18 (d, J=10.7 Hz, 1H), 3.84 (dd, J=3.4 and 11.7 Hz, 1H), 3.40-3.20 (m, 5H), 2.60-2.20 (m, 4H), 1.60-1.10 (m, 14H), 1.40 (m, 9H), 0.96 (s, 3H), and 0.79 (s, 3H). LRMS (ESI) m/z 799.6 [(M+H)$^+$; calcd for C$_{40}$H$_{59}$N$_6$O$_9$S: 799.4].

EXAMPLE 55

(5R,7S,10S)—N-{(1R,2S)-1-[({[Benzyl(methyl)amino]sulfonyl}amino)carbonyl]-2-vinylcyclopropyl}-10-tert-butyl-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxamide (III-240)

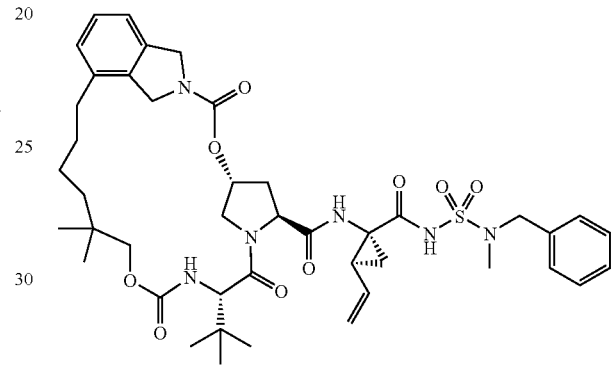

III-240

EXAMPLE 55 was prepared according to the procedure used for EXAMPLE 53 except that N-benzyl-N-methylsulfamide [*J. Med. Chem.*, 1967, 10(4), 636.] was used in place of N,N-dimethylsulfamide. $^1$H NMR (500 MHz, CDCl$_3$, ppm) δ 9.95 (s, 1H), 7.32 (m, 5H), 7.22 (t, J=7.6 Hz, 1H), 7.09 (d, J=7.6 Hz, 1H), 7.05 (d, J=7.3 Hz, 1H), 6.85 (s, 1H), 5.80 (m, 1 H), 5.56 (d, J=9.8 Hz, 1H), 5.34 (m, 1H), 5.26 (dd, J=0.9 and 17.3 Hz, 1H), 5.17 (dd, J=1.2 and 10.2 Hz, 1H), 4.71 (q, J=14.8 Hz, 2H), 4.6-4.1 (m, 6H), 4.18 (d, J=10.8 Hz, 1H), 3.85 (dd, J=3.4 and 11.7 Hz, 1H), 3.25 (d, J=10.8 Hz, 1H), 2.76 (s, 3H), 2.63 (m, 1H), 2.52 (m, 1H), 2.35 (m, 2H), 2.10 (m, 2H), 1.98 (m, 1H), 1.48 (m, 3H), 1.30 (m, 3H), 1.12 (m, 1 H), 1.03 (m, 9H), 0.96 (s, 3H), and 0.79 (s, 3H). LRMS (ESI) m/z 835.6 [(M+H)$^+$; calcd for C$_{43}$H$_{59}$N$_6$O$_9$S: 835.4].

Alternative Preparation of (1R,2R)-1-amino-N-(cyclopropylsulfonyl)-2-ethylcyclopropanecarboxamide Hydrochloride:

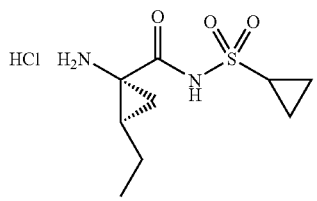

Step 1: tert-Butyl ((1R,2R)-1-{[(cyclopropylsulfonyl)amino]carbonyl}-2-ethylcyclopropyl)carbamate:

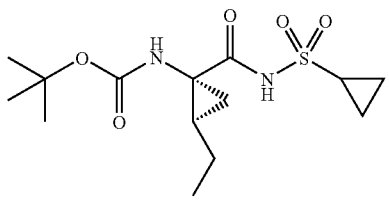

A hydrogenation vessel was charged with a methanol (1000 mL) slurry of tert-butyl ((1R,2S)-1-{[(cyclopropylsulfonyl)amino]carbonyl}-2-vinylcyclopropyl)carbamate (164 g, 0.50 mol) (Wang et al., U.S. Pat. No. 6,995,174) and 5% Ru/C (dry, 7.5 wt %, 12.4 g) and set stirring. The vessel was placed under nitrogen (20 psig) and vented to atmospheric pressure three times to remove residual oxygen. The vessel was then placed under hydrogen (50 psig). After 20 hours, the vessel was vented to atmospheric pressure. The reaction slurry was then transferred out of the reaction and filtered through SOLKA FLOK (34 grams, wetted w/100 mL methanol) to yield a clear, light brown solution. The SOLKA FLOK was rinsed with methanol (200 mL×2). The combined methanol solutions were concentrated under reduced pressure to yield crude product as a white solid (153 g). The crude product was slurried in ethyl acetate (800 mL), warmed to 40° C. and aged 30 minutes. The solution was then seeded, aged 30 minutes, and heptane (500 mL) was added via addition funnel over 30 minutes. The partially crystallized solid was cooled to room temperature and aged overnight after which additional heptane (500 mL) was added. After one hour, additional heptane (250 mL) was added via addition funnel, and the white slurry aged for one hour. The solution was filtered and the solid was rinsed with heptane/EtOAc (500 mL, 4:1) and dried under reduced pressure to give tert-butyl ((1R,2R)-1-{[(cyclopropylsulfonyl)amino]carbonyl}-2-ethylcyclopropyl)carbamate (125.9 g).

Step 2: (1R,2R)-1-amino-N-(cyclopropylsulfonyl)-2-ethylcyclopropanecarboxamide: Hydrochloride A solution of the product from Step 1 above (92 g, 0.28 mol) in DCM (1200 mL) was cooled to 0° C. and HCl bubbled through the solution for 10 min, the cooling bath removed and the reaction mixture stirred for 2 h. Nitrogen was bubbled through the reaction mixture for 5 min and the volatiles evaporated. The residue was azeotroped with DCM (×3) to give an off white powder (75 g).
LRMS (M+H)+ Calcd.=233. found 233.

Preparation of N-{[(1-but-3-en-1-ylcyclohexyl)methoxy]carbonyl}-3-methyl-L-valine:

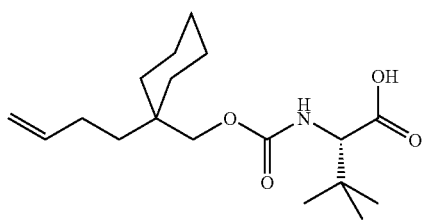

N-{[(1-But-3-en-1-ylcyclohexyl)methoxy]carbonyl}-3-methyl-L-valine was prepared according to the procedure for N-{[(2,2-dimethylhex-5-enyl)oxy]carbonyl}-3-methyl-L-valine by using methyl cyclohexanecarboxylate instead of ethyl isobutyrate in Step 1. LRMS (ESI) m/z 326.3 [(M+H)+; calcd for $C_{18}H_{32}NO_4$: 326.2].

Preparation of N-{[(1-but-3-en-1-ylcyclopentyl)methoxy]carbonyl}-3-methyl-L-valine:

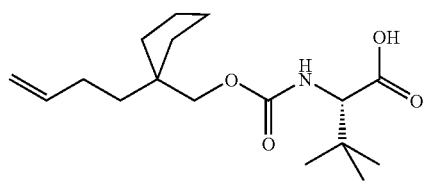

N-{[(1-But-3-en-1-ylcyclopentyl)methoxy]carbonyl}-3-methyl-L-valine was prepared according to the procedure for N-{[(2,2-dimethylhex-5-enyl)oxy]carbonyl}-3-methyl-L-valine by using methyl cyclopentanecarboxylate instead of ethyl isobutyrate in Step 1. LRMS (ESI) m/z 312.3 [(M+H)+; calcd for $C_{17}H_{30}NO_4$: 312.2].

Preparation of N-{[(1-but-3-en-1-ylcyclobutyl)methoxy]carbonyl}-3-methyl-L-valine:

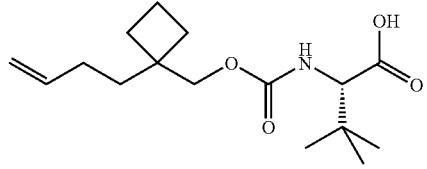

N-{[(1-But-3-en-1-ylcyclobutyl)methoxy]carbonyl}-3-methyl-L-valine was prepared according to the procedure for N-{[(2,2-dimethylhex-5-enyl)oxy]carbonyl}-3-methyl-L-valine by using ethyl cyclobutanecarboxylate instead of ethyl isobutyrate in Step 1. LRMS (ESI) m/z 298.3 [(M+H)+; calcd for $C_{16}H_{28}NO_4$: 298.2].

Preparation of N-{[(1-but-3-en-1-ylcyclopropyl)methoxy]carbonyl}-3-methyl-L-valine:

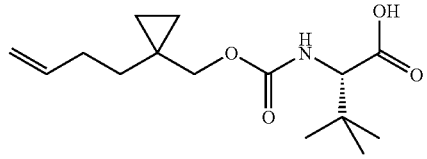

Step 1: Ethyl 2-(diethoxyphosphoryl)hex-5-enoate:

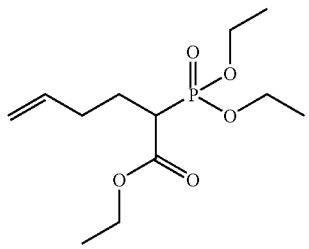

To a stirred suspension of NaH (60% dispersion in mineral oil, 9.37 g, 234 mmol) in dry THF (100 mL), at 22° C. and under nitrogen, was added dropwise triethyl phosphonoacetate (26.5 mL, 134 mmol). Stirred for 30 minutes, this reaction was added dropwise 4-bromo-1-butene (24.4 mL, 241 mmol), then refluxed at 80° C. for 5 hours. Quenched at 22° C. with 1N aqueous NH$_4$Cl (40 mL), the reaction was then concentrated. The residue was diluted with water (200 mL) and extracted with ether (3×200 mL). The combined ether layer was washed with water (70 mL), brine (70 mL), dried over Na$_2$SO$_4$, filtered and concentrated. The residue was flash chromatographed on 120 g silica gel 60, eluting with 20-90% EtOAc/Hexane, to give the title compound (17.5 g, 47.1%). LRMS (ESI) m/z 279.3 [(M+H)$^+$; calcd for C$_{12}$H$_{24}$O$_5$P: 279.1].

Step 2: Ethyl 1-but-3-en-1-ylcyclopropanecarboxylate:

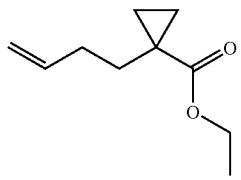

To a stirred suspension of NaH (60% dispersion in mineral oil, 3.02 g, 75.5 mmol) in dry benzene (100 mL), at 22° C. and under nitrogen, was added dropwise ethyl 2-(diethoxyphosphoryl)hex-5-enoate with anhydrous EtOH (0.044 mL, 0.76 mmol) over 30 minutes. Stirred for 30 minutes, this reaction, cooled at 0° C. and attached with a dry ice/acetone condenser, was added via cannula ethylene oxide (12.7 g, 289.3 mmol), then refluxed at 50° C. for 5 hours. Quenched at 22° C. with 1N aqueous NH$_4$Cl (100 mL), the reaction solution was extracted with Et$_2$O (3×200 mL). The combined Et$_2$O layers were washed with aqueous saturated NaHCO$_3$ (100 mL), water (70 mL), brine (70 mL), dried over Na$_2$SO$_4$, filtered and concentrated. The residue was flash chromatographed on 120 g silica gel 60, eluting with 20-100% EtOAc/Hexane, to give the title product (5.07 g, 48%). LRMS (ESI) m/z 169.2 [(M+H)$^+$; calcd for C$_{10}$H$_{17}$O$_2$: 169.1].

Step 3: N-{[(1-But-3-en-1-ylcyclopropyl)methoxy]carbonyl}-3-methyl-L-valine:

N-{[(1-But-3-en-1-ylcyclopropyl)methoxy]carbonyl}-3-methyl-L-valine was prepared according to the procedure for N-{[(2,2-dimethylhex-5-enyl)oxy]carbonyl}-3-methyl-L-valine (Steps 2 and 3) by using ethyl 1-but-3-en-1-ylcyclopropanecarboxylate-instead of ethyl 2,2-dimethylhex-5-enoate in Step 2. LRMS (ESI) m/z 284.3 [(M+H)$^+$; calcd for C$_{15}$H$_{26}$NO$_4$: 284.2].

Preparation of (2S)-(1-methylcyclohexyl){[(pent-4-en-1-yloxy)carbonyl]amino}acetic acid:

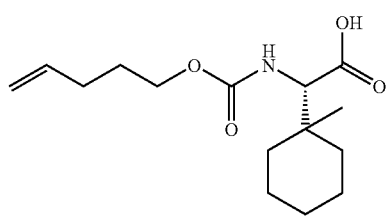

Step 1: 1-Methylcyclohexanecarboxaldehyde:

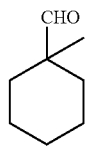

To a solution of cyclohexanecarboxaldehyde (10.8 mL, 89.15 mmol) in DCM (500 mL) cooled to 0° C. was added potassium tert-butoxide (13.0 g, 115.9 mmol) and methyl iodide (16.65 mL, 267.5 mmol). After 30 min at this temperature, the mixture was warmed to RT and stirring was continued for an additional 5 h. The reaction was then poured into brine and extracted with DCM. The organic layer was dried over MgSO$_4$ and the solvent was then removed carefully in vacuo to yield 9.4 g (83%) of crude 1-methylcyclohexanecarboxaldehyde which was ~80% pure and was used directly in the next reaction.

Step 2: (2S)-Amino(1-methylcyclohexyl)acetic Acid Hydrochloride:

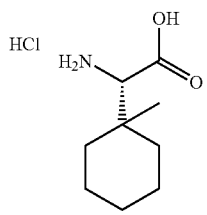

Using the asymmetric Strecker method of Chakraborty (Chakraborty, T. K., Hussain, K. A., Reddy, G. V.; Tetrahedron 51, 33, 1995, 9179-9190) (2S)-amino(1-methylcyclohexyl)acetic acid hydrochloride was prepared.

To a solution of (2S)-amino(1-methylcyclohexyl)acetic acid hydrochloride (9.3 g, 73.7 mmol) in CHCl$_3$ (700 mL) was added (R)-(−)-2-phenylglycinol (10.1 g, 73.7 mmol). After stirring for 1 h, the mixture was cooled to 0° C. and trimethylsilylcyanide (19.65 mL, 147.4 mmol) was added.

The reaction was then warmed to RT and stirred for 2 d. Brine was then added and the mixture was extracted with DCM. The organic layer was dried over MgSO₄ and the solvent was removes in vacuo to yield 28 g of crude silylated material. The mixture was then taken up in DCM (250 mL) and stirred vigorously with 4 N HCl (100 mL) for 24 h. The organic layer was then washed with aq. NaHCO₃, dried over MgSO₄, and the solvent was removed in vacuo to yield 16 g of crude desilylated material. The aqueous layer was then basified with concentrated NaOH and extracted with EtOAc. The organic layer was then dried over MgSO4 and the solvent was removed in vacuo to yield 3.3 g of crude material. The combined crude material was purified on silica (isco, 120 g, 0-30% EtOac/hex) to yield 5.0 g (25%) of (2R)-{[(1R)-2-hydroxy-1-phenylethyl]amino}(1-methylcyclohexyl)acetonitrile.

To solution of (2R)-{[(1R)-2-hydroxy-1-phenylethyl] amino}(1-methylcyclohexyl)acetonitrile (4.8 g, 17.6 mmol) in DCM (100 mL) and MeOH (50 mL) cooled to 0° C. was added lead tetraacetate (9.37 g, 21.15 mmol). After 30 min, the reaction was warmed to RT and stirred for 24 h. The mixture was then quenched with pH 7 phosphate buffer and stirred for 1 h. The solids were then removed by filtration, and the mixture was extracted with DCM. The organic layer was dried over MgSO₄ and the solvent was removed in vacuo. The crude material was then taken up in concentrated HCl (100 mL) and heated to reflux for 48 h. After cooling to RT, the aqueous layer was washed with Et₂O 2× and DCM 3×. The water was then removed in vacuo (10 mmHg at 50° C.) to yield (2S)-amino(1-methylcyclohexyl)acetic acid-HCl salt (3.35 g, 91%) as an off-white solid. LRMS (ESI) m/z 172.2 [(M+H)⁺; calcd for C₉H₁₇NO₂: 172.2].

Step 3: (2S)-(1-Methylcyclohexyl){[(pent-4-en-1-yloxy)carbonyl]amino}acetic Acid:

(2S)-(1-methylcyclohexyl) {[(pent-4-en-1-yloxy)carbonyl]amino}acetic acid was prepared according to the procedure for 3-methyl-N-[(pent-4-enyloxy)carbonyl]-L-valine by using (2S)-amino(1-methylcyclohexyl)acetic acid-HCl instead of t-butylglycine. LRMS (ESI) m/z 347.3 [(M+Na+CH3CN)⁺; calcd for C₁₇H₂₈N₂NaO₄: 347.2].

Preparation of (2S)-({[(2,2-dimethylhex-5-en-1-yl)oxy]carbonyl}amino)(1-methylcyclohexyl)acetic Acid:

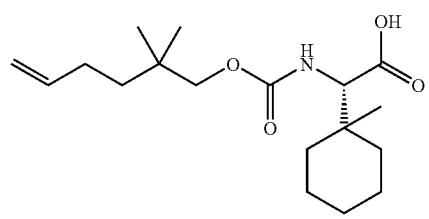

(2S)-({[(2,2-Dimethylhex-5-en-1-yl)oxy]carbonyl}amino)(1-methylcyclohexyl)acetic acid was prepared according to the procedure for 3-methyl-N-[(pent-4-enyloxy)carbonyl]-L-valine using (2S)-amino(1-methylcyclohexyl)acetic acid-HCl and 2,2-dimethylhex-5-en-1-ol. LRMS (ESI) m/z 326.3 [(M+H)⁺; calcd for C₁₈H₃₂NO₄: 326.2].

Preparation of (2S)-4,4,4-trifluoro-2-{[(hex-5-en-1-yloxy)carbonyl]amino}butanoic Acid:

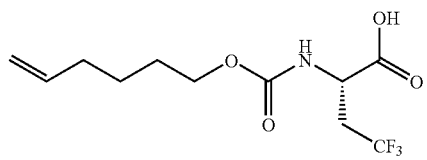

(2S)-4,4,4-trifluoro-2-{[(hex-5-en-1-yloxy)carbonyl] amino}butanoic acid was prepared according to the procedure for 3-methyl-N-[(pent-4-enyloxy)carbonyl]-L-valine using (2S)-2-amino-4,4,4-trifluorobutanoic acid and 5-hexenol. LRMS (ESI) m/z 284.3 [(M+H)⁺; calcd for C₁₁H₁₇F₃NO₄: 284.1].

Preparation of O-(tert-butyl)-N-{[(2,2-dimethylhex-5-en-1-yl)oxy]carbonyl}-L-serine:

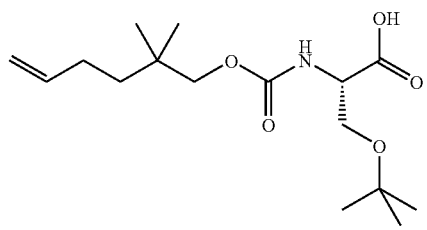

O-(tert-Butyl)-N-{[(2,2-dimethylhex-5-en-1-yl)oxy]carbonyl}-L-serine was prepared according to the procedure for 3-methyl-N-[(pent-4-enyloxy)carbonyl]-L-valine using O-(tert-butyl)-L-serine and 2,2-dimethylhex-5-en-1-ol. ¹H NMR (500 MHz, CDCl₃, ppm) δ 5.75-5.86 (m, 1H), 4.90-5.04 (m, 2H), 4.02 (m, 1H), 3.57-3.90 (m, 4H), 1.98-2.05 (m, 2H), 1.27-1.36 (m, 2H), 1.14 (s, 9H), 1.01 (d, J=6.5 Hz, 1H), and 6.09 (s, 6H).

Preparation of (2S)-cyclohexyl({[(2,2-dimethylhex-5-en-1-yl)oxy]carbonyl}amino)acetic Acid:

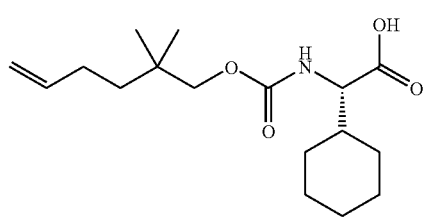

(2S)-Cyclohexyl({[(2,2-dimethylhex-5-en-1-yl)oxy]carbonyl}amino)acetic acid was prepared according to the procedure for 3-methyl-N-[(pent-4-enyloxy)carbonyl]-L-valine using (2S)-amino(cyclohexyl)acetic acid and 2,2-dimethylhex-5-en-1-ol. LRMS (ESI) m/z 312.3 [(M+H)+; calcd for $C_{17}H_{30}NO_4$: 312.2].

Preparation of 3-methyl-N-[(pent-4-yn-1-yloxy)carbonyl]-L-valine:

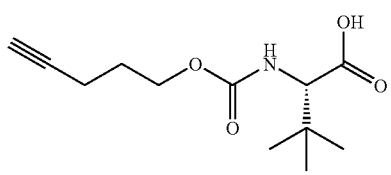

3-Methyl-N-[(pent-4-yn-1-yloxy)carbonyl]-L-valine was prepared according to the procedure for 3-methyl-N-[(pent-4-enyloxy)carbonyl]-L-valine by using pent-4-yn-1-ol instead of 4-pentenol. LRMS (ESI) m/z 242.2 [(M+H)+; calcd for $C_{12}H_{20}NO_4$: 242.1].

Preparation of N-[(hex-5-yn-1-yloxy)carbonyl]-3-methyl-L-valine:

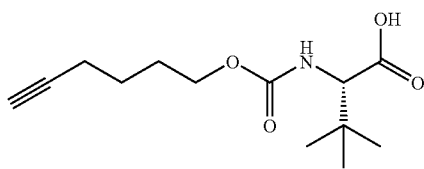

N-[(Hex-5-yn-1-yloxy)carbonyl]-3-methyl-L-valine was prepared according to the procedure for 3-methyl-N-[(pent-4-enyloxy)carbonyl]-L-valine by using hex-5-yn-1-ol instead of 4-pentenol. LRMS (ESI) m/z 256.2 [(M+H)+; calcd for $C_{13}H_{22}NO_4$: 256.1].

Preparation of N-{[isopropyl(pent-4-en-1-yl)amino]carbonyl}-3-methyl-L-valine:

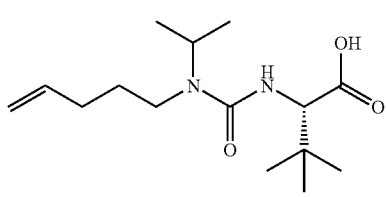

Step 1: N-Isopropylpent-4-en-1-amine:

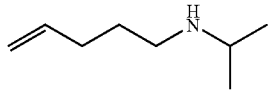

5-Bromo-1-pentene (42.3 mmol) was added to isopropylamine (423 mmol), and the mixture was stirred at 60° C. for 48 h in the dark in a sealed tube. Then the volatiles were evaporated at reduced pressure and the crude residue was dissolved in 50 mL of diethyl ether and washed twice with water. The organic phase was dried over $Na_2SO_4$. Evaporation of the solvent gave N-isopropylpent-4-en-1-amine as brownish oil (40%) which was used without any further purification.

Step 2: Methyl N-{[isopropyl(pent-4-en-1-yl)amino]carbonyl}-3-methyl-L-valinate:

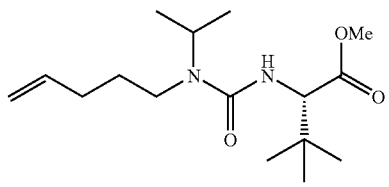

To a solution (60 nM) of L-tert-leucine methyl-ester hydrochloride and $NaHCO_3$ (8 eq) in dry THF, a solution 20% w/w of phosgene in toluene (5 eq) was added dropwise at 0° C. and the reaction mixture was stirred at that temperature for 30 minutes. Then the solid was filtered-off and the filtrate evaporated at reduced pressure. The resulting crude yellow oil was taken-up in dry THF (0.3 M) and added dropwise to a stirred solution (0.2 M) of N-isopropylpent-4-en-1-amine and TEA (1 eq). The reaction mixture was stirred at room temperature overnight. Then the mixture was taken-up in EtOAc and washed twice with water and brine. The organic phase was dried over $Na_2SO_4$ and the volatiles evaporated at reduced pressure. The crude was purified by flash chromatography eluting with petroleum ether (8) EtOAc (2) using Nynhydrin as stain. Methyl N-{[isopropyl(pent-4-en-1-yl)amino]carbonyl}-3-methyl-L-valinate was obtained as light yellow oil (43%).

Step 3: N-{[Isopropyl(pent-4-en-1-yl)amino]carbonyl}-3-methyl-L-valine

To a solution (0.1 M) of methyl N-{[isopropyl(pent-4-en-1-yl)amino]carbonyl}-3-methyl-L-valinate in a 1:1 mixture of water and dioxane, LiOH (4 eq) was added and the resulting mixture was stirred at room temperature for 6 h. The reaction mixture was then concentrated at reduced pressure and the crude residue was dissolved in EtOAc. The organic phase was washed with water. The aqueous phase was brought to pH=2 and re-extracted with EtOAc. After drying over $Na_2SO_4$ and evaporation of the volatiles, N-{[isopropyl(pent-4-en-1-yl)amino]carbonyl}-3-methyl-L-valine was recovered as a brownish solid (100%) and used without any further purification. LRMS (ESI) m/z 285 [(M+H)$^+$; calcd for $C_{15}H_{29}N_2O_3$: 285.2].

Preparation of N-{[Hex-5-en-1-yl(isopropyl)amino]carbonyl}-3-methyl-L-valine:

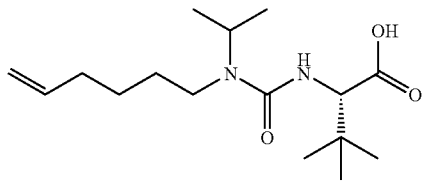

N-{[Hex-5-en-1-yl(isopropyl)amino]carbonyl}-3-methyl-L-valine was prepared according to the procedure described for N-{[isopropyl(pent-4-en-1-yl)amino]carbonyl}-3-methyl-L-valine by using 6-bromo-1-hexene in Step 1. LRMS (ESI) m/z 299 [(M+H)$^+$; calcd for $C_{16}H_{31}N_2O_3$: 299.2].

Preparation of 3-Methyl-N-{[pent-4-en-1-yl(propyl)amino]carbonyl}-L-valine:

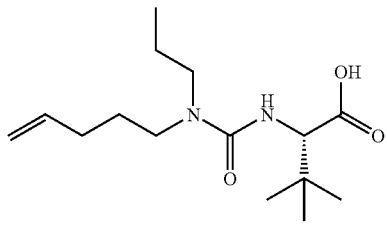

3-Methyl-N-{[pent-4-en-1-yl(propyl)amino]carbonyl}-L-valine was prepared according to the procedure described for N-{[isopropyl(pent-4-en-1-yl)amino]carbonyl}-3-methyl-L-valine by using n-propylamine in Step 1. LRMS (ESI) m/z 285 [(M+H)$^+$; calcd for $C_{15}H_{29}N_2O_3$: 285.2].

EXAMPLE 56

HCV NS3 Protease Time-Resolved Fluorescence (TRF) Assay

The NS3 protease TRF assay was performed in a final volume of 100 µl in assay buffer containing 50 mM HEPES, pH 7.5, 150 mM NaCl, 15% glycerol, 0.15% TRITON X-100, mM DTT, and 0.1% PEG 8000. The NS3 protease was pre-incubated with various concentrations of inhibitors for 10-30 minutes. The peptide substrate for the assay is Ac—C(Eu)-DDMEE-Abu-[COO]—XSAK(QSY7)-NH$_2$ (SEQ ID No. 1) where Eu is an europium-labeled group, Abu is 1-aminobutanoic acid which connects an ester linkage with 2-hydroxy propanoic acid (X). Hydrolysis of the peptide by NS3 protease activity causes in separation of the fluorophore from the quencher, resulting in an increase in fluorescence. Activity of the protease was initiated by adding the TRF peptide substrate (final concentration 50-100 nM). The reaction was quenched after 1 hour at room temperature with 100 µl of 500 mM MES, pH 5.5. Product fluorescence was detected using either a VICTOR V2 or FUSION fluorimeter (PERKIN ELMER Life and Analytical Sciences) with excitation at 340 nm and emission at 615 nm with 50-400 µs delay. Testing concentrations of different enzyme forms was selected with a signal to background ratio of 10-30. The inhibition constants were derived using a four-parameter fit.

Compounds in Examples 1-55 were tested to have a Ki value of less than 100 nM in the NS3 protease TRF assay as described above.

What is claimed is:

1. A compound of formula (I):

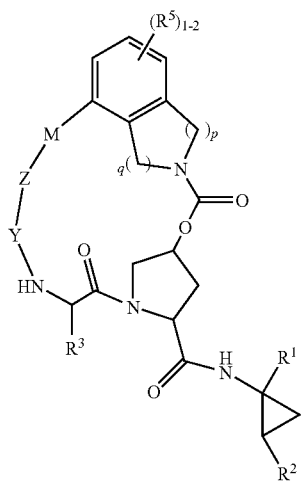

or a pharmaceutically acceptable salt thereof, wherein:
p and q are both 1;
$R^1$ is $CONR^{10}SO_2R^6$;
$R^2$ is $C_1$-$C_6$ alkyl or $C_2$-$C_6$ alkenyl, wherein said alkyl or alkenyl is optionally substituted with 1 to 3 halo;
$R^3$ is $C_5$-$C_6$ cycloalkyl or $C_1$-$C_8$ alkyl optionally substituted with 1 to 3 halo substitutents;
Het is a 5- or 6-membered saturated cyclic ring having 1 or 2 heteroatoms selected from N, O and S, wherein said ring is optionally substituted with 1 to 3 substituents selected from halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo$(C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^4$ is H, $C_1$-$C_8$ alkyl, $C_3$-$C_8$ cycloalkyl$(C_1$-$C_8)$alkyl, or aryl$(C_1$-$C_8)$alkyl; wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo$(C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^5$ is H, F or Cl;
$R^6$ is $C_3$-$C_6$ cycloalkyl;
Y is C(=O);
Z is O, $CH_2$, NH or $N(CH_3)$;
M is $C_1$-$C_8$ alkylene or $C_2$-$C_8$ alkenylene, wherein said alkylene or alkenylene is optionally substituted with 1 or 2 substituents selected from the group consisting of $C_1$-$C_8$ alkyl, $C_3$-$C_8$ cycloalkyl$(C_1$-$C_8$ alkyl) or aryl$(C_1$-$C_8$ alkyl), and 2 adjacent substituents of M, if present, are optionally taken together to form a 3- to 6-membered cyclic ring containing 0-2 heteroatoms selected from N, O, and S; and each $R^7$ is independently H, $C_1$-$C_6$ alkyl, $C_3$-$C_6$ cycloalkyl, $C_3$-$C_6$ cycloalkyl$(C_1$-$C_5)$alkyl, aryl, aryl$(C_1$-$C_4)$alkyl, heteroaryl, heteroaryl$(C_1$-$C_4$ alkyl), heterocyclyl, or heterocyclyl$(C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo$(C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1$-$C_8$ alkyl, $C_3$-$C_8$ cycloalkyl, $C_3$-$C_8$ cycloalkyl$(C_1$-$C_8$ alkyl), aryl, aryl$(C_1$-$C_4$ alkyl), heteroaryl, heterocyclyl, heteroaryl$(C_1$-$C_4$ alkyl), or heterocyclyl$(C_1$-$C_8$ alkyl), wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo$(C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and)$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing 0-3 heteroatoms selected from N, O and S;

$R^9$ is $C_1$-$C_8$ alkyl, $C_3$-$C_8$ cycloalkyl, $C_3$-$C_8$ cycloalkyl$(C_1$-$C_8$ alkyl), $C_1$-$C_8$ alkoxy, $C_3$-$C_8$ cycloalkoxy, aryl, aryl$(C_1$-$C_4$ alkyl), heteroaryl, heterocyclyl, heteroaryl$(C_1$-$C_4$ alkyl), or heterocyclyl$(C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing 0-3 heteroatoms selected from N, O and S;

or $R^8$ and $R^9$ are optionally taken together, with the nitrogen atom to which they are attached, to form a 4- to 8-membered monocyclic ring containing 0-2 additional heteroatoms selected from N, O and S; and $R^{10}$ is H or $C_1$-$C_6$ alkyl.

2. A compound of formula (I):

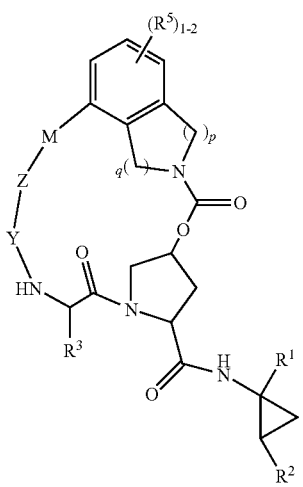

or a pharmaceutically acceptable salt or hydrate thereof, wherein:

p and q are both 1;

$R^1$ is $CO_2R^{10}$, $CONR^{10}SO_2R^6$, $CONR^{10}SO_2NR^8R^9$, or tetrazolyl;

$R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

Het is a 5- or 6-membered saturated cyclic ring having 1 or 2 heteroatoms selected from N, O and S, wherein said ring is optionally substituted with 1 to 3 substituents selected from halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^4$ is H, $C_1$-$C_8$ alkyl, $C_3$-$C_8$ cycloalkyl($C_1$-$C_8$)alkyl, or aryl($C_1$-$C_8$)alkyl; wherein aryl is phenyl or naphthyl and said alkyl, cycloalkyl, or aryl is optionally substituted with 1 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^5$ is H, halo, $OR^{10}$, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, or alkyl is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein 2 adjacent substituents of said cycloalkyl, cycloalkoxy, aryl, heteroaryl or heterocyclyl, if present, are optionally taken together to form a 3- to 6-membered cyclic ring containing 0-3 heteroatoms selected from N, O and S;

$R^6$ is $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl ($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is $C(=O)$, $SO_2$, or $C(=N—CN)$;

Z is $C(R^{10})_2$, O, or $N(R^4)$;

M is $C_1$-$C_{12}$ alkylene or $C_2$-$C_{12}$ alkenylene, wherein said alkylene or alkenylene is substituted with 2 substituents selected from the group consisting of $C_1$-$C_8$ alkyl, $C_3$-$C_8$ cycloalkyl($C_1$-$C_8$ alkyl), and aryl($C_1$-$C_8$ alkyl); and the 2 adjacent substituents of M are optionally taken together to form a 3- to 6-membered cyclic ring containing 0-3 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$O_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo($C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing 0-3 heteroatoms selected from N, O and S;

$R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing 0-3 heteroatoms selected from N, O and S;

or $R^8$ and $R^9$ are optionally taken together, with the nitrogen atom to which they are attached, to form a 4- to 8-membered monocyclic ring containing 0-2 additional heteroatoms selected from N, O and S; and each $R^{10}$ is independently H or $C_1$-$C_6$ alkyl.

3. The compound of claim 2, wherein $R^1$ is $CONHSO_2R^6$.

4. The compound of claim 3, wherein $R^6$ is $C_3$-$C_6$ cycloalkyl.

5. The compound of claim 2, wherein $R^2$ is $C_2$-$C_4$ alkenyl.

6. The compound of claim 2, wherein Y is C=O and Z is O.

7. The compound of claim 2, wherein $R^3$ is $C_1$-$C_8$ alkyl optionally substituted with 1 to 3 substituents selected from halo and $OR^{10}$.

8. The compound of claim 7, wherein $R^3$ is unsubstituted $C_1$-$C_8$ alkyl.

9. The compound of claim 2, wherein $R^3$ is $C_3$-$C_8$ cycloalkyl optionally substituted with 1 to 3 substituents selected from halo and $OR^{10}$.

10. The compound of claim 9, wherein $R^3$ is unsubstituted $C_3$-$C_8$ cycloalkyl.

11. The compound of claim 2, wherein:
$R^1$ is $CONHSO_2R^6$;
$R^6$ is $C_3$-$C_6$ cycloalkyl;
$R^2$ is $C_2$-$C_4$ alkenyl;
Y is C=O;
Z is O; and
$R^3$ is $C_1$-$C_8$ alkyl or $C_3$-$C_8$ cycloalkyl, where said $R^3$ is optionally substituted with 1 to 3 substituents selected from halo and $OR^{10}$.

12. A pharmaceutical composition comprising an effective amount of a compound of any one of claim 1 or 2, and a pharmaceutically acceptable carrier.

13. The pharmaceutical composition of claim 12, further comprising a second therapeutic agent selected from the group consisting of a HCV antiviral agent, an immunomodulator, and an anti-infective agent.

14. The pharmaceutical composition of claim 13, wherein the HCV antiviral agent is an antiviral selected from the group consisting of a HCV protease inhibitor and a HCV NS5B polymerase inhibitor.

15. A method of inhibiting HCV NS3 protease activity in a subject in need thereof, comprising administering a compound of any one of claim 1 or 2.

16. A method of preventing or treating infection by HCV in a subject in need thereof, comprising administering a compound of any one of claim 1 or 2.

17. The method of claim 16, further comprising administering at least one second therapeutic agent selected from the group consisting of a HCV antiviral agent, an immunomodulator, and an anti-infective agent.

18. The method of claim 17, wherein the HCV antiviral agent is an antiviral selected from the group consisting of a HCV protease inhibitor and a HCV NS5B polymerase inhibitor.

* * * * *

UNITED STATES PATENT AND TRADEMARK OFFICE
CERTIFICATE OF CORRECTION

PATENT NO. : 8,216,999 B2  
APPLICATION NO. : 12/325965  
DATED : July 10, 2012  
INVENTOR(S) : M. Katharine Holloway et al.

It is certified that error appears in the above-identified patent and that said Letters Patent is hereby corrected as shown below:

In The Claims

Column 189, lines 40-58
delete the entire text.

Column 190, line 12 to Column 191, line 25
delete the entire text.

Signed and Sealed this
Tenth Day of February, 2015

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Protease Substrate
<221> NAME/KEY: ACETYLATION
<222> LOCATION: 1
<221> NAME/KEY: AMIDATION
<222> LOCATION: 11
<221> NAME/KEY: SITE
<222> LOCATION: 1
<223> OTHER INFORMATION: Europium label
<221> NAME/KEY: MOD_RES
<222> LOCATION: 7
<223> OTHER INFORMATION: Xaa = Abu
<221> NAME/KEY: SITE
<222> LOCATION: 8
<223> OTHER INFORMATION: Xaa = 2-hydroxy propanoic acid
<221> NAME/KEY: SITE
<222> LOCATION: (11)...(11)
<223> OTHER INFORMATION: QSY-7 label
<221> NAME/KEY: THIOLEST
<222> LOCATION: (7)...(8)
```

```
<400> SEQUENCE: 1

Cys Asp Asp Met Glu Glu Xaa Xaa Ser Ala Lys
1               5                   10
```